(12) United States Patent
McCarthy et al.

(10) Patent No.: US 10,370,388 B2
(45) Date of Patent: *Aug. 6, 2019

(54) HETEROCYCLIC COMPOUNDS AND METHODS OF THEIR USE

(71) Applicant: NOVARTIS AG, Basel (CH)

(72) Inventors: Thomas David McCarthy, Westport, CT (US); Alan Naylor, Royston (GB)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,375

(22) Filed: Feb. 6, 2017

(65) Prior Publication Data
US 2017/0145032 A1 May 25, 2017

Related U.S. Application Data

(63) Continuation of application No. 14/370,737, filed as application No. PCT/AU2013/000003 on Jan. 4, 2013, now Pat. No. 9,624,243.

(30) Foreign Application Priority Data

Jan. 6, 2012 (AU) .............................. 2012900057

(51) Int. Cl.
| A61K 31/4439 | (2006.01) |
| A61K 31/40 | (2006.01) |
| C07D 498/10 | (2006.01) |
| C07D 403/04 | (2006.01) |
| C07D 471/04 | (2006.01) |
| C07D 471/10 | (2006.01) |
| C07D 487/04 | (2006.01) |
| C07D 487/10 | (2006.01) |
| C07D 205/04 | (2006.01) |
| C07D 207/16 | (2006.01) |
| C07D 207/22 | (2006.01) |
| C07D 209/18 | (2006.01) |
| C07D 209/42 | (2006.01) |
| C07D 209/94 | (2006.01) |
| C07D 401/04 | (2006.01) |
| C07D 401/12 | (2006.01) |
| C07D 409/04 | (2006.01) |
| C07D 498/04 | (2006.01) |
| C07D 207/14 | (2006.01) |
| C07D 413/04 | (2006.01) |

(52) U.S. Cl.
CPC ............ *C07D 498/10* (2013.01); *A61K 31/40* (2013.01); *A61K 31/4439* (2013.01); *C07D 205/04* (2013.01); *C07D 207/14* (2013.01); *C07D 207/16* (2013.01); *C07D 207/22* (2013.01); *C07D 209/18* (2013.01); *C07D 209/42* (2013.01); *C07D 209/94* (2013.01); *C07D 401/04* (2013.01); *C07D 401/12* (2013.01); *C07D 403/04* (2013.01); *C07D 409/04* (2013.01); *C07D 413/04* (2013.01); *C07D 471/04* (2013.01); *C07D 471/10* (2013.01); *C07D 487/04* (2013.01); *C07D 487/10* (2013.01); *C07D 498/04* (2013.01)

(58) Field of Classification Search
None
See application file for complete search history.

(56) References Cited

U.S. PATENT DOCUMENTS

| 3,654,034 | A | 4/1972 | Welstead |
| 5,401,851 | A | 3/1995 | Boyd et al. |
| 5,612,360 | A | 3/1997 | Boyd et al. |
| 5,789,434 | A | 8/1998 | Kluender et al. |
| 2006/0258728 | A1 | 11/2006 | Tani et al. |
| 2014/0378430 | A1 | 12/2014 | McCarthy et al. |
| 2015/0011565 | A1 | 1/2015 | McCarthy et al. |
| 2015/0218180 | A1 | 8/2015 | McCarthy et al. |
| 2016/0145213 | A1 | 5/2016 | McCarthy et al. |

FOREIGN PATENT DOCUMENTS

| JP | 08092207 A | | 7/1995 | |
| WO | WO 95/09859 | * | 4/1995 | ............. A61K 31/69 |
| WO | 1995/022524 A1 | | 8/1995 | |
| WO | 1997/02032 A1 | | 1/1997 | |
| WO | 2003/0459912 A1 | | 6/2003 | |
| WO | 2004/004665 A2 | | 1/2004 | |
| WO | 2004/022529 A1 | | 3/2004 | |
| WO | 2005/046575 A2 | | 5/2005 | |

(Continued)

OTHER PUBLICATIONS

Cas Registry No. 1340356-88-8.
Cas Registry No. 1275418-10-4.
Cas Registry No. 1274920-10-3.
Cas Registry No. 1274568-52-3.
Cas Registry No. 1272108-06-1.
Cas Registry No. 1270817-82-7.
Cas Registry No. 1104778-25-7.
Cas Registry No. 1101927-58-5.
Chakrabarty, Endocrinology, 2008, 149(7): 3452-3460.

(Continued)

*Primary Examiner* — Samantha L Shterengarts
(74) *Attorney, Agent, or Firm* — Wendy F. Ballard

(57) ABSTRACT

The present invention relates to heterocyclic compounds useful for antagonizing angiotensin II Type 2 ($AT_2$) receptor. More particularly the invention relates to pyrrolidine and azetidine compounds, compositions containing them and their use in methods of treating or preventing disorders or diseases associated with $AT_2$ receptor function including neuropathic pain, inflammatory pain, conditions associated with neuronal hypersensitivity, impaired nerve conduction velocity, cell proliferation disorders, disorders associated with an imbalance between bone resorption and bone formation and disorders associated with aberrant nerve regeneration.

26 Claims, 3 Drawing Sheets

(56) References Cited

FOREIGN PATENT DOCUMENTS

| WO | 2007/053406 A1 | 5/2007 |
|---|---|---|
| WO | 2009/039069 A1 | 3/2009 |
| WO | 2010/017401 A1 | 2/2010 |
| WO | 2011/073376 A1 | 6/2011 |

OTHER PUBLICATIONS

Clere, Int'l J. Cancer, 2010, 127: 2279-2291.
Izu, J. Biol. Chem., 2009, 248(4): 4857-4864.
Steckelings, Peptides, 2005, 26: 1401-1409.
Wallinder, Bior & Med. Chem., 2008, 16: 6841-6849.
Wan, J. Med. Chem., 2004, 47: 5995-6008.
Wexler, J. Med. Chem., 1996, 39(3): 625-656.
Zhang, Biorg. & Med. Chem., 2007, 15(7): 2749-2758.
Cas Reg. No. 1099657-10-9.

International Preliminary Report on Patentability for related application PCT/AU2013/000003, filed on Jan. 4, 2013 and prepared on May 6, 2014.
International Search Report for related application PCT/AU2013/000003, filed on Jan. 4, 2013 and dated Mar. 20, 2013.
Database Registry Chemical Abstracts Service, Columbus, Ohio, Accession No. RN 178866-91-6, Entered STN: Jul. 25, 1996.
Ito, Nobuyuki, Cancer Science 94(1), (2003) 3-8.
Damour, D. et al., "Synthesis of Novel Proline and γ-Lactam Derivatives as Non-Peptide Mimics of Somatostatin / Sandostatin", Tetrahedron, 1999, vol. 55, pp. 10135-10154.
CAS Registry No. 1026515-71-8; STN Entry Date Jun. 8, 2008; 1H-Pyrrole-1-carboxamide, 4-(2,5-difluorophenyl)-N-[(3S,4S)-4-fluoro-3-pyrrolidinyl]-2,5-dihydro-2-(hydroxymethyl)-N-phenyl-, (2S)-.
CAS Registry No. 1025884-33-6; Entry Date Jun. 5, 2008; 1H-Pyrrole-1-carboxamide, 4-(2,5-difluorophenyl)-N-[(3R,4R)-4-fluoro-1-methyl-3-pyrrolidinyl]-2,5-dihydro-2-(hydroxymethyl)-N-phenyl-, (2S)-.

* cited by examiner

HETEROCYCLIC COMPOUNDS AND METHODS OF THEIR USE

This application is a continuation application of U.S. application Ser. No. 14/370,737 filed on Jan. 4, 2013; which is a U.S. national Phase filing of International application Serial No. PCT/AU2013/000003 filed on Jan. 4 2013 and claims priority to Australian provisional Application No. 2012900057, filed Jan. 12, 2012; the content of which is incorporated herein by reference in their entirety.

FIELDS OF THE INVENTION

The present invention relates generally to compounds that are useful in antagonizing the angiotensin II type 2 ($AT_2$) receptor. More particularly, the invention relates to heterocyclic compounds of formula (I) and their use as $AT_2$ receptor antagonists. Pharmaceutical compositions comprising the compounds and their use in modulating the $AT_2$ receptor and therapies that require modulation of the $AT_2$ receptor are described.

BACKGROUND OF THE INVENTION

Although $AT_2$ receptor has been known since the 1980s, much less is known about its biological function than the angiotensin. II type 1 ($AT_1$) receptor, which has been studied for its functional effects on vasoconstriction, aldosterone release and cardiovascular growth [Wexler et al., 1996]. However, more recently the $AT_2$ receptor has been implicated in the differentiation and regeneration of neuronal tissue [Steckelings et al., 2005; Chakrabarty et al., 2008], cell proliferation and angiogenesis [Clere et al., 2010] and maintenance of bone mass [Izu et al., 2009].

$AT_2$ receptor antagonists have also recently been associated with the treatment of pain, particularly inflammatory pain [WO 2007/106938] and neuropathic pain [WO 2006/066361], two types of pain which are difficult to treat or relieve. Impaired nerve conduction velocity is also associated with nerve damage and has been implicated in peripheral neuropathies, Carpel Tunnel Syndrome, ulnar neuropathy, Guillian-Barré Syndrome, fascioscapulohumeral muscular dystrophy and spinal disc herneation. Impaired nerve conduction velocity can result in diminished reflex responses and altered peripheral sensation such as parathesia and in some cases pain and $AT_2$ receptor antagonists have been shown to restore nerve conduction velocity [WO 2011/088504].

While there are effective therapies for treating nociceptive pain, inflammatory and neuropathic pain are often resistant to these therapies. In addition, current therapies of neuropathic pain, inflammatory pain, impaired nerve conduction velocity and other types of pain that are difficult to treat, have serious side effects, for example, cognitive changes, sedation, nausea and in the case of narcotic drugs, tolerance and dependence. There is a need for further therapies that treat or prevent neuropathic pain, inflammatory pain, impaired nerve conduction velocity and other painful conditions that are currently difficult to treat.

Cell proliferation and angiogenesis are important biological functions in normal tissue. However, uncontrolled cell proliferation and angiogenesis can lead to tumors and other proliferative disorders. While there are some effective chemotherapies available for tumors, many result in unpleasant side effects and/or have high toxicity for normal cells.

Further therapies for reducing or preventing abnormal cell proliferation in a controlled manner are required and $AT_2$ receptor antagonists have been shown to have antiproliferative activity [Clere et al., 2010].

Osteoporosis is a significant problem in older populations, especially in post-menopausal women. Current therapies for osteoporosis rely on calcium supplementation. However, the control of bone formation and bone resorption is complex and further therapies for improving bone mass are required and $AT_2$ receptor antagonists have been shown to increase bone mass [Izu et al., 2009].

The role of the $AT_2$ receptor in modulating neuronal outgrowth and associated effects of $AT_2$ receptor antagonists on reducing neuronal outgrowth, indicates that $AT_2$ receptor antagonists may be useful therapeutics in diseases characterized by aberrant nerve regeneration [Chakrabarty et al., 2008].

The present invention is predicated in part on the discovery of heterocyclic azetidine and pyrrolidine compounds that have $AT_2$ receptor antagonist activity.

SUMMARY OF THE INVENTION

In a first aspect of the present invention there is provided a compound of formula (I):

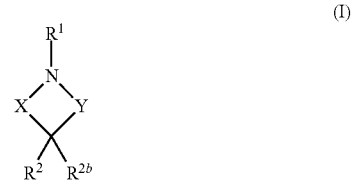

(I)

wherein:

X is absent and Y is —CHR³CH₂—, —CH₂CHR³—, —CHR³CHR⁴CH₂—, —CH₂CHR³CHR⁴—, —CH₂CH₂CHR³—, —CR³═CHCH₂—, —CH═CHR³CH₂— or —CH₂CH═CR³—; or X is —CHR⁵— and Y is —CHR³—, —CHR³CHR⁴—, —CH₂CHR³—, —CHR³CR⁴—; —CR³═CH— or —CH═CR³—; wherein when Y is —CHR³CR⁴═, $R^{2b}$ is absent; or X is —CH₂CHR⁵— or C(═O)CHR⁵— and Y is —CHR³—;

R¹ is —C(═O)CHR⁶R⁷, —C(═O)NR⁶R⁷, —C(═O)CH₂CHR⁶R⁷, —C(═O)CH═CR⁶R⁷, —C(═S)CHR⁶R⁷, —C(═S)NR⁶R⁷, —C(═S)CH₂CHR⁶R⁷, —C(═S)CH═CR⁶R⁷, —C(═NR⁸)CHR⁶R⁷, —C(═NR⁸)NR⁶R⁷, —C(═NR⁸)CH₂CHR⁶R⁷ and —C(═NR⁸)CH═CR⁶R⁷;

R² is —C$_{1-6}$alkyl, —C$_{2-6}$alkenyl, —C$_{2-6}$alkynyl, —OR⁸, —SR⁸, —N(R⁸)₂, —C(═O)R⁸, —C(═O)N(R⁸)₂, —N(R⁸)C(═O)R⁸, —N(R⁸)C(═O)N(R⁸)₂, —N(R⁸)SO₂R⁸, —SO₂N(R⁸)₂, —N(R⁸)SO₂N(R⁸)₂, —W— cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, ═CH—C(═O)-J-R¹⁰, ═CHC(═O)NH-J-R¹⁰, —OCH₂CHR¹⁰CH₂R¹⁰ or —OCH₂C(R¹⁰)═CHR¹⁰;

$R^{2b}$ is hydrogen;

R³ is a carboxylic acid, —CH₂CO₂H, —C(═O)C(═O)OH, —CH₂OH, —C(O)NH₂, —CN, —CH₂C(O)NH₂, —CH₂CN, a -carboxylic acid bioisostere or —CH₂carboxylic acid bioisostere;

$R^4$ is hydrogen or $R^3$ and $R^4$ together form a group:

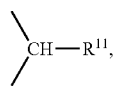

where $R^{11}$ is a carboxylic acid, —$CH_2CO_2H$, —$C(=O)$ $C(=O)OH$, —$CH_2OH$, —$C(O)NH_2$, —$CN$, —$CH_2C(O)$ $NH_2$, —$CH_2CN$, a carboxylic acid bioisostere or —$CH_2$carboxylic acid bioisostere;

$R^5$ is hydrogen or together with $R^2$ forms a fused aryl, heterocyclyl or heteroaryl ring, optionally substituted with one or two optional substituents selected from —$C_{1-6}$alkyl, —$C_{2-6}$alkenyl, —$C_{2-6}$alkynyl, cycloalkyl, cycloalkenyl, aryl, heterocyclyl, heteroaryl, —$C_{1-6}$alkyleneR$^{10}$, —$C_{2-6}$alkenyleneR$^{10}$, —$C_{2-6}$allcynyleneR$^{10}$, —$OCHF_2$, —$OR^9$, —$OC_{1-6}$alkyleneR$^{10}$, —$OC_{2-6}$alkenyleneR$^{10}$, —$OC_{2-6}$alkynyleneR$^{10}$, —$SO_2NHR^9$, —$NHSO_2R^9$, —$NHC(=O)NHR^9$, —$NHC(=O)OR^9$ or —$CH(OH)CH(OH)R^9$;

$R^6$ and $R^7$ are independently hydrogen, —$C_{1-6}$alkyl, cycloalkyl, cycloalkenyl, aryl, heterocyclyl, heteroaryl, —$CH_2$aryl, —$CH_2$cycloalkyl, —$CH_2$cycloalkenyl, —$CH_2$heterocyclyl or —$CH_2$heteroaryl; provided that $R^6$ and $R^7$ are not both hydrogen;

$R^8$ is hydrogen, —$C_{1-8}$alkyl, —$C_{1-8}$fluoroalkyl, aryl, $C_{1-8}$alkylenearyl, —$C_{2-8}$alkenylenearyl or —$C_{2-8}$alkynylenearyl;

$R^9$ is —$C_{1-6}$alkyl, —$C_{2-6}$alkenyl, —$C_{2-6}$alkynyl, cycloalkyl, cycloalkenyl, aryl, heterocyclyl, heteroaryl, arylcycloalkyl-, arylcycloalkenyl-, arylaryl-, arylheterocyclyl- or arylheteroaryl-;

W is a covalent bond, —O—, —S—, —SO—, —$SO_2$— $N(R^8)$—, —$C(=O)$—, —$N(R^8)C(=O)$—, —$C(=O)N$ $(R^8)$—, —$C_{2-4}$alkenylene-, —$C_{2-4}$alkynylene-, —$C_{1-3}$alkyleneQC$_{1-3}$alkylene-, -$QC_{1-4}$alkylene-, -$QC_{2-4}$alkenylene-, -$QC_{2-4}$alkynylene-, —$C_{2-4}$alkenyleneQ-, —$C_{2-4}$alkynyleneQ-QC$_{1-4}$alkyleneQ-, -$QC_{2-4}$alkenyleneQ- or —$OC_{2-4}$alkynyleneQ-;

Q is —O—, —S—, —SO—, —$SO_2$—N$(R^8)$—, —$C(=O)$—, —$N(R^8)C(=O)$—, —$C(=O)N(R^8)$—,

Z is cycloalkyl-, -cycloalkenyl-, -aryl-, -heterocyclyl- or -heteroaryl-;

J is a covalent bond or —$C_{1-6}$alkylene-, —$C_{2-6}$alkenylene- or —$C_{2-6}$alkynylene, in which one —$CH_2$— group in the alkylene, alkenylene or alkynylene group may be replaced by —O—, —S—, —S(O)—, —$S(O)_2$—N(R$^8$)—, —C(=O)NH— or —NHC(=O)—;

$R^{10}$ is cycloalkyl, cycloalkenyl, aryl, heterocyclyl or heteroaryl; and wherein each cycloalkyl, cycloalkenyl, aryl, heterocyclyl and heteroaryl may be optionally substituted;

or a pharmaceutically acceptable salt thereof.

In another aspect, the present invention provides a pharmaceutical composition comprising the compounds of formula (I) or a pharmaceutically acceptable salt thereof and a pharmaceutically acceptable carrier.

In a further aspect of the invention, there is provided a method of treating or preventing neuropathic pain in a subject comprising administering a compound of formula (I) or a pharmaceutically acceptable salt thereof.

In yet a further aspect of the invention there is provided a method of treating or preventing a condition characterized by neuronal hypersensitivity in a subject comprising administering a compound of formula (I) or a pharmaceutically acceptable salt thereof.

In yet another aspect of the invention, there is provided a method of treating or preventing inflammatory pain in a subject comprising administering a compound of formula (I) or a pharmaceutically acceptable salt thereof.

In a further aspect, the present invention provides a method of treating or preventing impaired nerve conduction velocity in a subject comprising administering a compound of formula (I) or a pharmaceutically acceptable salt thereof.

In yet a further aspect of the invention there is provided a method of producing analgesia in a subject comprising administering a compound of formula (I) or a pharmaceutically acceptable salt thereof.

In still another aspect of the invention there is provided a method of treating or preventing a cell proliferative disorder in a subject comprising administering a compound of formula (I) or a pharmaceutically acceptable salt thereof.

In a further aspect the present invention provides a method of treating or preventing a disorder associated with an imbalance between bone resorption and bone formation in a subject comprising administering a compound of formula (I) or a pharmaceutically acceptable salt thereof.

In yet another aspect the present invention provides a method of treating a disorder associated with aberrant nerve regeneration in a subject comprising administering a compound of formula (I) or a pharmaceutically acceptable salt thereof.

DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

As used herein, the term "$AT_2$ receptor" means an angiotensin II type 2 ($AT_2$) receptor polypeptide that can bind angiotensin II and/or one or more other ligands. The term "$AT_2$ receptor" encompasses vertebrate homologs of $AT_2$ receptor family members, including, but not limited to, mammalian, reptilian and avian homologs. Representative mammalian homologs of $AT_2$ receptor family members include, but are not limited to, murine and human homologs.

The term "antagonist" as used herein refers to a compound that decreases or inhibits the biological activity and/or function of an $AT_2$ receptor, including binding to the $AT_2$ receptor and blocking access to angiotensin II, inhibiting a gene that expresses $AT_2$ receptor, or inhibiting an expression product of that gene. By the term "selective", is meant that the compound binds to and/or inhibits $AT_2$ receptor activity to a greater extent than binding and inhibition of the $AT_1$ receptor. In some instances, selective refers to binding and/or inhibition of the $AT_2$ receptor with little or no binding at the $AT_1$ receptor.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

By "condition characterized by neuronal hypersensitivity" is meant conditions that have symptoms of pain related to neuronal hypersensitivity and/or allodynia. Examples of this type of condition include fibromyalgia and irritable bowel syndrome.

By "disorder associated with aberrant nerve regeneration" is meant disorders in which there is abnormal axon outgrowth in neurons. This abnormal outgrowth may be associated with painful conditions including breast pain, interstitial cystitis, vulvodynia and cancer chemotherapy-induced neuropathies.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "hyperalgesia" is meant an increased response to a stimulus that is normally painful. A hyperalgesia condition is one that is associated with pain caused by a stimulus that is not normally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

The term "nociceptive pain" refers to the normal, acute pain sensation evoked by activation of nociceptors located in non-damaged skin, viscera and other organs in the absence of sensitization.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and inflammatory bowel disease including Crohn's disease and colitis, as well as other inflammatory diseases including carditis, dermatitis, myositis, neuritis and collagen vascular diseases.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, $28^{th}$ Edition, W. B. Saunders Company, Philadelphia, Pa.). The goal of treatment of pain is to reduce the degree of severity of pain perceived by a treatment subject.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies' Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association. Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including paresthesia. As used herein, "paresthesia" refers to a sensation of tingling, prickling, weakness or numbness in a subject's skin. It is also known as "pins and needles" or a limb "falling asleep". Paresthesia may be transient, acute or chronic and may occur alone or be accompanied by other symptoms such as pain.

As used herein, the term "cell proliferative disorder" refers to diseases or conditions where unwanted or damaged cells are not removed by normal cellular process, or diseases or conditions in which cells undergo aberrant, unwanted or inappropriate proliferation. Disorders characterized by inappropriate cell proliferation include, for example, inflammatory conditions such as inflammation arising from acute tissue injury including, for example, acute lung injury, cancer including cancers characterized by tumors, autoimmune disorders, tissue hypertrophy and the like.

The term "disorder associated with an imbalance between bone resorption and bone formation" includes disorders where there is insufficient development of bone mass, excessive bone resorption and insufficient bone formation during remodelling. An exemplary disorder associated with an imbalance between bone resorption and bone formation is osteoporosis.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

The term "fluoroalkyl" as used herein refers to an alkyl group in which one or more hydrogen atoms of the alkyl group is replaced with a fluoro atom. Where appropriate, the alkyl group may have a specified number of carbon atoms, for example, $C_{1-6}$fluoroalkyl which includes fluoroalkyl groups having 1, 2, 3, 4, 5 or 6 carbon atoms in a linear or branched arrangement. Examples of fluoroalkyl groups include fluoromethyl, difluoromethyl, trifluoromethyl, 1-fluoroethyl, 2-fluoroethyl, 1,1-difluoroethyl, 2,2-fluoroethyl, 1,1,2-trifluoroethyl, 2,2,2-trifluoroethyl, 1,1,2,2,2-pentafluoroethyl, 3-fluoropropyl, 3,3-difluoropropyl, 3,3,3-trifluoropropyl, 4-fluorobutyl, 4,4-difluorobutyl, 4,4,4-trifluorobutyl, 5-fluoropentyl, 5,5-difluoropentyl, 5,5,5-trifluoropentyl, 6-fluorohexyl, 6,6-difluorohexyl or 6,6,6-trifluorohexyl and the like.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "alkylene" refers to a divalent saturated hydrocarbon chain having 1 to 6 carbon atoms. Where appropriate, the alkylene group may have a specified number of carbon atoms, for example, $C_{1-6}$alkylene includes alkylene groups having 1, 2, 3, 4, 5 or 6 carbon atoms in a linear arrangement. Examples of suitable alkylene groups include, but are not limited to, —$CH_2$—, —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—.

As used herein, the term "alkenylene" refers to a divalent unsaturated hydrocarbon chain having 2 to 6 carbon atoms and at least one double bond. Where appropriate, the alkenylene group may have a specified number of carbon atoms, for example, $C_{2-6}$alkenylene includes alkenylene groups having 2, 3, 4, 5 or 6 carbon atoms in a linear arrangement. The double bonds may be in either E or Z configuration. Examples of suitable alkenylene groups include, but are not limited to, —CH=CH—, —CH=CHCH$_2$—, —CH$_2$CH=CH—, —CH=CHCH$_2$CH$_2$—, —CH$_2$CH=CHCH$_2$—, —CH$_2$CH$_2$CH=CH—, —CH=CHCH$_2$CH$_2$CH$_2$—, —CH$_2$CH=CHCH$_2$CH$_2$—, —CH$_2$CH=CHCH$_2$CH$_2$—, —CH$_2$CH$_2$CH=CHCH$_2$—, —CH$_2$CH$_2$CH=CHCH$_2$—, —CH$_2$CH$_2$CH$_2$CH=CH—, —CH$_2$CH$_2$CH$_2$CH=CH—, —CH$_2$CH$_2$CH$_2$CH=CH—.

As used herein, the term "alkynylene" refers to a divalent unsaturated hydrocarbon chain having 2 to 6 carbon atoms and at least one triple bond. Where appropriate, the alkynylene group may have a specified number of carbon atoms, for example, $C_{2-6}$alkynylene includes alkynylene groups having 2, 3, 4, 5 or 6 carbon atoms in a linear arrangement. Examples of suitable alkynylene groups include, but are not limited to, —C≡C—, —C≡CCH$_2$—, —CH$_2$C≡C—, —C≡CCH$_2$CH$_2$—, —CH$_2$C≡CCH$_2$—, —CH$_2$CH$_2$C≡C—, —C≡CCH$_2$CH$_2$CH$_2$—, —CH$_2$C≡CCH$_2$CH$_2$—, —CH$_2$CH$_2$C≡CCH$_2$—, —CH$_2$CH$_2$CH$_2$C≡C—, —C≡CCH$_2$CH$_2$GH$_2$CH$_2$—, —CH$_2$C≡CCH$_2$CH$_2$CH$_2$—, —CH$_2$CH$_2$C≡CCH$_2$CH$_2$—, —CH$_2$CH$_2$CH$_2$C≡CCH$_2$— and —CH$_2$CH$_2$CH$_2$CH$_2$C≡C—.

In some embodiments, one or more "—CH$_2$—" groups in an alkylene, alkenylene or alkynylene group may be replaced by a heteroatom or a group containing a heteroatom including —O—, —S—, —NH—, —NR—, —S(O)—, —S(O)$_2$—, —C(=O)—, —C(=O)NH— and —NHC(=O)—.

The term "benzyl" where used herein refers to a phenylmethylene group, $C_6H_5CH_2$—.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), S(O)$_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl and tetrazolyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (=O), —OH, —SH, $C_{2-6}$alkenylO—, $C_{3-6}$cycloalkylO—, $C_{1-6}$alkylS—, $C_{2-6}$alkenylS—, $C_{3-6}$cycloalkylS—, —$CO_2H$, —$CO_2C_{1-6}$alkyl, —$NH_2$, —NH($C_{1-6}$alkyl), —N($C_{1-6}$alkyl)$_2$, —NH(phenyl), —N(phenyl)$_2$, oxo, —CN, —$NO_2$, -halogen, —$CF_3$, —$OCF_3$, —$SCF_3$, —$CHF_2$, —$OCHF_2$, —$SCHF_2$, -phenyl, -heterocyclyl, -heteroaryl, —Oheteroaryl, —Oheterocyclyl, —Ophenyl, —C(O)phenyl, —C(O)$C_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —$CO_2H$, —$CO_2CH_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The term "carboxylic acid bioisotere" refers to a group which is physiochemically or topologically similar to carboxylic acid or carboxylate group. Examples of suitable carboxylic acid or carboxylate isosteres include, but are not limited to, tetrazole, tetrazolate, —CONH-tetrazole, oxadiazole, phosphate (—$PO_3H_2$), —C(OH)(CF$_3$)$_2$, N-(aryl or heteroaryl)-sulfonamides, acylsulfonamides and sulfonic acid (—$SO_3H$) [See Patani and LaVoie, 1996]. Examples of sulfonamide isosteric equivalents of carboxy groups include —$CONHSO_2R^a$, —$CONHSO_2N(R^a)_2$, —$SO_2NHCOR^a$, —$SO_2NHCONHR^a$, —$SO_2NHR^a$ and —$NHSO_2R^a$, where $R^a$ is selected from the group consisting of $C_{1-6}$alkyl, $C_{2-6}$alkenyl, $C_{3-8}$cycloalkyl, aryl, heterocyclyl, heteroaryl and —$CF_3$.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

Compounds of the Invention

In a first aspect of the present invention there is provided a compound of formula (I):

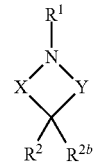

wherein:

X is absent and Y is —CHR$^3$CH$_2$—, —CH$_2$CHR$^3$—, —CHR$^3$CHR$^4$CH$_2$—, —CH$_2$CHR$^3$CHR$^4$—, —CH$_2$CH$_2$CHR$^3$—, —CR$^3$=CHCH$_2$—, —CH=CHR$^3$CH$_2$— or —CH$_2$CH=CR$^3$—; or X is —CHR$^5$ and Y is —CHR$^3$—, —CHR$^3$CHR$^4$—, —CH$_2$CHR$^3$—, —CHR$^3$CR$^4$=, —CR$^3$=CH— or —CH=CR$^3$—; wherein when Y is —CHR$^3$CR$^4$=, R$^{2b}$ is absent; or X is —CH$_2$CHR$^5$— or C(=O)CHR$^5$— and Y is —CHR$^3$—;

R$^1$ is —C(=O)CHR$^6$R$^7$, —C(=O)NR$^6$R$^7$, —C(=O)CH$_2$CHR$^6$R$^7$, —C(=O)CH=CR$^6$R$^7$, —C(=S)CHR$^6$R$^7$, —C(=S)NR$^6$R$^7$, —C(=S)CH$_2$CHR$^6$R$^7$, —C(=S)CH=CR$^6$R$^7$, —C(=NR$^8$)CHR$^6$R$^7$, —C(=NR$^8$)NR$^6$R$^7$, —C(=NR$^8$)CH$_2$CHR$^6$R$^7$ and —C(=NR$^8$)CH=CR$^6$R$^7$;

R$^2$ is —C$_{1-6}$alkyl, —C$_{2-6}$alkenyl, —C$_{2-6}$alkynyl, —OR$^8$, —SR$^8$, —N(R$^8$)$_2$, —C(=O)R$^8$, —C(=O)N(R$^8$)$_2$, —N(R$^8$)C(=O)R$^8$, —N(R$^8$)C(=O)N(R$^8$)$_2$, —N(R$^8$)SO$_2$R$^8$, —SO$_2$N(R$^8$)$_2$, —N(R$^8$)SO$_2$N(R$^8$)$_2$, —W-cycloalkyl, —W-cycloalkynyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, =CH—C(=O)-J-$R^{10}$, =CHC(=O)NH-J-$R^{10}$, —OCH$_2$CHR$^{10}$CH$_2$R$^{10}$ or —OCH$_2$C(R$^{10}$)=CHR$^{10}$;

$R^{2b}$ is hydrogen;

$R^3$ is a carboxylic acid, —CH$_2$CO$_2$H, —C(=O)C(=O)OH, —CH$_2$OH, —C(O)NH$_2$, —CN, —CH$_2$C(O)NH$_2$, —CH$_2$CN, a -carboxylic acid bioisostere or —CH$_2$carboxylic acid bioisostere;

$R^4$ is hydrogen or $R^3$ and $R^4$ together form a group:

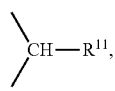

where $R^{11}$ is a carboxylic acid, —CH$_2$CO$_2$H, —C(=O)C(=O)OH, —CH$_2$OH, —C(O)NH$_2$, —CN, —CH$_2$C(O)NH$_2$, —CH$_2$CN, a carboxylic acid bioisostere or —CH$_2$carboxylic acid bioisostere;

$R^5$ is hydrogen or together with $R^2$ forms a fused aryl, heterocyclyl or heteroaryl ring, optionally substituted with one or two optional substituents selected from —C$_{1-6}$alkyl, —C$_{2-6}$alkenyl, —C$_{2-6}$alkynyl, cycloalkyl, cycloalkenyl, aryl, heterocyclyl, heteroaryl, —C$_{1-6}$alkyleneR$^{10}$, —C$_{2-6}$alkenyleneR$^{10}$, —C$_{2-6}$alkynyleneR$^{10}$, —OCF$_3$, —OCHF$_2$, —OR$^9$, —OC$_{1-6}$alkyleneR$^{10}$, —OC$_{2-6}$alkenyleneR$^{10}$, —OC$_{2-6}$alkynyleneR$^{10}$, —SO$_2$NHR$^9$, —NHSO$_2$R$^9$, —NHC(=O)NHR$^9$, —NHC(=O)OR$^9$ or —CH(OH)CH(OH)R$^9$;

$R^6$ and $R^7$ are independently hydrogen, —C$_{1-6}$alkyl, cycloalkyl, cycloalkenyl, aryl, heterocyclyl, heteroaryl, —CH$_2$aryl, —CH$_2$cycloalkyl, —CH$_2$cycloalkenyl, —CH$_2$heterocyclyl or —CH$_2$heteroaryl; provided that $R^6$ and $R^7$ are not both hydrogen;

$R^8$ is hydrogen, —C$_{1-8}$alkyl, C$_{1-8}$fluoroalkyl, aryl, —C$_{1-8}$alkylenearyl, —C$_{2-8}$alkenylenearyl or —C$_{2-4}$alkynylenearyl;

$R^9$ is —C$_{1-6}$alkyl, —C$_{2-6}$alkenyl, —C$_{2-6}$alkynyl, cycloalkyl, cycloalkenyl, aryl, heterocyclyl, heteroaryl, arylcycloalkyl-, arylcycloalkenyl-, arylaryl-, arylheterocyclyl- or arylheteroaryl-;

W is a covalent bond, —O—, —S—, —SO—, —SO$_2$—N(R$^8$)—, —C(=O)—, —N(R$^8$)C(=O)—, —C(=O)N(R$^8$)—, —C$_{1-4}$alkylene-, —C$_{2-4}$alkenylene-, —C$_{2-4}$alkynylene-, —C$_{1-3}$alkyleneQC$_{1-3}$alkylene-, -QC$_{1-4}$alkylene-, -QC$_{2-4}$alkenylene-, -QC$_{2-4}$alkynylene-, —C$_{1-4}$alkyleneQ-, —C$_{2-4}$alkenyleneQ-, —C$_{2-4}$alkynyleneQ-QC$_{1-4}$alkyleneQ-, -QC$_{2-4}$alkenyleneQ- or —QC$_{2-4}$alkynyleneQ-;

Q is —O—, —S—, —SO—, —SO$_2$—N(R$^8$)—, —C(=O)—, —N(R$^8$)C(=O)—, —C(=O)N(R$^8$)—,

Z is -cycloalkyl-, -cycloalkenyl-, -aryl-, -heterocyclyl- or -heteroaryl-;

J is a covalent bond or —C$_{1-6}$alkylene-, —C$_{2-6}$alkenylene- or —C$_{2-6}$alkynylene, in which one —CH$_2$— group in the alkylene, alkenylene or alkynylene group may be replaced by —O—, —S—, —S(O)—, —S(O)$_2$—N(R$^8$)—, —C(=O)—, —C(=O)NH— or —NHC(=O)—;

$R^{10}$ is cycloalkyl, cycloalkenyl, aryl, heterocyclyl or heteroaryl; and wherein each cycloalkyl, cycloalkenyl, heterocyclyl and heteroaryl may be optionally substituted;

or a pharmaceutically acceptable salt thereof.

In a particular embodiment, the compound of formula (I) is a compound of formula (Ia):

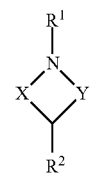

(Ia)

wherein:

X is absent and Y is —CHR$^3$CH$_2$—, —CH$_2$CHR$^3$—, —CHR$^3$CHR$^4$CH$_2$—, —CH$_2$CHR$^3$CHR$^4$—, —CH$_2$CH$_2$CHR$^3$—, —CR$^3$=CHCH$_2$—, —CH=CHR$^3$CH$_2$— or —CH$_2$CH=CR$^3$—; or X is —CHR$^5$ and Y is —CHR$^3$—, —CHR$^3$CHR$^4$—, —CH$_2$CHR$^3$—, —CR$^3$=CH— or —CH=CR$^3$—; or X is —CH$_2$CHR$^5$— or C(=O)CHR$^5$— and Y is —CHR$^3$—;

$R^1$ is —C(=O)CHR$^6$R$^7$, —C(=O)NR$^6$R$^7$, —CHCH$_2$CHR$^6$R$^7$, —C(=O)CH=CR$^6$R$^7$, —C(=S)CHR$^6$R$^7$, —C(=S)NR$^6$R$^7$, —C(=S)CH$_2$CR$^6$R$^7$, —C(=S)CH=CR$^6$R$^7$, —C(=NR$^8$)CHR$^6$R$^7$, —C(=NR$^8$)NR$^6$R$^7$, —C(=NR$^8$)CH$_2$CHR$^6$R$^7$ or —C(=NR$^8$)CH=CR$^6$R$^7$;

$R^2$ is —C$_{1-6}$alkyl, —C$_{2-6}$alkenyl, —C$_{2-6}$alkynyl, —OR$^8$, —SR$^8$, —N(R$^8$)$_2$, —C(=O)R$^8$, —C(=O)N(R$^8$)$_2$, —N(R$^8$)C(=O)R$^8$, —N(R$^8$)C(=O)N(R$^8$)$_2$, —N(R$^8$)SO$_2$R$^8$, —SO$_2$N(R$^8$)$_2$, —N(R$^8$)SO$_2$N(R$^8$)$_2$, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or *W—Z—W-heteroaryl, =CH—C(=O)-J-R$^{10}$, =CHC(=O)NH-J-R$^{10}$, —OCH$_2$CHR$^{10}$CH$_2$R$^{10}$ or —OCH$_2$C(R$^{10}$)=CHR$^{10}$;

$R^3$ is a carboxylic acid, —CH$_2$CO$_2$H, —C(=O)C(=O)OH or a carboxylic acid bioisostere;

$R^4$ is hydrogen or $R^3$ and $R^4$ together form a group:

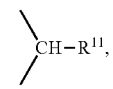

where $R^{11}$ is a carboxylic acid, —CH$_2$CO$_2$H, —C(=O)C(=O)OH, or carboxylic acid bioisostere;

$R^5$ is hydrogen or together with $R^2$ forms a fused aryl, heterocyclyl or heteroaryl ring, optionally substituted with one or two optional substituents selected from —C$_{1-6}$alkyl, —C$_{2-6}$alkenyl, —C$_{2-6}$alkynyl, cycloalkyl, cycloalkenyl, aryl, heterocyclyl, heteroaryl, —C$_{1-6}$alkyleneR$^{10}$, —C$_{2-6}$alkenyleneR$^{10}$, —C$_{2-6}$alkynyleneR$^{10}$, —OCF$_3$, —OCHF$_2$, —OR$^9$, —OC$_{1-6}$alkyleneR$^{10}$, —OC$_{2-6}$alkenyleneR$^{10}$, —OC$_{2-6}$alkynyleneR$^{10}$, —SO$_2$NHR$^9$, —NHSO$_2$R$^9$, —NHC(=O)NHR$^9$, —NHC(=O)OR$^9$ or —CH(OH)CH(OH)R$^9$;

$R^6$ and $R^7$ are independently hydrogen, —C$_{1-6}$alkyl, cycloalkyl, cycloalkenyl, aryl, heterocyclyl, heteroaryl, —CH$_2$aryl, —CH$_2$cycloalkyl, —CH$_2$cycloalkenyl, —CH$_2$heterocyclyl or —CH$_2$heteroaryl; provided that $R^6$ and $R^7$ are not both hydrogen;

$R^8$ is hydrogen, —C$_{1-6}$alkyl, aryl or —C$_{1-6}$alkylenearyl;

$R^9$ is —C$_{1-6}$alkyl, —C$_{2-6}$alkenyl, —C$_{2-6}$alkynyl, cycloalkyl, cycloalkenyl, aryl, heterocyclyl, heteroaryl, arylcycloalkyl-, arylcycloalkenyl-, arylaryl-, arylheterocyclyl- or arylheteroaryl-;

W is a covalent bond, —O—, —S—, —SO—, —SO$_2$—N(R$^8$)—, —C(=O)—, —N(R$^8$)C(=O)—, —C(=O)N (R⁸)—, —C₁₋₄alkylene-, —C₂₋₄alkenylene-, —C₂₋₄alkynylene-, —C₁₋₃alkyleneQC₁₋₃alkylene-, -QC₁₋₄alkylene-, -QC₂₋₄alkenylene-, -QC₂₋₄alkynylene-, —C₁₋₄alkyleneQ-, —C₂₋₄alkenyleneQ-, —C₂₋₄alkynyleneQ- QC₁₋₄alkyleneQ-, -QC₂₋₄alkenyleneQ- or —OC₂₋₄alkynyleneQ-;

Q is —O—, —S—, —SO—, —SO₂—N(R⁸)—, —C(=O)—, —N(R⁸)C(=O)—, —C(=O)N(R⁸)—,

Z is -cycloalkyl-, -cycloalkenyl-, -aryl-, -heterocyclyl- or -heteroaryl-;

J is a covalent bond or —C₁₋₆alkylene-, —C₂₋₆alkenylene- or —C₂₋₆alkynylene, in which one —CH₂— group in the alkylene, alkenylene or alkynylene group may be replaced by —O—, —S—, —S(O)—, —S(O)₂—N(R⁸)—, —C(=O)—, —C(=O)NH— or —NHC(=O)—;

R¹⁰ is cycloalkyl, cycloalkenyl, aryl, heterocyclyl or heteroaryl; and wherein each cycloalkyl, cycloalkenyl, aryl, heterocyclyl and heteroaryl may be optionally substituted;

or a pharmaceutically acceptable salt thereof.

In particular embodiments of formula (I) or formula (Ia), one or more of the following applies:

X is absent and Y is —CHR³CH₂—;

X is —CH₂— or —CHR⁵— and Y is —CHR³—, —CHR³CH₂—, —CHR³CR⁴=, —CH₂CHR³—, —CH=CR³— or —CR³=CH—, wherein when Y is —CHR³CR⁴=, R²ᵇ is absent,

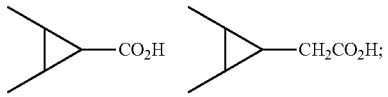

or

X is —CH₂CH₂—, —CH₂CHR⁵— or —C(=O)CHR⁵— and Y is —CHR³—;

R¹ is —C(=O)CHR⁶R⁷, —C(=O)NR⁶R⁷, especially —C(=O)CH(aryl)(aryl), —C(=O)CH(aryl)(cycloalkyl), —C(=O)CH(cycloalkyl)(cycloalkyl), —C(=O)CH(aryl)(alkyl), —C(=O)N(aryl)(aryl), —C(=O)N(aryl)(cycloalkyl), —C(=O)N(cycloalkyl)(cycloalkyl) or —C(=O)N(aryl)(alkyl), where each aryl or cycloalkyl group is optionally substituted; more especially —C(=O)CH(phenyl)(phenyl), —C(=O)CH(phenyl)(cyclohexyl), —C(=O)N(phenyl)(phenyl) or —C(=O)N(phenyl)(cyclohexyl), wherein each phenyl or cyclohexyl group is optionally substituted with one or more substituents selected from —C₁₋₃alkyl, —OC₁₋₃alkyl and halo, especially methyl, methoxy and fluoro; most especially where R¹ is —C(=O)CH(phenyl)(phenyl) and —C(=O)N(phenyl)(phenyl);

R² is cycloalkyl, cycloalkenyl, aryl, heterocyclyl, heteroaryl, heterocyclylaryl, -heterocyclylC₁₋₃alkylenearyl, —C₁₋₄alkylenecycloalkyl, —C₁₋₄alkylenecycloalkenyl, —C₁₋₄alkylenearyl, —C₁₋₄alkyleneheterocyclyl, —C₁₋₄alkyleneheteroaryl, —C₂₋₄alkenylenecycloalkyl, —C₂₋₄alkenylenecycloalkenyl, —C₂₋₄alkenylenearyl, —C₂₋₄alkenyleneheterocyclyl, —C₂₋₄alkenyleneheteroaryl, —C₂₋₄alkynylenecycloalkyl, —C₂₋₄alkynylenecycloalkenyl, —C₂₋₄alkynylenearyl, —C₂₋₄alkynyleneheterocyclyl, —C₂₋₄alkynyleneheteroaryl, =CHC(=O)NHCH₂cycloalkyl, =CHC(=O)NHCH₂cycloalkenyl, =CHC(=O)NHCH₂aryl, =CHC(=O)NHCH₂heterocyclyl, =CHC(=O)NHCH₂heteroaryl, —Ocycloalkyl, —Ocycloalkenyl, —Oaryl, —Oheterocyclyl, —Oheteroaryl, —OC₁₋₃alkylenecycloalkyl, —OC₁₋₃alkylenecycloalkenyl, —OC₁₋₃alkylenearyl, —OC₁₋₃alkyleneheterocyclyl, —OC₁₋₃alkyleneheteroaryl, —OC₂₋₃alkenylenecycloalkyl, —OC₂₋₃alkenylenecycloalkenyl, —OC₂₋₃alkenylenearyl, —OC₂₋₃alkenyleneheterocyclyl, —OC₂₋₃alkenyleneheteroaryl, —OC₂₋₃alkynylenecycloalkyl, —OC₂₋₃alkynylenecycloalkenyl, —OC₂₋₃alkynylenearyl, —OC₂₋₃alkynyleneheterocyclyl, —OC₁₋₃alkylenecycloalkylaryl, —OarylOaryl, —OarylOC₁₋₃alkylenearyl, —Scycloalkyl, —Scycloalkenyl, —Saryl, —Sheterocyclyl, —Sheteroaryl, —SC₁₋₃alkylenecycloalkyl, —SC₁₋₃alkylenecycloalkenyl, —SC₁₋₃alkylenearyl, —SC₁₋₃alkyleneheterocyclyl, —SC₁₋₃alkyleneheteroaryl, —SC₂₋₃alkenylenecycloalkyl, —SC₂₋₃alkenylenecycloalkenyl, —SC₂₋₃alkenylenearyl, —SC₂₋₃alkenyleneheterocyclyl, —SC₂₋₃alkenyleneheteroaryl, —SC₂₋₃alkynylenecycloalkyl, —SC₂₋₃alkynylenecycloalkenyl, —SC₂₋₃alkynylenearyl, —SC₂₋₃alkynyleneheterocyclyl, —SC₂₋₃alkynyleneheteroaryl, —SC₁₋₃alkylenecycloalkylaryl, —SO₂cycloalkyl, —SO₂cycloalkenyl, —SO₂aryl, —SO₂heterocyclyl, —SO₂heteroaryl, —SO₂C₁₋₃alkylenecycloalkyl, —SO₂C₁₋₃alkylenecycloalkenyl, —SO₂C₁₋₃alkylenearyl, —SO₂C₁₋₃alkyleneheterocyclyl, —SO₂C₁₋₃alkyleneheteroaryl, —SO₂C₂₋₃alkenylenecycloalkyl, —SO₂C₂₋₃alkenylene cycloalkenyl, —SO₂C₂₋₃alkenylenearyl, —SO₂C₂₋₃alkenyleneheterocyclyl, —SO₂C₂₋₃alkenyleneheteroaryl, —SO₂C₂₋₃alkynylenecycloalkyl, —SO₂C₂₋₃alkynylenecycloalkenyl, —SO₂C₂₋₃alkynylenearyl, —SO₂C₂₋₃alkynyleneheterocyclyl, —SO₂C₂₋₃alkynyleneheteroaryl, —SO₂C₁₋₃alkylenecycloalkylaryl, —NHC₁₋₈alkyl, —NHC₂₋₈alkenyl, —NHC₂₋₈alkynyl, —NHcycloalkyl, —NHcycloalkenyl, —NHaryl, —NHheterocyclyl, —NHheteroaryl, —NHC₁₋₃alkylenecycloalkyl, —NH C₁₋₃alkylenecycloalkenyl, —NHC₁₋₃alkylenearyl, —NH C₁₋₃alkyleneheterocyclyl, —NHC₁₋₃alkyleneheteroaryl, —NHC₂₋₃alkenylenecycloalkyl, —NHC₂₋₃alkenylenecycloalkenyl, —NHC₂₋₃alkenylenearyl, —NHC₂₋₃alkenyleneheterocyclyl, —NHC₂₋₃alkenyleneheteroaryl, —NH C₂₋₃alkynylenecycloalkyl, —NHC₂₋₃alkynylenecycloalkenyl, —NHC₂₋₃alkynylenearyl, —NHC₂₋₃alkynyleneheterocyclyl, —NHC₂₋₃alkynyleneheteroaryl, —NHC(=O)cycloalkyl, —NHC(=O)cycloalkenyl, —NHC(=O)aryl, —NHC(=O)heterocyclyl, —NHC(=O)heteroaryl, —NHC(=O)C₁₋₃alkylenecycloalkyl, —NHC(=O)C₁₋₃alkylenecycloalkenyl, —NHC(=O)C₁₋₃alkylenearyl, —NHC(=O) C₁₋₃alkyleneheterocyclyl, —NHC(=O) C₁₋₃alkyleneheteroaryl, —NHC(=O)C₂₋₃alkenylenecycloalkyl, —NHC(=O)C₂₋₃alkenylenecycloalkenyl, —NHC(=O)C₂₋₃alkenylenearyl, —NHC(=O)C₂₋₃alkenyleneheterocyclyl, —NHC(=O)C₂₋₃alkenyleneheteroaryl, —NHC(=O)C₂₋₃alkynylenecycloalkyl, —NHC(=O)C₂₋₃alkynylenecycloalkenyl, —NHC(=O)C₂₋₃alkynylenearyl, —NHC(=O)C₂₋₃alkynyleneheterocyclyl, —NHC(=O)C₂₋₃alkynyleneheteroaryl, —N(CH₃)C₁₋₈alkyl, —N(CH₃)C₂₋₈alkenyl, —N(CH₃)C₂₋₈alkynyl, —N(CH₃)cycloalkyl, —N(CH₃)cycloalkenyl, —N(CH₃)aryl, —N(CH₃)heterocyclyl, —N(CH₃)heteroaryl, —N(CH₃)C₁₋₃alkylenecycloalkyl, —N(CH₃)C₁₋₃alkylenecycloalkenyl, —N(CH₃)C₁₋₃alkylenearyl, —N(CH₃)C₁₋₃alkyleneheterocyclyl, —N(CH₃)C₁₋₃alkyleneheteroaryl, —N(CH₃) C₂₋₃alkenylenecycloalkyl, —N(CH₃) C₂₋₃alkenylenecycloalkenyl, —N(CH₃)C₂₋₃alkenylenearyl, —N(CH₃)C₂₋₃alkenyleneheterocyclyl, —N(CH₃)C₂₋₃alkenyleneheteroaryl, —N(CH₃)C₂₋₃alkynylenecycloalkyl, —N(CH₃)C₂₋₃alkynylenecycloalkenyl, —N(CH₃)C₂₋₃alkynylenearyl, —N(CH₃)C₂₋₃alkynyleneheterocyclyl, —N(CH₃)C₂₋₃alkynyleneheteroaryl, —N(CH₃)C(=O)cycloalkyl, —N(CH₃)C(=O)cycloalkenyl, —N(CH₃)C(=O)

aryl, —N(CH₃)C(=O)heterocyclyl, —N(CH₃)C(=O)heteroaryl, —N(CH₃)C(=O)C$_{1-3}$alkylenecycloalkyl, —N(CH₃)C(=O)C$_{1-3}$alkylenecycloalkenyl, —N(CH₃)C(=O)C$_{1-3}$alkylenearyl, —N(CH₃)C(=O)C$_{1-3}$alkyleneheterocyclyl, —N(CH₃)C(=O)C$_{1-3}$alkyleneheteroaryl, —N(CH₃)C(=O)C$_{2-3}$alkenylenecycloalkyl, —N(CH₃)C(=O)C$_{2-3}$alkenylenecycloalkenyl, —N(CH₃)C(=O)C$_{2-3}$alkenylenearyl, —N(CH₃)C(=O)C$_{2-3}$alkenyleneheterocyclyl, —N(CH₃)C(=O)C$_{2-3}$alkenyleneheteroaryl, —N(CH₃)C(=O)C$_{2-3}$alkynylenecycloalkyl, —N(CH₃)C(=O)C$_{2-3}$alkynylenecycloalkenyl, —N(CH₃)C(=O)C$_{2-3}$alkynylenearyl, —N(CH₃)C(=O)C$_{2-3}$alkynyleneheterocyclyl, —N(CH₃)C(=O)C$_{2-3}$alkynyleneheteroaryl, —N(C(=O)CH₃)cycloalkyl, —N(C(=O)CH₃)cycloalkenyl, —N(C(=O)CH₃)aryl, —N(C(=O)CH₃)heterocyclyl, —N(C(=O)CH₃)heteroaryl, —N(C(=O)CH₃)C$_{1-3}$alkylenecycloalkyl, —N(C(=O)CH₃)C$_{1-3}$alkylenecycloalkenyl, —N(C(=O)CH₃)C$_{1-3}$alkylenearyl, —N(C(=O)CH₃)C$_{1-3}$alkyleneheterocyclyl, —N(C(=O)CH₃)C$_{1-3}$alkyleneheteroaryl, —N(C(=O)CH₃)C$_{2-3}$alkenylenecycloalkyl, —N(C(=O)CH₃)C$_{2-3}$alkenylenecycloalkenyl, —N(C(=O)CH₃)C$_{2-3}$alkenylenearyl, —N(C(=O)CH₃)C$_{2-3}$alkenyleneheterocyclyl, —N(C(=O)CH₃)C$_{2-3}$alkenyleneheteroaryl, —N(C(=O)CH₃)C$_{2-3}$alkynylenecycloalkyl, —N(C(=O)CH₃)C$_{2-3}$alkynylenecycloalkenyl, —N(C(=O)CH₃)C$_{2-3}$alkynylenearyl, —N(C(O)CH₃)C$_{2-3}$alkynyleneheterocyclyl, —N(C(O)CH₃)C$_{2-3}$alkynyleneheteroaryl, —N(SO₂CH₃)cycloalkyl, —N(SO₂CH₃)cycloalkenyl, —N(SO₂CH₃)aryl, —N(SO₂CH₃)heterocyclyl, —N(SO₂CH₃)heteroaryl, —N(SO₂CH₃)C$_{1-3}$alkylenecycloalkyl, —N(SO₂CH₃)C$_{1-3}$alkylenecycloalkenyl, —N(SO₂CH₃)C$_{1-3}$alkylenearyl, —N(SO₂CH₃)C$_{1-3}$alkyleneheterocyclyl, —N(SO₂CH₃)C$_{1-3}$alkyleneheteroaryl, —N(SO₂CH₃)C$_{2-3}$alkenylenecycloalkyl, —N(SO₂CH₃)C$_{2-3}$alkenylenecycloalkenyl, —N(SO₂CH₃)C$_{2-3}$alkenylenearyl, —N(SO₂CH₃)C$_{2-3}$alkenyleneheterocyclyl, —N(SO₂CH₃)C$_{2-3}$alkenyleneheteroaryl, —N(SO₂CH₃)C$_{2-3}$alkynylenecycloalkyl, —N(SO₂CH₃)C$_{2-3}$alkynylenecycloalkenyl, —N(SO₂CH₃)C$_{2-3}$alkynylenearyl, —N(SO₂CH₃)C$_{2-3}$alkynyleneheterocyclyl, —N(SO₂CH₃)C$_{2-3}$alkynyleneheteroaryl, —N(CH₂CF₃)cycloalkyl, —N(CH₂CF₃)cycloalkenyl, —N(CH₂CF₃)aryl, —N(CH₂CF₃)heterocyclyl, —N(CH₂CF₃)heteroaryl, —N(CH₂CF₃)C$_{1-3}$alkylenecycloalkyl, —N(CH₂CF₃)C$_{1-3}$alkylenecycloalkenyl, —N(CH₂CF₃)C$_{1-3}$alkylenearyl, —N(CH₂CF₃)C$_{1-3}$alkyleneheterocyclyl, —N(CH₂CF₃)C$_{1-3}$alkyleneheteroaryl, —N(CH₂CF₃)C$_{2-3}$alkenylenecycloalkyl, —N(CH₂CF₃)C$_{2-3}$alkenylenecycloalkenyl, —N(CH₂CF₃)C$_{2-3}$alkenylenearyl, —N(CH₂CF₃)C$_{2-3}$alkenyleneheterocyclyl, —N(CH₂CF₃)C$_{2-3}$alkenyleneheteroaryl, —N(CH₂CF₃)C$_{2-3}$alkynylenecycloalkyl, —N(CH₂CF₃)C$_{2-3}$alkynylenecycloalkenyl, —N(CH₂CF₃)C$_{2-3}$alkynylenearyl, —N(CH₂CF₃)C$_{2-3}$alkynyleneheterocyclyl, —N(CH₂CF₃)C$_{2-3}$alkynylene heteroaryl, —OCH₂CH(phenyl)CH₂(phenyl), —OCH₂C(phenyl)=CH(phenyl), —CH₂C(=O)NHCH₂cycloalkyl, —CH₂C(=O)NHCH₂cycloalkenyl, —CH₂C(=O)NHCH₂aryl, —CH₂C(=O)NHCH₂heterocyclyl, —CH₂C(=O)NHCH₂heteroaryl, —C(=O)NHC$_{1-3}$alkylenecycloalkyl, —C(=O)NHC$_{1-3}$alkylenecycloalkenyl, —C(=O)NHC$_{1-3}$alkylenearyl, —C(=O)NHC$_{1-3}$alkyleneheterocyclyl, —C(=O)NHC$_{1-3}$alkyleneheteroaryl, —CH₂SO₂C$_{0-3}$alkylenecycloalkyl, —CH₂SO₂C$_{0-3}$alkylenecycloalkenyl, —CH₂SO₂C$_{0-3}$alkyleneheterocyclyl, —CH₂SO₂C$_{0-3}$alkyleneheteroaryl, —CH₂SO₂C$_{0-3}$alkylenearyl, —CH₂OC$_{1-3}$alkylenecycloalkyl, —CH₂OC$_{1-3}$alkylenecycloalkenyl, —CH₂OC$_{1-3}$alkylenearyl, —CH₂OC$_{1-3}$alkyleneheterocyclyl, —CH₂OC$_{1-3}$alkyleneheteroaryl, —CH₂SC$_{1-3}$alkylenecycloalkyl, —CH₂SC$_{1-3}$alkylenecycloalkenyl, —CH₂SC$_{1-3}$alkylenearyl, —CH₂SC$_{1-3}$alkyleneheterocyclyl, —CH₂SC$_{1-3}$alkyleneheteroaryl, —CH₂SC$_{2-3}$alkenylenecycloalkyl, —CH₂SC$_{2-3}$alkenylenecycloalkenyl, —CH₂SC$_{2-3}$alkenylenearyl, —CH₂SC$_{2-3}$alkenyleneheterocyclyl, —CH₂SC$_{2-3}$alkenyleneheteroaryl, —CH₂SC$_{2-3}$alkynylenecycloalkyl, —CH₂SC$_{2-3}$alkynylenecycloalkenyl, —CH₂SC$_{2-3}$alkynylenearyl, —CH₂SC$_{2-3}$alkynyleneheterocyclyl, —CH₂SC$_{2-3}$alkynyleneheteroaryl or —NHC(=O)N(aryl)₂, especially —OCH₂phenyl, —CH₂Ophenyl, —OCH₂CH₂phenyl, —OCH₂CH₂CH₂phenyl, —OCH₂CH₂CH₂-(4-fluorophenyl), —CH₂CH=CHphenyl, —OCH₂CH=CHphenyl, —C≡CCH₂CH₂phenyl, =CHC(=O)NHCH₂phenyl, —OCH₂cyclopropyl, —OCH₂-(2-phenyl)cyclopropyl, —OCH₂-4-oxazole, —CH₂-4-(3-methyl-2-phenyl)oxazole, -1-azetidine, -1-(3-benzyloxy)azetidine, -1-(3-phenyl)azetidine, —N(CH₃)(CH₂CH₂CH₃), —N(CH₃)(CH₂CH₂CH₂C(CH₃)₃), —N(CH₃)(CH₂C≡CH), —N(CH₃)(CH₂C≡CC(CH₃)₃), —N(CH₃)CH₂CH₂CH₂phenyl, —N(CH₂CF₃)CH₂CH₂CH₂-(4-fluorophenyl), —N(CH₃)CH₂CH₂phenyl, —N(CH₃)CH₂CH₂CH₂-(4-fluorophenyl), —N(CH₃)CH₂CH₂(4-fluorophenyl), —N(CH₃)CH₂CH₂O-(4-fluorophenyl), —N(CH₃)CH₂C≡C-(3-methyl-4-methoxyphenyl), -1-piperazine, -1-(4-phenyl)piperazine, -1-(4-benzyl)piperazine, -1-(3-benzyl)piperazine, -1-(4-methyl-3-phenyl)piperazine, -4-morpholine, -4-(2-phenyl)morpholine, -4-(2-benzyl)morpholine, -4-(3-benzyl)morpholine, —N(CH₃)cyclopropyl, —N(CH₃)-(2-phenyl)cyclopropyl, —OCH₂C(phenyl)=CH(phenyl), —OCH₂CH(phenyl)CH₂(phenyl), —Ophenyl, —O-(4-benzyloxy)phenyl, —O-(3-benzyloxy)phenyl, —O-(2-benzyloxy)phenyl, —O-(4-phenoxy)phenyl, —O-(3-phenoxy)phenyl, —O-(2-phenoxy)phenyl; —OCH₂—C≡Cphenyl, —CH₂C(=O)NHCH₂phenyl, —C(=O)NHCH₂phenyl, —C(=O)NHCH₂CH₂phenyl, —NHCH₂CH₂CH₂phenyl, —NHCH₂CH₂phenyl, —CH₂CH₂CH₂phenyl, —CH₂CH₂CH₂CH₂phenyl, —CH₂OCH₂phenyl, —CH₂Ophenyl, -1-piperidine, -1-(4-phenyl)piperidine, -1-(3-phenyl)piperidine, -1-(3-benzyl)piperidine, -2-(phenyl)pyrrolidine, -3-(phenyl)pyrrolidine, —CH₂OCH₂CH₂phenyl, —CH₂CH₂OCH₂phenyl, -2-oxazole, -2-(5-phenyl)oxazole, -2-(5-benzyl)oxazole, —CH₂SO₂CH₂CH₂phenyl, -1-pyrrolidine, -1-(2-benzyl)pyrrolidine, —N(CH₃)CH₂cyclopropyl, —N(CH₃)CH₂-(2-phenyl)cyclopropyl, —N(CH₃)(CH₂)₃phenyl, —N(CH₃)(CH₂)₃(4-fluorophenyl), —N(CH₃)(CH₂)₃(4-methoxy-3-methylphenyl), —N(CH₃)(CH₂)₄phenyl, —N(CH₃)(CH₂)₃pyridine, —NHC(=O)N(phenyl)(phenyl), —OCH₂-4-oxazole, —OCH₂-4-(2-phenyl)oxazole, —O-4-oxazole, —O-4-(2-phenyl)oxazole, —NHC(=O)CH=CHphenyl, —N(CH₃)C(=O)CH=CHphenyl, —NHC(O)CH₂CH₂phenyl, —N(CH₃)C(=O)CH₂CH₂phenyl, —N(C(=O)CH₃)CH₂CH₂CH₂phenyl, N(SO₂CH₃)CH₂CH₂CH₂phenyl, —CH₂SO₂CH₂phenyl, —CH₂SO₂phenyl, —CH₂SCH₂CH₂phenyl, —CH₂SCH₂phenyl, —CH₂Sphenyl, —CH₂SCH₂CH₂CH₂phenyl, —SO₂CH₂CH₂phenyl, —SCH₂CH₂phenyl, —SO₂CH₂CH₂phenyl, —SCH₂CH₂-(4-fluorophenyl), —SO₂CH₂CH₂CH₂-(4-fluorophenyl), -1-(5-phenyl-1,2,3-triazolyl), -1-(5-benzyl-1,2,3-triazolyl), -4-(5-benzyl-3-oxo-morpholinyl), -2-(3-phenylthiophenyl), -2-(4-phenyl-1,3-thiazolyl),

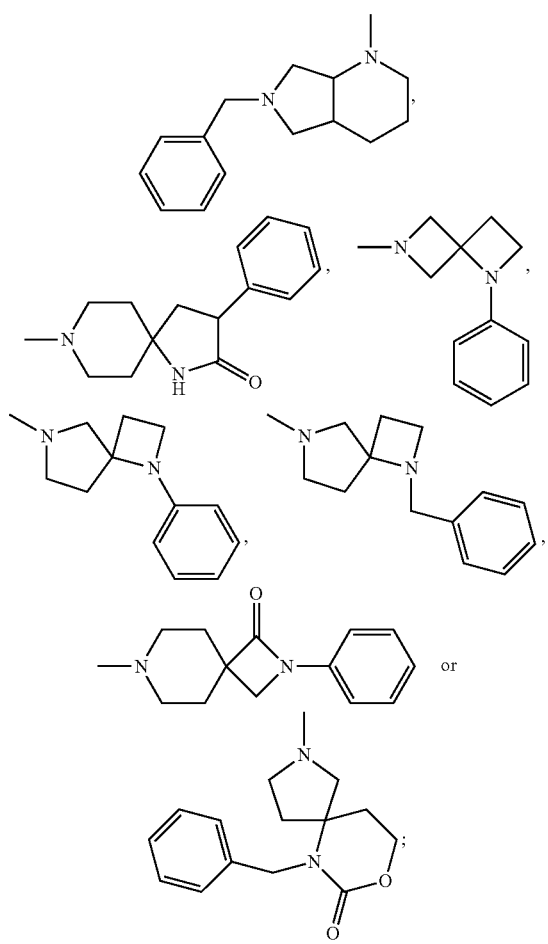

$R^{2b}$ is hydrogen, $R^3$ is —CO$_2$H, —CH$_2$CO$_2$H, —C(═O)C(═O)OH, —C(═O)NHSO$_2$C$_{1-6}$alkyl, —C(═O)NHSO$_2$N(C$_{1-6}$alkyl)$_2$, —C(═O)NHSO$_2$phenyl, —C(═O)NHSO$_2$CF$_3$, —SO$_3$H, PO$_3$H$_2$, tetrazolyl, —CH$_2$NHSO$_2$C$_{1-6}$alkyl, —CH$_2$OH, —C(═O)NH$_2$ or CN, especially —CO$_2$H, —CH$_2$CO$_2$H, —CH$_2$OH, —C(═O)NHSO$_2$C$_{1-4}$alkyl, —C(═O)NHSO$_2$N(C$_{1-3}$alkyl)$_2$, —C(═O)NHSO$_2$phenyl, tetrazolyl, —CH$_2$NHSO$_2$(C$_{1-4}$alkyl), —C(═O)NH$_2$ or CN, —C(═O)NHSO$_2$CF$_3$, more especially —CO$_2$H;

$R^4$ is hydrogen or $R^3$ and $R^4$ together form:

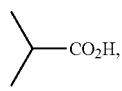

especially where $R^4$ is hydrogen;

$R^5$ is hydrogen or together with $R^2$ forms an aryl, heteroaryl or heterocyclyl ring selected from:

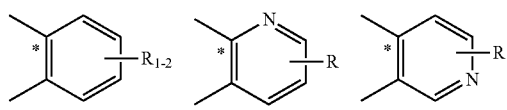

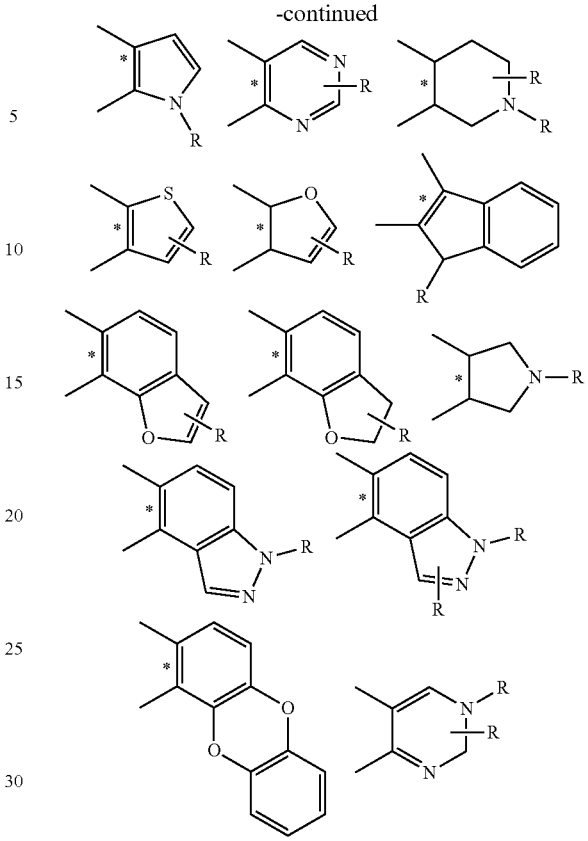

where* indicates the fused bond, and R is selected from —C$_{1-3}$alkyl, —OC$_{1-3}$alkyl, —OCF$_3$, —OCHF$_2$, —OCH$_2$phenyl, —CH═CHphenyl, —CH$_2$CH$_2$phenyl, —CH(OH)CH(OH)phenyl, —SO$_2$NHphenyl, —NHSO$_2$phenyl, —NHC(O)NHphenyl, —NHC(O)Ophenyl, —CH$_2$phenyl, —Ophenyl, —OCH$_2$CH═CHphenyl, —OCH$_2$CH$_2$phenyl, —OCH$_2$CH$_2$CH$_2$phenyl and -phenyl;

$R^6$ and $R^7$ are independently selected from phenyl and cyclohexyl, especially where both $R^6$ and $R^7$ are phenyl;

$R^8$ is hydrogen, methyl, ethyl or phenyl.

In some embodiments, especially when $R^3$ appears on the carbon atom of Y that is adjacent in the ring to the ring nitrogen, $R^3$ has an S stereochemistry.

In some embodiments, $R^2$ and $R^3$ are cis relative to one another, that is, they are positioned on the same face of the N-containing 4- or 5-membered ring.

In some embodiments, the group $R^2$ contains at least one stereocentre. In embodiments where $R^2$ comprises a cyclohexyl or 6-membered heterocyclyl ring, substituted in the position adjacent to the attachment to the azetidine or pyrrolidine ring, one stereoisomer may be preferred over the other stereoisomer.

In one embodiment, the compound of formula (I) is a compound of formula (II):

wherein X is absent and Y is —CHR³CHR⁴CH₂—, —CH₂CHR³CHR⁴— or —CH₂CH₂CHR³— or X is —CHR⁵— and Y is —CHR³—, —CHR³CHR⁴—, —CHR³CR⁴=, —CH₂CHR³—, —CR³=CH— or —CH=CR³—, wherein when Y is —CHR³CR⁴=, R²$^b$ is absent; or X is —CH₂CH⁵— and Y is —CHR³— and R¹, R², R³, R⁴ and R⁵ are as defined for formula (I).

In particular embodiments of compound of formula (II): R¹ is —C(=O)CH(phenyl)(phenyl), —C(=O)CH(phenyl)(cycloalkyl), —C(=O)CH(cycloalkyl)(cycloalkyl), —C(=O)N(phenyl)(phenyl), —C(=O)N(phenyl)(cycloalkyl) or —C(=O)N(cycloalkyl)(cycloalkyl), especially —C(=O)CH(phenyl)(phenyl) or —C(=O)N(phenyl)(phenyl);

R² is cycloalkyl, cycloalkenyl, aryl, heterocyclyl, heteroaryl, -heterocyclylaryl, -heterocyclyl C₁₋₃alkylenearyl, —C₁₋₄alkylenecycloalkyl, —C₁₋₄alkylenecycloalkenyl, —C₁₋₄alkylenearyl, —C₁₋₄alkyleneheterocyclyl, —C₁₋₄alkyleneheteroaryl, —C₂₋₄alkenylenecycloalkyl, —C₂₋₄alkenylenecycloalkenyl, —C₂₋₄alkenylenearyl, —C₂₋₄alkenyleneheterocyclyl, —C₂₋₄alkenyleneheteroaryl, —C₂₋₄alkynylenecycloalkyl, —C₂₋₄alkynylenecycloalkenyl, —C₂₋₄ alkynylenearyl, —C₂₋₄alkynyleneheterocyclyl, —C₂₋₄alkynyleneheteroaryl, =CHC(=O)NHCH₂cycloalkyl, =CHC(=O)NHCH₂cycloalkyl, =CHC(=O)NHCH₂aryl, =CHC(=O)NHCH₂heterocyclyl, =CHC(=O)NHCH₂heteroaryl, —Ocycloalkyl, —Ocycloalkenyl, —Oaryl, —Oheterocyclyl, —Oheteroaryl, —OC₁₋₃alkylenecycloalkyl, —OC₁₋₃alkylenecycloalkenyl, —OC₁₋₃alkylenearyl, —OC₁₋₃alkyleneheterocyclyl, —OC₁₋₃alkyleneheteroaryl, —OC₂₋₃alkenylenecycloalkyl, —OC₂₋₃alkenylenecycloalkenyl, —OC₂₋₃alkenylenearyl, —OC₂₋₃alkenyleneheterocyclyl, —OC₂₋₃alkenyleneheteroaryl, —OC₂₋₃alkynylenecycloalkyl, —OC₂₋₃alkynylenecycloalkenyl, —OC₂₋₃alkynylenearyl, —OC₂₋₃alkynyleneheterocyclyl, —OC₂₋₃alkynyleneheteroaryl, —OC₁₋₃alkylenecycloalkylaryl, —OarylOaryl, —OarylOC₁₋₃alkylenearyl, —Scycloalkyl, —Scycloalkenyl, —Saryl, —Sheterocyclyl, —Sheteroaryl, —SC₁₋₃alkylenecycloalkyl, —SC₁₋₃alkylenecycloalkenyl, —SC₁₋₃alkylenearyl, —SC₁₋₃alkyleneheterocyclyl, —SC₁₋₃alkyleneheteroaryl, —SC₂₋₃alkenylenecycloalkyl, —SC₂₋₃alkenylenecycloalkenyl, —SC₂₋₃alkenylenearyl, —SC₂₋₃alkenyleneheterocyclyl, —SC₂₋₃alkenyleneheteroaryl, —SC₂₋₃alkynylenecycloalkyl, —SC₂₋₃alkynylenecycloalkenyl, —SC₂₋₃alkynylenearyl, —SC₂₋₃alkynyleneheterocyclyl, —SC₂₋₃alkynyleneheteroaryl, —SC₁₋₃alkylenecycloalkylaryl, —SO₂cycloalkyl, —SO₂cycloalkenyl, —SO₂aryl, —SO₂heterocyclyl, —SO₂heteroaryl, —SO₂C₁₋₃ alkylenecycloalkyl, —SO₂C₁₋₃alkylenecycloalkenyl, —SO₂C₁₋₃alkylenearyl, —SO₂C₁₋₃alkyleneheterocyclyl, —SO₂C₁₋₃alkyleneheteroaryl, —SO₂C₂₋₃alkenylenecycloalkyl, —SO₂C₂₋₃alkenylenecycloalkenyl, —SO₂C₂₋₃alkenylenearyl, —SO₂C₂₋₃alkenyleneheterocyclyl, —SO₂C₂₋₃alkenyleneheteroaryl, —SO₂C₂₋₃alkynylenecycloalkyl, —SO₂C₂₋₃alkynylenecycloalkenyl, —SO₂C₂₋₃ alkynylenearyl, —SO₂C₂₋₃alkynyleneheterocyclyl, —SO₂C₂₋₃alkynyleneheteroaryl, —SO₂C₁₋₃alkylenecycloalkylaryl, —NHC₁₋₈alkyl, —NHC₂₋₈alkenyl, —NHC₂₋₈alkynyl, —NHcycloalkyl, —NHcycloalkenyl, —NHaryl, —NHheterocyclyl, —NHheteroaryl, —NHC₁₋₃alkylenecycloalkyl, —NHC₁₋₃alkylenecycloalkenyl, —NHC₁₋₃alkylenearyl, —NHC₁₋₃alkyleneheterocyclyl, —NHC₁₋₃alkyleneheteroaryl, —NHC₂₋₃alkenylenecycloalkyl, —NHC₂₋₃alkenylenecycloalkenyl, —NHC₂₋₃alkenylenearyl, —NHC₂₋₃alkenyleneheterocyclyl, —NHC₂₋₃alkenyleneheteroaryl, —NHC₂₋₃alkynylenecycloalkyl, —NHC₂₋₃alkynylenecycloalkenyl, —NHC₂₋₃alkynylenearyl, —NHC₂₋₃alkynyleneheterocyclyl, —NHC₂₋₃alkynyleneheteroaryl, —NHC(=O)cycloalkyl, —NHC(=O)cycloalkenyl, —NHC(=O)aryl, —NHC(=O)heterocyclyl, —NHC(=O)heteroaryl, —NHC(=O)C₁₋₃alkylenecycloalkyl, —NHC(=O)C₁₋₃alkylenecycloalkenyl, —NHC(=O)C₁₋₃alkylenearyl, —NHC(=O)C₁₋₃alkyleneheterocyclyl, —NHC(=O)C₁₋₃alkyleneheteroaryl, —NHC(=O)C₂₋₃ alkenylenecycloalkyl, —NHC(=O)C₂₋₃alkenylenecycloalkenyl, —NHC(=O)C₂₋₃alkenylenearyl, —NHC(=O)C₂₋₃alkenyleneheterocyclyl, —NHC(=O)C₂₋₃ alkenyleneheteroaryl, —NHC(=O)C₂₋₃alkynylenecycloalkyl, —NHC(=O)C₂₋₃alkynylenecycloalkenyl, —NHC(=O)C₂₋₃alkynylenearyl, —NHC(=O)C₂₋₃alkynyleneheterocyclyl, —NHC(=O)C₂₋₃alkynyleneheteroaryl, —N(CH₃)C₁₋₈alkyl, —N(CH₃)C₂₋₈alkenyl, —N(CH₃)C₂₋₈alkynyl, —N(CH₃)cycloalkyl, —N(CH₃)cycloalkenyl, —N(CH₃)aryl, —N(CH₃)heterocyclyl, —N(CH₃)heteroaryl, —N(CH₃)C₁₋₃alkylenecycloalkyl, —N(CH₃)C₁₋₃alkylenecycloalkenyl, —N(CH₃)C₁₋₃alkylenearyl, —N(CH₃)C₁₋₃alkyleneheterocyclyl, —N(CH₃)C₁₋₃alkyleneheteroaryl, —N(CH₃)C₂₋₃alkenylenecycloalkyl, —N(CH₃)C₂₋₃alkenylenecycloalkenyl, —N(CH₃)C₂₋₃alkenylenearyl, —N(CH₃)C₂₋₃alkenyleneheterocyclyl, —N(CH₃)C₂₋₃alkenyleneheteroaryl, —N(CH₃)C₂₋₃alkynylenecycloalkyl, —N(CH₃)C₂₋₃alkynylenecycloalkenyl, —N(CH₃)C₂₋₃alkynylenearyl, —N(CH₃)C₂₋₃alkynyleneheterocyclyl, —N(CH₃)C₂₋₃alkynyleneheteroaryl, —N(CH₃)C(=O)cycloalkyl, —N(CH₃)C(=O)cycloalkenyl, —N(CH₃)C(=O)aryl, —N(CH₃)C(=O)heterocyclyl, —N(CH₃)C(=O)heteroaryl, —N(CH₃)C(=O)C₁₋₃alkylenecycloalkyl, —N(CH₃)C(=O)C₁₋₃alkylenecycloalkenyl, —N(CH₃)C(=O)C₁₋₃alkylenearyl, —N(CH₃)C(=O)C₁₋₃alkyleneheterocyclyl, —N(CH₃)C(=O)C₁₋₃alkyleneheteroaryl, —N(CH₃)C(=O)C₂₋₃alkenylenecycloalkyl, —N(CH₃)C(=O)C₂₋₃alkenylenecycloalkenyl, —N(CH₃)C(=O)C₂₋₃alkenylenearyl, —N(CH₃)C(=O)C₂₋₃alkenyleneheterocyclyl, —N(CH₃)C(=O)C₂₋₃alkenyleneheteroaryl, —N(CH₃)C(=O)C₂₋₃alkynylenecycloalkyl, —N(CH₃)C(=O)C₂₋₃alkynylenecycloalkenyl, —N(CH₃)C(=O)C₂₋₃alkynylenearyl, —N(CH₃)C(=O)C₂₋₃alkynyleneheterocyclyl, —N(CH₃)C(=O)C₂₋₃alkynyleneheteroaryl, —N(C(=O)CH₃)cycloalkyl, —N(C(=O)CH₃)cycloalkenyl, —N(C(=O)CH₃)aryl, —N(C(=O)CH₃)heterocyclyl, —N(C(=O)CH₃)heteroaryl, —N(C(=O)CH₃)C₁₋₃alkylenecycloalkyl, —N(C(=O)CH₃)C₁₋₃alkylenecycloalkenyl, —N(C(=O)CH₃)C₁₋₃alkylenearyl, —N(C(=O)CH₃)C₁₋₃alkyleneheterocyclyl, —N(C(=O)CH₃)C₁₋₃alkyleneheteroaryl, —N(C(=O)CH₃)C₂₋₃alkenylenecycloalkyl, —N(C(=O)CH₃)C₂₋₃alkenylenecycloalkenyl, —N(C(=O)CH₃)C₂₋₃alkenylenearyl, —N(C(=O)CH₃)C₂₋₃alkenyleneheterocyclyl, —N(C(=O)CH₃)C₂₋₃alkenyleneheteroaryl, —N(C(=O)CH₃)C₂₋₃alkynylenecycloalkyl, —N(C(=O)CH₃)C₂₋₃alkynylenecycloalkenyl, —N(C(=O)CH₃)C₂₋₃alkynylenearyl, —N(C(O)CH₃)C₂₋₃alkynyleneheterocyclyl, —N(C(O)CH₃)C₂₋₃alkynyleneheteroaryl, —N(SO₂CH₃)cycloalkyl, —N(SO₂CH₃)cycloalkenyl, —N(SO₂CH₃)aryl, —N(SO₂CH₃)heterocyclyl, —N(SO₂CH₃)heteroaryl, —N(SO₂CH₃)C₁₋₃alkylenecycloalkyl, —N(SO₂CH₃)C₁₋₃alkylenecycloalkenyl, —N(SO₂CH₃)C₁₋₃alkylenearyl, —N(SO₂CH₃)C₁₋₃alkyleneheterocyclyl, —N(SO₂CH₃)C₁₋₃alkyleneheteroaryl, —N(SO₂CH₃)C₂₋₃alkenylenecycloalkyl, —N(SO₂CH₃)C₂₋₃alkenylenecycloalkenyl, —N(SO₂CH₃)C₂₋₃alkenylenearyl, —N(SO₂CH₃)C₂₋₃alkenyleneheterocyclyl, —N(SO₂CH₃)C₂₋₃alkenyleneheteroaryl, —N(SO₂CH₃)

C$_{2-3}$alkynylenecycloalkyl, —N(SO$_2$CH$_3$)C$_{2-3}$alkynylenecycloalkenyl, —N(SO$_2$CH$_3$)C$_{2-3}$alkynylenearyl, —N(SO$_2$CH$_3$)C$_{2-3}$alkynyleneheterocyclyl, —N(SO$_2$CH$_3$)C$_{2-3}$alkynyleneheteroaryl, —N(CH$_2$CF$_3$)cycloalkyl, —N(CH$_2$CF$_3$)cycloalkenyl, —N(CH$_2$CF$_3$)aryl, —N(CH$_2$CF$_3$)heterocyclyl, —N(CH$_2$CF$_3$)heteroaryl, —N(CH$_2$CF$_3$)C$_{1-3}$alkylenecycloalkyl, —N(CH$_2$CF$_3$)C$_{1-3}$alkylenecycloalkenyl, —N(CH$_2$CF$_3$)C$_{1-3}$alkylenearyl, —N(CH$_2$CF$_3$)C$_{1-3}$alkyleneheterocyclyl, —N(CH$_2$CF$_3$)C$_{1-3}$alkyleneheteroaryl, —N(CH$_2$CF$_3$)C$_{2-3}$alkenylenecycloalkyl, —N(CH$_2$CF$_3$)C$_{2-3}$alkenylenecycloalkenyl, —N(CH$_2$CF$_3$)C$_{2-3}$alkenylenearyl, —N(CH$_2$CF$_3$)C$_{2-3}$alkenyleneheterocyclyl, —N(CH$_2$CF$_3$)C$_{2-3}$alkenyleneheteroaryl, —N(CH$_2$CF$_3$)C$_{2-3}$alkynylenecycloalkyl, —N(CH$_2$CF$_3$)C$_{2-3}$alkynylenecycloalkenyl, —N(CH$_2$CF$_3$)C$_{2-3}$alkynylenearyl, —N(CH$_2$CF$_3$)C$_{2-3}$alkynyleneheterocyclyl, —N(CH$_2$CF$_3$)C$_{2-3}$alkynyleneheteroaryl, —OCH$_2$CH(phenyl)CH$_2$(phenyl), —OCH$_2$C(phenyl)=CH(phenyl), —CH$_2$C(=O)NHCH$_2$cycloalkyl, —CH$_2$C(=O)NHCH$_2$cycloalkenyl, —CH$_2$C(=O)NHCH$_2$aryl, —CH$_2$C(=O)NHCH$_2$heterocyclyl, —CH$_2$C(=O)NHCH$_2$heteroaryl, —C(=O)NHC$_{1-3}$alkylenecycloalkyl, —C(=O)NHC$_{1-3}$alkylenecycloalkenyl, —C(=O)NHC$_{1-3}$alkylenearyl, —C(=O)NHC$_{1-3}$alkyleneheterocyclyl, —C(=O)NHC$_{1-3}$alkyleneheteroaryl, —CH$_2$SO$_2$C$_{0-3}$alkylenecycloalkyl, —CH$_2$SO$_2$C$_{0-3}$alkylenecycloalkenyl, —CH$_2$SO$_2$C$_{0-3}$alkylenearyl, —CH$_2$SO$_2$C$_{0-3}$alkyleneheterocyclyl, —CH$_2$SO$_2$C$_{0-3}$alkyleneheteroaryl, —CH$_2$OC$_{1-3}$alkylenecycloalkyl, —CH$_2$OC$_{1-3}$alkylenecycloalkenyl, —CH$_2$OC$_{1-3}$alkylenearyl, —CH$_2$OC$_{1-3}$alkyleneheterocyclyl, —CH$_2$OC$_{1-3}$alkyleneheteroaryl, —CH$_2$SC$_{1-3}$alkylenecycloalkyl, —CH$_2$SC$_{1-3}$alkylenecycloalkenyl, —CH$_2$SC$_{1-3}$alkylenearyl, —CH$_2$SC$_{1-3}$alkyleneheterocyclyl, —CH$_2$SC$_{1-3}$alkyleneheteroaryl, —CH$_2$SC$_{2-3}$alkenylenecycloalkyl, —CH$_2$SC$_{2-3}$alkenylenecycloalkenyl, —CH$_2$SC$_{2-3}$alkenylenearyl, —CH$_2$SC$_{2-3}$alkenyleneheterocyclyl, —CH$_2$SC$_{2-3}$alkenyleneheteroaryl, —CH$_2$SC$_{2-3}$alkynylenecycloalkyl, —CH$_2$SC$_{2-3}$alkynylenecycloalkenyl, —CH$_2$SC$_{2-3}$alkynylenearyl, —CH$_2$SC$_{2-3}$alkynyleneheterocyclyl, —CH$_2$SC$_{2-3}$alkynyleneheteroaryl or —NHC(=O)N(aryl)$_2$, especially —OCH$_2$phenyl, —CH$_2$Ophenyl, —OCH$_2$CH$_2$phenyl, —OCH$_2$CH$_2$CH$_2$phenyl, —OCH$_2$CH$_2$CH$_2$-(4-fluorophenyl), —CH$_2$CH=CHphenyl, —OCH$_2$CH=CHphenyl, —C≡CCH$_2$CH$_2$phenyl, —CHC(=O)NHCH$_2$phenyl, —OCH$_2$-(2-phenyl)cyclopropyl, —OCH$_2$-4-oxazole, —CH$_2$-4-(3-methyl-2-phenyl)oxazole, -1-azetidine, -1-(3-benzyloxy)azetidine, -1-(3-phenyl)azetidine, —N(CH$_3$)(CH$_2$CH$_2$CH$_3$), —N(CH$_3$)(CH$_2$CH$_2$CH$_2$C(CH$_3$)$_3$), —N(CH$_3$)(CH$_2$C≡CH), —N(CH$_3$)(CH$_2$C≡CC(CH$_3$)$_3$), —N(CH$_3$)CH$_2$CH$_2$CH$_2$phenyl, —N(CH$_2$CF$_3$)CH$_2$CH$_2$CH$_2$-(4-fluorophenyl)-N(CH$_3$)CH$_2$CH$_2$phenyl, —N(CH$_3$)CH$_2$CH$_2$CH$_2$-(4-fluorophenyl), —N(CH$_3$)CH$_2$C≡Cphenyl, —N(CH$_3$)CH$_2$C≡C-(3-methyl-4-methoxyphenyl), —N(CH$_3$)CH$_2$CH$_2$-(4-fluorophenyl), —N(CH$_3$)CH$_2$CH$_2$-(4-fluorophenyl), -1-piperazine, -1-(4-phenyl)piperazine, -1-(4-benzyl)piperazine, -1-(3-benzyl)piperazine, -1-(4-methyl-3-phenyl)piperazine, -4-morpholine, -4-(2-phenyl)morpholine, -4-(2-benzyl)morpholine, -4-(3-benzyl)morpholine, —N(CH$_3$)cyclopropyl, —N(CH$_3$)-(2-phenyl)cyclopropyl, —OCH$_2$C(phenyl)=CH(phenyl), —OCH$_2$CH(phenyl)CH$_2$(phenyl), —Ophenyl, —O-(4-benzyloxy)phenyl, —O-(3-benzyloxy)phenyl, —O-(2-benzyloxy)phenyl, —O-(4-phenoxy)phenyl, —O-(3-phenoxy)phenyl, —O-(2-phenoxy)phenyl, —OCH$_2$—C≡Cphenyl, —CH$_2$C(=O)NHCH$_2$phenyl, —C(=O)NHCH$_2$phenyl, —C(=O)NHCH$_2$CH$_2$phenyl, —NHCH$_2$CH$_2$CH$_2$phenyl, —NHCH$_2$CH$_2$phenyl, —CH$_2$CH$_2$CH$_2$phenyl, —CH$_2$CH$_2$CH$_2$CH$_2$phenyl, —CH$_2$OCH$_2$phenyl, —CH$_2$Ophenyl, -1-piperidine, -1-(4-phenyl)piperidine, -1-(3-phenyl)piperidine, -1-(3-benzyl)piperidine, -2-(phenyl)pyrrolidine, -3-(phenyl)pyrrolidine, —CH$_2$OCH$_2$CH$_2$phenyl, —CH$_2$CH$_2$OCH$_2$phenyl, -2-oxazole, -2-(5-phenyl)oxazole, -2-(5-benzyl)oxazole, —CH$_2$SO$_2$CH$_2$CH$_2$phenyl, -1-pyrrolidine, -1-(2-benzyl)pyrrolidine, —N(CH$_3$)CH$_2$cyclopropyl, —N(CH$_3$)CH$_2$-(2-phenyl)cyclopropyl, —N(CH$_3$)(CH$_2$)$_3$phenyl, —N(CH$_3$)(CH$_2$)$_3$(4-fluorophenyl), —N(CH$_3$)(CH$_2$)$_3$(4-methoxy-3-methylphenyl), —N(CH$_3$)(CH$_2$)$_4$phenyl, —N(CH$_3$)(CH$_2$)$_3$pyridine, —NHC(=O)N(phenyl)(phenyl), —OCH$_2$-4-oxazole, —OCH$_2$-4-(2-phenyl)oxazole, —O-4-oxazole, —O4-(2-phenyl)oxazole, —NHC(=O)CH=CHphenyl, —N(CH$_3$)C(=O)CH=CHphenyl, —NHC(O)CH$_2$CH$_2$phenyl, —N(CH$_3$)C(=O)CH$_2$CH$_2$phenyl, —N(C(=O)CH$_3$)CH$_2$CH$_2$CH$_2$phenyl, N(SO$_2$CH$_3$)CH$_2$CH$_2$CH$_2$phenyl, —CH$_2$SO$_2$CH$_2$phenyl, —CH$_2$SO$_2$phenyl, —CH$_2$SCH$_2$CH$_2$phenyl, —CH$_2$SCH$_2$phenyl, —CH$_2$S phenyl, —CH$_2$SCH$_2$CH$_2$CH$_2$phenyl, —SO$_2$CH$_2$CH$_2$CH$_2$phenyl, —SCH$_2$CH$_2$phenyl, —SO$_2$CH$_2$CH$_2$phenyl, —SCH$_2$CH$_2$-(4-fluorophenyl), —SO$_2$CH$_2$CH$_2$CH$_2$-(4-fluorophenyl), -1-(5-phenyl-1,2,3-triazolyl), -1-(5-benzyl-1,2,3-triazolyl), -4-(5-benzyl-3-oxo-morpholinyl), -2-(3-phenylthiophenyl), -2-(4-phenyl-1,3-thiazolyl),

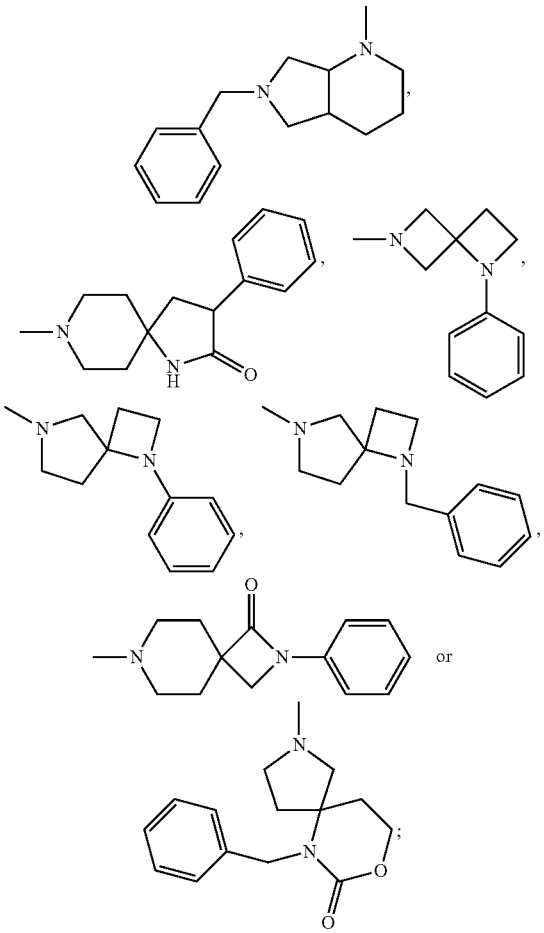

$R^{2b}$ is hydrogen;
$R^3$ is —CO$_2$H, —CH$_2$CO$_2$H, —CH$_2$OH, —C(=O)C(=O)OH, —C(=O)NHSO$_2$C$_{1-6}$alkyl, —C(=O)NHSO$_2$N(C$_{1-6}$alkyl)$_2$, —C(=O)NHSO$_2$phenyl, —C(=O)NHSO$_2$CF$_3$, —SO$_3$H, PO$_3$H$_2$, tetrazolyl, —CH$_2$NHSO$_2$C$_{1-6}$ alkyl, —CH$_2$OH, —C(=O)NH$_2$ or —CN especially —CO$_2$H, —CH$_2$CO$_2$H, —C(=O)NHSO$_2$C$_{1-4}$alkyl, —C(=O)NHSO$_2$(C$_{1-3}$alkyl)$_2$, —C(=O)NHSO$_2$phenyl, tetrazolyl, —CH$_2$NHSO$_2$C$_{1-4}$alkyl, —C(=O)NH$_2$, CN or —C(=O)NHSO$_2$CF$_3$, more especially —CO$_2$H;
$R^4$ is hydrogen or $R^3$ and $R^4$ together form:

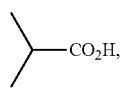

especially hydrogen;
$R^5$ is hydrogen or together with $R^2$ forms an aryl, heteroaryl or heterocyclyl ring selected from:

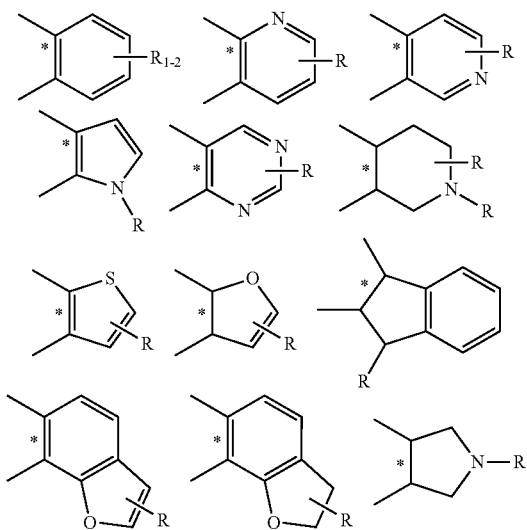

where* indicates the fused bond, and R is selected from —C$_{1-3}$alkyl, —OC$_{1-3}$alkyl, —OCF$_3$, —OCHF$_2$, —OCH$_2$phenyl, —CH=CHphenyl, —CH$_2$CH$_2$phenyl, —CH(OH)CH(OH)phenyl, —SO$_2$NHphenyl, —NHSO$_2$phenyl, —NHC(O)NHphenyl, —NHC(O)Ophenyl, —CH$_2$phenyl, —Ophenyl, —OCH$_2$CH=CHphenyl, —OCH$_2$CH$_2$phenyl, —OCH$_2$CH$_2$CH$_2$phenyl and -phenyl;
especially where $R^5$ and $R^2$ together forms one of:

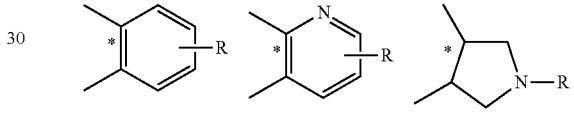

where R is selected from —C$_{1-3}$alkyl, —OC$_{1-3}$alkyl, —OCF$_3$, —OCHF$_2$, —OCH$_2$phenyl, —CH=CHphenyl, —CH$_2$CH$_2$phenyl, —CH(OH)CH(OH)phenyl, —C≡Cphenyl, —SO$_2$NHphenyl, —NHSO$_2$phenyl, —NHC(O)NHphenyl, —NHC(O)Ophenyl, —CH$_2$phenyl, —Ophenyl, —OCH$_2$CH=CHphenyl, —OCH$_2$CH$_2$phenyl, —OCH$_2$CH$_2$CH$_2$phenyl and -phenyl especially —OCH$_2$phenyl or —CH$_2$phenyl;
Particular compounds of formula (II) are:

| Compound | X | Y | $R^1$ | $R^2$ | $R^3$ | Relative $R^2/R^3$ | $R^4$ | $R^3/R^4$ | $R^5$ | $R^2/R^5$ |
|---|---|---|---|---|---|---|---|---|---|---|
| 1 | —CR$^5$— | —CH=CR$^3$— | —C(O)CH(phenyl)$_2$ | — | —CO$_2$H | — | H | — | — | (pyridine with OCH$_2$phenyl substituent) |
| 2 | —CHR$^5$— | —CHR$^3$CHR$^4$— | —C(O)CH(phenyl)$_2$ | benzyloxy | —CO$_2$H (S) | cis | H | — | H | — |
| 3 | —CHR$^5$— | —CHR$^3$CHR$^4$— | —C(O)CH(phenyl)$_2$ | benzyloxy | —CO$_2$H (S) | trans | H | — | H | — |
| 4 | —CHR$^5$— | —CHR$^3$CHR$^4$— | —C(O)CH(phenyl)$_2$ | phenylCH$_2$CH$_2$O— | —CO$_2$H (S) | cis | H | — | H | — |
| 5 | —CHR$^5$— | —CHR$^3$CHR$^4$— | —C(O)CH(phenyl)$_2$ | phenylCH= | —CO$_2$H (S) | cis | H | — | H | — |

-continued

| Compound | X | Y | $R^1$ | $R^2$ | $R^3$ | Relative $R^2/R^3$ | $R^4$ | $R^3/R^4$ | $R^5$ | $R^2/R^5$ |
|---|---|---|---|---|---|---|---|---|---|---|
| 6 | —CHR$^5$— | —CHR$^3$CHR$^4$— | —C(O)CH(phenyl)$_2$ | CHCH$_2$O—phenylCH$_2$CH$_2$CH$_2$O— | —CO$_2$H (S) | cis | H | — | H | — |
| 7 | —CHR$^5$— | —CHR$^3$CHR$^4$— | —C(O)CH(phenyl)$_2$ | phenylCH$_2$CH$_2$O— | —CO$_2$H (S) | trans | H | — | H | — |
| 8 | —CHR$^5$— | —CHR$^3$CHR$^4$— | —C(O)CH(phenyl)$_2$ | phenylCH=CHCH$_2$O— | —CO$_2$H (S) | trans | H | — | H | — |
| 9 | —CHR5— | —CHR3CHR4— | —C(0)CH(phenyl)$_2$ | phenylCH$_2$CH$_2$CH$_2$O— | —CO2H (S) | trans | H | — | H | — |
| 10 | —CHR$^5$— | —CHR$^3$CHR$^4$— | —C(O)CH(phenyl)$_2$ | =CHC(O)NHCH$_2$phenyl | —CO$_2$H (S) | — | H | — | H | — |
| 11 | —CR$^5$— | —CR$^3$=CH— | —C(O)CH(phenyl)$_2$ | — | —CO$_2$H | — | — | — | — | (2-methyl-phenoxymethyl-phenyl) |
| 12 | —CR$^5$— | —CR$^3$=CH— | —C(O)CH(phenyl)$_2$ | — | —C(O)C(O)OH | — | — | — | H | (2-methyl-phenoxymethyl-phenyl) |
| 13 | —CR$^5$— | —CR$^3$=CH— | —C(O)N(phenyl)$_2$ | — | —CO$_2$H | — | — | — | — | (2-methyl-phenoxymethyl-phenyl) |
| 14 | —CR$^5$— | —CH=CR$^3$— | —C(O)N(phenyl)$_2$ | — | —C(O)C(O)OH | — | — | — | — | (2-methyl-phenoxymethyl-phenyl) |

-continued

| Compound | X | Y | R¹ | R² | R³ | Relative R²/R³ | R⁴ | R³/R⁴ | R⁵ | R²/R⁵ |
|---|---|---|---|---|---|---|---|---|---|---|
| 15 | —CR⁵— | —CHR³CHR⁴— | —C(O)CH(phenyl)₂ | — | —CO₂H (R/S) | — | H | — | — | 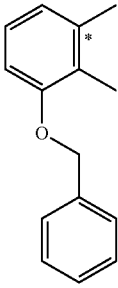 |
| 16 | —CHR⁵— | —CHR³CHR⁴— | —C(O)CH(phenyl)₂ | 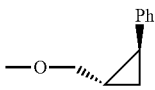 | —CO₂H (S) | cis | H | — | H | |
| 17 | —CHR⁵— | —CHR³CHR⁴— | —C(O)CH(phenyl)₂ | 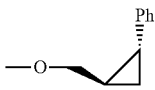 | —CO₂H (S) | cis | H | — | H | |
| 18 | —CHR⁵— | —CHR³CHR⁴— | —C(O)CH(phenyl)₂ | —OCH₂-(2-phenyl)-5-methyl-4-oxazole | —CO₂H (S) | cis | H | — | H | — |
| 19 | —CHR⁵— | —CHR³CHR⁴— | —C(O)CH(phenyl)₂ | -1-(3-benzyloxy)azetidine | —CO₂H (S) | cis | H | — | H | — |
| 20 | —CHR⁵— | —CHR³CHR⁴— | —C(O)CH(phenyl)₂ | -1-(3-phenyl)azetidine | —CO₂H (S) | cis | H | — | H | — |
| 21 | —CHR⁵— | —CHR³CHR⁴— | —C(O)CH(phenyl)₂ | —N(CH₃)CH₂CH₂CH₂phenyl | —CO₂H (S) | cis | H | — | H | — |
| 22 | —CHR⁵— | —CHR³CHR⁴— | —C(O)CH(phenyl)₂ | —N(CH₃)CH₂CH₂phenyl | —CO₂H (S) | cis | H | — | H | — |
| 23 | —CHR⁵— | —CHR³CHR⁴— | —C(O)CH(phenyl)₂ | -1-(4-phenyl)-piperazine | —CO₂H (S) | cis | H | — | H | — |
| 24 | —CHR⁵— | —CHR³CHR⁴— | —C(O)CH(phenyl)₂ | -1-(4-methyl-3R-phenyl)piperazine | —CO₂H (S) | cis | H | — | H | — |
| 25 | —CHR⁵— | —CHR³CHR⁴— | —C(O)CH(phenyl)₂ | -1-(4-methyl-3S-phenyl)piperazine | —CO₂H (S) | cis | H | — | H | — |
| 26 | —CHR⁵— | —CHR³CHR⁴— | —C(O)CH(phenyl)₂ | -4-(2R-phenyl)morpholine | —CO₂H (S) | cis | H | — | H | — |
| 27 | —CHR⁵— | —CHR³CHR⁴— | —C(O)CH(phenyl)₂ | -4-(2S-phenyl)morpholine | —CO₂H (S) | cis | H | — | H | — |
| 28 | —CHR⁵— | —CHR³CHR⁴— | —C(O)CH(phenyl)₂ | -4-(2S-benzyl)morpholine | —CO₂H (S) | cis | H | — | H | — |
| 29 | —CHR⁵— | —CHR³CHR⁴— | —C(O)CH(phenyl)₂ | —N(CH₃)-(2-phenyl)cyclopropyl | —CO₂H (S) | cis | H | — | H | — |
| 30 | —CHR⁵— | —CHR³CHR⁴— | —C(O)CH(phenyl)₂ | —N(CH₃)-(2-phenyl)Cyclopropyl | —CO₂H (S) | cis | H | — | H | — |
| 31 | —CHR⁵— | —CHR³CHR⁴— | —C(O)CH(phenyl)₂ | —OCH₂C(phenyl)=CH(phenyl) | —CO₂H (S) | cis | H | — | H | — |
| 32 | —CHR⁵— | —CHR³CHR⁴— | —C(O)CH(phenyl)₂ | —OCH₂CH(phenyl)CH₂(phenyl) | —CO₂H (S) | cis | H | — | H | — |
| 33 | —CHR⁵— | —CHR³CHR⁴— | —C(O)CH(phenyl)₂ | —O-(2-benyzloxy)phenyl | —CO₂H (S) | cis | H | — | H | — |
| 34 | —CHR⁵— | —CHR³CHR⁴— | —C(O)CH(phenyl)₂ | —O-(3-phenoxy)phenyl | —CO₂H (S) | cis | H | — | H | — |
| 35 | —CHR⁵— | —CHR³CHR⁴— | —C(O)CH(phenyl)₂ | —O-(2-phenoxy)phenyl | —CO₂H (S) | cis | H | — | H | — |
| 36 | —CHR⁵— | —CHR³CHR⁴— | —C(O)CH(phenyl)₂ | —OCH₂C≡C-phenyl | —CO₂H (S) | cis | H | — | H | — |
| 37 | —CHR⁵— | —CHR³CHR⁴— | —C(O)CH | —OCH₂CH=CH | —CO₂H (R) | cis | H | — | — | — |

-continued

| Compound | X | Y | R¹ | R² | R³ | Relative R²/R³ | R⁴ | R³/R⁴ | R⁵ | R²/R⁵ |
|---|---|---|---|---|---|---|---|---|---|---|
| 38 | —CHR⁵— | —CHR³CHR⁴— | —C(O)CH(phenyl)₂ | —OCH₂CH₂CH₂phenyl | —CO₂H (R) | cis | H | — | H | — |
| 39 | —CH₂CHR⁵— | —CHR³— | —C(O)CH(phenyl)₂ | —OCH₂CH=CHphenyl | —CO₂H (S) | cis | H | — | H | — |
| 40 | —CH₂CHR⁵— | —CHR³— | —C(O)CH(phenyl)₂ | —OCH₂CH₂CH₂phenyl | —CO₂H (S) | cis | H | — | H | — |
| 41 | — | —CHR³CHR⁴CH₂— | —C(O)CH(phenyl)₂ | —CH₂CH=CHphenyl | —CO₂H (S) | cis | H | — | H | — |
| 42 | — | —CHR³CHR⁴CH₂— | —C(O)CH(phenyl)₂ | —CH₂CH₂CH₂phenyl | —CO₂H (S) | cis | — | — | — | — |
| 43 | —CR⁵— | —CHR³CHR⁴— | —C(O)CH(phenyl)₂ | — | — | — | — | — | —CH(CO₂H)— | 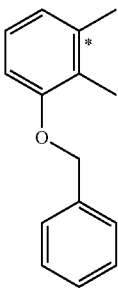 |
| 44 | —CHR⁵— | —CHR³CHR⁴— | —C(O)CH(phenyl)₂ | —C(O)NHCH₂phenyl | —CO₂H (S) | cis | H | — | H | — |
| 45 | —CHR⁵— | —CHR³CHR⁴— | —C(O)CH(phenyl)₂ | —C(O)NHCH₂CH₂phenyl | —CO₂H (S) | cis | H | — | H | — |
| 46 | —CHR⁵— | —CHR³CHR⁴— | —C(O)CH(phenyl)₂ | —NHCH₂CH₂phenyl | —CO₂H (S) | cis | H | — | H | — |
| 47 | —CHR⁵— | —CHR³CHR⁴— | —C(O)CH(phenyl)₂ | -1-(4-phenyl)piperidine | —CO₂H (S) | cis | H | — | H | — |
| 48 | —CHR⁵— | —CHR³CHR⁴— | —C(O)CH(phenyl)₂ | -1-(3S-phenyl)piperidine | —CO₂H (S) | cis | H | — | H | — |
| 49 | —CHR⁵— | —CHR³CHR⁴— | —C(O)CH(phenyl)₂ | -1-(3R-phenyl)piperidine | —CO₂H (S) | cis | H | — | H | — |
| 50 | —CHR⁵— | —CHR³CHR⁴— | —C(O)CH(phenyl)₂ | -1-(3R/S-phenyl)piperidine | —CO₂H (S) | cis | H | — | H | — |
| 51 | —CHR⁵— | —CHR³CHR⁴— | —C(O)CH(phenyl)₂ | -1-(3R-benzyl)piperidine | —CO₂H (S) | cis | H | — | H | — |
| 52 | —CHR⁵— | —CHR³CHR⁴— | —C(O)CH(phenyl)₂ | -1-(3S-benzyl)piperidine | —CO₂H (S) | cis | H | — | H | — |
| 53 | —CHR⁵— | —CHR³CHR⁴— | —C(O)CH(phenyl)₂ | -1-(3R/S-benzyl)piperidine | —CO₂H (S) | cis | H | — | H | — |
| 54 | —CHR⁵— | —CHR³CHR⁴— | —C(O)CH(phenyl)₂ | —CH₂OCH₂phenyl | —CO₂H (S) | cis | H | — | H | — |
| 55 | —CHR⁵— | —CHR³CHR⁴— | —C(O)CH(phenyl)₂ | —CH₂CH₂OCH₂phenyl | —CO₂H (S) | cis | H | — | H | — |
| 56 | —CHR⁵— | —CHR³CHR⁴— | —C(O)CH(phenyl)₂ | -2-(5-phenyl)oxazolyl | —CO₂H (S) | cis | H | — | H | — |
| 57 | —CHR⁵— | —CHR³CHR⁴— | —C(O)CH(phenyl)₂ | -2-(5-benzyl)oxazolyl | —CO₂H (S) | cis | H | — | H | — |
| 58 | —CHR⁵— | —CHR³CHR⁴— | —C(O)CH(phenyl)₂ | —CH₂SO₂CH₂CH₂phenyl | —CO₂H (S) | cis | H | — | H | — |
| 59 | —CHR⁵— | —CHR³CHR⁴— | —C(O)CH(phenyl)₂ | -1-(2S-benzyl)pyrrolidinyl | —CO₂H (S) | cis | H | — | H | — |
| 60 | —CHR⁵— | —CHR³CHR⁴— | —C(O)CH(phenyl)₂ | -1-(2R-benzyl)pyrrolidinyl | —CO₂H (S) | cis | H | — | H | — |
| 61 | —CHR⁵— | —CHR³CHR⁴— | —C(O)CH(phenyl)₂ | -1-(2R/S-benzyl)pyrrolidinyl | —CO₂H (S) | cis | H | — | H | — |
| 62 | —CHR⁵— | —CHR³CHR⁴— | —C(O)CH(phenyl)(cyclohexyl) | —N(CH₃)CH₂CH₂CH₂phenyl | —CO₂H (S) | cis | H | — | H | — |
| 63 | —CHR⁵— | —CHR³CHR⁴— | —C(O)CH(phenyl)₂ | 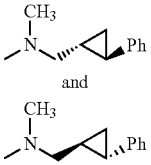 | —CO₂H (S) | cis | H | — | H | — |

-continued

| Compound | X | Y | R¹ | R² | R³ | Relative R²/R³ | R⁴ | R³/R⁴ | R⁵ | R²/R⁵ |
|---|---|---|---|---|---|---|---|---|---|---|
| 64 | —CHR⁵— | —CHR³CHR⁴— | —C(O)CH(phenyl)₂ | —NHC(O)N(phenyl)₂ | —CO₂H (S) | cis | H | — | H | — |
| 65 | —CHR⁵— | —CHR³CHR⁴— | —C(O)CH(phenyl)₂ | 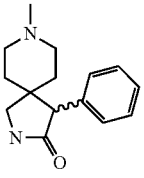 | —CO₂H (S) | cis | H | — | H | — |
| 66 | —CHR⁵— | —CH₂CHR³— | —C(O)CH(phenyl)₂ | —N(CH₃)CH₂CH₂CH₂phenyl | —CO₂H (S/R) | cis | — | — | H | — |
| 67 | —CHR⁵— | —CH₂CHR³— | —C(O)CH(phenyl)₂ | —N(CH₃)CH₂CH₂CH₂phenyl | —CO₂H (S/R) | trans | — | — | H | — |
| 68 | —CHR⁵— | —CHR³CHR⁴— | —C(O)CH(phenyl)₂ | 1-(2S-benzyl)piperidine | —CO₂H (S) | cis | H | — | H | — |
| 69 | —CHR⁵— | —CHR³CHR⁴— | —C(O)CH(phenyl)₂ | 1-(2R-benzyl)piperidine | —CO₂H (S) | cis | H | — | H | — |
| 70 | —CHR⁵— | —CHR³CHR⁴— | —C(O)CH(phenyl)₂ | 1-(2R/S-benzyl)piperidine | —CO₂H (S) | cis | H | — | H | — |
| 71 | —CHR⁵— | —CHR³CHR⁴— | —C(O)CH(phenyl)₂ | —OCH₂-4-(2-phenyl)oxazolyl | —CO₂H (S) | cis | H | — | H | — |
| 72 | —CHR⁵— | —CHR³CHR⁴— | —C(O)CH(phenyl)₂ | 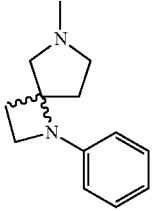 | —CO₂H (S) | cis | H | — | H | — |
| 73 | —CHR⁵— | —CHR³CHR⁴— | —C(O)CH(phenyl)₂ | 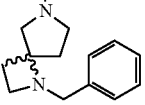 | —CO₂H (S) | cis | H | — | H | — |
| 74 | —CHR⁵— | —CHR³CHR⁴— | —C(O)CH(phenyl)₂ | 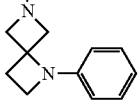 | —CO₂H (S) | cis | H | — | H | — |
| 75 | —CHR⁵— | —CHR³CHR⁴— | —C(O)CH(phenyl)₂ | 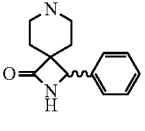 | —CO₂H (S) | cis | H | — | H | — |
| 76 | —CHR⁵— | —CHR³CHR⁴— | —C(O)CH(phenyl)₂ | —OCH₂CH₂CH₂phenyl | —CO₂H (R) | cis | H | — | H | — |
| 77 | —CH₂CHR⁵— | —CHR³— | —C(O)CH(phenyl)₂ | — | —CO₂H (R) | — | — | — | — | 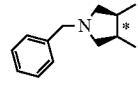 |
| 78 | —CH₂CHR⁵— | —CHR³— | —C(O)CH(phenyl)₂ | — | —CO₂H (R) | — | — | — | — | 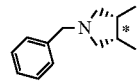 |
| 79 | —CHR⁵— | —CHR³CHR⁴— | —C(O)CH(phenyl)₂ | —O-4-(2-phenyl)oxazolyl | —CO₂H (S) | cis | H | — | H | — |
| 80 | —CHR⁵— | —CHR³CHR⁴— | —C(O)N(phenyl)₂ | —OCH₂CH₂CH₂phenyl | —CO₂H (S) | cis | H | — | H | — |
| 81 | —CHR⁵— | —CHR³CHR⁴— | —C(O)CH(phenyl)₂ | -1-(3R-benzyl)piperidine | —CO₂H (S) | trans | H | — | H | — |

-continued

| Compound | X | Y | R¹ | R² | R³ | Relative R²/R³ | R⁴ | R³/R⁴ | R⁵ | R²/R⁵ |
|---|---|---|---|---|---|---|---|---|---|---|
| 82 | —CHR⁵— | —CHR³CHR⁴— | —C(O)CH(phenyl)₂ | -1-(3R/S-benzyl) piperidine | —CO₂H (S) | trans | H | — | H | — |
| 83 | —CHR⁵— | —CHR³CHR⁴— | —C(O)CH(phenyl)₂ | -1-(3S-benzyl) piperidine | —CO₂H (S) | trans | H | — | H | — |
| 84 | —CHR⁵— | —CHR³CHR⁴— | —C(O)CH(phenyl)₂ | [structure: benzyl-octahydropyrrolo-pyridine] | —CO₂H (S) | cis | H | — | H | — |
| 85 | —CHR⁵— | —CHR³CHR⁴— | —C(O)CH(phenyl)₂ | [structure: benzyl-octahydropyrrolo-pyridine stereoisomer] | —CO₂H (S) | cis | H | — | H | — |
| 86 | —CHR⁵— | —CHR³CHR⁴— | —C(O)CH(phenyl)₂ | -3R-phenylpyrrolidine | —CO₂H (S) | cis | H | — | H | — |
| 87 | —CHR⁵— | —CHR³CHR⁴— | —C(O)CH(phenyl)₂ | -3S-phenylpyrrolidine | —CO₂H (S) | cis | H | — | H | — |
| 88 | —CHR⁵— | —CHR³CHR⁴— | —C(O)CH(phenyl)₂ | -4-(2S-benzyl) morpholine | —CO₂H (S) | cis | H | — | H | — |
| 89 | —CHR⁵— | —CHR³CHR⁴— | —C(O)CH(phenyl)₂ | -4-(2R-benzyl) morpholine | —CO₂H (S) | cis | H | — | H | — |
| 90 | —CHR⁵— | —CHR³CHR⁴— | —C(O)CH(phenyl)₂ | —N(CH₃)(CH₂)₄-phenyl | —CO₂H (S) | cis | H | — | H | — |
| 91 | —CHR⁵— | —CHR³CHR⁴— | —C(O)CH(phenyl)₂ | —N(CH₃)(CH₂)₃(4-fluorophenyl) | —CO₂H (S) | cis | H | — | H | — |
| 92 | —CHR⁵— | —CHR³CHR⁴— | —C(O)CH(phenyl)₂ | —N(CH₃)(CH₂)₃-(4-methoxy-3-methylphenyl) | —CO₂H (S) | cis | H | — | H | — |
| 93 | —CHR⁵— | —CHR³CHR⁴— | —C(O)CH(phenyl)₂ | —N(CH₃)(CH₂)₃(3-pyridine) | —CO₂H (S) | cis | H | — | H | — |
| 94 | —CHR⁵— | —CHR³CHR⁴— | —C(O)CH(Phenyl)₂ | —NHC(O)CH=CH phenyl | —CO₂H (S) | cis | H | — | H | — |
| 95 | —CHR⁵— | —CHR³CHR⁴— | —C(O)CH(Phenyl)₂ | —N(CH₃)C(O)CH=CH phenyl | —CO₂H (S) | cis | H | — | H | — |
| 96 | —CHR⁵— | —CHR³CHR⁴— | —C(O)CH(Phenyl)₂ | —NHC(O)CH₂CH₂ phenyl | —CO₂H (S) | cis | H | — | H | — |
| 97 | —CHR⁵— | —CHR³CHR⁴— | —C(O)CH(Phenyl)₂ | —N(CH₃)C(O)CH₂CH₂ phenyl | —CO₂H (S) | cis | H | — | H | — |
| 98 | —CHR⁵— | —CHR³CHR⁴— | —C(O)CH(Phenyl)₂ | —N(C(O)CH₃)CH₂CH₂CH₂phenyl | —CO₂H (S) | cis | H | — | H | — |
| 99 | —CHR⁵— | —CHR³CHR⁴— | —C(O)CH(Phenyl)₂ | —N(SO₂CH₃)CH₂CH₂CH₂phenyl | —CO₂H (S) | cis | H | — | H | — |
| 100 | —CHR⁵— | —CHR³CHR⁴— | —C(O)CH(Phenyl)₂ | -1-(5-phenyl-1,2,3-triazolyl) | —CO₂H (S) | cis | H | — | H | — |
| 101 | —CHR⁵— | —CHR³CHR⁴— | —C(O)CH(Phenyl)₂ | -1-(5-benzyl-1,2,3-triazolyl) | —CO₂H (S) | cis | H | — | H | — |
| 102 | —CHR⁵— | —CHR³CHR⁴— | —C(O)CH(Phenyl)₂ | -4-(5-benzyl-3-oxo-morpholinyl) | —CO₂H (S) | cis | H | — | H | — |
| 103 | —CHR⁵— | —CHR³CHR⁴— | —C(O)CH(Phenyl)₂ | —OCH₂CH₂CH₂ phenyl | —CH₂OH (S) | cis | H | — | H | — |
| 104 | —CHR⁵— | —CHR³CHR⁴— | —C(O)CH(Phenyl)₂ | —OCH₂CH₂CH₂-(4-fluorophenyl) | —CO₂H (S) | cis | H | — | H | — |
| 105 | —CHR⁵— | —CHR³CHR⁴— | —C(O)CH(Phenyl)₂ | —N(CH₃)CH₂C≡C-(3-methyl-4-methoxyphenyl) | —CO₂H (S) | cis | H | — | H | — |
| 106 | —CHR⁵— | —CHR³CHR⁴— | —C(O)CH(Phenyl)₂ | —CH₂CH₂CH₂CH₂ phenyl | —CO₂H (S) | cis | H | — | H | — |
| 107 | —CHR⁵— | —CHR³CHR⁴— | —C(O)CH(Phenyl)₂ | -2-(3-phenylthio-phenyl) | —CO₂H (S) | cis | H | — | H | — |
| 108 | —CHR⁵— | —CHR³— | —C(O)CH(Phenyl)₂ | —OCH₂CH₂CH₂ phenyl | —CH₂OH (S/R) | trans | H | — | H | — |
| 109 | —CHR⁵— | —CHR³— | —C(O)CH(Phenyl)₂ | —OCH₂CH₂CH₂ phenyl | —CH₂OH (S/R) | cis | H | — | H | — |
| 110 | —CH₂CHR⁵— | —CHR³— | —C(O)CH(Phenyl)₂ | —OCH₂CH=CH phenyl | —CO₂H (S) | trans | H | — | H | — |
| 111 | —CH₂CHR⁵— | —CHR³— | —C(O)CH(Phenyl)₂ | —OCH₂CH₂CH₂ phenyl | —CO₂H (S) | trans | H | — | H | — |
| 112 | —CHR⁵— | —CHR³CHR⁴— | —C(O)CH(Phenyl)₂ | —OCH₂CH₂CH₂ phenyl | —C(O)NHSO₂N(CH₃)₂ (S) | cis | H | — | H | — |
| 113 | —CHR⁵— | —CHR³CHR⁴— | —C(O)CH(Phenyl)₂ | —N(CH₃)CH₂CH₂CH₂ phenyl | —C(O)NHSO₂N(CH₃)₂ (S) | cis | H | — | H | — |

-continued

| Compound | X | Y | R¹ | R² | R³ | Relative R²/R³ | R⁴ | R³/R⁴ | R⁵ | R²/R⁵ |
|---|---|---|---|---|---|---|---|---|---|---|
| 114 | —CHR⁵— | —CHR³CHR⁴— | —C(O)CH(Phenyl)₂ | —N(CH₃)CH₂CH₂CH₂-(4-fluorophenyl) | —C(O)NHSO₂N(CH₃)₂ (S) | cis | H | — | H | — |
| 115 | —CHR⁵— | —CHR³CHR⁴— | —C(O)CH(Phenyl)₂ | (spiro structure with N-methyl pyrrolidine fused to N-benzyl oxazinone) | —CO₂H (S) | cis | H | — | H | — |
| 116 | —CHR⁵— | —CHR³CHR⁴— | —C(O)CH(Phenyl)₂ | —N(CH₃)CH₂C≡C-phenyl | —CO₂H (S) | cis | H | — | H | — |
| 117 | —CHR⁵— | —CHR³CHR⁴— | —C(O)CH(Phenyl)₂ | —CH₂Ophenyl | —CO₂H (S) | cis | H | — | H | — |
| 118 | —CHR⁵— | —CHR³CHR⁴— | —C(O)CH(Phenyl)₂ | —CH₂SO₂CH₂phenyl | —CO₂H (S) | cis | H | — | H | — |
| 119 | —CHR⁵— | —CHR³CHR⁴— | —C(O)CH(Phenyl)₂ | —CH₂SO₂phenyl | —CO₂H (S) | cis | H | — | H | — |
| 120 | —CHR⁵— | —CHR³CHR⁴— | —C(O)CH(Phenyl)₂ | —CH₂SCH₂CH₂phenyl | —CO₂H (S) | cis | H | — | H | — |
| 121 | —CHR⁵— | —CHR³CHR⁴— | —C(O)CH(Phenyl)₂ | —CH₂SCH₂phenyl | —CO₂H (S) | cis | H | — | H | — |
| 122 | —CHR⁵— | —CHR³CHR⁴— | —C(O)CH(Phenyl)₂ | —CH₂Sphenyl | —CO₂H (S) | cis | H | — | H | — |
| 123 | —CHR⁵— | —CHR³CHR⁴— | —C(O)CH(Phenyl)₂ | -2-(4-phenyl-1,3-thiazolyl) | —CO₂H (S) | cis | H | — | H | — |
| 124 | —CHR⁵— | —CHR³CHR⁴— | —C(O)CH(Phenyl)₂ | —SCH₂CH₂CH₂phenyl | —CO₂H (S) | cis | H | — | H | — |
| 125 | —CHR⁵— | —CHR³CHR⁴— | —C(O)CH(Phenyl)₂ | —SO₂CH₂CH₂CH₂phenyl | —CO₂H (S) | cis | H | — | H | — |
| 126 | —CHR⁵— | —CHR³CHR⁴— | —C(O)CH(Phenyl)₂ | —N(CH₃)CH₂CH₂O-(4-fluorophenyl) | —CO₂H (S) | cis | H | — | H | — |
| 127 | —CHR⁵— | —CHR³CHR⁴— | —C(O)CH(Phenyl)₂ | —CH₂N(CH₃)CH₂CH₂-(4-fluorophenyl) | —CO₂H (S) | cis | H | — | H | — |
| 128 | —CHR⁵— | —CHR³CHR⁴— | —C(O)CH(Phenyl)₂ | —N(CH₂CF₃)CH₂CH₂CH₂-(4-fluorophenyl) | —CO₂H (S) | cis | H | — | H | — |
| 129 | —CHR⁵— | —CHR³CHR⁴— | —C(O)CH(Phenyl)₂ | —OCH₂CH₂CH₂phenyl | -tetrazolyl (S) | cis | H | — | H | — |
| 130 | —CHR⁵— | —CHR³CHR⁴— | —C(O)CH(Phenyl)₂ | —OCH₂CH₂CH₂phenyl | —CH₂NHSO₂CH₃ (S) | cis | H | — | H | — |
| 131 | —CHR⁵— | —CHR³CHR⁴— | —C(O)CH(Phenyl)₂ | —SCH₂CH₂phenyl | —CO₂H (S) | cis | H | — | H | — |
| 132 | —CHR⁵— | —CHR³CHR⁴— | —C(O)CH(Phenyl)₂ | —SO₂CH₂CH₂phenyl | —CO₂H (S) | cis | H | — | H | — |
| 133 | —CHR⁵— | —CHR³CHR⁴— | —C(O)CH(Phenyl)₂ | —SCH₂CH₂-(4-fluorophenyl) | —CO₂H (S) | cis | H | — | H | — |
| 134 | —CHR⁵— | —CHR³CHR⁴— | —C(O)CH(Phenyl)₂ | —SO₂CH₂CH₂CH₂-(4-fluorophenyl) | —CO₂H (S) | cis | H | — | H | — |
| 135 | —CHR⁵— | —CHR³CHR⁴— | —C(O)CH(Phenyl)₂ | —OCH₂CH₂CH₂phenyl | —C(O)NHSO₂CH₃ (S) | cis | H | — | H | — |
| 136 | —CHR⁵— | —CHR³CHR⁴— | —C(O)CH(Phenyl)₂ | —N(CH₃)CH₂CH₂CH₂-(4-fluorophenyl) | —C(O)NH₂ (S) | cis | H | — | H | — |
| 137 | —CHR⁵— | —CHR³CHR⁴— | —C(O)CH(Phenyl)₂ | —N(CH₃)CH₂CH₂CH₂-(4-fluorophenyl) | —CN (S) | cis | H | — | H | — |
| 138 | —CHR⁵— | —CHR³CHR⁴— | —C(O)CH(Phenyl)₂ | —N(CH₃)CH₂CH₂CH₂-(4-fluorophenyl) | -tetrazolyl (S) | cis | H | — | H | — |
| 139 | —CHR⁵— | —CHR³CR⁴= | —C(O)CH(phenyl)₂ | -2-(3-phenylthio-phenyl) | —CO₂H (S) | — | H | — | H | — |
| 140 | —CHR⁵— | —CHR³CR⁴= | —C(O)CH(phenyl)₂ | —C≡CCH₂CH₂phenyl | —CO₂H (S) | — | H | — | H | — |
| 141 | —CHR⁵— | —CHR³CR⁴= | —C(O)CH(phenyl)₂ | -2-(4-phenyl-1,3-thiazolyl) | —CO₂H (S) | — | H | — | H | — |
| 142 | —CHR⁵— | —CHR³— | —C(O)CH(phenyl)₂ | —OCH₂CH₂CH₂phenyl | —CO₂H (S/R) | trans | H | — | H | — |
| 143 | —CHR⁵— | —CHR³— | —C(O)CH(phenyl)₂ | —OCH₂CH₂CH₂phenyl | —CO₂H (S/R) | cis | H | — | H | — |
| 144 | —CHR⁵— | —CHR³CHR⁴— | —C(O)CH(phenyl)₂ | -4-(2R-phenyl)morpholine | —CO₂H (S) | cis | H | — | H | — |
| 145 | —CHR⁵— | —CHR³CHR⁴— | —C(O)CH(phenyl)₂ | -4-(2S-phenyl)morpholine | —CO₂H (S) | cis | H | — | H | — |

-continued

| Compound | X | Y | $R^1$ | $R^2$ | $R^3$ | Relative $R^2/R^3$ | $R^4$ | $R^3/R^4$ | $R^5$ | $R^2/R^5$ |
|---|---|---|---|---|---|---|---|---|---|---|
| 146 | —$CHR^5$— | —$CHR^3CHR^4$— | —C(O)CH(phenyl)$_2$ | —N(CH$_3$)(CH$_2$C≡CH) | —CO$_2$H (S) | cis | H | — | H | — |
| 147 | —$CHR^5$— | —$CHR^3CHR^4$— | —C(O)CH(phenyl)$_2$ | —N(CH$_3$)(CH$_2$CH$_2$CH$_3$) | —CO$_2$H (S) | cis | H | — | H | — |
| 148 | —$CHR^5$— | —$CHR^3CHR^4$— | —C(O)CH(phenyl)$_2$ | —N(CH$_3$)(CH$_2$C≡CC(CH$_3$)$_3$) | —CO$_2$H (S) | cis | H | — | H | — |
| 149 | —$CHR^5$— | —$CHR^3CHR^4$— | —C(O)CH(phenyl)$_2$ | —N(CH$_3$)(CH$_2$CH$_2$CH$_2$C(CH$_3$)$_3$) | —CO$_2$H (S) | cis | H | — | H | — |

Particular compounds of the formula (II) include compounds 2, 3, 5, 6, 8, 9, 15, 16, 17, 21, 22, 23, 28, 34, 35, 36, 46, 48, 49, 50, 51, 53, 54, 55, 56, 58, 60, 61, 62, 63, 64, 65, 66, 67, 68, 69, 70, 75, 76, 84, 85, 86, 87, 90, 91, 92, 93, 94, 95, 96, 97, 98, 99, 100, 101, 102, 103, 104, 105, 106, 107, 108, 109, 112, 114, 115, 116, 118, 119, 120, 121, 122, 124, 125, 126, 131, 132, 133, 134, 135, 136, 137, 138, 139, 140, 142 and 143, especially 2, 3, 5, 6, 9, 15, 16, 21, 22, 23, 28, 48, 49, 50, 51, 53, 54, 55, 56, 58, 61, 63, 70, 84, 85, 87, 90, 91, 92, 93, 97, 98, 100, 101, 102, 106, 107, 112, 114, 115, 118, 121, 122, 124, 126, 135, 136, 137, 138, and 143.

In some embodiments, the compounds of formula (I) are selective AT$_2$ receptor antagonists. In particular embodiments, the selective AT$_2$ receptor antagonists have an IC$_{50}$ at the AT$_2$ receptor of ≤100 nM and an IC$_{50}$ at the AT$_1$ receptor of >100,000 nM (10 μM) using the assay methodologies described in Biological Examples 1 and 2.

The compounds of the invention are made by methods known in the art from commercially available starting materials.

For preparation of pyrrolidine derivatives, starting materials include suitably protected carboxylic acids such as trans-4-hydroxyproline ethyl ester and 4-hydroxy-indol-2-yl carboxylic acid methyl ester. For preparation of azetidine derivatives, a suitable starting material includes 3-hydroxy-azetidine-2-carboxylic acid methyl ester.

$R^2$ may be introduced by alkylation reactions such as reaction of an alkyl or aryl chloride in the presence of base. In some instances, the base used may be a hindered alkoxide such as tert-butoxide. In some instances where epimerization of a group alpha to the carboxylic acid is a problem, silver oxide mediated alkylation may be used.

$R^1$ may be introduced either before the introduction of $R^2$ or after the introduction of $R^2$. If $R^2$ is introduced prior to the introduction of $R^1$, it may be necessary to protect the ring nitrogen during the alkylation reaction. Suitable nitrogen protecting groups are known in the art, for example, in Greene & Wutz, Protective Groups in Organic Synthesis, Third Edition, John Wiley & Sons, 1999. A suitable nitrogen protecting group is t-butoxycarbonyl (Boc). Alternatively other reactive alkyl or aryl groups, such as phenoxy groups may be introduced by reaction of the 4-hydroxy substituent with the phenolic hydroxyl group in the presence of triphenylphosphine (PPh$_3$) and DBAD.

$R^1$ may be introduced by amide formation with a suitable carboxylic acid and the ring nitrogen. Amide formation is well known in the art and may involve the activation of the carboxylic acid, for example, the carboxy group is activated by formation of a carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-ethyl-3-(dimethylaminopropyl)carbodiimide (EDCI), 1-hydroxybenzotriazole (HOBt), 1-hydroxy-7-azabenzotriazole (HOAt), ethyl-2-cyano-2-cyano-2-(hydroxyimino)acetate (Oxyma Pure), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chloro-1H-benzotriazol-1-yl)-1,1,3,3-tetramethyluronium tetrafluorophosphate (HCTU), O-benzotriazol-1-yl-N,N,N'N'-tetramethyluronium tetrafluoroborate (TBTU), (benzotriazol-1-yloxy) tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethylidenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU).

Compounds in which $R^2$ is a substituted amino group may be prepared from 4-aminoproline. 4-Aminoproline may be prepared from commercially available 4-hydroxyproline by reductive amination of a ketone resulting from the oxidation of the 4-hydroxy group. The amino group may be further alkylated, acylated or sulfonated with one or two substituents. When the amine is bulky, for example, a secondary amine or the amino of a heterocyclic ring, this method provides good yields. In an alternative approach, the hydroxyl group of the 4-hydroxyproline may be mesylated and reacted with an amine nucleophile. This approach may be used when the amino nucleophile is a primary amine group. After introduction of the amino substituent, the amino group may be alkylated to provide a tertiary amine such as a N-methylalkylphenyl substituent.

In some cases, where the bond to $R^2$ is with the nitrogen atom of a heterocyclic ring, the starting material may be 4-oxo-proline methyl ester or an N-protected or N-derivative thereof and the reaction proceeds at elevated temperature, such as between 100 and 110° C.

The mesylate may also be used to prepare compounds in which $R^2$ is a thiol or sulfoxide group. For example the mesylate formed from 4-hydroxy-proline methyl ester may be reacted with PhC(O)SH to provide a protected thiol group as $R^2$. The thiol may be deprotected with mild base such as K$_2$CO$_3$. The free thiol may then be alkylated or arylated by methods known in the art such as reaction with an alkyl halide. The thio group may also be oxidised to provide a sulfoxide, for example, with m-CPBA.

When the pyrrolidine ring has a double bond in the 3,4-position, this may also be formed from reaction of 4-oxo-proline with a compound such as PhNTf$_2$. The triflate formed may then be further reacted with another group such as a heterocycle via its borate or an alkyne in the presence of a catalyst such as CuI, Pd(PPh$_3$)$_2$Cl$_2$.

In some instances, $R^2$ may be formed into a heterocyclyl ring in situ by cyclization of a disubstituted amino group.

For example, the 4-oxo-proline may be aminated with a hydroxy containing alkyl amine, followed by acylation of the nitrogen atom with an chloroalkylacyl chloride. The remaining chloride is able to be used in a cyclization reaction in the presence of $Cs_2CO_3$.

Triazoles may be prepared by reaction of 4-azo-proline with an alkyne in the presence of a suitable catalyst such as Cp*Ru (COD)Cl.

$R^3$ may be a carboxy group or may be manipulated, for example by reduction with a reagent such as $LiAlH_2Cl$, $NaBH_4/ClCO_2Et$ or $BH_3$ THF, to give a primary alcohol. Acyl sulfonamides may also be prepared by reaction with appropriate amines such as $NH_2SO_2N(CH_3)_2$.

The substituents of $R^2$ and $R^5$ that have reactive functional groups such as double bonds or triple bonds may be further manipulated to provide variation in the $R^2$ or $R^5$ substituents. For example, double bonds may be reduced to alkylene groups, or may be oxidized such as with meta-chloroperoxybenzoic acid (MCPBA) to give epoxides or reacted with diiodomethane to provide cyclopropyl groups. Triple bonds may be selectively reduced to provide double bonds and catalysts may be selected to provide either cis or trans geometric isomers as known in the art.

Substituents may be introduced onto a ring formed by $R^2$ and $R^5$ in a similar manner as discussed for the introduction of $R^2$ above.

Methods of the Invention

In one aspect of the present invention, there is provided a method of treating or preventing the symptoms of a neuropathic condition in a subject comprising administering a compound of formula (I) or a pharmaceutically acceptable salt thereof.

The compounds of formula (I) are effective in the prevention or attenuation of the symptoms of neuropathic conditions including primary and secondary neuropathic conditions. In accordance with the present invention, the compounds of formula (I) can act to treat, prevent or attenuate one or more symptoms associated with neuropathic conditions including, but not limited to, hyperesthesia, hyperalgesia, allodynia and/or spontaneous burning pain. In some embodiments, the compound of formula (I) is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is neuropathic pain. Accordingly, in a related aspect, the invention provides methods for preventing and/or attenuating neuropathic pain in an individual, comprising administering to the individual a pain-preventing or -attenuating effective amount of an $AT_2$ receptor antagonist, which is suitably in the form of a pharmaceutical composition.

There are many possible causes of neuropathy and neuropathic pain and it will be understood that the present invention contemplates the treatment or prevention of symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcer-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several anti-retroviral drugs ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barre syndrome.

In another aspect of the invention there is provided a method of treating or preventing a condition characterized by neuronal hypersensitivity in a subject comprising administering a compound of formula (I) or a pharmaceutically acceptable salt thereof.

In some embodiments, the condition characterized by neuronal hypersensitivity is a hyperalgesic condition such as fibromyalgia. In other embodiments, the condition is irritable bowel syndrome which is characterized by neuronal hypersensitivity in the gut.

In another aspect of the invention there is provided a method of treating or preventing a disorder associated with aberrant nerve regeneration comprising administering a compound of formula (I) or a pharmaceutically acceptable salt thereof.

In some embodiments, the disorder associated with aberrant nerve regeneration also includes neuronal hypersensitivity. For example, disorders associated with aberrant nerve regeneration are breast pain, interstitial cystitis and vulvodynia. In other embodiments, the disorder is a cancer chemotherapy-induced neuropathy.

In another aspect of the invention, there is provided a method of treating or preventing inflammatory pain in a subject comprising administering a compound of formula (I) or a pharmaceutically acceptable salt thereof.

Pain related to inflammation may be acute or chronic and can be due to a number of conditions that are characterized by inflammation including, without limitation, burns such as chemical, frictional or chemical burns, autoimmune diseases such as rheumatoid arthritis and osteoarthritis, inflammatory bowel disease such as Crohn's disease and colitis, and other inflammatory diseases such as inflammatory bowel disease, carditis, dermatitis, myositis, neuritis and collagen vascular diseases.

In a further aspect, the present invention provides a method of treating or preventing impaired nerve conduction velocity in a subject comprising administering a compound of formula (I) or a pharmaceutically acceptable salt thereof.

Impaired neuronal conduction velocity is a symptom of nerve dysfunction or damage and may be present as a symptom of a large number of diseases or disorders, particularly diseases or disorders that exhibit paresthesia as a symptom. In some embodiments, the impaired nerve conduction velocity is associated with a neuropathic condition as described above. In other embodiments, the impaired nerve conduction velocity is associated with Carpel Tunnel Syndrome, ulnar neuropathy, Guillian-Barré Syndrome, fascioscapulohumeral muscular dystrophy and spinal disc herneation.

Nerve conduction velocity is assessed by evaluating the electrical conduction of motor and sensory nerves in the body. Motor nerve conduction velocity is measured by stimulation of a peripheral nerve and measuring the time taken for the electrical impulse to be detected in the muscle associated with the nerve. The time taken is measured in milliseconds and is converted to a velocity (m/s) by taking into account the distance travelled. Sensory nerve conduction is assessed in a similar manner with stimulation of a peripheral nerve and recording at a sensory site such as a finger or paw pad.

In yet a further aspect of the invention there is provided a method of producing analgesia in a subject comprising administering a compound of formula (I) or a pharmaceutically acceptable salt thereof.

In some embodiments, the subject is a subject having a neuropathic condition, an inflammatory condition, impaired nerve conduction velocity, a condition characterized by neuronal hypersensitivity or a disorder associated with aberrant nerve regeneration. In other embodiments, the subject is a subject at risk of developing neuropathic pain, inflammatory pain, pain related to impaired nerve conduction velocity, a condition characterized by neuronal hypersensitivity or a disorder associated with aberrant nerve regeneration.

In still another aspect of the invention there is provided a method of treating or preventing a cell proliferative disorder in a subject comprising administering a compound of formula (I) or a pharmaceutically acceptable salt thereof.

In some embodiments, the cell proliferative disorder is a cancer, especially where the cancer is selected from leukaemia, melanoma, prostate cancer, breast cancer, ovarian cancer, basal cell carcinoma, squamous cell carcinoma, sarquoides, fibrosarcoma, colon cancer, lung cancer and other solid tumour cancers.

In other embodiments, the cell proliferative disorder is a non-cancerous proliferative disorder. Examples of such non-cancerous proliferative disorders include dermatological disorders such as warts, keloids, psoriasis, proud flesh disorder and also the reduction in scar tissue and cosmetic remodelling.

In a further aspect the present invention provides a method of treating or preventing a disorder associated with an imbalance between bone resorption and bone formation in a subject comprising administering a compound of formula (I) or a pharmaceutically acceptable salt thereof.

In some embodiments, the disorder associated with an imbalance between bone resorption and bone formation is osteoporosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 mg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. "Treatment" may also reduce the severity of an existing condition. The term "prophylaxis" does not necessarily mean that the subject will not eventually contract a disease condition. The term "prophylaxis" may be considered to include delaying the onset of a particular condition. Accordingly, treatment and prophylaxis include amelioration of the symptoms of a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body.

In some embodiments, the compounds of formula (I) or their pharmaceutically acceptable salts are administered together with another therapy to treat neuropathic or inflammatory pain or the underlying condition that is causing the neuropathic or inflammatory pain or another therapy to treat conditions characterized by neuronal sensitivity, disorders associated with aberrant nerve regeneration, proliferative disorders or disorders associated with an imbalance between bone resorption and bone formation. In some embodiments, the amount of the second drug may be reduced when administration is together with a compound of formula (I) or a pharmaceutically acceptable salt thereof.

Suitable additional drugs to treat pain include opiates such as morphine, codeine, dihydrocodeine, hydrocodone, acetyl-dihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenytoin, carbamazebine, levocarnitine, tricyclic antidepressants such as amitryptiline and sodium channel blockers such as lidocaine.

Examples of chemotherapy drugs for proliferative disorders include cisplatin, carboplatin, camptothecin, carmustine, cyclophosphamide, dactinomycin, daunorubicin, dexamethasone, docetaxel, doxorubicin, etoposide, epirubicin, everolimus, gemcitibine, goserelin, trastuzumab (Herceptin®), idarubicin, interferon-alfa, irinotecan, methotrexate, mitomycin, oxaliplatin, paclitaxel, raloxifene, streptozocin, tamoxifen, topotecan, vinblastine, vincristine, abiraterone, fluorouracil, denosumab, imatinib, geftinib, lapatinib, pazopanib, rituximab, sunitinib, erlotinib and vorinistat.

Examples of drugs to treat disorders associated with an imbalance between bone formation and bone resorption include bisphosphonates such as sodium alendronate, risedronate and ibandronate, raloxifene, calcitonin, teriparatide, strontium ranelate or calcium supplements.

Examples of drugs used to treat conditions characterized by neuronal hypersensitivity, such as irritable bowel syndrome, include 5HT$_3$ receptor antagonists such as alosetron (Lotronex®).

The AT$_2$ receptor antagonists of the invention are also useful in combination with radiotherapy in cancer patients.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles' comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention will now be described with reference to the following Examples which illustrate some preferred aspects of the present invention. However, it is to be understood that the particularity of the following description of the invention is not to supersede the generality of the preceding description of the invention.

EXAMPLES

Abbreviations

Figure 1:
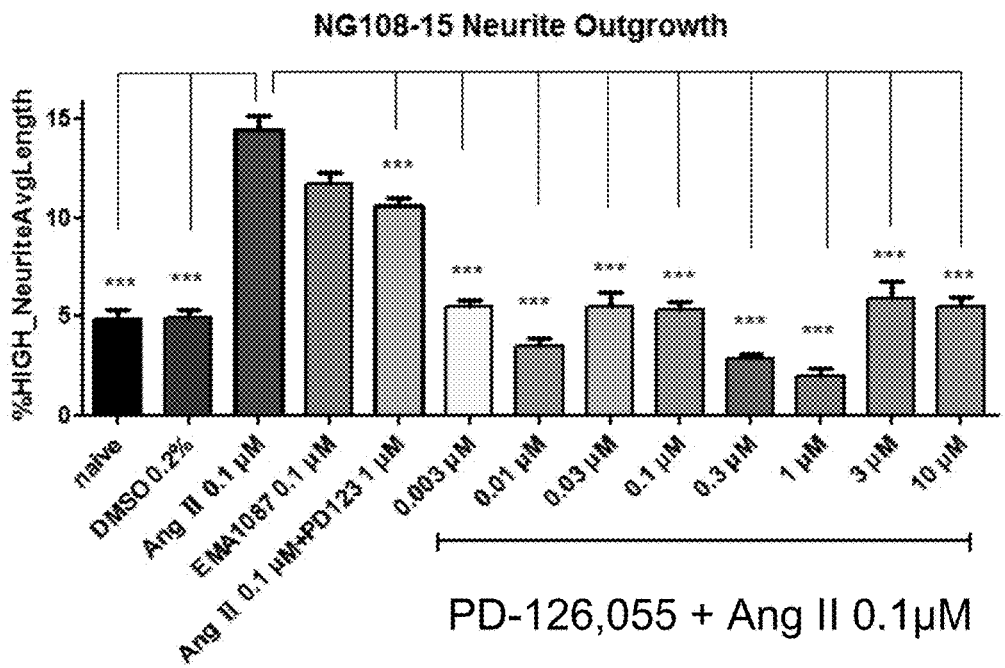
FIG. 1 is a graphical representation of the inhibition of neurite outgrowth in the presence of angiotensin II 0.1 μM and known selective $AT_2$ receptor antagonist PD-126,055 at 0.003 μM, 0.01 μM, 0.03 μM, 0.1 μM, 0.3 μM, 1 μM, 3 μM and 10 μM.

| | |
|---|---|
| DCM | dichloromethane |
| DBAD | dibenzyl azodicarboxylate |
| RT | room temperature |
| PE | petroleum ether |
| EA or EtOAc | ethyl acetate |
| THF | tetrahydrofuran |
| $Et_2O$ | diethyl ether |
| MeOH | methanol |
| $Et_3N$ | triethylamine |
| DMAP | 4-dimethylaminopyridine |
| DMSO | dimethylsulfoxide |
| Bn | benzyl |
| Bz | benzoyl |
| TLC | thin layer chromatography |
| DCE | 1,2-dichloroethane |
| DMF | dimethylformamide |
| NaH | sodium hydride |

| | |
|---|---|
| TFA | trifluoroacetic acid |
| EDCI | 1-ethyl-3-(3-dimethylaminopropyl)carbodiimide |
| AcOH | acetic acid |
| TEA | triethylamine |
| Boc | t-butyloxycarbonyl |
| TBAI | tetrabutylammonium iodide |
| HCHO | formaldehyde |
| MsCl | mesyl chloride |
| PCC | pyridinium chlorochromate |
| EDTA | ethylenediamine tetraacetic acid |
| DIPEA | diisopropylethylamine |
| CuI | copper iodide |
| IPA | isopropylamine |
| CDI | 1,1-carbonyldiimidazole |
| LDA | Lithium diisopropylamide |
| HATU | O-(7-azabenzotriazol-1-yl)-N,N,N',N'-tetramethyluronium tetrafluroroborate |

General Methods Used in the Synthesis Examples

LC-MS (Agilent):
1. LC: Agilent Technologies 1200 series, Binary Pump, Diode Array Detector. Ultimate AQ-C18, 3 μm, 2.1×50 mm column. Mobile phase: B (MeOH) and A (0.07% HCOOH aqueous solution). Flow Rate: 0.4 mL/min at 25° C. Detector: 214 nm, 254 nm. Gradient stop time, 5 min. Timetable:

| T (min) | B (%) | A (%) |
|---|---|---|
| 0 | 10 | 90 |
| 0.2 | 10 | 90 |
| 1.2 | 95 | 5 |
| 2.8 | 95 | 5 |
| 3 | 10 | 90 |
| 5 | 10 | 90 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 μg/mL, then filtered through a 0.22 μM filter membrane. Injection volume: 1~10 μL.

LC-MS (Waters):
1. LC: Waters 2695, Quaternary Pump, Waters 2996 Photodiode Array Detector. Xbridge-C18, 3.5 μm, 2.1× 50 mm column. Mobile Phase: B (MeOH) and A (0.07% HCOOH aqueous solution). Flow Rate: 0.3 mL/min at 30° C. Detector: 214 nm, 254 nm. Gradient stop time, 10 min. Timetable:

| T (min) | B (%) | A (%) |
|---|---|---|
| 0 | 10 | 90 |
| 2.5 | 75 | 25 |
| 5.0 | 95 | 5 |
| 7.5 | 95 | 5 |
| 7.6 | 10 | 90 |
| 10 | 10 | 90 |

2. MS: Micromass QZ, TIC: 100~900 m/z, Ion Source: ES, Capillary: 3 kV, Cone: 3V, Extractor: 3V, Drying gas flow: 600 L/hr, cone: 50 L/hr, Desolvation temperature: 300° C., Source temperature: 100° C.
3. Sample preparation: samples were dissolved in methanol at 1~10 μg/mL, then filtered through a 0.22 μm filter membrane. Injection volume: 1~10 μL.

LC-MS (Agilent, P-2) (Positive Ion Mode) or LC-MS (Agilent, N-2) (Negative Ion Mode):
1. LC: Agilent Technologies 1200 series, Binary Pump, Diode Array Detector. Xbridge-C18, 2.5 μm, 2.1×30 mm column. Mobile phase: B (MeOH) and A (0.07% HCOOH aqueous solution). Flow Rate: 0.5 mL/min at 30° C. Detector: 214 nm, 254 nm. Gradient stop time, 5 min. Timetable:

| T (min) | B (%) | A (%) |
|---|---|---|
| 0 | 80 | 20 |
| 0.2 | 80 | 20 |
| 0.8 | 5 | 95 |
| 2.8 | 5 | 95 |
| 3 | 80 | 20 |
| 5 | 80 | 20 |

4. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
5. Sample preparation: samples were dissolved in methanol at 1~10 μg/mL, then filtered through a 0.22 μm filter membrane. Injection volume: 1~10 μL.

LC-MS (Agilent, P-1) (Positive Ion Mode) or LC-MS (Agilent, N-1) (Negative Ion Mode) (Low Polarity Samples):
1. LC: Agilent Technologies 1200 series, Binary Pump, Diode Array Detector. Xbridge-C18, 2.5 μm, 2.1×30 mm column. Mobile phase: B (MeOH) and A (0.07% HCOOH aqueous solution). Flow Rate: 0.4 mL/min at 30° C. Detector: 214 nm, 254 nm. Gradient stop time, 6 min. Timetable:

| T (min) | B (%) | A (%) |
|---|---|---|
| 0 | 80 | 20 |
| 0.2 | 80 | 20 |
| 0.8 | 5 | 95 |
| 3.8 | 5 | 95 |
| 4 | 80 | 20 |
| 6 | 80 | 20 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 μg/mL, then filtered through a 0.22 μm filter membrane. Injection volume: 1~10 μL.

Analytical HPLC:
1. (Referred to as "Aligent") Agilent Technologies 1200 series, Quaternary Pump, Diode Array Detector. Ultimate AQ-C18, 5 μm, 4.6×250 mm column. Mobile Phase: B (MeOH) and A (0.07% TFA aqueous solution). Flow Rate: 1.00 mL/min at 30° C. Detector: 214 nm, 254 nm. Gradient stop time: 20 min. Timetable:

| T (min) | B (%) | A (%) |
|---|---|---|
| 0 | 40 | 60 |
| 3 | 40 | 60 |
| 5 | 60 | 40 |
| 7 | 80 | 20 |
| 8 | 95 | 5 |
| 15 | 95 | 5 |

-continued

| T (min) | B (%) | A (%) |
|---|---|---|
| 17 | 40 | 60 |
| 20 | 40 | 60 |

2. Sample preparation: samples were dissolved in methanol at ~1 mg/mL, then filtered through a 0.22 μm filter membrane. Injection volume: 1~10 pt.

Referred to as "July-L" or "SYN-001"

1. Agilent Technologies 1200 series, Quaternary Pump, Diode Array Detector. Waters Nova-pak C18, 4 μm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 15 min. Timetables:

Method Name: SYN-901 (High Polarity)

| T (min) | C (%) | D (%) |
|---|---|---|
| 0 | 5 | 95 |
| 2 | 5 | 95 |
| 5 | 12 | 88 |
| 6 | 40 | 60 |
| 7 | 95 | 5 |
| 10 | 95 | 5 |
| 12 | 60 | 40 |
| 13 | 5 | 95 |
| 15 | 5 | 95 |

Method Name: JULY-L (Average and Low Polarity)

| T (min) | C (%) | D (%) |
|---|---|---|
| 0 | 20 | 80 |
| 2 | 20 | 80 |
| 4 | 40 | 60 |
| 5 | 70 | 30 |
| 6 | 95 | 5 |
| 10 | 95 | 5 |
| 11 | 70 | 20 |
| 12 | 20 | 80 |
| 15 | 20 | 80 |

2. Sample preparation: samples were dissolved in methanol at ~1 mg/mL, then filtered through a 0.22 μm filter membrane. Injection volume: 1~10 μL.

Referred to as "ZSJ-2"

1. Agilent Technologies 1200 series, Quaternary Pump, Diode Array Detector. Waters Nova-pak C18, 4 μm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 30 min. Timetable:

Method Name: ZSJ-2

| T (min) | C (%) | D (%) |
|---|---|---|
| 0 | 20 | 80 |
| 28 | 95 | 5 |
| 30 | 70 | 30 |

2. Sample preparation: samples were dissolved in methanol at ~1 mg/mL, then filtered through a 0.22 μm filter membrane. Injection volume: 1~10 μL.

Example 1: Compound 2 (2S,4S)-4-(benzyloxy)-1-(2,2-diphenylacetyl)pyrrolidine-2-carboxylic acid 1. Procedure for the Preparation of Compound 26

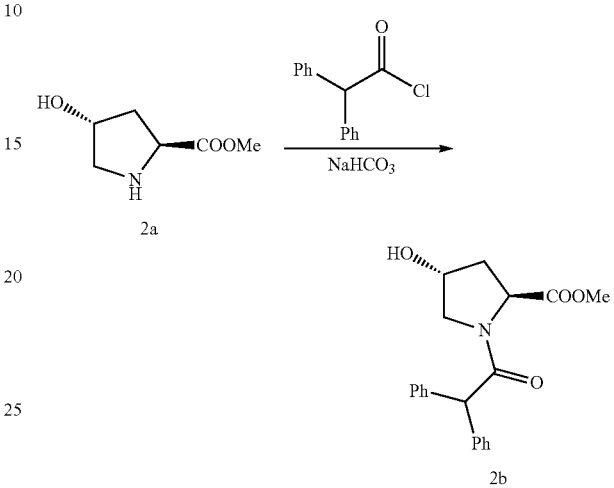

A solution of diphenylacetic acid (5.0 g, 23.6 mmol) in thionyl chloride (30 mL) was heated at reflux for 30 min. The mixture was then concentrated in vacuo and the residue was dissolved in ether (10 mL) and added to a mixture of compound 2a (3.76 g, 25.9 mmol) and NaHCO$_3$ (5.95 g, 70.8 mmol) in water (50 mL) and ether (20 mL) at 0° C. After addition, the mixture was stirred at RT for 2 h, TLC (EA:PE=1:1) showed the starting material was consumed. The product was collected by filtration and the obtained filter cake was dissolved in EA (50 mL), washed with brine (30 mL×3), dried over Na$_2$SO$_4$, filtered and concentrated in vacuo to give 2b as a white solid (6.5 g, 74%). LC-MS (Agilent): R$_t$ 4.86 min; m/z calculated for C$_{20}$H$_{21}$NO$_4$ [M+H]$^+$ 340.2, [M+Na]$^+$ 362.1, found [M+H]$^+$ 340.2, [M+Na]$^+$ 362.1.

2. Procedure for the Preparation of Compound 2c

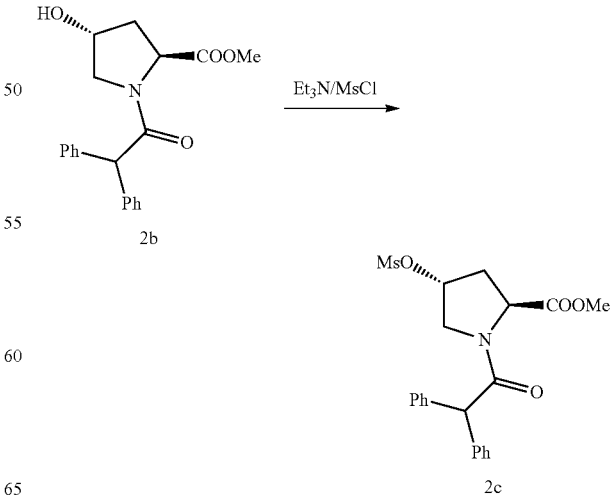

To a stirred solution of 2b (2.0 g, 5.9 mmol) and Et₃N (1.2 g, 11.8 mmol) in DCM (20 mL) was added MsCl (0.81 g, 7.1 mmol) at 0° C. After addition, the reaction was stirred at RT for 1 h. TLC (PE:EA=2:1) showed the starting material was consumed. DCM (10 mL) and water (20 mL) were added and the DCM layer was separated, washed with brine (20 mL×3) then dried over Na₂SO₄. The solvent was removed in vacuo to give 2c as a yellow solid (2.0 g, 81%). LC-MS (Agilent): $R_t$ 4.82 min; m/z calculated for $C_{21}H_{23}NO_6S$ [M+H]⁺ 418.1, [M+Na]⁺ 440.1, found [M+H]⁺ 418.0, [M+Na]⁺ 440.0.

3. Procedure for the Preparation of Compound 2d

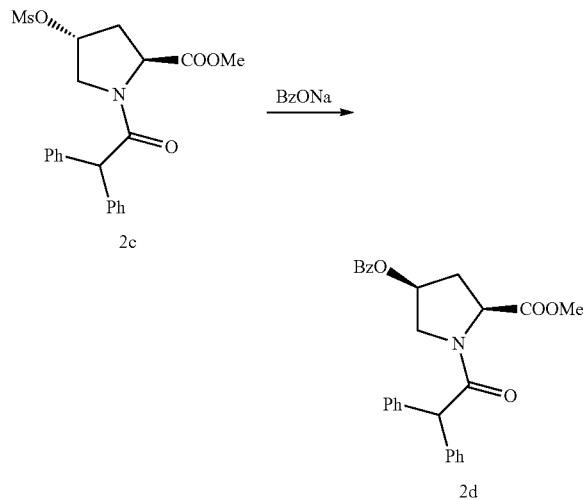

To a stirred solution of 2c (2.0 g, 4.8 mmol) in DMSO (20 mL) was added BzONa (1.4 g, 9.6 mmol) at RT. The mixture was then heated at 90° C. overnight. TLC (PE:EA=2:1) showed the starting material was consumed. The mixture was cooled to RT, added to EA (30 mL) and washed with cold water (200 mL). The organic phase was washed with brine (2×20 mL), dried over Na₂SO₄, filtered and concentrated in vacuo. The residue was purified by chromatography (PE:EA=10:1) to give 2d as an off-white solid (1.5 g, 70%). LC-MS (Agilent): $R_t$ 5.25 min; m/z calculated for $C_{27}H_{25}NO_5$ [M+H]⁺ 444.2, [M+Na]⁺ 466.2, found [M+H]⁺ 444.1, [M+Na]⁺ 466.1.

4. Procedure for the Preparation of Compound 2e

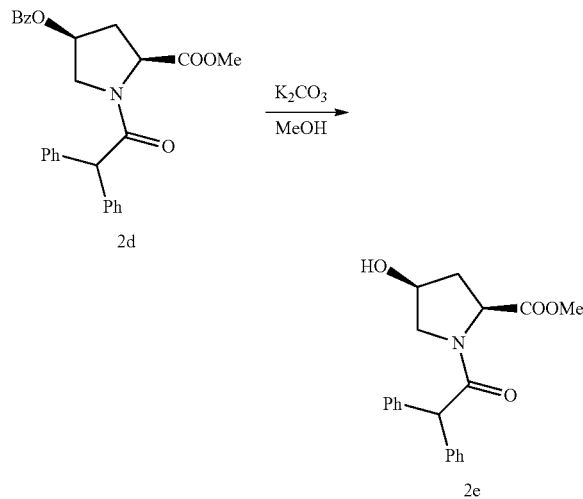

To a stirred solution of 2d (8.0 g, 18.0 mmol) in MeOH (150 mL) was added K₂CO₃ (2.5 g, 18.0 mmol) at 0° C. and the mixture was stirred at RT for 1 h, TLC (PE:EA=2:1) showed the starting material was consumed. The mixture was poured into EA (200 ml), washed with water (300 mL) and brine (150 mL×2), then dried over Na₂SO₄, filtered and concentrated in vacuo. The residue was purified by chromatography (PE:EA=3:1) to give 2e as an off-white solid (5.6 g, 88%). LC-MS (Agilent): $R_t$ 4.78 min; m/z calculated for $C_{20}H_{21}NO_4$ [M+H]⁺ 340.2, [M+Na]⁺ 362.1, found [M+H]⁺ 340.0, [M+Na]⁺ 362.0.

5. Procedure for the Preparation of Compound 2f

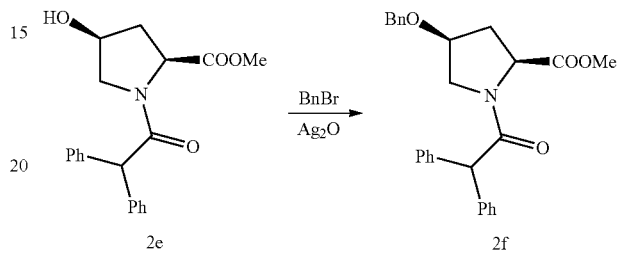

To a stirred suspension of Ag₂O (409 mg, 1.77 mmol) in DCM (10 mL) was added 2e (500 mg, 1.47 mmol) at 0° C. BnBr (303 mg, 1.77 mmol) was added to the reaction mixture at 0° C. After addition, the reaction was stirred at RT overnight. TLC (PE:EA=1:1) showed the starting material was consumed. The mixture was filtered and the filtrate was concentrated in vacuo. The residue was purified by chromatography (PE:EA=0:1 to 5:1) to give the product as a clear oil (250 mg, 40%). LC-MS (Agilent): $R_t$ 5.30 min; m/z calculated for $C_{27}H_{27}NO_4$ [M+H]⁺ 430.2, [M+Na]⁺ 452.2, found [M+H]⁺ 430.1, [M+Na]⁺ 452.1.

6. Procedure for the Preparation of Compound 2

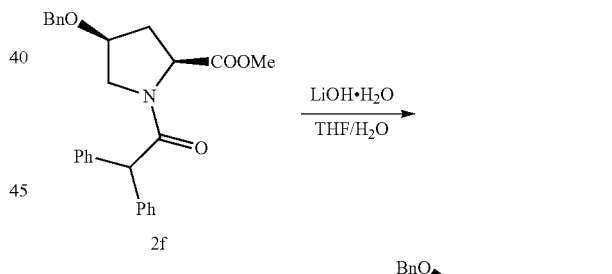

To a stirred solution of 2f (250 mg, 0.58 mmol) in THF (7 mL) was added an solution of LiOH.H₂O (37 mg, 0.87 mmol) in water (3 mL) at 0° C. After addition, the reaction was stirred overnight at 25° C. TLC (MeOH:DCM=1:10) showed the starting material was consumed. Water (5 mL) and Et₂O (10 mL) were added to the mixture and the organic phase separated. The aqueous phase was acidified with 1M HCl to pH 3-4 and the solution was extracted with EA (2×10 mL). The organic layer was washed with brine (3×10 mL)

and the organic phase dried (Na$_2$SO$_4$) and evaporated to give 200 mg of the crude product. 100 mg of the crude product was purified by preparative TLC (MeOH:DCM=1:20) to give 59 mg of pure 2. LC-MS (Agilent): R$_t$ 5.09 min; adz calculated for C$_{19}$H$_{25}$NO$_5$ [M+H]$^+$ 416.2, [M+Na]$^+$ 438.2, found [M+H]$^+$ 416.2, [M+Na]$^+$ 438.1. HPLC (214 and 254 nm): R$_t$ 13.38 min.

Example 2: Compound 3 (2S,4R)-4-(benzyloxy)-1-(2,2-diphenylacetyl)pyrrolidine-2-carboxylic acid 1. Procedure for the Preparation of Compound 2a

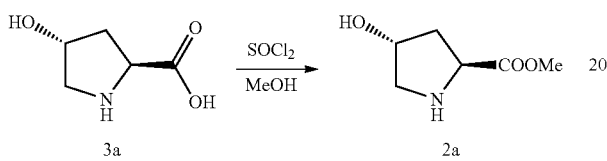

To a stirred mixture of 3a (5.0 g, 38:1 mmol) in MeOH (50 mL) was added SOCl$_2$ (5 mL) dropwise and the mixture was heated at reflux for 7 h, TLC (DCM:MeOH=10:1) showed the starting material was consumed. The MeOH was removed in vacuo to give 2a (6.0 g) as white solid, which was used for the next step directly. LC-MS (Agilent): R$_t$ 0.87 min; m/z calculated for C$_6$H$_{11}$NO$_3$[M+H]$^+$ 146.1, found [M+H]$^+$ 146.1.

2. Procedure for the Preparation of Compound 3b

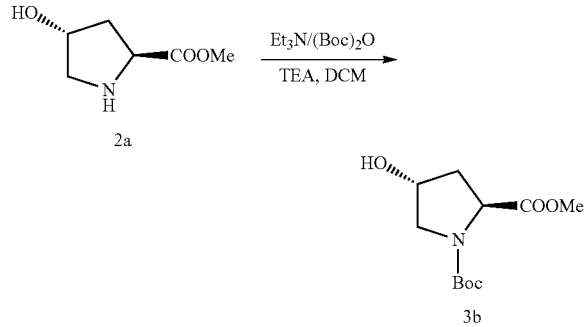

To a stirred solution of 2a (4.0 g, 27.5 mmol) and Et$_3$N (3.3 g, 33.1 mmol) in DCM (40 mL) was added (Boc)$_2$O (7.22 g, 33.1 mmol) at 0° C. under N$_2$ and the mixture was stirred at RT for 5 h, TLC (DCM:MeOH=20:1) showed the starting material was consumed. The reaction was quenched with water (30 mL), the layers were separated and the aqueous phase was extracted with DCM (20 mL×2). The combined organic extracts were washed by brine, dried over Na$_2$SO$_4$ and concentrated in vacuo. Recrystallization from hexane/DCM then gave 3b as white solid (4.2 g, 62%). LC-MS (Agilent): R$_t$ 4.96 min; m/z calculated for C$_{11}$H$_{19}$NO$_5$ [M+Na]$^+$ 268.1, [2M+Na]$^+$ 513.3, found [M+Na]$^+$ 268.1, [2M+Na]$^+$ 513.3.

3. Procedure for the Preparation of Compound 3c

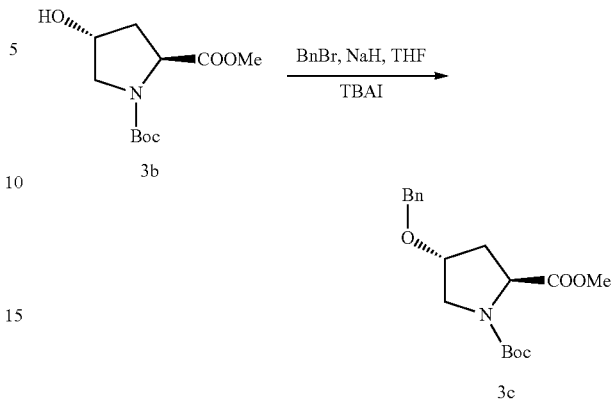

To a stirred suspension of 3b (2.5 g, 10.2 mmol), BnBr (1.5 mL, 12.2 mmol) and TBAI (1.13 g, 3.06 mmol) in THF (50 mL) was added NaH (60% w/w dispersion in mineral oil, 0.45 g, 11.2 mmol) at 0° C. and the mixture was stirred at RT overnight, TLC (PE:EA=2:1) showed that the starting material was consumed. The mixture was poured into water (40 mL) and extracted with EA (30 mL×2). The combined organic extracts were washed with brine, dried over Na$_2$SO$_4$ and concentrated in vacuo. Purification by silica column (PE:EA=10:1 to 4:1) gave 3c as yellow oil (1.7 g, 50%). LC-MS (Agilent): R$_t$ 5.35 min; m/z calculated for C$_{18}$H$_{25}$NO$_5$ [M+Na]$^+$ 358.2, [2M+Na]$^+$ 693.3, found [M+Na]$^+$ 358.2, [2M+Na]$^+$ 693.4.

4. Procedure for the Preparation of Compound 3d

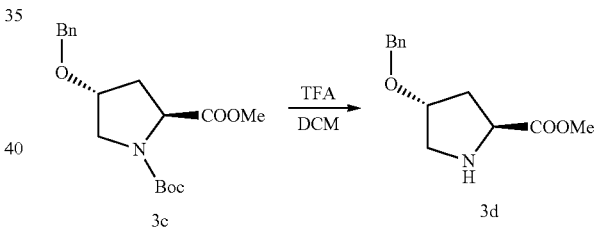

To a stirred solution of 3c (800 mg, 2.38 mmol) in DCM (6 mL) was added TFA (1.36 g, 12.0 mmol) and the mixture was stirred at RT for 2 h, then heated at 35° C. for 3 h, TLC (DCM:MeOH=20:1) showed that the starting material was consumed. Water (15 mL) and DCM (15 mL) were added and the aqueous phase was adjusted to pH 8 with NaHCO$_3$ (aq). The layers were separated and the aqueous layer was extracted with DCM (10 mL). The combined organic extracts were washed with brine, dried over Na$_2$SO$_4$ and the solvent was removed in vacuo to give 3d (380 mg, 67%) as a yellow oil. LC-MS (Agilent): R$_t$ 4.12 min; m/z calculated for C$_{13}$H$_{17}$NO$_3$[M+H]$^+$ 236.1, found [M+H]$^+$ 236.1.

5. Procedure for the Preparation of Compound 3e

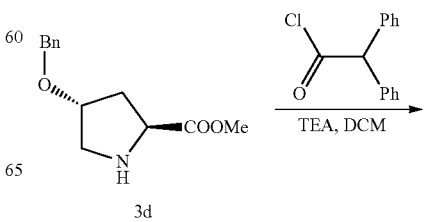

-continued

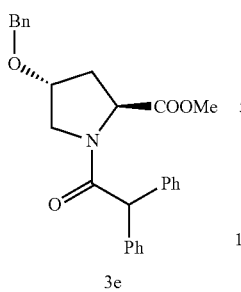

3e

To a solution of diphenylacetic acid (1.14 g, 5.3 mmol) in DCM (15 mL) at 0° C. was added two drops of DMF followed by oxalyl chloride (1.0 g, 8.0 mmol) and the mixture was stirred at RT for 5 h then concentrated in vacuo. The residue was dissolved in DCM (15 mL) and a mixture of 3d (1.15 g, 4.8 mmol) and Et$_3$N (0.73 g, 7.1 mmol) in DCM (20 mL) was added at 0° C. The mixture was then stirred at RT overnight, TLC (PE:EA=2:1) showed that the starting material was consumed. Water (30 mL) was added and the layers were separated. The aqueous phase was extracted with DCM (20 mL) and the combined organic extracts were washed with NaHCO$_3$ (saturated aqueous solution), brine and dried over Na$_2$SO$_4$. The solvent was removed in vacuo and purification by silica column (PE:EA=20:1 to 4:1) gave the product as a yellow oil (600 mg, 30%). LC-MS (Agilent): R$_t$ 5.25 min; m/z calculated for C$_{27}$H$_{27}$NO$_4$ [M+H]$^+$ 430.1, found [M+H]$^+$ 430.1.

6. Procedure for the Preparation of Compound 3

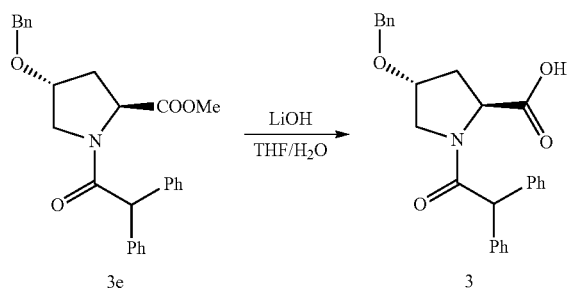 [SMILES: COC(=O)[C@@H]1C[C@@H](OCc2ccccc2)CN1C(=O)C(c1ccccc1)c1ccccc1 ; "LiOH" ; "THF/H2O" ; O=C(O)[C@@H]1C[C@@H](OCc2ccccc2)CN1C(=O)C(c1ccccc1)c1ccccc1]

To a stirred mixture of 3e (600 mg, 1.4 mmol) in THF (5 mL) and H$_2$O (2 mL) was added LiOH (146.7 mg, 3.5 mmol) and the mixture was stirred at RT for 5 h, TLC (PE:EA=1:1) showed that the starting material was consumed. Most of the THF was removed in vacuo, water (10 mL) was added and the mixture was acidified to pH 2-3 with 1 M aqueous HCl and extracted with EA (10 mL×2). The combined organic extracts were washed with brine, dried over Na$_2$SO$_4$ and concentrated in vacuo. Purification by column chromatography then prep-TLC (EA:DCM=1:1) gave 3 (90 mg, 17%) as a white solid.

LC-MS (Agilent): R$_t$ 5.22 min; m/z calculated for C$_{26}$H$_{25}$NO$_4$ [M+H]$^+$ 416.1, found [M+H]$^+$ 416.1. HPLC (214 and 254 nm): R$_t$ 13.49 min.

Example 3: Compound 5 (2S,4S)-4-cinnamyloxy-1-(2,2-diphenylacetyl)pyrrolidine-2-carboxylic acid 1. Procedure for the Preparation of Compound 5a

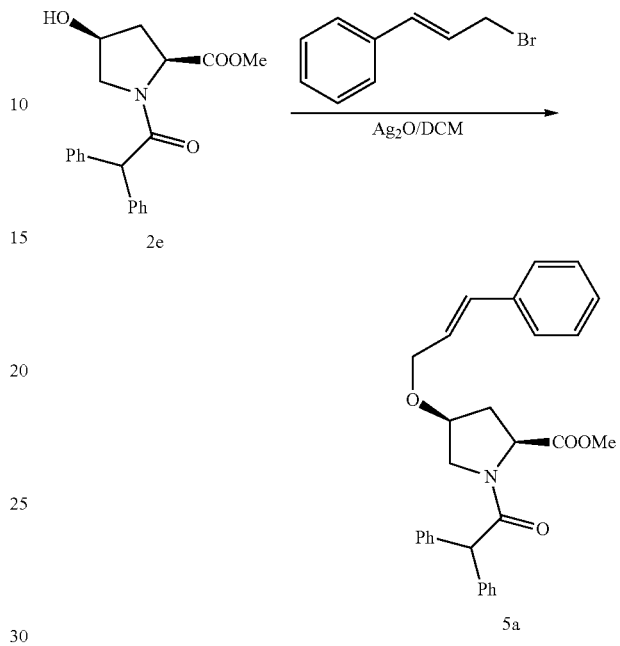

To a stirred suspension of 2e (2.0 g, 5.89 mmol) and Ag$_2$O (1.64 g, 7.07 mmol) in DCM (25 mL) at 0° C. was added cinnamyl bromide (1.4 g, 7.07 mmol) at 0° C. and the mixture was stirred at RT overnight, TLC (PE:EA=1:1) showed most of the starting material was consumed. The reaction was filtered and the filtrate was concentrated in vacuo. The residue was purified by chromatography (PE:EA=10:1 to 5:1) to give 5a as a colorless oil (270 mg, 10%). LC-MS (Agilent): R$_t$ 5.43 min; m/z calculated for C$_{29}$H$_{29}$NO$_4$ [M+H]$^+$ 456.2, [M+Na]$^+$ 478.2, found [M+H]$^+$ 456.1, [M+Na]$^+$ 478.1.

2. Procedure for the Preparation of Compound 5

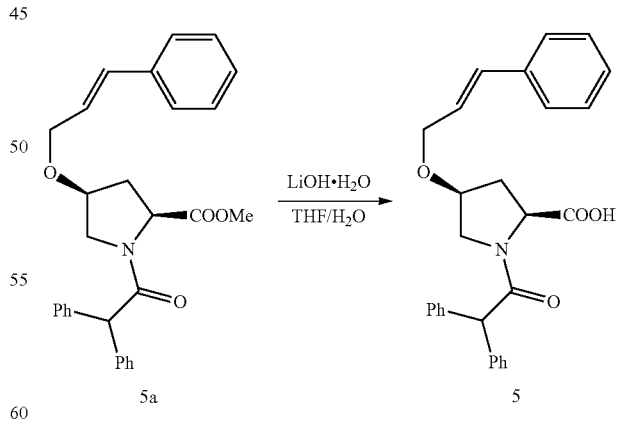

To a stirred solution of 5a (270 mg, 0.59 mmol) in THF (7 mL) and H$_2$O (3 mL) was added LiOH.H$_2$O (37 mg, 0.87 mmol) at 0° C. and the mixture was stirred at 0° C. for 0.5 hour, TLC (MeOH:DCM=1:10) showed the starting material was consumed. The mixture was concentrated in vacuo to remove most of the THF and water (10 mL) and Et$_2$O (10 mL) were added. The mixture was acidified with 1M HCl to pH 7 and then basified with sodium bicarbonate to pH 10 and the phases separated. DCM (10 mL) was added to the aqueous phase and the mixture was acidified to pH 3-4 with 1M HCl and the organic layer was separated, washed with water (5 mL×1), brine (5 mL×2), dried over Na$_2$SO$_4$, filtered and concentrated in vacuo to give the product (150 mg) as a white solid. The crude product was purified by prep-TLC to give 5 as a white solid (130 mg). LC-MS (Agilent): R$_t$ 5.26 min; m/z calculated for C$_{28}$H$_{27}$NO$_4$ [M+H]$^+$ 442.2, [M+Na]$^+$ 464.2, found [M+H]$^+$ 442.1, [M+Na]$^+$ 464.1. HPLC (214 and 254 nm): R$_t$ 13.63 min.

Example 4: Compound 6 (2S,4S)-1-2,2-diphenylacetyl)-4-(3-phenylpropoxy)pyrrolidine carboxylic acid

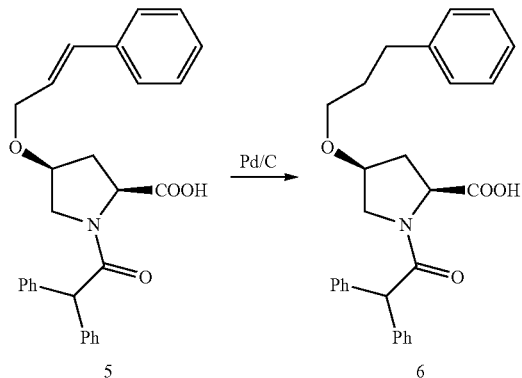 [SMILES: O=C(O)[C@@H]1C[C@H](OC/C=C/c2ccccc2)CN1C(=O)C(c1ccccc1)c1ccccc1 ; "Pd/C" ; O=C(O)[C@@H]1C[C@H](OCCCc2ccccc2)CN1C(=O)C(c1ccccc1)c1ccccc1]

To a stirred solution of 5 (120 mg, 0.27 mmol) in EA (3 mL) was added 10% Pd/C (12 mg) and the mixture was stirred at RT under a H$_2$ atmosphere (1 atm pressure) overnight, TLC (MeOH:DCM=1:20) showed the starting material was consumed. The mixture was filtered and the filtrate was concentrated in vacuo to give the crude product, which was purified by column chromatography (DCM: EA=10:1 to 8:1) to give 6 (60 mg, 50%) as a colorless oil. LC-MS (Agilent): R$_t$ 5.26 min; m/z calculated for C$_{28}$H$_{29}$NO$_4$ [M+H]$^+$ 444.2, found 444.2. HPLC (214 and 254 nm): R$_t$ 13.75 min.

Example 5: Compound 8 (2S,4R)-4-(cinnamyloxy)-1-(2,2-diphenylacetyl)pyrrolidine-2-carboxylic acid 1. Procedure for the Preparation of Compound 8a

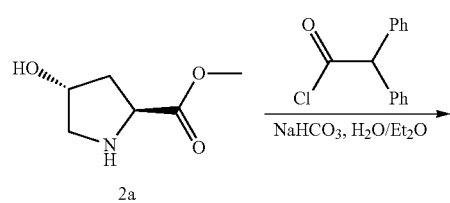

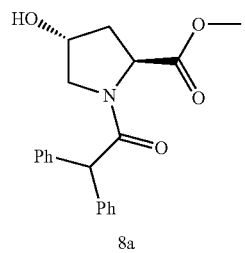

A solution of diphenylacetic acid (5.0 g, 23.6 mmol) in thionyl chloride (30 mL) was heated at reflux for 30 min. The mixture was then concentrated in vacuo and the residue was dissolved in ether (10 mL) and added to a mixture of 2a (3.76 g, 25.9 mmol) and NaHCO$_3$ (5.95 g, 70.8 mmol) in water (50 mL) and ether (20 mL) at 0° C. After addition, the mixture was stirred at RT for 2 h, TLC (EA:PE=1:1) showed the starting material was consumed. The product was collected by filtration and the obtained cake was dissolved in EA (50 mL), washed with brine (30 mL×3), dried over Na$_2$SO$_4$, filtered and concentrated in vacuo to give 8a (6.5 g, 74%) as a white solid. LC-MS (Agilent): R$_t$ 4.86 min; m/z calculated for C$_{20}$H$_{21}$NO$_4$ [M+H]$^+$ 340.2, [M+Na]$^+$ 362.1, found [M+H]$^+$ 340.2, [M+Na]$^+$ 362.1.

2. Procedure for the Preparation of Compound 8b

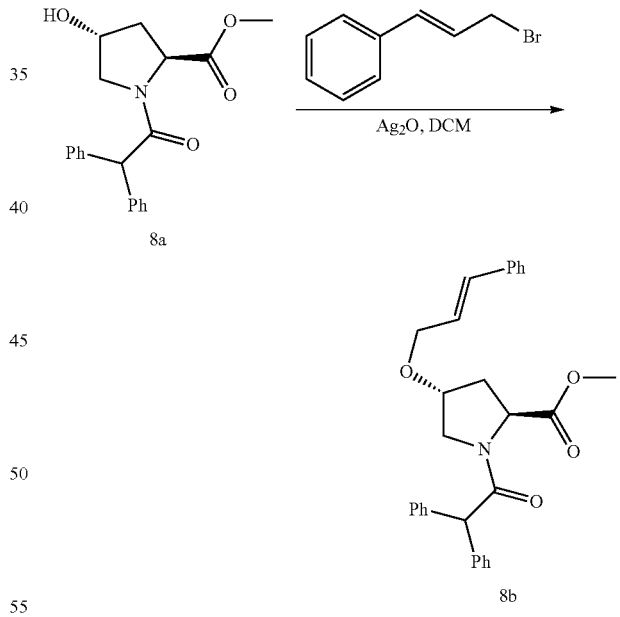

To a solution of 8a (1.0 g, 2.9 mmol) in DCM (10 mL) was added Ag$_2$O (806 mg, 3.48 mmol) at 0° C. and the mixture was stirred at RT for 30 min. A solution of cinnamyl bromide (685.8 mg, 3.48 mmol) in DCM (2 mL) was then added and the mixture was stirred at RT overnight. The Ag$_2$O was removed by filtration and the filtrate was concentrated in vacuo. Purification by silica column (PE:EA=10:1 to 4:1) gave 8b as yellow solid (100 mg, 8%). LC-MS (Agilent): R$_t$ 5.34 min; m/z calculated for C$_{29}$H$_{29}$NO$_4$ [M+H]$^+$ 456.1, [M+Na]$^+$ 478.1, found [M+H]$^+$ 456.1, [M+23]$^+$ 478.1.

3. Procedure for the Preparation of Compound 8

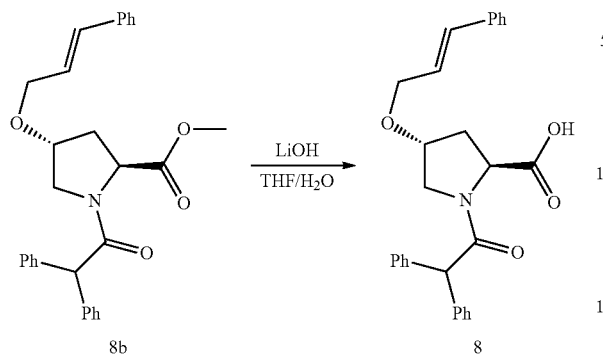

To a mixture of 8b (170 mg, 0.37 mmol) in THF/H$_2$O (3 mL/1 mL) was added LiOH (40 mg, 0.93 mmol) and the mixture was stirred at RT for 5 h, TLC (PE:EA=2:1) showed that the starting material was consumed. Most of the THF was removed in vacuo, water (10 mL) and Et$_2$O (10 mL) were added and the layers were separated. The aqueous phase was adjusted to pH 2-3 with 1 M aqueous HCl and extracted with DCM (15 mL×2). The combined organic extracts were washed with brine, dried over Na$_2$SO$_4$ and the solvent was removed in vacuo. Purification by prep-TLC (DCM:MeOH=10:1) gave 8 as a white solid (80 mg, 49%). LC-MS (Agilent): R$_t$ 5.34 min; m/z calculated for C$_{28}$H$_{27}$NO$_4$ [M+H]$^+$ 442.1, found [M+H]$^+$ 442.1. HPLC (214 and 254 nm): R$_t$ 13.71 min.

Example 6: Compound 9 (2S,4R)-1-(2,2-diphenylacetyl)-4-(3-phenylpropoxy)pyrrolidine-2-carboxylic acid

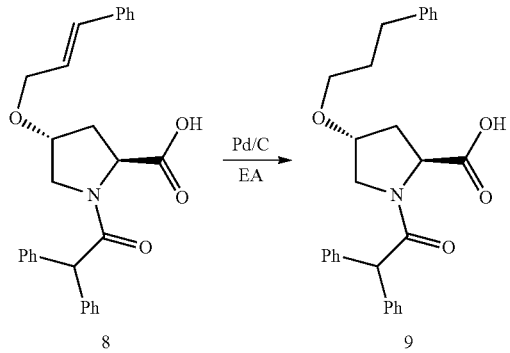 [SMILES: O=C(O)[C@@H]1C[C@@H](OC/C=C/c2ccccc2)CN1C(=O)C(c1ccccc1)c1ccccc1 ; "EA" ; "Pd/C" ; O=C(O)[C@@H]1C[C@@H](OCCCc2ccccc2)CN1C(=O)C(c1ccccc1)c1ccccc1]

To a solution of 8 (100 mg, 0.23 mmol) in EA (5 mL) was added 10% Pd/C (10 mg) and the mixture was stirred at RT under a hydrogen atmosphere (1 atm pressure) overnight. The mixture was filtered through Celite and the filtrate was concentrated in vacuo. Purification by prep-TLC (DCM:MeOH=10:1) gave 9 as a white solid (93 mg, 93%). LC-MS (Agilent): R$_t$ 5.40 min; m/z calculated for C$_{28}$H$_{29}$NO$_4$ [M+H]$^+$ 444.2, [M+Na]$^+$ 466.2, found [M+H]$^+$ 444.2, [M+Na]$^+$ 466.2. HPLC (214 and 254 nm): Rt 13.86 min.

Example 7: Compound 15 4-(benzyloxy)-1-(2,2-diphenylacetyl)indoline-2-carboxylic acid 1. Procedure for the Preparation of Compound 15b

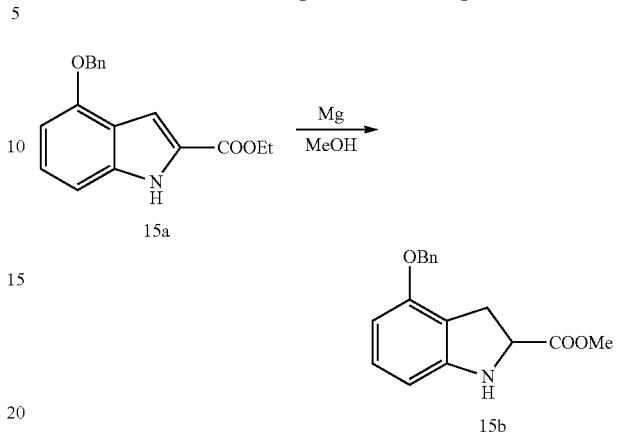

To a stirred solution of 15a (200 mg, 0.68 mmol) in MeOH (10 mL) was added Mg pieces (65 mg, 2.7 mmol) at RT under N$_2$ and the mixture was stirred overnight at RT. TLC (EA:PE=1:10) showed the starting material was consumed. The mixture was poured into a cold 2 M aqueous HCl solution (4 mL) and then stirred until it became a clear solution. The Mixture was basified to pH 8~9 with a saturated aqueous NaHCO$_3$ solution and then concentrated in vacuo to remove most of the MeOH. The residue was dissolved in EA, washed with water (5 mL) and brine (5 mL×2), dried over Na$_2$SO$_4$, then filtered and concentrated in vacuo to give 15b (180 mg, 94%) as an off-white solid. LC-MS (Agilent): R$_t$ 4.96 min; m/z calculated for C$_{17}$H$_{17}$NO$_3$ [M+H]$^+$ 284.1, [M+Na]$^+$ 306.1, found [M+H]$^+$ 284.1, [M+Na]$^+$ 306.1.

2. Procedure for the Preparation of Compound 15c

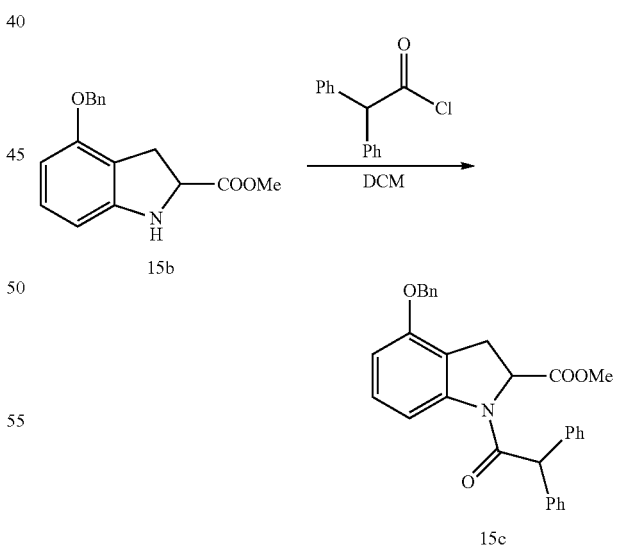

To a solution of 15b (180 mg, 0.64 mmol), Et$_3$N (129 mg, 1.28 mmol), and DMAP (8 mg, 0.06 mmol) in DCM (10 mL) was added diphenylacetyl chloride (175 mg, 0.76 mmol) at 0° C. The mixture was then warmed to RT and stirred for 5 h, TLC (DCM) showed the starting material was consumed. Iced water was added to quench the reaction, the organic layer was separated, washed with brine (5 mL×2), dried over Na₂SO₄, then filtered and concentrated in vacuo. The residue was purified by chromatography (PE:DCM=10:1 to 1:2) to give 15c (220 mg, 56%) as an off-white solid. LC-MS (Agilent): R_t 5.50 min; m/z calculated for $C_{31}H_{27}NO_4$ [M+H]⁺ 478.2, [M+Na]⁺ 500.2, found [M+H]⁺ 478.2, [M+Na]⁺ 500.2.

3. Procedure for the Preparation of Compound 15

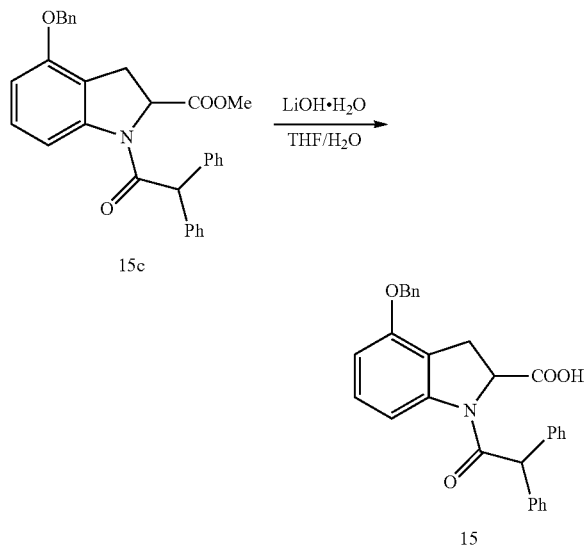

To a solution of 15c (50 mg, 0.10 mmol) in THF (0.7 mL) was added a solution of LiOH.H₂O (7 mg, 0.16 mmol) in water (0.3 mL) at 0° C. and the mixture was stirred at RT overnight, TLC (MeOH:DCM=1:10) showed the starting material was consumed. The reaction was repeated on a larger batch of ester (170 mg, 0.36 mmol) and the reaction mixtures were combined and concentrated in vacuo to remove most of the THF. The residue was dissolved in EA (10 mL), acidified to pH 4-5 using 1 M HCl and the organic phase washed with water (5 mL), brine (5 mL×2) and dried over Na₂SO₄. The solvent was removed in vacuo and the crude product was washed with hexane and Et₂O to give pure 15 (150 mg, 70%) as a white solid. LC-MS (Agilent): R_t 5.52 min; m/z calculated for $C_{30}H_{25}NO_4$ [M+H]⁺ 464.2, [M+Na]⁺ 486.2, found [M+H]⁺ 464.2, [M+Na]⁺ 486.1. HPLC (214 and 254 nm): R_t 14.08 min.

Example 8: Compound 17 (2S,4S)-1-(2,2-diphenylacetyl)-4-(((1R,2S)-2-phenylcyclopropyl)methoxy)pyrrolidine-2-carboxylic acid and (2S,4S)-1-(2,2-diphenylacetyl)-4-(((1S,2R)-2-phenylcyclopropyl)methoxy)pyrrolidine-2-carboxylic acid 1. Procedure for the Preparation of Compound 17b

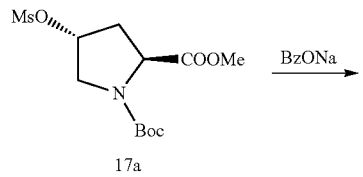

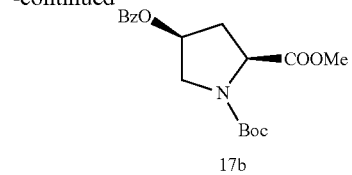

To a stirred solution of 17a (2.0 g, 6.2 mmol) in DMSO (20 mL) was added BzONa (1.8 g, 12.4 mmol) at RT and the mixture was stirred at 90° C. for 6 h, TLC (PE:EA=2:1) showed the starting material was consumed. The mixture was cooled to RT. The reaction was repeated (140 g, 434 mmol) and the two reaction mixtures were combined and poured into water (10 L) and EA (2 L). The layers were separated and the aqueous phase was extracted with EA (0.5 L). The combined organic extracts were washed with brine (1 L×3), dried over Na₂SO₄, filtered and concentrated in vacuo to give crude 17b (150 g) as an off-white solid which was used in next step directly. LC-MS (Agilent): R_t 3.20 min; m/z calculated for $C_{18}H_{23}NO_6$ [M+H-Boc]⁺ 250.1, [M+Na]⁺ 372.1, found [M+H-Boc]⁺ 250.1, [M+Na]⁺ 372.1.

2. Procedure for the Preparation of Compound 17c

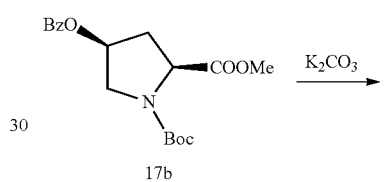

To a stirred solution of 17b (1.0 g, 2.86 mmol) in MeOH (20 mL) was added K₂CO₃ (0.4 g, 2.86 mmol) at 0° C. and the mixture was stirred at RT for 0.5 h, TLC (PE:EA=1:1) showed the reaction was complete. The reaction was repeated (150 g, 429 mmol) and the two reaction mixtures were combined and filtered. The filtrate was concentrated in vacuo to remove most of the MeOH, the residue was dissolved in EA (500 mL), washed with water (250 mL), brine (250 mL×2), dried over Na₂SO₄, filtered and concentrated in vacuo. The residue was purified by chromatography (PE:EA=1:0 to 0:1) to give 17c as an off-white solid (70 g, 65%). LC-MS (Agilent): R_t 2.97 min; m/z calculated for $C_{11}H_{19}NO_5$ [M+H-Boc]⁺ 146.1, [M+H-t-Bu]⁺ 190.1, [M+Na]⁺, 268.1, found [M+H-Boc]⁺ 146.1, [M+H-t-Bu]⁺ 190.1, [M+Na]⁺, 268.1.

3. Procedure for the Preparation of Compound 17d

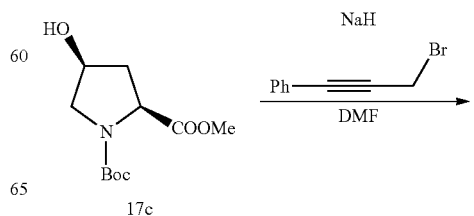

-continued

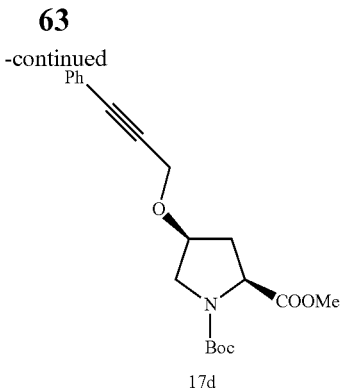

17d

To a stirred solution of the 17c (3.5 g, 14.3 mmol) in DMF (35 mL) was added NaH (60% w/w dispersion in mineral oil, 0.63 g, 15.7 mmol) at 0° C. under a $N_2$ atmosphere and the mixture was stirred at RT for 1 hour then re-cooled to 0° C. The bromide (3.1 g, 15.7 mmol) was added and the mixture was warmed to RT slowly and then stirred overnight, TLC (PE:EA=1:1) showed the starting material was consumed. The mixture was partitioned between EA (100 mL) and water (300 mL), the layers were separated and the aqueous layer was extracted with EA (80 mL×2). The combined organic layers were washed with brine, dried over $Na_2SO_4$ and concentrated in vacuo and the residue was purified by chromatography (PE:EA=10:0 to 1:20) to give 17d as a colorless oil (1.0 g, 19%). LC-MS (Agilent): $R_t$ 3.25 min; m/z calculated for $C_{20}H_{25}NO_5$ $[M+H-Boc]^+$ 260.1, $[M+Na]^+$ 382.2, found $[M+H-Boc]^+$ 260.1, $[M+Na]^+$ 382.1.

4. Procedure for the Preparation of Compound 17e

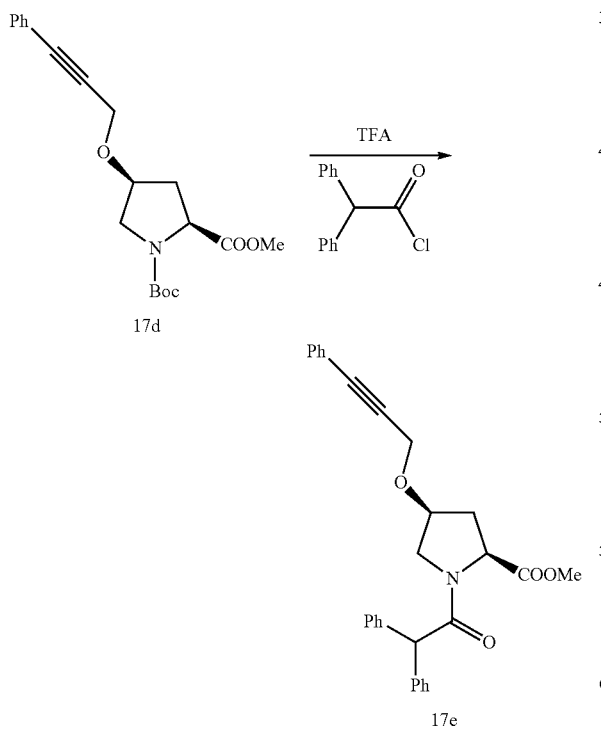

17e

To a stirred solution of compound 17d (1.0 g, 3.8 mmol) in DCM (10 mL) was added. TFA (1.7 g, 15.2 mmol) at 0° C. and the mixture was stirred at 0° C. for 4 hour, TLC (PE:EA=4:1) showed the starting material was consumed. The mixture was concentrated in vacuo, the residue was partitioned between DCM (30 mL) and a saturated aqueous $NaHCO_3$ solution (30 mL). The organic layer was separated and washed with brine, dried over $Na_2SO_4$ and filtered. The filtrate was treated with $Et_3N$ (422 mg, 4.17 mmol), cooled to 0° C. and diphenylacetyl chloride (867 mg, 3.8 mmol) was added in portions. The mixture was stirred at 0~5° C. for 10 min, TLC (PE:EA=2:1) showed the reaction was complete. Ice-water (40 mL) was added and the DCM layer was separated, washed with brine, dried over $Na_2SO_4$ and concentrated in vacuo. The residue was purified by chromatography (PE:EA=50:0 to 10:1) to give 17e (300 mg, 17%). LC-MS (Agilent): $R_t$ 3.04 min; m/z calculated for $C_{29}H_{27}NO_4$ $[M+H]^+$ 454.2, found $[M+H]^+$ 454.2.

5. Procedure for the Preparation of Compound 17f

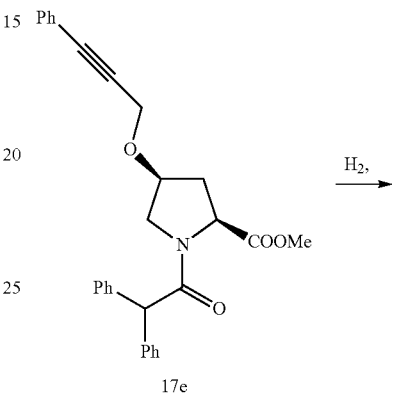

17e

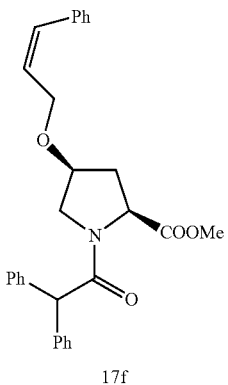

17f

To a stirred solution of 17e (150 mg, 0.33 mmol) in EA (3 mL) was added Lindlar catalyst (15 mg) and the mixture was stirred at RT under a $H_2$ balloon overnight, LCMS showed the reaction was complete. The mixture was filtered and the filtrate was concentrated in vacuo to give 17f as a thick oil (150 mg). LC-MS (Agilent): $R_t$ 3.37 min; m/z calculated for $C_{29}H_{29}NO_4$ $[M+H]^+$ 456.2, $[M+Na]^+$ 478.2, found $[M+H]^+$ 456.2, $[M+Na]^+$ 478.2.

6. Procedure for the Preparation of Compound 17g

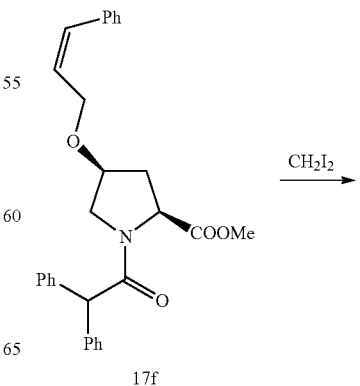

17f

-continued

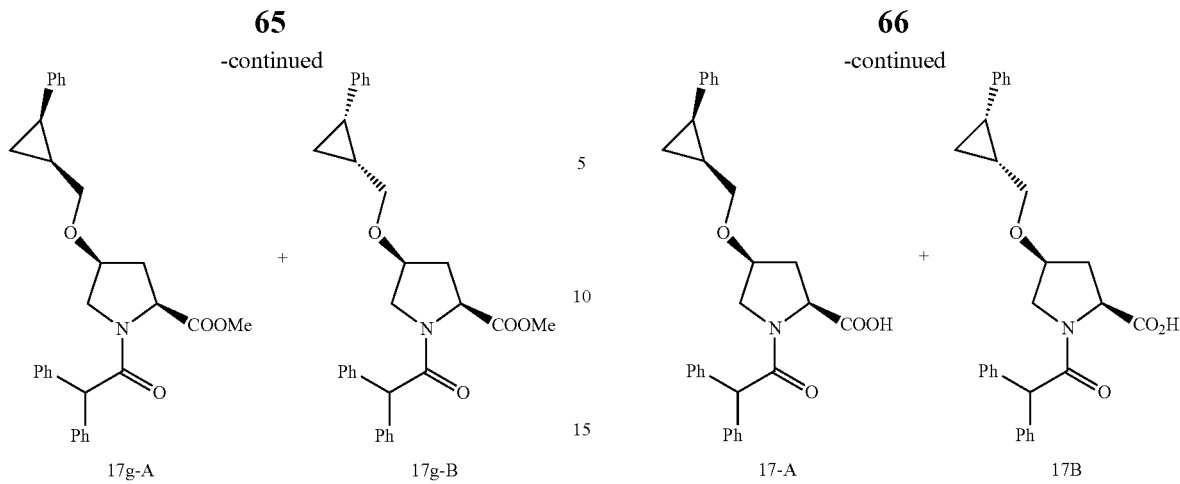

17g-A 17g-B 17-A 17B

A stirred solution of compound 17f (100 mg, 0.22 mmol) in dry DCE (10 mL) was cooled to −5° C. under a N$_2$ atmosphere. A ZnEt$_2$ solution (1 M in hexane, 0.44 mL, 0.44 mmol) was added followed by CH$_2$I$_2$ (235 mg, 0.88 mmol) and the mixture was warmed to RT slowly and stirred overnight, TLC showed the reaction was complete. The mixture was concentrated in vacuo, the residue was partitioned between ether (20 mL) and water (20 mL) and the aqueous phase was acidified to pH 2-3 with a 1 M aqueous HCl solution. The layers were separated and the aqueous layer was extracted again with ether (20 mL). The combined organic extracts were washed with brine, dried over Na$_2$SO$_4$, filtered and concentrated in vacuo to give crude product as the two indicated diastereoisomers (100 mg) as a yellow oil, which was used in next step directly.

7. Procedure for the Preparation of Compound 17

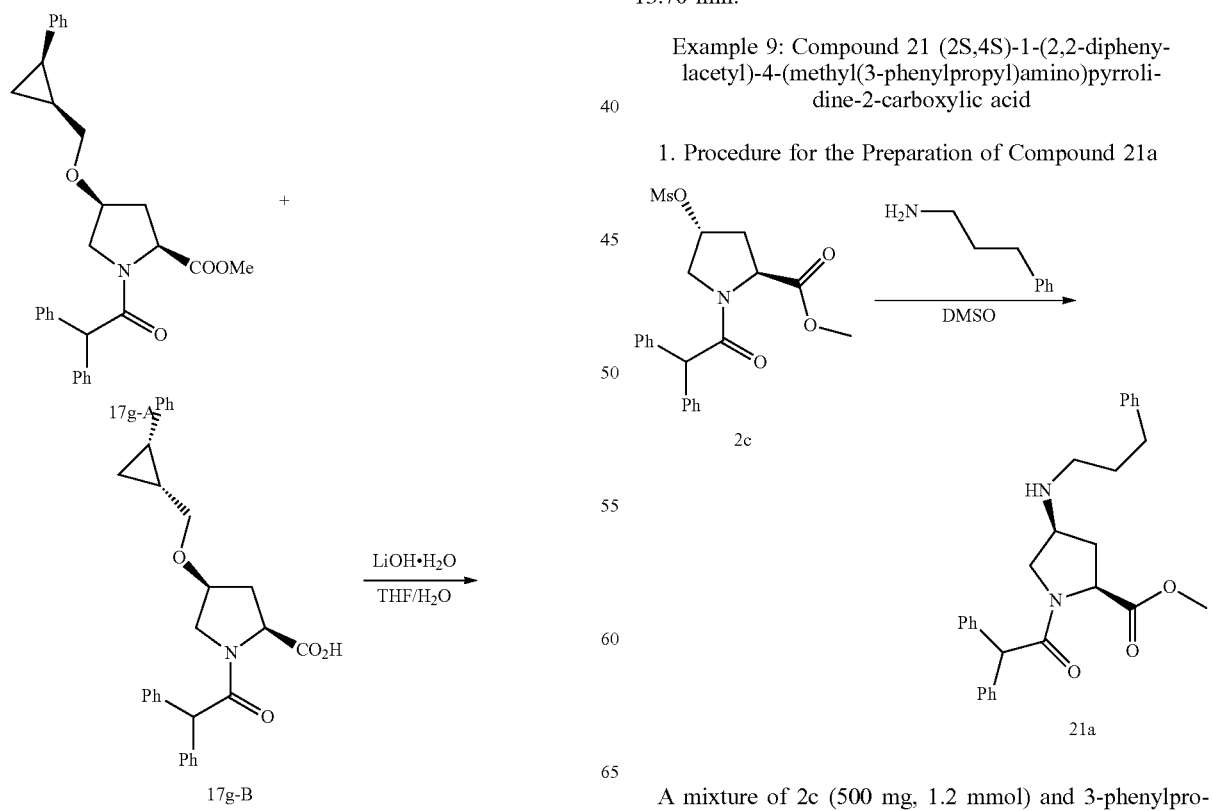

To a stirred solution of 17 g-A and 17 g-B (100 mg, 0.20 mmol) in THF (5 mL) and was added LiOH.H$_2$O/H$_2$O (25 mg, 0.6 mmol/1 mL) and the mixture was stirred at RT overnight, TLC (PE:EA=4:1) showed the reaction was complete. The mixture was concentrated in vacuo to remove most of the THF and the residue was partitioned between DCM (20 mL) and water (20 mL). The aqueous layer was acidified to pH 3~4 with a 1 M aqueous HCl solution, the layers were separated and the aqueous layer was extracted again with DCM (20 mL). The combined organic extracts were washed with brine, dried over Na$_2$SO$_4$, filtered and concentrated in vacuo. The residue was purified by flash chromatography (DCM:MeOH=50:1) to give the product as a mixture of the indicated diastereoisomers as a white solid (80 mg, 77%). LC-MS (Agilent): R$_t$ 3.28 min; m/z calculated for C$_{29}$H$_{29}$NO$_4$ [M+H]$^+$ 456.2, [M+Na]$^+$ 478.2, found [M+H]$^+$ 456.2, [M+Na]$^+$ 478.2. HPLC (214 and 254 nm): R$_t$ 13.70 min.

Example 9: Compound 21 (2S,4S)-1-(2,2-diphenylacetyl)-4-(methyl(3-phenylpropyl)amino)pyrrolidine-2-carboxylic acid 1. Procedure for the Preparation of Compound 21a

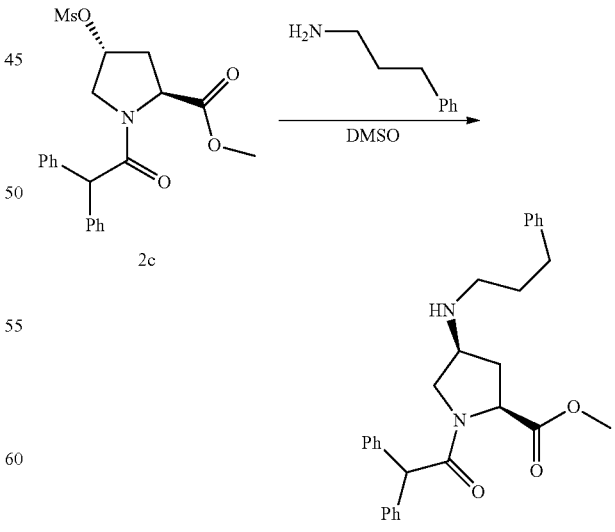

A mixture of 2c (500 mg, 1.2 mmol) and 3-phenylpropylamine (487 mg, 3.6 mmol) in DMSO/DMA/NMP (1:1:1, 10 mL) was heated at 110° C. overnight, TLC (DCM: MeOH=20:1) showed that most of the starting material was consumed. The mixture was poured into water (50 mL) and extracted with EA (20 mL×2). The combined organic extracts were washed with brine, dried over $Na_2SO_4$, filtered and concentrated in vacuo. Purification by silica column gave 21a (300 mg, 55%) as a yellow oil. LC-MS (Agilent): $R_t$ 2.96 min; m/z calculated for $C_{29}H_{32}N_2O_3$ $[M+H]^+$ 457.2, found $[M+H]^+$ 457.2.

2. Procedure for the Preparation of Compound 21b

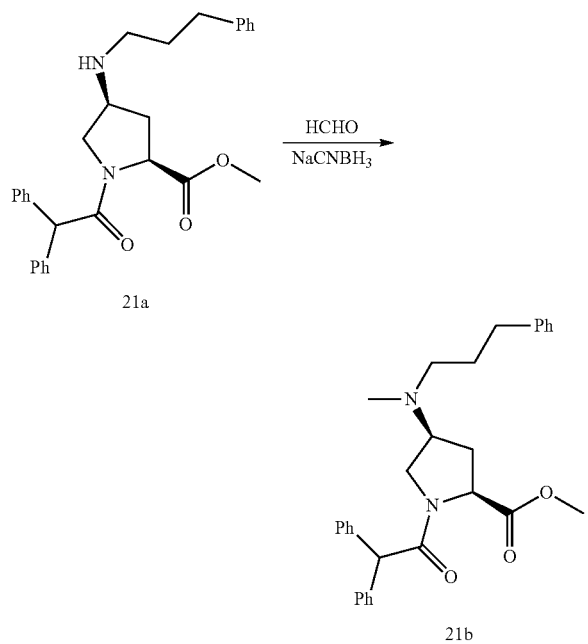

To a solution of compound 21a (300 mg, 0.66 mmol) in $CH_3CN$ (8 mL) was added 37% aqueous HCHO (160.0 mg, 1.97 mmol) and $NaCNBH_3$ (103.9 mg, 1.65 mmol) and the mixture was stirred at RT for 3 h, TLC (DCM:MeOH=20:1) showed that the starting material was consumed. Water (20 mL) was added and the mixture was extracted with EA (15 mL×2). The combined organic extracts were washed with brine, dried over $Na_2SO_4$, concentrated in vacuo and the residue was purified by silica column (DCM:MeOH=100:1 to 50:1) to give 21b (280 mg, 90%) as a yellow solid. LC-MS (Agilent): $R_t$ 2.95 min; m/z calculated for $C_{30}H_{34}N_2O_3$ $[M+H]^+$ 471.2, found $[M+H]^+$ 471.3.

3. Procedure for the Preparation of Compound 21

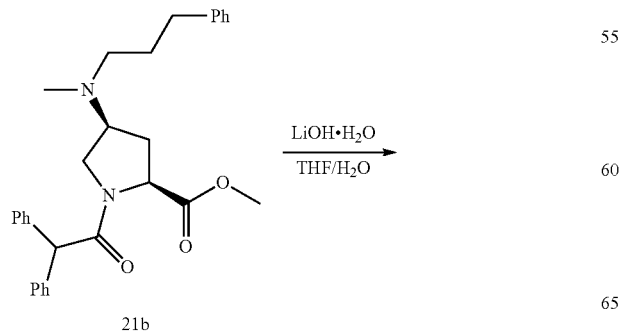

To a stirred mixture of 21b (280 mg, 0.6 mmol) in THF/water (6 mL/2 mL) was added $LiOH·H_2O$ (75.0 mg, 1.8 mmol) and the mixture was stirred at RT overnight, TLC showed that the starting material was consumed. Most of the THF was removed in vacuo and the residue was partitioned between water (20 mL) and $Et_2O$ (10 mL). The $Et_2O$ layer was discarded, DCM (10 mL) was added and the aqueous layer was acidified to pH 2-3 with a 1 M aqueous HCl solution. The organic layer was separated and the aqueous layer was extracted again with DCM (10 mL). The combined organic extracts were washed with brine, dried over $Na_2SO_4$, filtered and concentrated in vacuo to give crude 21 (180 mg). Purification by prep-HPLC gave pure 21 (60.0 mg, 22%) as a white solid. LC-MS (Agilent): $R_t$ 3.14 min; m/z calculated for $C_{29}H_{32}N_2O_3$ $[M+H]^+$ 457.2, found $[M+H]^+$ 457.2. HPLC (214 and 254 nm): $R_t$ 14.30 min.

Example 10: Compound 22 (2S,4S)-1-(2,2-diphenylacetyl)-4-(methyl(phenylethylamino)pyrrolidine-2-carboxylic acid 1. Procedure for the Preparation of Compound 22a

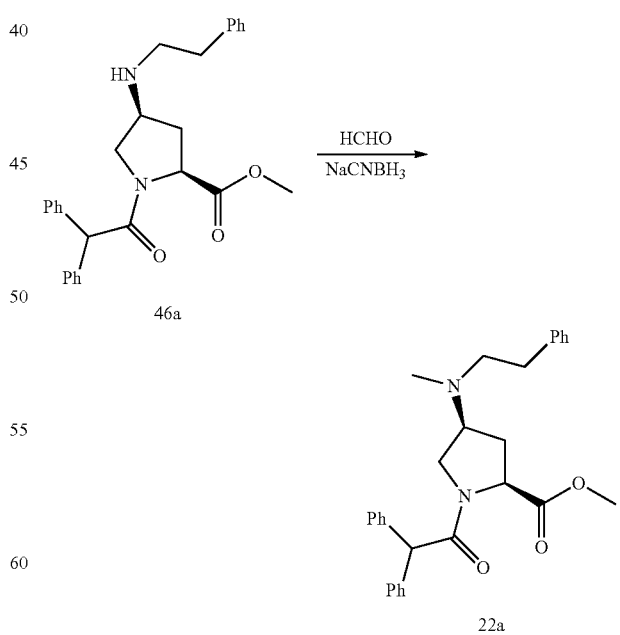

The reaction of Example 9, 2. was repeated with 46a (380.0 mg, 0.86 mmol) in $CH_3CN$ (8 mL), 37% aqueous HCHO (210 mg, 2.6 mmol) and $NaCNBH_3$ (135.0 mg, 2.2 mmol) to give 22a (260 mg, 66%) as a yellow solid. LC-MS (Agilent): $R_t$ 2.60 min; m/z calculated for $C_{29}H_{32}N_2O_3$ [M+H]$^+$ 457.3, found [M+H]$^+$ 457.3.

2. Procedure for the Preparation of Compound 22

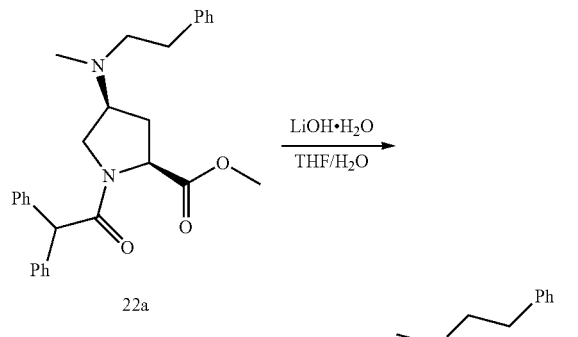

Hydrolysis of 22a (260 mg, 0.57 mmol) as performed using the method of Example 9, 3. using 3 equivalents of LiOH.H$_2$O (71.8 mg, 1.71 mmol). Purification by prep-HPLC gave 22 (160.0 mg, 64%) as a white solid. LC-MS (Agilent): $R_t$ 3.09 min; m/z calculated for $C_{28}H_{30}N_2O_3$ [M+H]$^+$ 443.3, found [M+H]$^+$ 443.3. HPLC (214 and 254 nm): $R_t$ 12.66 min.

Example 11: Compound 23 (2S,4S)-1-(2,2-diphenylacetyl)-4-(4-phenylpiperazine)pyrrolidine-2-carboxylic acid 1. Procedure for the Preparation of Compound 23b

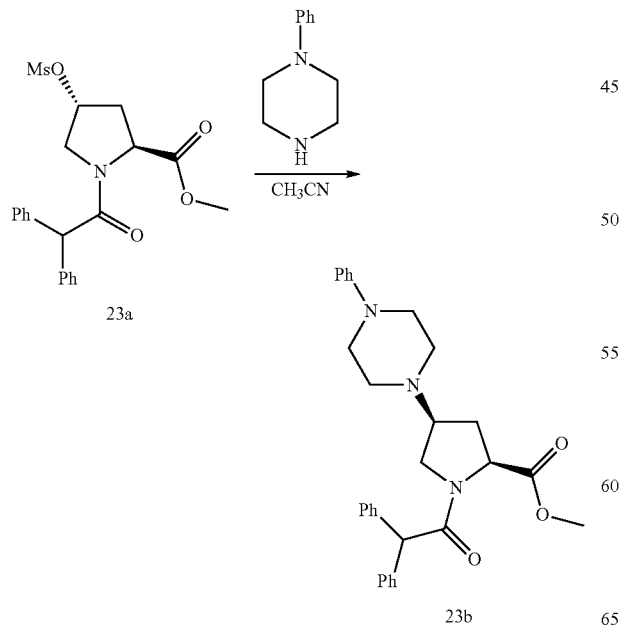

A mixture of compound 23a (1.5 g, 3.5 mmol) and N-phenylpiperazine (1.75 g, 10.7 mmol) in CH$_3$CN (10 mL) was heated at 110° C. overnight, TLC (DCM:MeOH=20:1) showed that the reaction was complete. The mixture was poured into water (50 mL) and extracted with EA (20 mL×2). The combined organic extracts were washed with brine, dried over Na$_2$SO$_4$, filtered and concentrated in vacuo to give 23b (600 mg 35%) as a yellow solid. LC-MS (Agilent): $R_t$ 3.16 min; m/z calculated for $C_{30}H_{33}N_3O_3$ [M+H]$^+$ 484.3, found [M+H]$^+$ 484.3.

2. Procedure for the Preparation of Compound 23

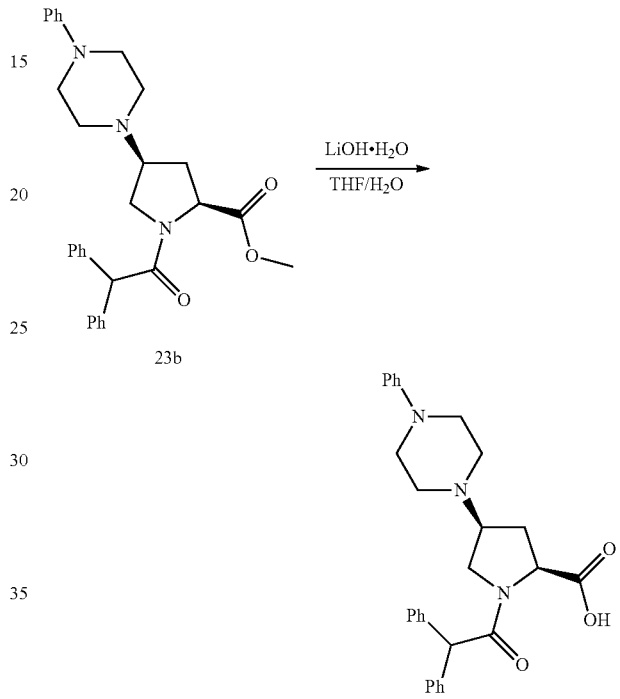

Hydrolysis of 23b (450 mg, 0.93 mmol) was performed using the method of Example 9, 3. using about 3 equivalents of LiOH.H$_2$O (117.4 mg, 2.8 mmol). Recrystallization from DCM/hexane gave 23 (200 mg, 45%) as a white solid. LC-MS (Agilent): $R_t$ 3.17 min; m/z calculated for $C_{29}H_{31}N_3O_3$ [M+H]$^+$ 470.3, found [M+H]$^+$ 470.3. HPLC (214 and 254 nm): Rt 14.25 mini.

Example 12: Compound 28 (2S,4S)-4-((S)-3-benzylmorpholino)-1-(2,2-diphenylacetyl)pyrrolidine-2-carboxylic acid 1. Procedure for the Preparation of Compound 28b

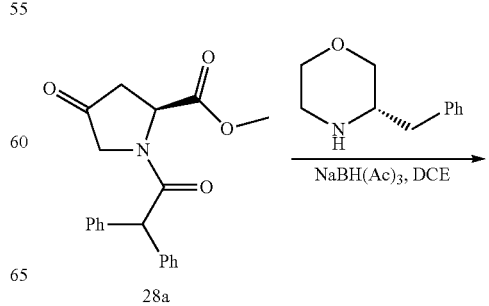

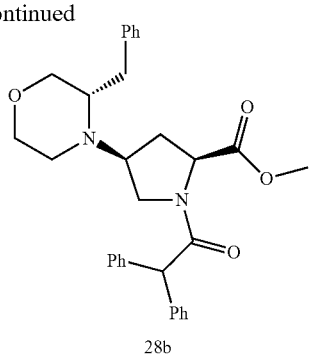

28b

To a solution of 28a (762 mg, 2.26 mmol) and (S)-3-benzylmorpholine (400 mg, 2.26 mmol) in DCE (10 mL) was added AcOH (0.2 mL) and the mixture was stirred at RT for 40 min. The mixture was cooled to 0° C., NaBH(OAc)$_3$ (954 mg, 4.5 mmol) was added and stirring was continued at RT overnight, TLC (PE:EA=2:1) showed that the starting material was consumed. Water (20 mL) was added and the pH was adjusted to 7-8 with Na$_2$CO$_3$. The organic phase was separated and the aqueous layer was extracted with DCM (20 mL). The combined organic extracts were washed with brine, dried over Na$_2$SO$_4$, filtered and concentrated in vacuo. Purification by silica column (PE:EA=10:1 to 4:1) gave 28b (400 mg, 36%) as a white solid. LC-MS (Agilent): R$_t$ 3.26 min; m/z calculated for C$_{31}$H$_{34}$N$_2$O$_4$ [M+H]$^+$ 499.3, found [M+H]$^+$ 499.3.

2. Procedure for the Preparation of Compound 28

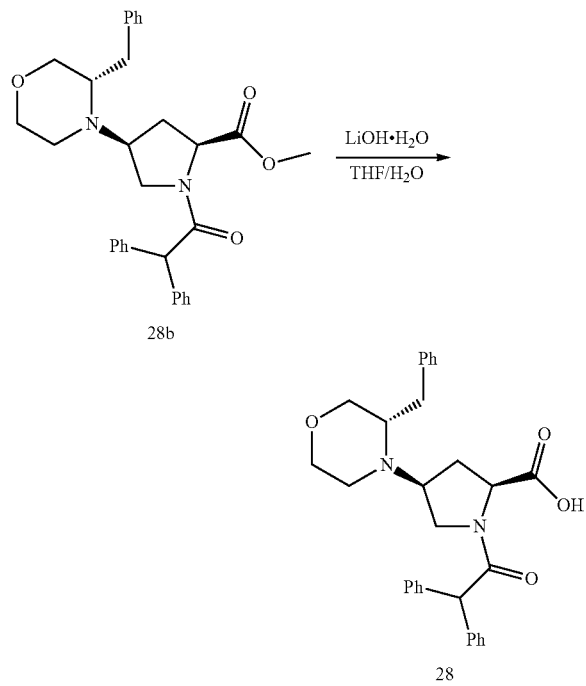

To a mixture of compound 28b (400 mg, 0.8 mmol) in THF/water (6 mL/2 mL) was added LiOH·H$_2$O (101 mg, 2.4 mmol) and the mixture was stirred at RT overnight, TLC showed the starting material was consumed. Most of the THF was removed in vacuo and the residue was partitioned between water (20 mL) and Et$_2$O (15 mL) and the aqueous phase was adjusted to pH 2-3 with 1 M aqueous HCl solution, then to pH 8 with Na$_2$CO$_3$. The Et$_2$O phase was separated and discarded, DCM (10 mL) was added and the aqueous layer was acidified to pH 2-3 with a 1 M aqueous HCl solution. The organic layer was separated and the aqueous layer was extracted with DCM (20 mL). The combined organic extracts were washed with brine, dried over Na$_2$SO$_4$, filtered and concentrated in vacuo. Recrystallization from DCM/hexane gave 28 (200 mg, 51%) as a white solid. LC-MS (Agilent): R$_t$ 3.10 min; m/z calculated for C$_{30}$H$_{32}$N$_2$O$_4$ [M+H]$^+$ 485.3, found [M+H]$^+$ 485.3. HPLC (214 and 254 nm): R$_t$ 12.08 min.

Example 13: Compound 35 (2S,4S)-1-(2,2-diphenylacetyl)-4-(2-phenoxyphenoxy)-pyrrolidine-2-carboxylic acid 1. Procedure for the Preparation of Compound 35b

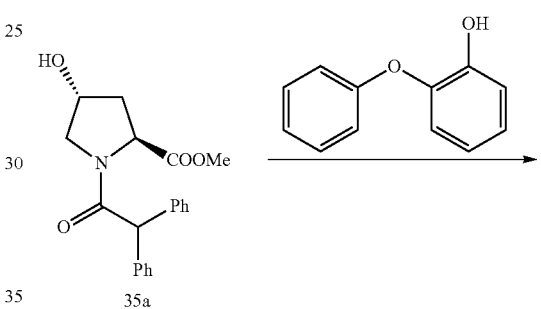

35a

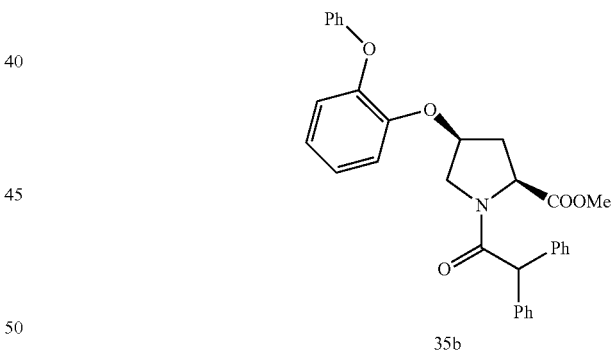

35b

To a stirred solution of 35a (3.00 g, 8.84 mmol), 2-phenoxyphenol (2.40 g 13.3 mmol) prepared by the method described in *Synthesis*, (1994, 1, p 28) and PPh$_3$ (4.6 g, 17.7 mmol) in DCM (60 mL) was added a solution of DBAD (5.3 g, 17.7 mmol) in DCM (30 mL) slowly at 0° C. under a N$_2$ atmosphere and the mixture was stirred at RT overnight, TLC (PE:EA=2:1) showed the starting material was consumed. The mixture was concentrated in vacuo and the residue was partially purified by chromatography (PE:EA=1:0 to 5:1) to give 35b (6.00 g) as a colorless oil, which was used in next step directly. LC-MS (Waters): R$_t$ 6.32 min; m/z calculated for C$_{32}$H$_{29}$NO$_5$ [M+H]$^+$ 508.2, [M+Na]$^+$ 530.2, found [M+H]$^+$ 508.1, [M+Na]$^+$ 530.1.

2. Procedure for the Preparation of Compound 35

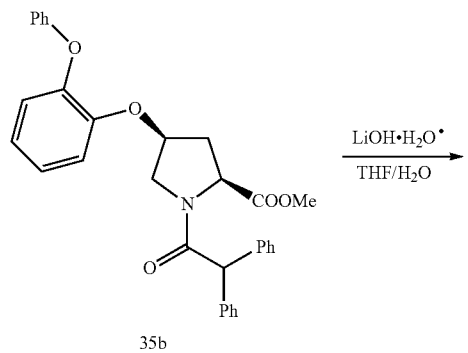

To a solution of compound 35b (6.00 g, 11.8 mmol) in THF (35 mL) was added a solution of LiOH.H$_2$O (0.74 g, 17.7 mmol) in water (15 mL) and the mixture was stirred at RT overnight, TLC (PE:EA=2:1) showed the starting material was consumed. Most of the THF was removed in vacuo and the residue was dissolved in water H$_2$O (10 mL) and washed with Et$_2$O (20 mL×2). EtOAc (20 mL) was added and the aqueous layer was acidified to pH 3~4 with a 1 M aqueous HCl solution. The layers were separated and the organic layer was washed with water (20 mL), brine (20 mL×2), dried over Na$_2$SO$_4$, filtered and concentrated in vacuo. The residue was purified by chromatography (PE to PE:EA=5:1) then prep-HPLC to give 35 (120 mg, 2%) as a white solid. LC-MS (Agilent): R$_t$ 3.43 min; m/z calculated for C$_{31}$H$_{27}$NO$_5$ [M+H]$^+$ 494.2, [M+Na]$^+$ 516.2, found [M+H]$^+$ 494.2, [M+Na]$^+$ 516.2. HPLC (JULY-L) (214 and 254 nm): R$_t$ 8.44 min.

Example 14: Compound 36 (2S,4S)-1-(2,2-diphenylacetyl)-4-((3-phenylprop-2-yn-1-yl)-oxy)pyrrolidine-2-carboxylic acid 1. Procedure for the Preparation of Compound 36b

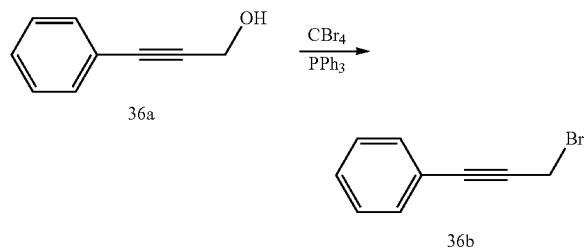

To a stirred solution of 36a (200 mg, 1.5 mmol) and PPh$_3$ (430 mg, 1.65 mmol) in THF (4 mL) was added CBr$_4$ (600 mg, 1.8 mmol) at 0° C. and the mixture was stirred at 0° C. for 2 h, TLC (PE:EA=1:1) showed the starting material was consumed. The reaction was repeated (4.8 g, 36 mmol) and the reaction mixtures were combined, then most of the THF was removed in vacuo and the residue was partitioned between EA (50 mL) and water (30 mL). The organic layer was separated, washed with brine (30 mL×2), dried over Na$_2$SO$_4$, filtered and concentrated in vacuo. The residue was purified by chromatography (PE) to give 36b (6.5 g, 90%) as a colorless oil.

2. Procedure for the Preparation of Compound 36d

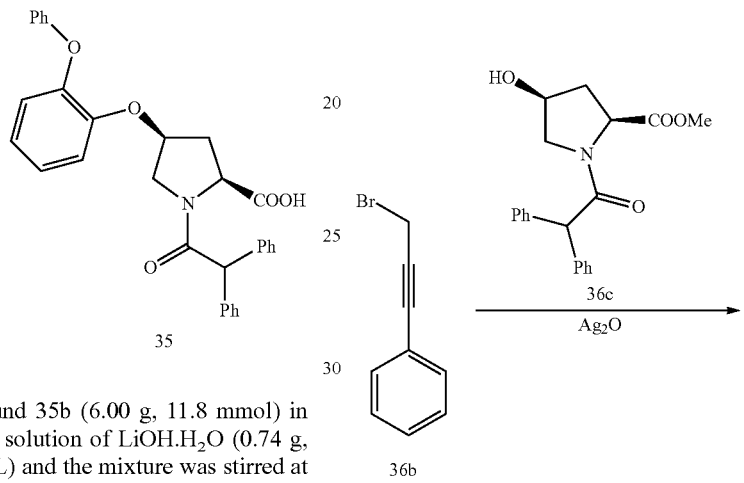

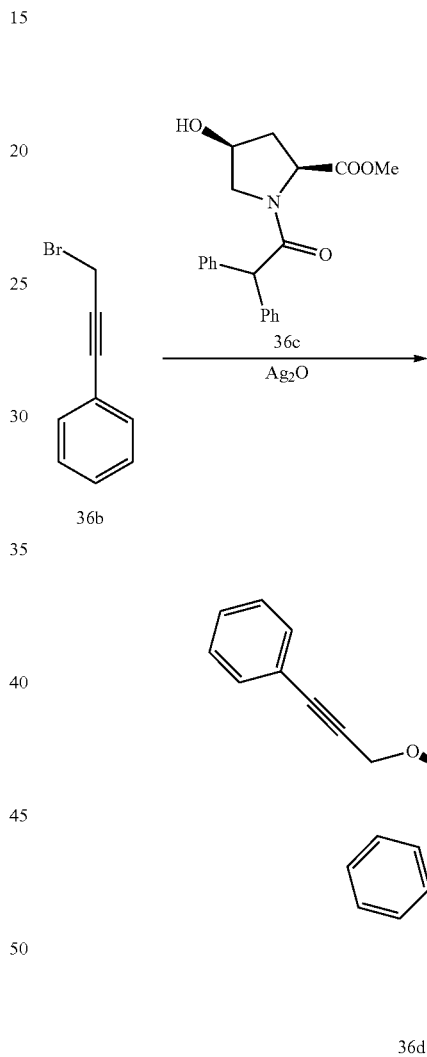

To a stirred suspension of 36c (100 mg, 0.29 mmol) and Ag$_2$O (81 mg, 0.35 mmol) in DCM (2 mL) was added compound 36b (67 mg, 0.35 mmol) at 0° C. and the mixture was stirred in the dark at RT overnight. The reaction was repeated (0.9 g, 2.6 mmol) and the reaction mixtures were combined, then the mixture was filtered and the filtrate was concentrated in vacuo. The residue was purified by chromatography (PE:EA=10:1 to 5:1) to give 36d (100 mg, 8%) as a colorless oil. LC-MS (Agilent): R$_t$ 3.29 min; m/z calculated for C$_{29}$H$_{27}$NO$_4$ [M+H]$^+$ 454.2, [M+Na]$^+$ 476.2, found [M+H]$^+$ 454.2, [M+Na]$^+$ 476.2.

3. Procedure for the Preparation of Compound 36

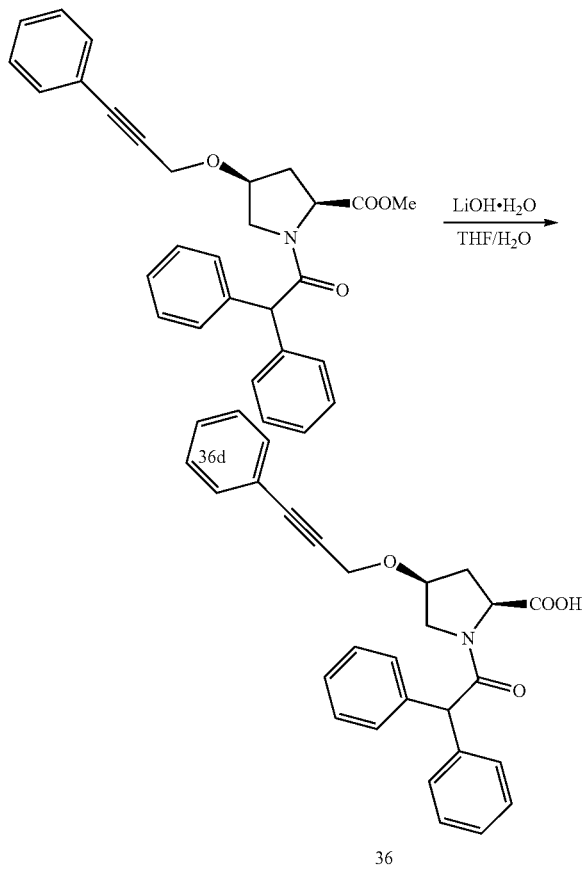

To a mixture of compound 36d (80 mg, 0.18 mmol) in THF/water (5 mL/2 mL) was added LiOH·H$_2$O (11 mg, 0.26 mmol) at 0° C. and the mixture was stirred at RT overnight, TLC (MeOH:DCM=1:10) showed the starting material was consumed. The mixture was concentrated in vacuo to remove most of the THF and the residue was partitioned between EA and water. The aqueous layer was acidified to pH 3~4 with a 1 M aqueous HCl solution and the EA layer was separated, washed with water (3 mL), brine (3 mL×2), dried over Na$_2$SO$_4$, filtered and concentrated in vacuo. The residue was purified by chromatography (DCM:MeOH=50:1) to give 36 (50 mg, 61%) as a white solid. LC-MS (Agilent): R$_t$ 3.29 min; m/z calculated for C$_{28}$H$_{25}$NO$_4$ [M−H]$^-$ 438.2, found [M−H]$^-$ 438.1. HPLC (214 and 254 nm): R$_t$ 13.55 min.

Example 15: Compound 46 (2S,4S)-1-(2,2-diphenylacetyl)-4-(phenethylamino)-pyrrolidine-2-carboxylic acid

1. Procedure for the Preparation of Compound 46a

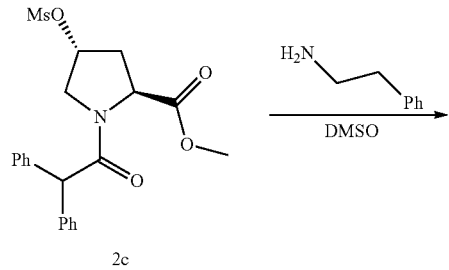

A mixture of 2c (1.5 g, 3.5 mmol) and phenethylamine (1.3 g, 10.8 mmol) in DMSO (10 mL) was heated at 100° C. overnight, TLC (DCM:MeOH=20:1) showed that most of the starting material was consumed. The mixture was poured into water and extracted with EA. The combined organic extracts were washed with brine, dried over Na$_2$SO$_4$, filtered and concentrated in vacuo to give 46a (500 mg, 31%) as a yellow solid. LC-MS (Agilent): R$_t$ 2.92 min; m/z calculated for C$_{28}$H$_{30}$N$_2$O$_3$ [M+H]$^+$ 443.2, found [M+H]$^+$ 443.2.

2. Procedure for the Preparation of Compound 46

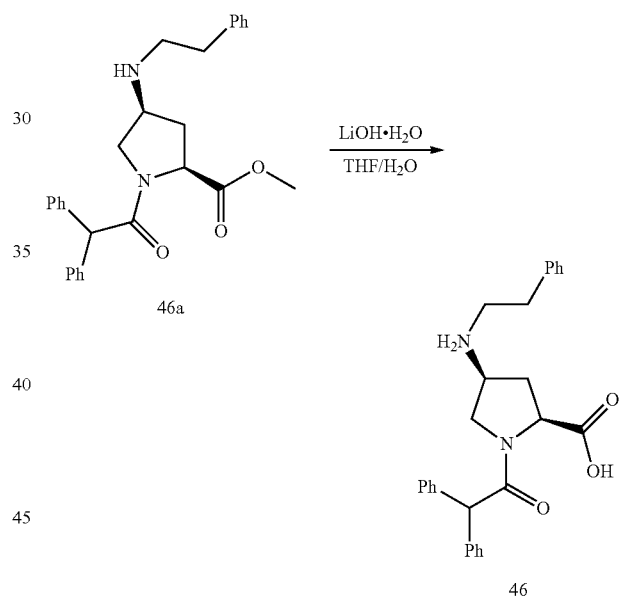

To a mixture of compound 46a (200 mg, 0.45 mmol) in THF/water (6 mL/2 mL) was added LiOH·H$_2$O (56.9 mg, 1.36 mmol) and the mixture was stirred at RT for 3 h, TLC showed that the starting material was consumed. Most of the THF was removed in vacuo and the residue was partitioned between water (20 mL) and Et$_2$O (10 mL). The pH of the aqueous phase was adjusted to 3-4 with a 1 M aqueous HCl solution and then to pH 8 with a saturated aqueous Na$_2$CO$_3$ solution. The layers were separated and the Et$_2$O layer discarded. DCM (10 mL) was added and the aqueous layer was acidified to pH 2-3 with a 1 M aqueous HCl solution. The layers were separated and the organic extract was washed with brine, dried over Na$_2$SO$_4$, filtered and concentrated in vacuo. Purification by prep-HPLC gave 46 (60.0 mg, 31%) as a white solid. LC-MS (Agilent): R$_t$ 3.10 min; m/z calculated for C$_{27}$H$_{28}$N$_2$O$_3$ [M+H]$^+$ 429.2, found [M+H]$^+$ 429.2. HPLC (214 and 254 nm): R$_t$ 11.78 min.

Example 16: Compound 48 (2S,4S)-1-(2,2-diphenylacetyl)-4-((S)-3-phenylpiperidine-1-yl)pyrrolidine-2-carboxylic acid 1. Procedure for the Preparation of Compound 48a

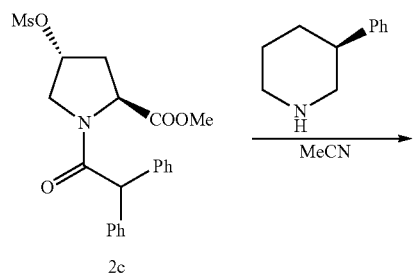

2c

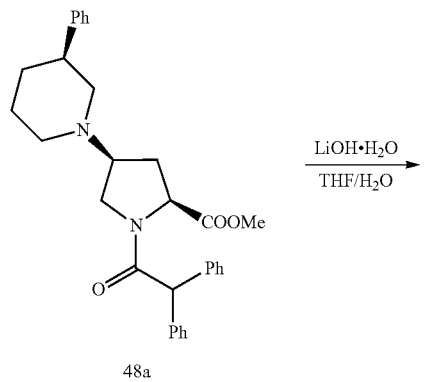

48a

A mixture of 2c (450 mg, 1.08 mmol) and (S)-3-phenyl piperidine (348 mg 2.16 mmol) in CH₃CN (5 mL) heated at 105° C. in a sealed tube overnight, TLC (PE:EA=1:1) showed most of the starting material was consumed. The mixture was cooled to RT, concentrated in vacuo and the residue was purified by chromatography (PE:EA=1:0 to 2:1) to give 48a (150 mg, 28%) as a white solid. LC-MS (Agilent): $R_t$ 3.40 min; m/z calculated for $C_{31}H_{34}N_2O_3$ [M+H]⁺ 483.3, found [M+H]⁺ 483.3.

2. Procedure for the Preparation of Compound 48

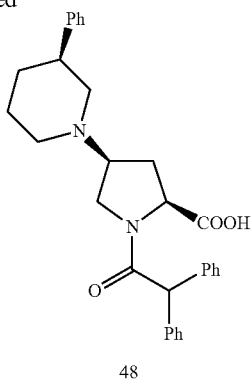

48

To a mixture of compound 48a (150 mg, 0.31 mmol) in THF/water (5 mL/1 mL) was added LiOH·H₂O (33 mg, 0.77 mmol) and the mixture was stirred at RT overnight, TLC (PE:EA=1:1) showed the starting material was consumed. Most of the THF was removed in vacuo and the residue was dissolved in water (15 mL), acidified to pH 3~4 with a 1 M aqueous HCl solution and extracted with chloroform (15 mL×2). The combined organic extracts were washed with brine (15 mL), dried over Na₂SO₄, filtered and concentrated in vacuo to give 48 (130 mg, 89%) as a white solid. LC-MS (Agilent): $R_t$ 3.55 min; m/z calculated for $C_{30}H_{32}N_2O_3$ [M+H]⁺ 469.2, found [M+H]⁺ 469.3. HPLC (JULY-L) (214 and 254 nm): $R_t$ 8.87 min.

Example 17: Compound 49 (2S,4S)-1-(2,2-diphenylacetyl)-4-((R)-3-phenylpiperidin-1-yl)pyrrolidine-2-carboxylic acid 1. Procedure for the Preparation of Compound 49a

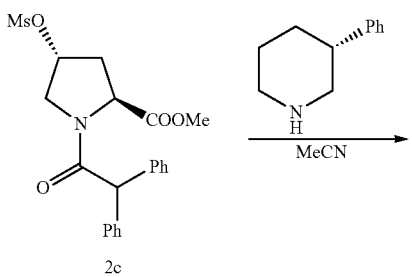

2c

49a

A mixture of 2c (450 mg, 1.08 mmol) and (R)-3-phenyl piperidine (348 mg 2.16 mmol) in CH₃CN (5 mL) was heated at 105° C. in a sealed tube overnight, TLC (PE:EA=1: 1) showed most of the starting material was consumed. The mixture was cooled to RT, concentrated in vacuo and the residue was purified by chromatography (PE:EA=1:0 to 2:1) to give 49a (170 mg, 31%) as a colorless oil. LC-MS (Agilent): $R_t$ 3.42 min; m/z calculated for $C_{31}H_{34}N_2O_3$ [M+H]$^+$ 483.3, found [M+H]$^+$ 483.3.

2. Procedure for the Preparation of Compound 49

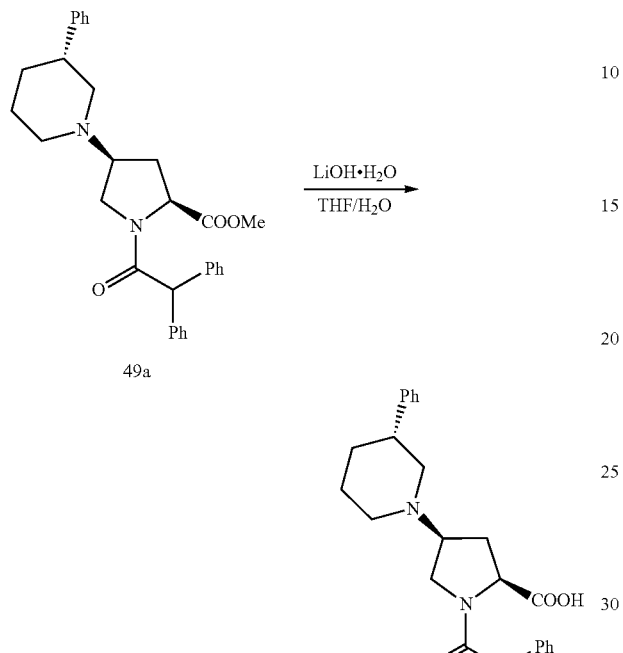

Hydrolysis of 49a (170 mg, 0.35 mmol) as performed with about 2 equivalents of LiOH·H$_2$O (37 mg, 0.77 mmol) as described in Example 16, 2. The resulting precipitate was collected by filtration, washed with water (5 mL×2), then ether (5 mL×2) and dried at 45° C. overnight to give 49 (90 mg, 55%) as a white solid. LC-MS (Agilent): $R_t$ 3.40 min; m/z calculated for $C_{30}H_{32}N_2O_3$ [M+H]$^+$ 469.2, found [M+H]$^+$ 469.3. HPLC (JULY-L) (214 and 254 nm): $R_t$ 8.61 min.

Example 18: Compound 53 (2S,4S)-4-(3-benzylpiperidin-1-yl)-1-(2,2-diphenylacetyl)-pyrrolidine-2-carboxylic acid 1. Procedure for the Preparation of Compound 53a

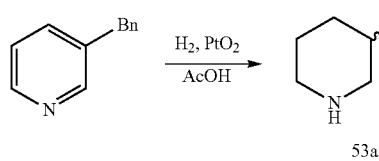

A mixture of 3-benzyl pyridine (1.0 g, 5.9 mmol) and PtO$_2$ (100 mg, 0.36 mmol) in AcOH (20 mL) was stirred at 30° C. under a H$_2$ atmosphere (0.6 Mpa) overnight, TLC (PE:EA=4:1) showed the starting material was consumed. The mixture was filtered and the filtrate was concentrated in vacuo. The residue was partitioned between EA (30 mL) and a saturated aqueous Na$_2$CO$_3$ solution (30 mL), the organic layer was separated, washed with brine, dried over Na$_2$SO$_4$, filtered and concentrated in vacuo to give 53a (1.0 g, 97%) as a yellow oil. LC-MS (Waters): $R_t$ 2.79 min; m/z calculated for $C_{12}H_{17}N$ [M+H]$^+$ 176.1, found [M+H]$^+$ 176.2.

2. Procedure for the Preparation of Compound 53b

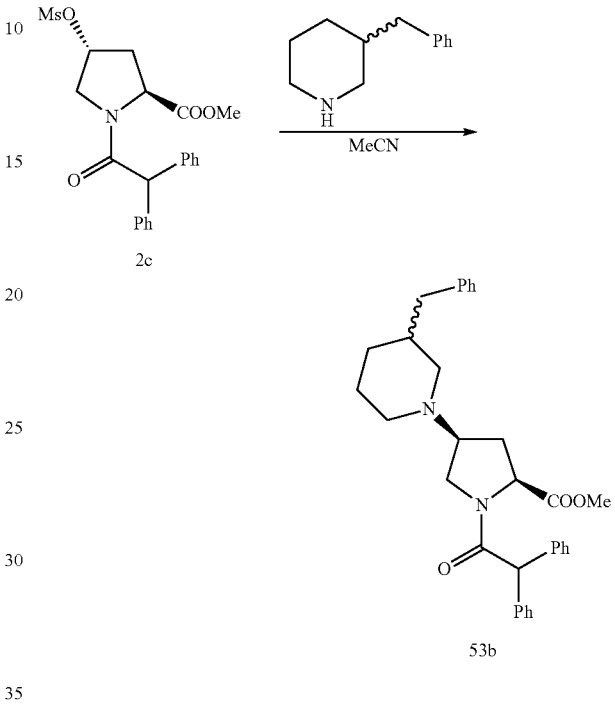

A mixture of compound 2c (1.2 g, 2.88 mmol) and 3-benzyl piperidine (compound 53a) (1.0 g 5.76 mmol) in CH$_3$CN (40 mL) was heated at 110° C. in a sealed tube overnight, TLC (PE:EA=1:1) showed the starting material was consumed. The mixture was cooled to RT, diluted with water and extracted with EA. The combined organic extracts were washed with brine (20 mL×2), dried over Na$_2$SO$_4$, filtered and concentrated in vacuo. The reaction was repeated (600 mg, 1.43 mmol) and the two crude products were combined and purified by chromatography (PE:EA=1:0 to 1:1) to give 53b as the indicated mixture of diastereoisomers (300 mg, 14%) as a yellow oil. LC-MS (Waters): $R_t$ 5.03 min; m/z calculated for $C_{32}H_{36}N_2O_3$ [M+H]$^+$ 497.3, found [M+H]$^+$ 497.1.

3. Procedure for the Preparation of Compound 53

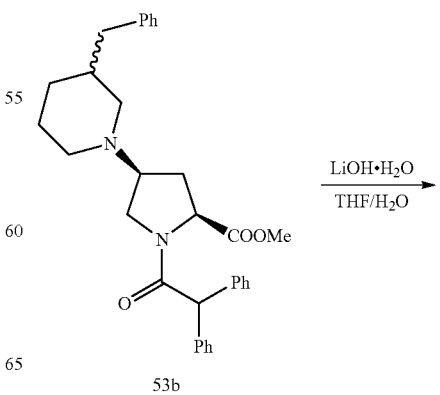

81

-continued

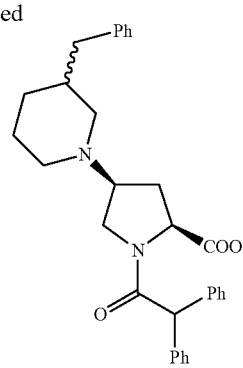

53

To a mixture of 53b (300 mg, 0.60 mmol) in THF/water (6 mL/2 mL) was added LiOH.H$_2$O (25.4 mg, 1.8 mmol) and the mixture was stirred at RT overnight, TLC (PE: EA=1:1) showed the starting material was consumed. Most of the THF was removed in vacuo and the residue was partitioned between EA and water. The aqueous layer was acidified to pH 2-3 with a 1 M aqueous HCl solution. The organic layer was separated, washed with water (10 mL), brine (10 mL×2), dried over Na$_2$SO$_4$, filtered and concentrated in vacuo. The residue was suspended in EA then heated at reflux for 30 min, cooled, the solid filtered and dried to give 53 as the indicated mixture of diastereoisomers (80 mg, 27%) as a white solid. LC-MS (Agilent): R$_t$ 3.26 min; m/z calculated for C$_{31}$H$_{34}$N$_2$O$_3$ [M+H]$^+$ 483.3, found [M+H]$^+$ 483.2. HPLC (JULY-L) (214 and 254 nm): R$_t$ 7.51 min.

Each enantiomer of 3-benzylpiperidine was prepared using methodology described in L. Micouin et al, *Tetrahedron Letters*, 1994, 35 (16), p. 2529-2532. Compounds 51 and 52 were prepared using the respective single enantiomer of 3-benzylpiperidine as starting material and applying the same methodology as for the preparation of Compound 53.

Example 19: Compound 61 (3'5,5'S)-2-benzyl-1'-(2,2-diphenylacetyl)-[1,3'-bipyrrolidine]-5'-carboxylic acid 1. Procedure for the Preparation of 2-Benzyl Pyrrolidine.

Racemic 2-benzyl pyrrolidine was synthesized using a modified literature procedure (the Sparteine chiral ligand was omitted), see: J. Am. Chem. Soc. 1994, 116, 3231 as follows:

A) Procedure for the Preparation of Boc-Protected Pyrrolidine

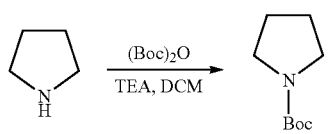 [SMILES: "(Boc)2O" ; C1CCNC1 ; CC(C)(C)OC(=O)N1CCCC1]

To a stirred mixture of pyrrolidine (10.0 g, 0.14 mol) in DCM (150 mL) at 0° C. was added TEA (15.6 g, 0.15 mol) followed by (Boc)$_2$O (30.6 g, 0.14 mol) and the mixture was stirred at RT for 1 h, TLC showed that pyrrolidine had disappeared. The mixture was washed with a 1 M aqueous HCl solution (100 mL), brine, dried over Na$_2$SO$_4$, filtered and concentrated in vacuo to give the product (24.0 g, 100%) as a colorless oil, which was used in the next step directly.

82

B) Procedure for the Preparation of Boc-Protected 2-Benzyl Pyrrolidine.

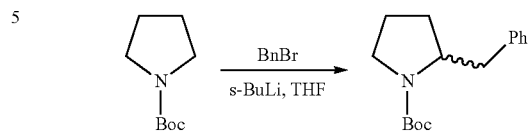

To a stirred solution of Boc-protected pyrrolidine (14.0 g, 80.0 mmol) in THF (200 mL) at −60° C. under N$_2$ was added s-BuLi (1.3 M solution in hexanes, 67.8 mL, 88 mmol) and the mixture was stirred at −60° C. for 1 h. A solution of BnBr (15.4 g, 0.09 mol) in THF (5 mL) was then added at −60° C. and stirring was continued at −60° C. for a further 3 h then at RT overnight. The reaction was quenched at 0° C. with a saturated aqueous NH$_4$Cl solution and extracted with EA. The organic extract was washed with brine, dried over Na$_2$SO$_4$, filtered and concentrated in vacuo. Purification by silica column (PE:EA=50:1 to 20:1) gave the product (6.0 g, 30%) as a yellow oil. LC-MS (Agilent): R$_t$ 3.55 min; m/z calculated for C$_{16}$H$_{23}$NO$_2$ [M−56+H]$^+$ 206.1, [M+H]$^+$ 262.2, [M+Na]$^+$ 284.1, found [M−56+H]$^+$ 206.1, [M+Na]$^+$ 284.1.

C) Procedure for the Preparation of Benzyl Pyrrolidine

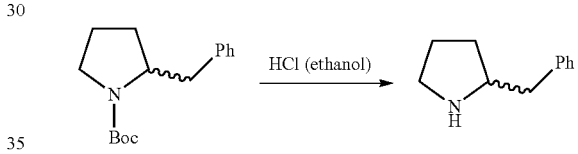

A mixture of Boc-protected 2-benzyl pyrrolidine (6.0 g, 23.0 mmol) in a 4 M HCl/ethanol solution (30 mL) was stirred at RT for 6 h, TLC (PE:EA=10:1) showed that most of the starting material had disappeared. The solvent was removed in vacuo, water (30 mL) and Et$_2$O (20 mL) were added and the layers were separated. The aqueous phase was basified to pH 7-8 with a saturated aqueous Na$_2$CO$_3$ solution and extracted with DCM (2×20 mL) and CHCl$_3$/IPA=3:1 (v/v) (2×20 mL). The combined organic extracts were dried over Na$_2$SO$_4$, filtered and concentrated in vacuo to give the product (2.0 g, 54%) as a colorless oil. LC-MS (Agilent): R$_t$ 2.82 min; m/z calculated for C$_{11}$H$_{13}$N [M+H]$^+$ 162.1, found [M+H]$^+$ 162.1.

2. Procedure for the Preparation of Compound 61b

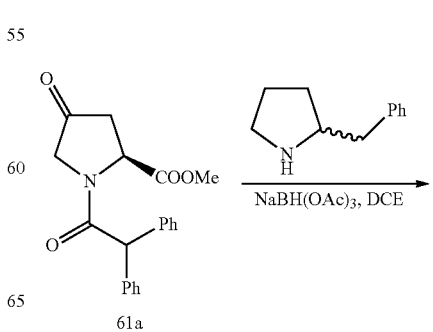

61a

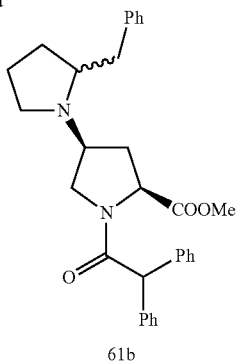

61b

To a solution of compound 61a (1.0 g, 2.96 mmol) and 2-benzyl pyrrolidine (0.47 g, 2.96 mmol) in DCE (20 mL) was added AcOH (0.2 mL) and the mixture was stirred at RT for 1 h. NaBH(OAc)$_3$ (0.94 g, 4.44 mmol) was then added at 0° C. and the mixture was stirred at RT overnight, TLC (PE:EA=1:1) showed that the starting material was consumed. Water (20 mL) was added, the layers were separated and the aqueous layer was extracted with DCM. The combined organic layers were washed with brine, dried over Na$_2$SO$_4$, filtered and concentrated in vacuo. Purification by silica column (PE:EA=10:1 to 3:1) gave 61b as the indicated mixture of diastereoisomers (320 mg, 23%) as a white solid. LC-MS (Agilent): R$_t$ 3.17 min; m/z calculated for C$_{31}$H$_{34}$N$_2$O$_3$ [M+H]$^+$ 483.2, found [M+H]$^+$ 483.2.

3. Procedure for the Preparation of Compound 61

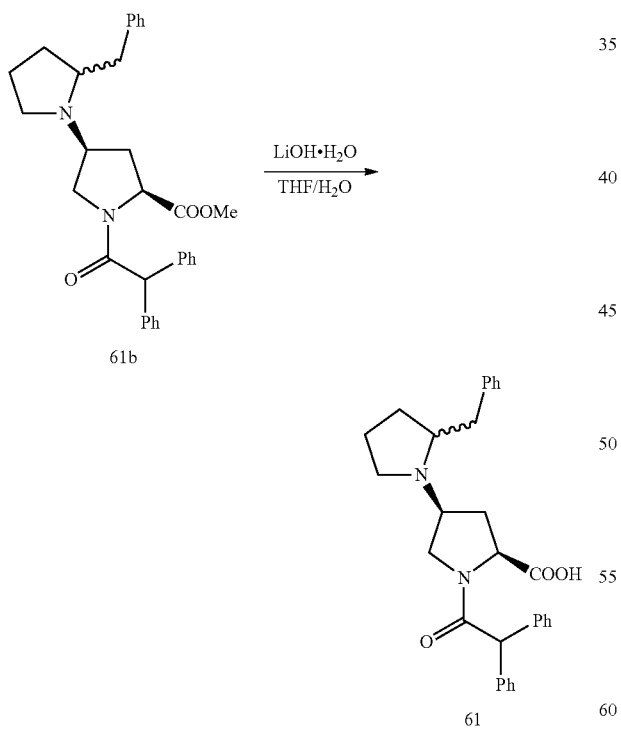

Hydrolysis of 61b (300 mg, 0.62 mmol) as performed as described in Example 9, 3. with about 3 equivalents of LiOH.H$_2$O (78.4 mg, 1.87 mmol), to give 61 (200 mg, 69%) as a yellow solid. The two diastereoisomers were separated by prep-HPLC to give compound 61-A (35 mg) and compound 61-B (35 mg) as white solids. The absolute stereochemistry of these diastereoisomers was not determined and therefore are referred to as 61-A and 61-B.

Data for Compound 61-A:
LC-MS (Agilent): R$_t$ 3.44 min; m/z calculated for C$_{30}$H$_{32}$N$_2$O$_3$ [M+H]$^+$ 469.2, found [M+H]$^+$ 469.2. HPLC (JULY-L) (214 and 254 nm): R$_t$ 7.39 min.

Data for Compound 61-B:
LC-MS (Agilent): R$_t$ 3.45 min; m/z calculated for C$_{30}$H$_{32}$N$_2$O$_3$ [M+H]$^+$ 469.2, found [M+H]$^+$ 469.2. HPLC (JULY-L) (214 and 254 nm): R$_t$ 7.61 min.

Example 20: Compound 62 (2S,4S)-1-(2-cyclohexyl-2-phenylacetyl)-4-(methyl(3-phenylpropyl)amino)pyrrolidine-2-carboxylic acid 1. Procedure for the Preparation of Compound 62b

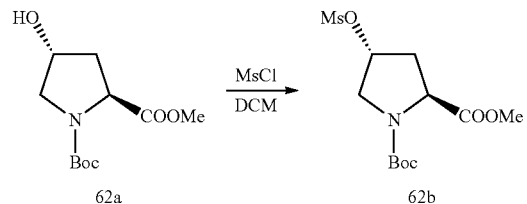

To a stirred solution of 62a (3.0 g, 12.2 mmol) and Et$_3$N (1.35 g, 13.4 mmol) in DCM (30 mL) at 0° C. was added MsCl (1.47 g, 12.8 mmol) and the mixture was stirred at 0° C. for 2 h, TLC (PE:EA=1:1) showed the starting material was consumed. The mixture was washed with water (20 mL×2), brine (20 mL), dried over Na$_2$SO$_4$, filtered and concentrated in vacuo to give 62b (3.9 g, 100%) as a yellow thick oil, which was used directly in next step.

2. Procedure for the Preparation of Compound 62c

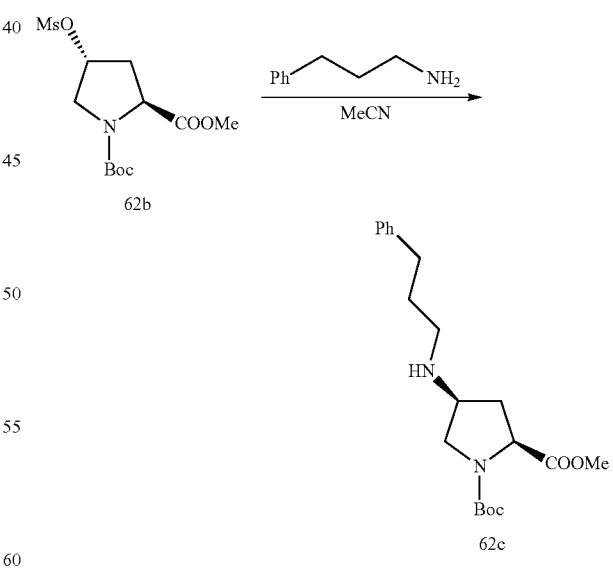

A solution of 62b (500 mg, 1.54 mmol) and 3-phenylpropylamine (522 mg, 3.86 mmol) in CH$_3$CN (5 mL) was heated at 110° C. in a sealed tube overnight and then allowed to cool to RT. The reaction was repeated (1.00 g, 3.08 mmol) and the reaction mixtures were combined and concentrated in vacuo. The residue was dissolved in EA, washed with brine then dried over. Na$_2$SO$_4$, filtered and concentrated in vacuo. Purification by chromatography (PE:EA=10:1 to 2:1) gave 62c (450 mg, 28%) as a yellow oil. LC-MS (Agilent): R$_t$ 3.11 min; m/z calculated for C$_{20}$H$_{30}$N$_2$O$_4$ [M+H]$^+$ 363.2, found [M+H]$^+$ 363.2.

3. Procedure for the Preparation of Compound 62d

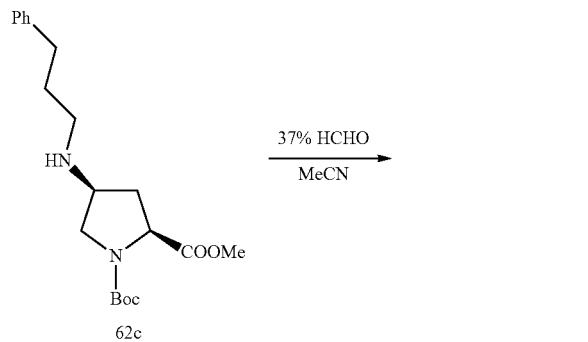

To a stirred solution of 62c (450 mg, 1.24 mmol) in MeCN (10 mL) was added a 37% aqueous solution of formaldehyde (252 mg, 3.10 mmol) followed by AcOH (2 drops) and the mixture was stirred at RT for 1 h. NaCNBH$_3$ (195 mg, 3.10 mmol) was added and the mixture was stirred at RT overnight, TLC (DCM:MeOH=10:1) showed the starting material was consumed. The mixture was partitioned between EA (30 mL) and water (20 mL), the organic layer was collected and washed with brine, dried over Na$_2$SO$_4$, filtered and concentrated in vacuo. The residue was purified by chromatography (PE:EA=10:1 to 2:1) to give 62d (90 mg, 19%) as a yellow oil. LC-MS (Agilent): R$_t$ 2.88 min; m/z calculated for C$_{21}$H$_{32}$N$_2$O$_4$ [M+H]$^+$ 377.2, found [M+H]$^+$ 377.2.

4. Procedure for the Preparation of Compound 62e

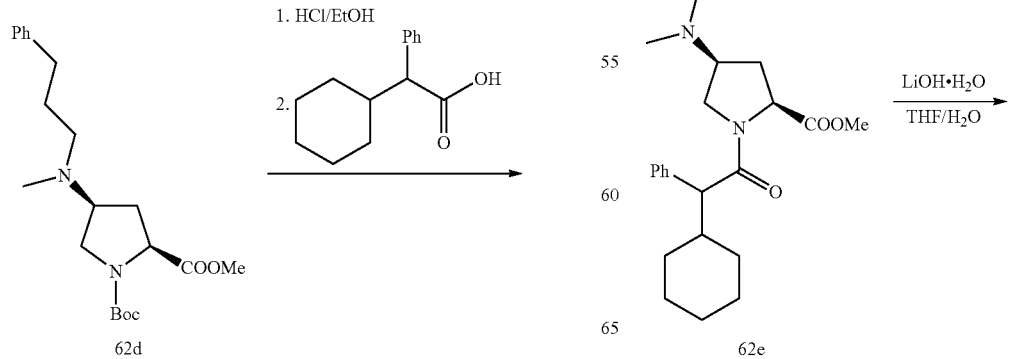

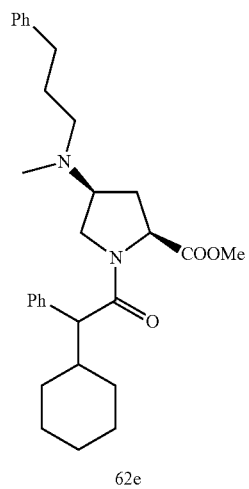

A suspension of compound 62d (90 mg, 0.24 mmol) in 4 M HCl/EtOH (10 mL) was stirred at RT for 4 h, TLC (DCM:MeOH=10:1) showed the starting material was consumed. The mixture was concentrated in vacuo, the residue was dissolved in water (10 mL) and washed with ether (10 mL×2). The aqueous layer was then basified to pH 9-10 with K$_2$CO$_3$ and extracted with DCM (10 mL×2). The combined organic extracts were dried over Na$_2$SO$_4$ and concentrated in vacuo. The residue was dissolved in DCM (10 mL) and cyclohexylphenyl acetic acid (50.4 mg, 0.23 mmol) and EDCI.HCl (76.6 mg, 0.40 mmol) were added followed by a catalytic amount of DMAP. The mixture was then stirred at RT overnight, TLC (DCM:MeOH=20:1) showed the reaction was complete. The mixture was washed with a saturated aqueous NaHCO$_3$ solution (10 mL×2), brine, dried over Na$_2$SO$_4$, filtered and concentrated in vacuo. Purification by chromatography (DCM:MeOH=1:0 to 20:1) gave 62e (60 mg, 52%) as a white solid. LC-MS (Agilent): R$_t$ 3.24 min; m/z calculated for C$_{30}$H$_{40}$N$_2$O$_3$ [M+H]$^+$ 477.3 found [M+H]$^+$ 477.3.

5. Procedure for the Preparation of Compound 62

-continued

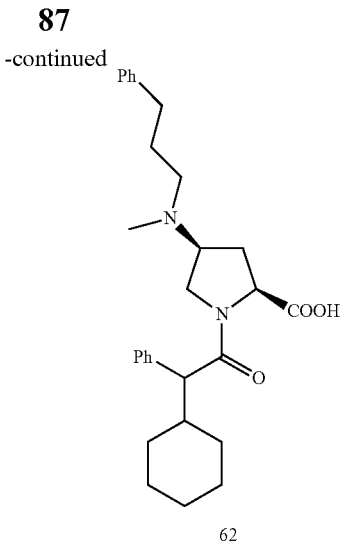

62

Hydrolysis of 62e (60 mg, 0.16 mmol) was performed as described in Example 2, 6. with 3 equivalents of LiOH.H$_2$O (15.8 mg, 0.48 mmol). After acidification, the organic layer was collected and washed with brine, dried over Na$_2$SO$_4$ and concentrated in vacuo to give 62 (36 mg, 49%) as a white solid. LC-MS (Agilent): R$_t$ 3.43 min; m/z calculated for C$_{29}$H$_{28}$N$_2$O$_3$ [M+H]$^+$ 463.3, found [M+H]$^+$ 463.3. HPLC (JULY-L) (214 and 254 nm): R$_t$ 7.96 min.

Example 21: Compound 63 (2S,4S)-1-(2,2-diphenylacetyl)-4-(methyl((2-phenylcyclopropyl)methyl)amino)pyrrolidine-2-carboxylic acid 1. Procedure for the Preparation of Compound 63f

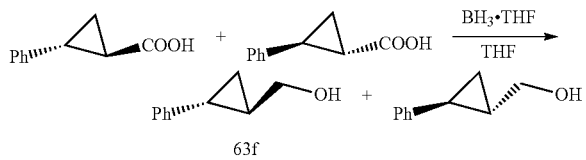

63f

To a stirred solution of racemic trans-2-phenyl-1-cyclopropanecarboxylic acid (2.00 g, 12.3 mmol) in dry THF (20 mL) at 0° C. was added BH$_3$.THF (1 M solution in THF, 14.8 mL, 14.8 mmol) and the mixture was allowed to warm slowly to RT and stirred for 4 h. More BH$_3$.THF (1 M solution in THF, 7.4 mL, 7.4 mmol) was added and stirring was continued at RT for 2 h, TLC (DCM:MeOH=20:1) showed the reaction was complete. The reaction was quenched with MeOH, water was added and the mixture was extracted with EA. The organic layer was separated and washed with brine (30 mL×2), dried over Na$_2$SO$_4$, filtered and concentrated to give 63f (1.6 g, 88%) as a yellow oil. LC-MS (Agilent): R$_t$ 3.27 min; m/z calculated for C$_{10}$H$_{12}$O [M+Na]$^+$ 171.1, found [M+Na]$^+$ 171.1.

2. Procedure for the Preparation of Compound 63g

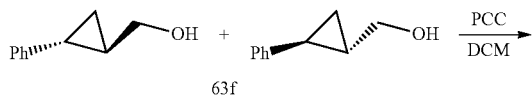

63f

-continued

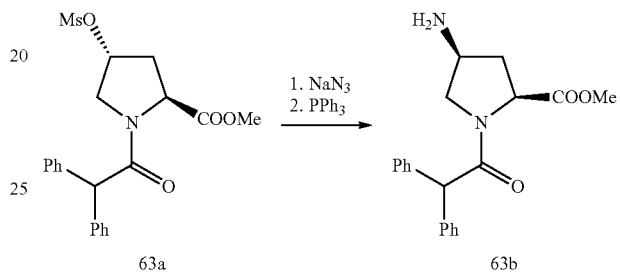

63g

To a solution of 63f (0.8 g, 5.39 mmol) in THF (30 mL) was added Celite (~3 g) followed by PCC (3.49 g, 16.2 mmol) and the mixture was stirred at RT overnight, TLC (PE:EtOAc=4:1) showed the reaction was complete. The mixture was then filtered through a plug of silica gel and rinsed with DCM. The filtrate was concentrated in vacuo to give the product (0.62 g, 78%) as a yellow oil.

3. Procedure for the Preparation of Compound 63b 63a    63b

To a solution of compound 63a (1.4 g, 3.35 mmol) in DMSO (15 mL) was added NaN$_3$ (0.43 g, 6.70 mmol) and the mixture was heated at 90° C. overnight, TLC (PE:EA=2:1) showed the reaction was complete. The reaction was partitioned between EA (30 mL) and water (60 mL), the layers was separated and the aqueous layer was extracted with EA (20 mL×2). The combined organic extracts were washed with brine (30 mL×2), dried over Na$_2$SO$_4$, filtered and concentrated to a volume of 2 mL. A mixture of THF/H$_2$O (10 mL/1 mL) was added followed by PPh$_3$ (1.4 g, 5.35 mmol) and the mixture was heated at reflux for 3 h, TLC (PE:EA=2:1) showed the starting material was consumed. The mixture was concentrated in vacuo to remove most of the THF and the residue was dissolved in a 0.5 M aqueous HCl solution (20 mL) and washed with EA (20 mL×2). The aqueous layer was then basified to pH 8 with K$_2$CO$_3$ and extracted with DCM (20 mL×4). The combined organic extracts were washed with brine, dried over Na$_2$SO$_4$ and concentrated in vacuo to give 63b (1.0 g, 90%) as a white solid. LC-MS (Agilent): R$_t$ 3.02 min; m/z calculated for C$_{20}$H$_{22}$N$_2$O$_3$ [M+H]$^+$ 339.2, found [M+H]$^+$ 339.2.

4. Procedure for the Preparation of Compound 63c

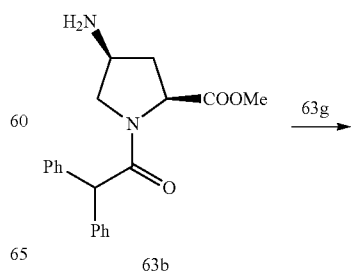

63b

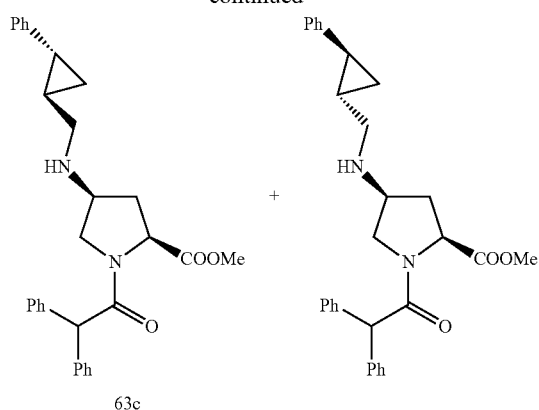

63c

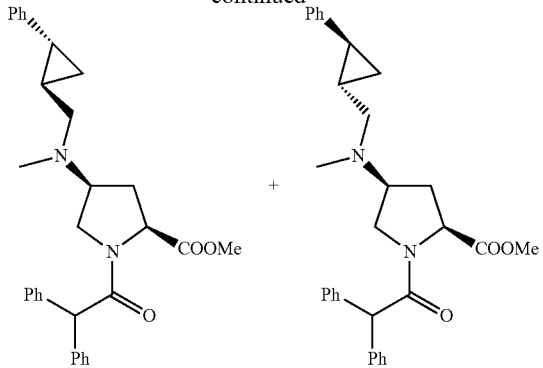

63d

To solution of compound 63b (600 mg, 1.77 mmol) and compound 63g (260 mg, 1.77 mmol) in DCE (30 mL) was added 2 drops of AcOH and the mixture was stirred at RT for 1 h. NaBH(OAc)$_3$ (451 mg, 2.13 mmol) was then added and stirring was continued at RT overnight, TLC (PE:EA=1:2) showed most of the starting material was consumed. The mixture was washed with brine, dried over Na$_2$SO$_4$, filtered and concentrated in vacuo. The residue was purified by chromatography to give 63c as a mixture of the indicated diastereoisomers (500 mg, 60%) as a yellow oil. LC-MS (Agilent): R$_t$ 3.22 min; m/z calculated for C$_{20}$H$_{32}$N$_2$O$_3$ [M+H]$^+$ 469.2, found [M+H]$^+$ 469.2.

5. Procedure for the Preparation of Compound 63d

To a solution of compound 63c (500 mg, 1.06 mmol) in MeCN (10 mL) was added a 37% aqueous formaldehyde solution (220 mg, 2.66 mmol) followed by 2 drops of AcOH and the mixture was stirred at RT for 1 h. NaCNBH$_3$ (168 mg, 2.66 mmol) was then added and stirring was continued at RT overnight, TLC (PE:EA=1:2) showed the starting material was consumed. To the reaction mixture was added 3-5 drops of NaHCO$_3$ to neutralize the mixture which was partitioned between EA and water. The organic layer was separated and washed with brine, dried over Na$_2$SO$_4$, filtered and concentrated in vacuo. The residue was purified by chromatography (PE:EA=10:1 to 2:1) to give 63d as a mixture of the indicated diastereoisomers (185 mg, 36%) as a yellow oil. LC-MS (Agilent): R$_t$ 148 min; m/z calculated for C$_{31}$H$_{34}$N$_2$O$_3$ [M+H]$^+$ 483.3, found [M+H]$^+$ 483.2.

6. Procedure for the Preparation of Compound 63

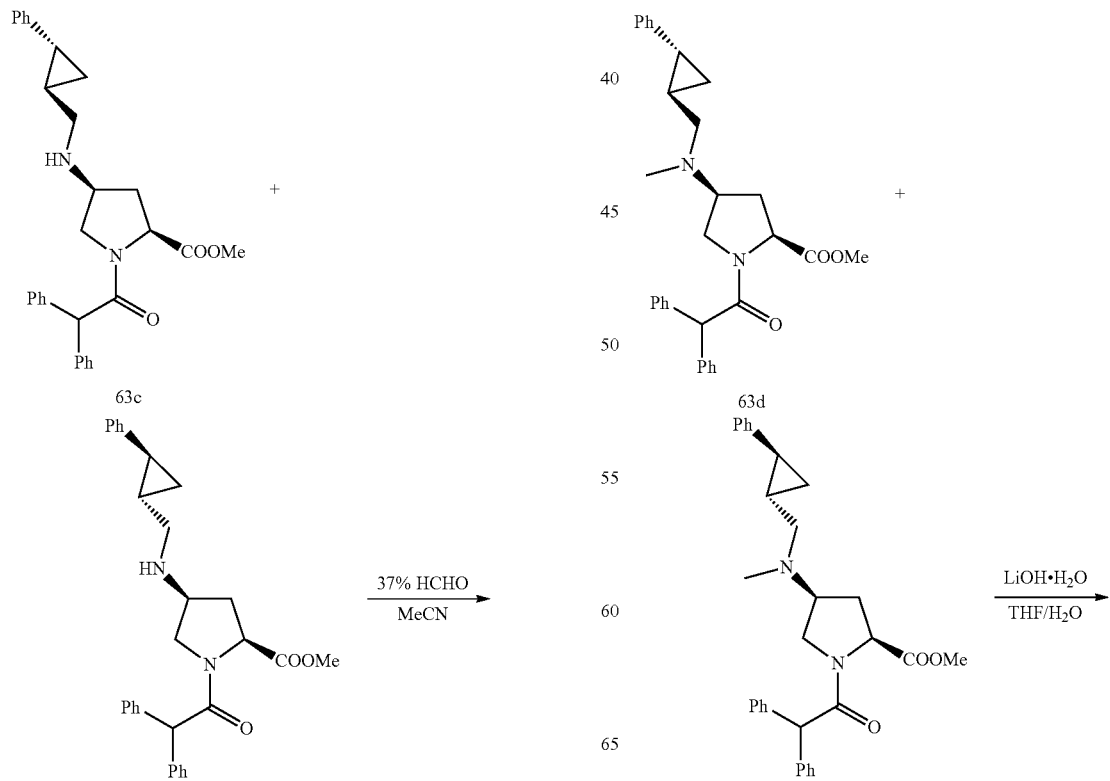

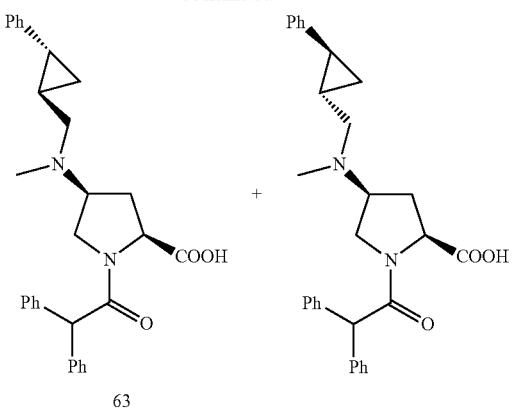

63

Hydrolysis of 63d (185 mg, 0.38 mmol) as performed as described in Example 16, 2. ith about 2.8 equivalents of LiOH·H$_2$O and the resulting precipitate was collected by filtration, washed with water (5 mL×2), then purified by prep-HPLC to give 63 as a mixture of the indicated diastereoisomers (51 mg, 28%) as a white solid. LC-MS (Agilent): R$_t$ 3.50 min; m/z calculated for C$_{30}$H$_{32}$N$_2$O$_3$ [M+H]$^+$ 469.2, found [M+H]$^+$ 469.3. HPLC (JULY-L) (214 and 254 nm): R$_t$ 8.76 min.

Example 22: Compound 64 (2S,4S)-1-(2,2-diphenylacetyl)-4-(3,3-diphenyluriedo)-pyrrolidine-2-carboxylic acid 1. Procedure for the Preparation of Compound 64b

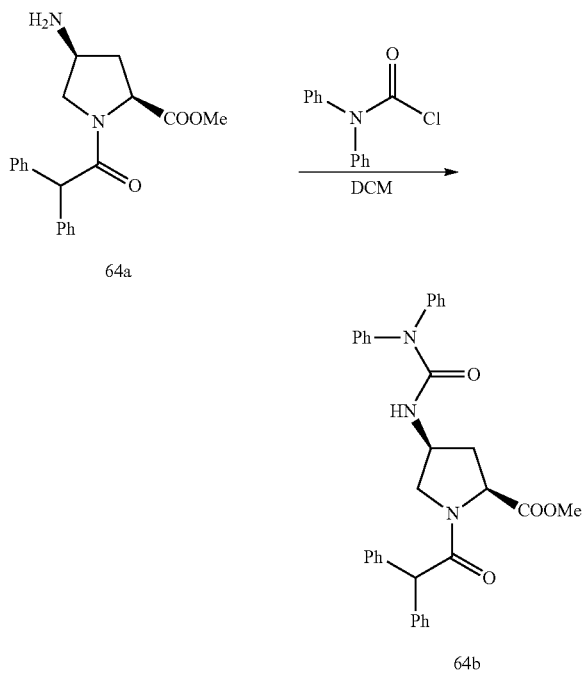

To a stirred solution of compound 64a (300 mg, 0.88 mmol) and Et$_3$N (96 mg, 0.96 mmol) in DCM (5 mL) was added diphenylcarbamoyl chloride (246 mg, 0.96 mmol) followed a catalytic amount of DMAP and the mixture was stirred at RT overnight, TLC (DCM:MeOH=10:1) showed the starting material was consumed. Water (10 mL) was added, the layers were separated and the aqueous layer was extracted with DCM (10 mL). The combined organic extracts were washed with brine (10 mL), dried over Na$_2$SO$_4$, filtered and concentrated in vacuo. The residue was purified by chromatography (PE:EA=4:1 to 2:1) to give 64b (210 mg, 44%) as a white solid. LC-MS (Agilent): R$_t$ 3.50 min; m/z calculated for C$_{31}$H$_{33}$N$_3$O$_4$ [M+H]$^+$ 534.2, [M+Na]$^+$ 556.2, found [M+H]$^+$ 534.2, [M+Na]+ 556.2.

2. Procedure for the Preparation of Compound 64

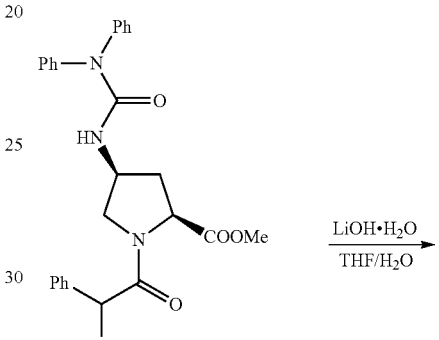

To a mixture of compound 64b (200 mg, 0.37 mmol) in THF (5 mL) and H$_2$O (1 mL) was added LiOH·H$_2$O (40 mg, 0.94 mmol) and the mixture was stirred at RT overnight, TLC (PE:EA=1:1) showed the starting material was consumed. Most of the THF was removed in vacuo and the residue was dissolved in water (20 mL), cooled to 0° C. and acidified to pH 2-3 with a 3 M aqueous HCl solution. The resulting precipitate was collected by filtration, washed with water (10 mL×2) and dried at 50° C. overnight to give 64 (140 mg, 72%) as a white solid. LC-MS (Agilent): R$_t$ 3.52 min; m/z calculated for C$_{32}$H$_{29}$N$_3$O$_4$ [M+H]$^+$ 520.2, [M+Na]$^+$ 542.2, found [M+H]$^+$ 520.2, [M+Na]$^+$ 542.2. HPLC (JULY-L) (214 and 254 nm): R$_t$ 8.15 min.

Example 23: Compound 65 (2S,4S)-1-(2,2-diphenylacetyl)-4-(3-oxo-4-phenyl-2,8-diazaspiro[4,5]decan-8-yl)pyrrolidine-2-carboxylic acid 1. Procedure for the Preparation of Compound 65a

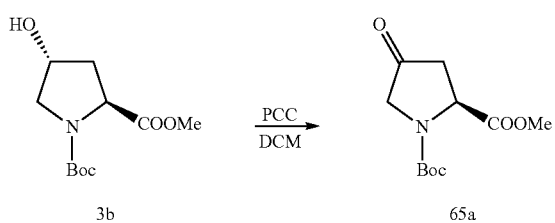 [SMILES: COC(=O)[C@@H]1C[C@@H](O)CN1C(=O)OC(C)(C)C ; "PCC" ; COC(=O)[C@@H]1CC(=O)CN1C(=O)OC(C)(C)C]

To a stirred solution of compound 3b (5.0 g, 20.4 mmol) in DCM (60 mL) was added Celite (8 g) then PCC (13.2 g, 61.2 mmol) and the mixture was stirred at RT overnight, TLC (PE:EA=2:1) showed the starting material was consumed. The mixture was filtered and the filtrate was concentrated in vacuo. The residue was purified by chromatography (PE:EA=1:0 to 4:1) to give 65a (3.6 g, 72%) as a thick yellow oil. LC-MS (Agilent): $R_t$ 3.17 min; m/z calculated for $C_{11}H_{17}NO_5$ [M+H-Boc]$^+$ 144.1, [M+H-t-Bu]$^+$ 188.1, found [M+H-Boc]$^+$ 144.1, [M+H-t-Bu]$^+$ 188.1.

2. Procedure for the Preparation of Compound 65b

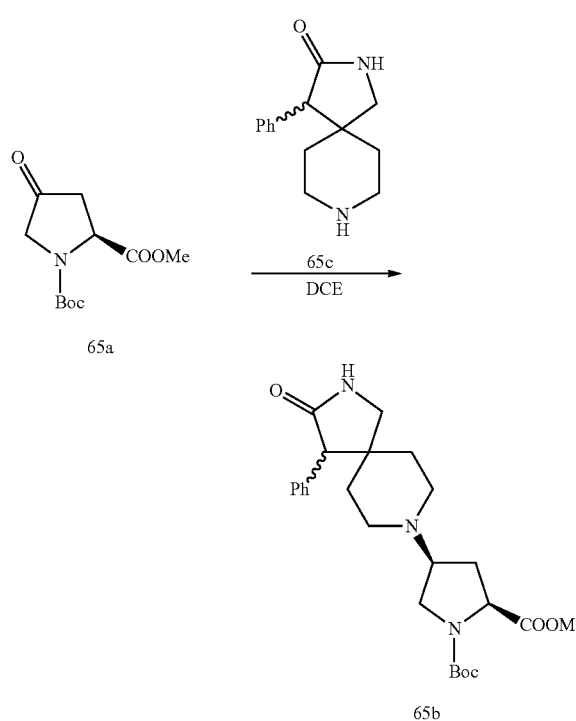

A solution of compound 65a (900 mg, 3.70 mmol) and the racemic piperidine 65c (710 mg, 3.08 mmol) in MeOH (15 mL) was stirred at RT for 30 min. NaCNBH$_3$ (233 mg, 3.70 mmol) was added followed by 3 drops of AcOH and stirring was continued at RT overnight, TLC (DCM:MeOH=10:1) showed the starting material was consumed. The mixture was concentrated in vacuo and the residue was partitioned between DCM (20 mL) and a saturated aqueous NaHCO$_3$ solution (10 mL). The organic layer was collected, dried over Na$_2$SO$_4$, filtered and concentrated in vacuo. The residue was purified by chromatography (DCM:MeOH=1:0 to 50:1) to give 65b* as the indicated mixture of diastereoisomers (450 mg, 26%) as a white solid. LC-MS (Agilent): $R_t$ 3.13 min; m/z calculated for $C_{25}H_{35}N_3O_5$ [M+H]$^+$ 458.3, found [M+H]$^+$ 458.3.

3. Procedure for the Preparation of Compound 65d

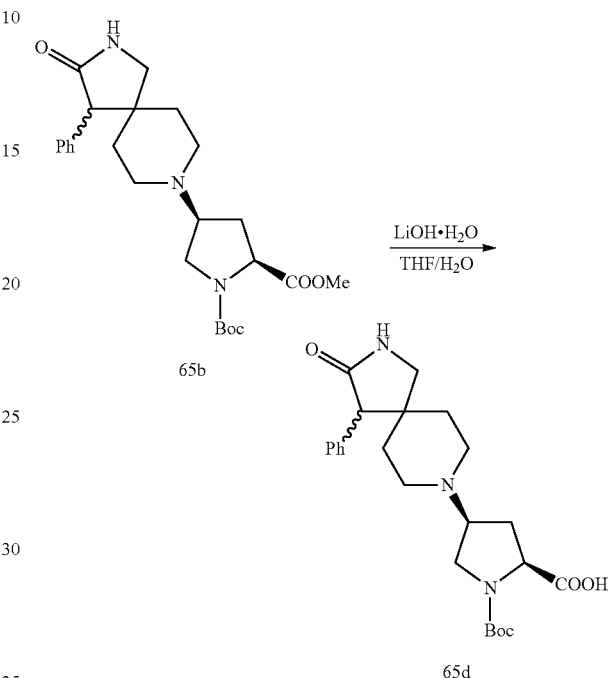

To a mixture of 65b (450 mg, 0.98 mmol) in THF (10 mL) and H$_2$O (2 mL) was added LiOH.H$_2$O (104 mg, 2.46 mmol) and the mixture was stirred at RT overnight, TLC (DCM:MeOH=10:1) showed the starting material was consumed. Most of the THF was removed in vacuo and the residue was dissolved in water (15 mL), cooled to 0° C., acidified to pH 2-3 with a 3 M aqueous HCl solution and then freeze-dried. Purification by flash chromatography (DCM:MeOH=10:1) gave 65d as the indicated mixture of diastereoisomers (320 mg, 73%) as a white solid. LC-MS (Agilent): $R_t$ 3.20 min; m/z calculated for $C_{24}H_{33}N_3O_5$ [M+H]$^+$ 444.2, found [M+H]$^+$ 444.2. HPLC (JULY-L) (214 and 254 nm): $R_t$ 8.08 min.

4. Procedure for the Preparation of Compound 65e

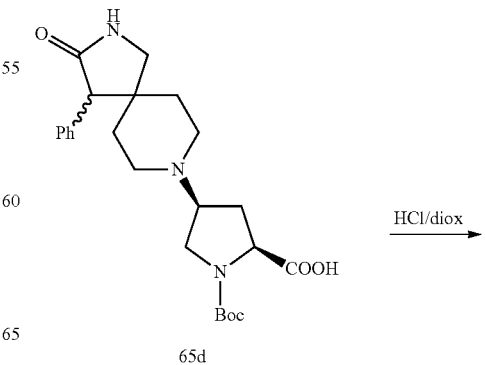

-continued

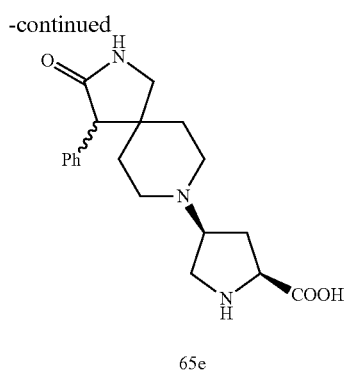

65e

To a stirred suspension of 65d (270 mg, 0.61 mmol) in a 4 M HCl/dioxane solution (5 mL) was added a 6 M aqueous HCl solution (0.5 mL). The resulting homogeneous mixture was then stirred at RT for 2 h, LCMS analysis showed the reaction was complete. The mixture was concentrated in vacuo to give crude 65e (250 mg) and a portion (80 mg) was purified by prep-HPLC to give pure 65e as the indicated mixture of diastereoisomers (40 mg, 59%) as a white solid. The remaining crude product was used directly in the next step. LC-MS (Agilent): $R_t$ 0.97 min; m/z calculated for $C_{19}H_{25}N_3O_3$ [M+H]$^+$ 344.2, found [M+H]$^+$ 344.2. HPLC (JULY-L) (214 and 254 nm): $R_t$ 3.19 min.

5. Procedure for the Preparation of Compound 65

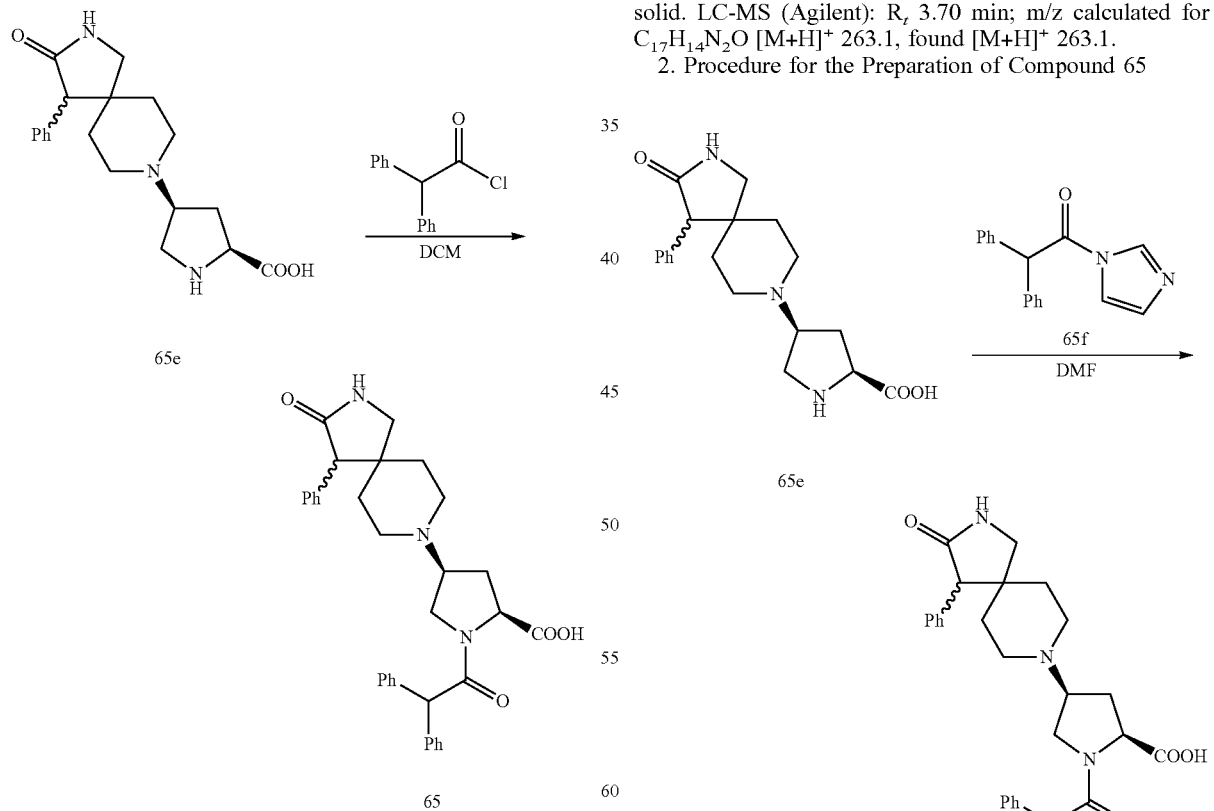

To a stirred mixture of crude 65e (130 mg, 0.34 mmol) and Et$_3$N (86 mg, 0.85 mmol) in DCM (10 mL) at 0° C. was added diphenylacetyl chloride (94 mg, 0.41 mmol) in DCM (2 mL) under a N$_2$ atmosphere and the mixture was stirred at 0° C. for 1 h, TLC (DCM:MeOH=10:1) showed a new product was formed. The mixture was partitioned between DCM/water (10 mL/15 mL) and the aqueous layer was acidified to pH 3 with a 6 M aqueous HCl solution. The organic layer was collected, concentrated in vacuo and the residue was purified by prep-HPLC to give 65 as the indicated mixture of diastereoisomers (8.5 mg, 5%) as a white solid. LC-MS (Agilent): $R_t$ 3.47 min; m/z calculated for $C_{33}H_{35}N_3O_4$ [M+H]$^+$ 538.3, found [M+H]$^+$ 538.3. HPLC (JULY-L) (214 and 254 nm): $R_t$ 8.50 min.

Example 24: Alternative Synthesis of Compound 65

1. Procedure for the Preparation of Compound 65f

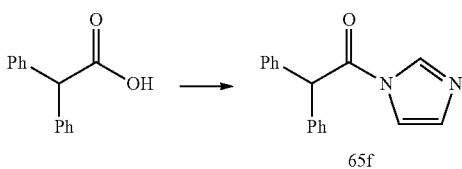 [SMILES: O=C(O)C(c1ccccc1)c1ccccc1 ; O=C(C(c1ccccc1)c1ccccc1)n1ccnc1]

To a stirred solution of diphenyl acetic acid (5.0 g, 23.5 mmol) in DCM (50 mL) at 0° C. was added CDI (4.6 g, 28.3 mmol) in portions and the mixture was stirred at RT for 1 h, TLC (DCM:MeOH=20:1) showed the starting material was consumed. The mixture was washed with water (30 mL×2) and brine (30 mL×2), dried over Na$_2$SO$_4$, filtered and concentrated in vacuo to give 65f (5.6 g, 90%) as a white solid. LC-MS (Agilent): $R_t$ 3.70 min; m/z calculated for $C_{17}H_{14}N_2O$ [M+H]$^+$ 263.1, found [M+H]$^+$ 263.1.

2. Procedure for the Preparation of Compound 65

To a stirred solution of pure 65e (27 mg, 0.079 mmol) in DMF (1 mL) was added tetra methyl guanidine (9.3 mg, 0.081 mmol) under a $N_2$ atmosphere and the mixture was stirred at RT for 1 h. Compound 65f (25 mg, 0.094 mmol) was added and stirring was continued at RT overnight. More compound 65f (24.7 mg, 0.094 mmol) was added stirring was continued at RT for another day. Water (10 mL) was added and the mixture was basified to pH 9 with $K_2CO_3$ and washed with ether. The aqueous layer was then acidified to pH 3-4 with a 1 M aqueous HCl solution and extracted with $CHCl_3$/i-PrOH (v/v=3/1, 15 mL×3). The combined organic extracts were concentrated in vacuo and the residue was purified by prep-HPLC to give 65 as the indicated mixture of diastereoisomers (7 mg, 16%) as a white solid. LC-MS (Agilent): $R_t$ 3.41 min; m/z calculated for $C_{33}H_{35}N_3O_4$ $[M+H]^+$ 538.3, found $[M+H]^+$ 538.3. HPLC (JULY-L) (214 and 254 nm): $R_t$ 8.50 min.

Example 25: Compound 70 (2S,4S)-4-(2-benzylpiperidin-1-yl)-1-(2,2-diphenylacetyl)-pyrrolidine-2-carboxylic acid 1. Procedure for the Preparation of Compound 70a

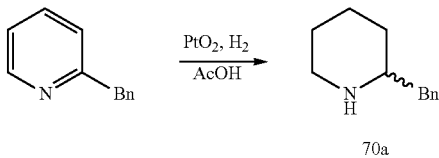 [SMILES: "AcOH" ; c1ccc(Cc2ccccn2)cc1 ; c1ccc(CC2CCCCN2)cc1]

A mixture of 2-benzyl pyridine (2.0 g, 1.08 mmol) and $PtO_2$ (200 mg, 0.72 mmol) in AcOH (20 mL) was stirred at RT under a $H_2$ atmosphere (0.6 Mpa) for 6 h, TLC (PE: EA=4:1) showed the starting material was consumed. The mixture was filtered and the filtrate was concentrated in vacuo. The residue was partitioned between DCM (30 mL) and water (30 mL) and the aqueous layer was basified to pH 8-9 with $K_2CO_3$. The organic layer was separated, washed with brine (15 mL), dried over $Na_2SO_4$, filtered and concentrated in vacuo to give 70a (1.9 g, 94%) as a colorless oil. LC-MS (Agilent): $R_t$ 2.77 min; m/z calculated for $C_{12}H_{17}N$ $[M+H]^+$ 176.1, found $[M+H]^+$ 176.2.

2. Procedure for the Preparation of Compound 70b

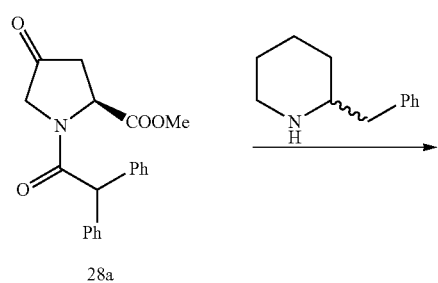

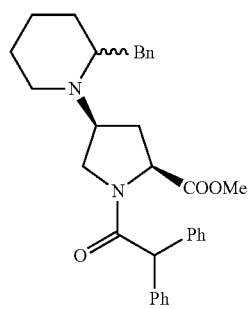

To a stirred solution of compound 28a (900 mg, 2.67 mmol) and 2-benzyl piperidine (compound 70a) (468 mg 2.67 mmol) in DCE (10 mL) was added AcOH (0.5 mL) and the mixture was stirred at RT for 30 min then cooled to 0° C. $NaBH(OAc)_3$ (849 mg, 4.01 mmol) was added and stirring was continued at RT overnight, TLC (PE:EA=1:1) showed most of the starting material was consumed. The mixture was partitioned between DCM (20 mL) and a saturated aqueous $NaHCO_3$ solution (20 mL). The organic layer was separated, washed with brine, dried over $Na_2SO_4$, filtered and concentrated in vacuo. The residue was purified by chromatography (DCM:EA=1:0 to 5:1) to give one diastereoisomer 70b-A (170 mg, 13%) as a white solid. Further elution then gave the other diastereoisomer 70b-B (150 mg, 12%) as a white solid. The absolute stereochemistry of these diastereoisomers was not determined and therefore are referred to as 70-A and 70-B.

LCMS for Compound 70b-A

LC-MS (Agilent): $R_t$ 3.42 min; m/z calculated for $C_{32}H_{36}N_2O_3$ $[M+H]^+$ 497.3, found $[M+H]^+$ 497.3.

LCMS for Compound 70b-B

LC-MS (Agilent): $R_t$ 3.39 min; m/z calculated for $C_{32}H_{36}N_2O_3$ $[M+H]^+$ 497.3, found $[M+H]^+$ 497.3.

3. Procedure for the Preparation of Compound 70-A

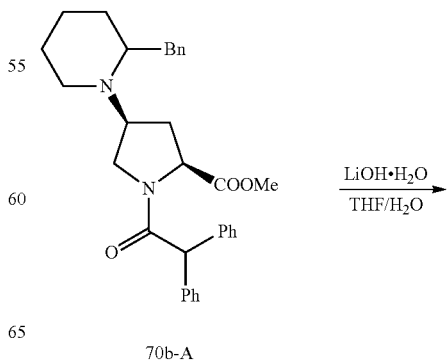

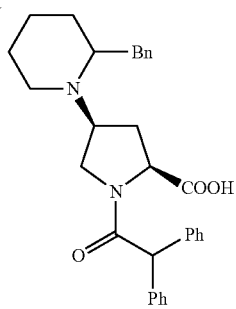

70-A

To a stirred solution of compound 70b-A (170 mg, 0.34 mmol) in THF/water (5 mL/1 mL) at 0° C. was added LiOH.H$_2$O (36 mg, 0.85 mmol) and the mixture was stirred at RT overnight, TLC (PE:EA=1:1) showed the starting material was consumed. Most of the THF was removed in vacuo and the residue was dissolved in water (15 mL), cooled in an ice-water bath and acidified to pH 3~4 with a 1 M aqueous HCl solution. The resulting precipitate was collected by filtration and re-crystallized from EA (20 mL) to give 70-A (23 mg, 14%) as a white solid. LC-MS (Agilent): R$_t$ 3.51 min; m/z calculated for C$_{31}$H$_{34}$N$_2$O$_3$ [M+H]$^+$ 483.3, found [M+H]$^+$ 483.3. HPLC (214 and 254 nm): R$_t$ 8.76 min.

4. Procedure for the Preparation of Compound 70-B

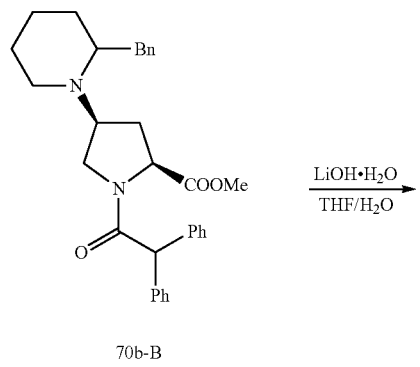

70b-B

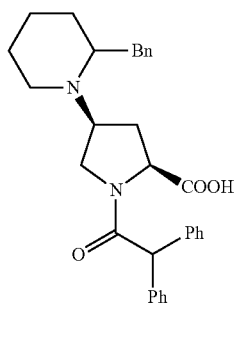

70-B

The hydrolysis reaction from 3. above was repeated for 70b-B (150 mg, 0.30 mmol) and after acidification, the aqueous mixture was then extracted with chloroform (15 mL×3) and the combined organic extracts were washed with brine (15 mL), dried over Na$_2$SO$_4$, filtered and concentrated in vacuo to give 70-B (120 mg, 83%) as a thick oil. LC-MS (Agilent): R$_t$ 3.68 min; m/z calculated for C$_{31}$H$_{34}$N$_2$O$_3$ [M+H]$^+$ 483.3, found [M+H]$^+$ 483.3. HPLC (JULY-L) (214 and 254 nm): R$_t$ 8.96 min.

Example 26: Compound 55 (2S,4R)-4-(2-(benzyloxy)ethyl)-1-(2,2-diphenylacetyl)-pyrrolidine-2-carboxylic acid 1. Procedure for the Preparation of 28a

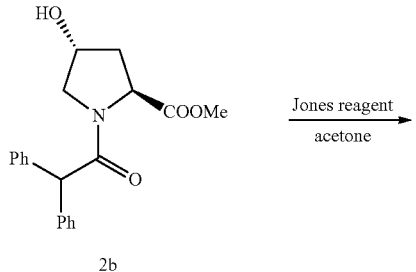

2b

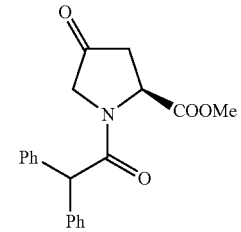

28a

To a solution of 2b (7.00 g, 20.6 mol) in acetone (70 mL) at 0° C. was added Jones reagent (2.6 M, 9.00 mL, 28.9 mol) and the mixture was allowed to warm to RT and stirred for 20 min, TLC (PE:EA=2:1) showed the starting material was consumed. The reaction was quenched with isopropanol, Celite (3 g) was added and the mixture was filtered. The filtrate was concentrated in vacuo and the residue was partitioned between EA (40 mL) and water (40 mL). The layers were separated and the organic phase was washed with a saturated aqueous NaHCO$_3$ solution (30 mL), brine (30 mL×2) then dried over Na$_2$SO$_4$, filtered and concentrated in vacuo. The residue was purified by chromatography (PE:EA=1:0 to 2:1) to give 28a (5.95 g, 85%) as a white solid. LC-MS (Agilent, P-2): R$_t$ 2.79 min; m/z calculated for C$_{20}$H$_{19}$NO$_4$ [M+H]$^+$ 338.1, found [M+H]$^+$ 338.1.

2. Procedure for the Preparation of 55a

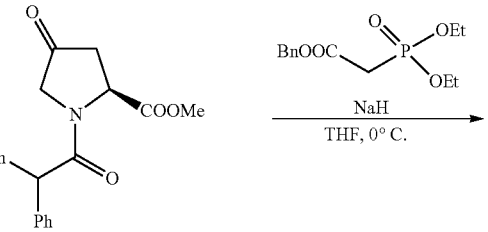

28a

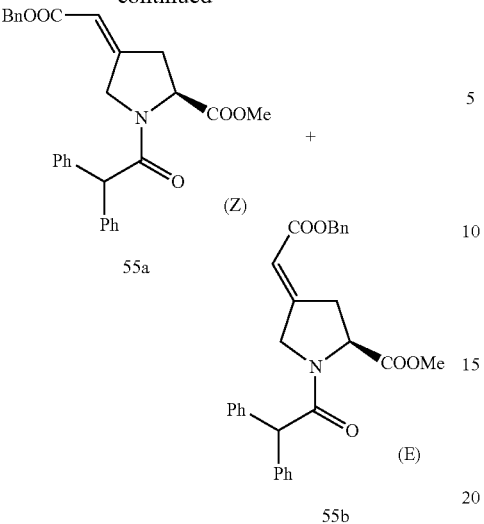

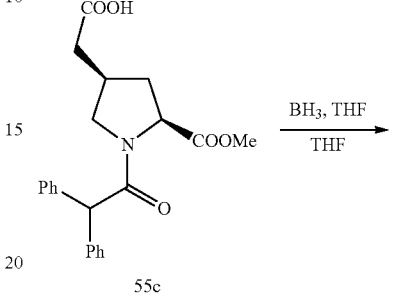

To a solution of benzyl 2-(diethoxyphosphoryl)acetate (1.68 g, 6.52 mmol) in dry THF (10 mL) at 0° C. was added NaH (60% dispersion in mineral oil, 260 mg, 6.52 mmol) in portions and the mixture was stirred at 0° C. for 30 min. A solution of 28a (2.00 g, 5.93 mmol) in THF (10 mL) was then added and stirring was continued at 0° C. for a further 40 min, TLC (PE:EA=2:1) showed that the starting material was consumed. The reaction was quenched with ice-water (40 mL) and the mixture was extracted with EA (20 mL×2). The combined organic extracts were washed with brine, dried over $Na_2SO_4$, filtered and concentrated in vacuo. The residue was purified by chromatography (PE:EA=1:0 to 5:1) to give the first eluting product 55a (1.0 g, 36%) and second eluting product 55b (1.8 g, 64%) as thick oils, which were assigned as Z and E isomers respectively. LC-MS (Agilent, P-2) for 55a: $R_t$ 3.02 min; m/z calculated for $C_{29}H_{27}NO_5$ $[M+H]^+$ 470.2, found $[M+H]^+$ 470.2. LC-MS (Agilent, P-2) for 55b: $R_t$ 3.01 min; m/z calculated for $C_{29}H_{27}NO_5$ $[M+H]^+$ 470.2, found $[M+H]^+$ 470.2.

3. Procedure for the Preparation of 55c

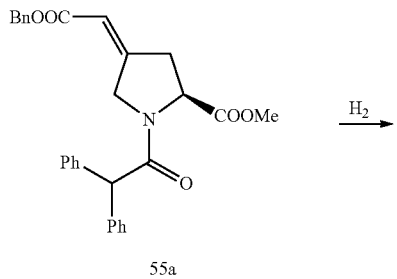

A mixture of 55a (1.00 g, 2.1 mmol) and 10% Pd/C (100 mg) in MeOH (20 mL) was stirred at RT under a, $H_2$ atmosphere (1 atm) overnight, TLC (PE:EA=2:1) showed that the starting material was consumed. The mixture was filtered and the filtrate was concentrated in vacuo to give 55c (0.75 g, 87%) as a white solid. LC-MS (Agilent, P-2): $R_t$ 2.70 min; m/z calculated for $C_{22}H_{23}NO_5$ $[M+H]^+$ 382.1, found $[M+H]^+$ 382.1.

4. Procedure for the Preparation of 55d

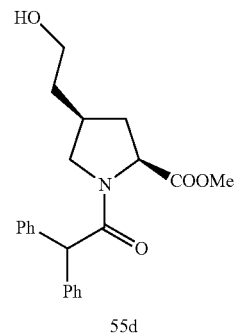

To a solution of 55c (0.70 g, 1.8 mmol) in dry THF (20 mL) at 0° C. under $N_2$ was added $BH_3$/THF (1 M solution in THF, 2.00 mL, 2.00 mmol) and the mixture was stirred at 0° C. for 1 h, TLC (DCM:MeOH=10:1) showed that the starting material was consumed. The reaction was quenched with MeOH (2 mL), a 3 M aqueous HCl solution (5 mL) was added and the mixture was stirred at RT for 1 h then partitioned between EA and brine. The layers were separated and the organic phase was dried over $Na_2SO_4$, filtered and concentrated in vacuo. The residue was purified by chromatography (PE:EA=1:0 to 1:1) to give 55d (500 mg, 76%) as a colorless oil. LC-MS (Agilent, P-2): $R_t$ 2.74 min; m/z calculated for $C_{22}H_{25}NO_4$ $[M+H]^+$ 368.2, found $[M+H]^+$ 368.2.

5. Procedure for the Preparation of 55e

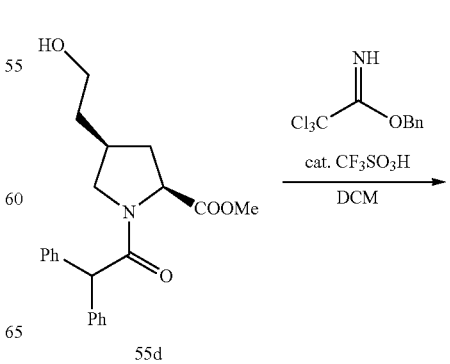

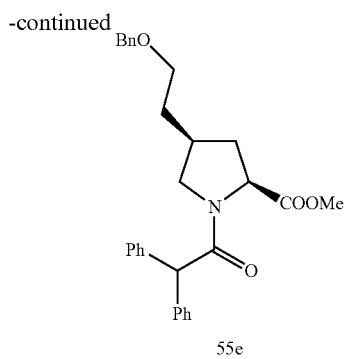

55e

To a solution of 55d (200 mg, 0.54 mmol) and benzyl 2,2,2-trichloroacetimidate (151 mg, 0.59 mmol) in DCM (10 mL) at RT was added 1 drop of $CF_3SO_3H$ and the mixture was stirred at RT overnight, TLC (DCM:MeOH=10:1) showed that the starting material was consumed. The mixture was washed with brine then dried over $Na_2SO_4$, filtered and concentrated in vacuo. The residue was purified by chromatography (PE:EA=1:0 to 4:1) to give 55e (120 mg, 50%) as a colorless oil. LC-MS (Agilent, P-2): $R_t$ 3.05 min; m/z calculated for $C_{29}H_{31}NO_4[M+H]^+$ 458.2, found $[M+H]^+$ 458.2.

6. Procedure for the Preparation of 55

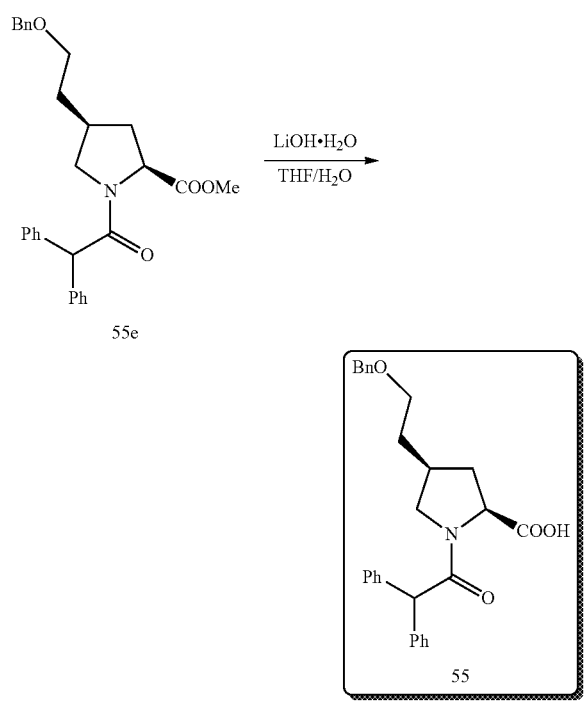

A mixture of 55e (120 mg, 0.26 mmol) and $LiOH \cdot H_2O$ (33 mg, 0.78 mmol) in THF/water (3 mL/1 mL) was stirred at RT overnight, TLC (PE:EA=2:1) showed that the starting material was consumed. Most of the THF was removed in vacuo and the residue was dissolved in water (20 mL), acidified to pH 3 with a 3 M aqueous HCl solution and extracted with DCM (20 mL×2). The combined organic extracts were washed with brine, dried over $Na_2SO_4$, filtered and concentrated in vacuo. The residue was purified by preparative HPLC to give 55 (90 mg, 78%) as a white solid. LC-MS (Agilent, P-2): $R_t$ 2.95 min; m/z calculated for $C_{28}H_{29}NO_4$ $[M+H]^+$ 444.2, found $[M+H]^+$ 444.2. HPLC (JULY-L) (214 and 254 nm): $R_t$ 9.25 min.

Example 27: Compound 67 (3R,4S)-1-(2,2-diphenylacetyl)-4-(methyl(3-phenylpropyl) amino)pyrrolidine-3-carboxylic acid and (3S,4R)-1-(2,2-diphenylacetyl)-4-(methyl(3-phenylpropyl) amino) pyrrolidine-3-carboxylic acid 1. Procedure for the Preparation of 67a

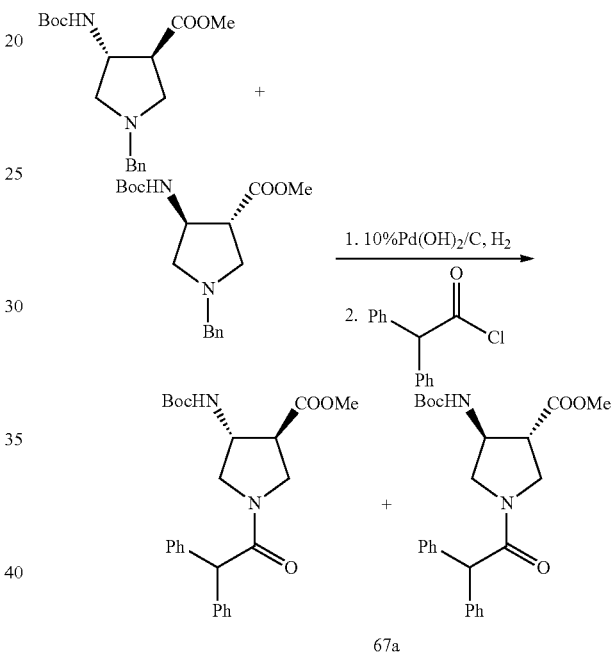

67a

To a solution of (3R,4S)-methyl-1-benzyl-4-(tert-butoxycarbonyl)amino-pyrrolidine-3-carboxylate (500 mg, 1.49 mmol) in MeOH (20 mL) was added Pearlman's catalyst (50 mg) and the mixture was stirred at RT under a $H_2$ atmosphere (1 atm) overnight, TLC (PE:EA=2:1) showed that the starting material was consumed. The mixture was filtered, the filtrate was concentrated in vacuo and the residue was dissolved in DCM (20 mL). Diphenyl acetic acid (347 mg, 1.64 mmol) and EDCI.HCl (343 mg, 1.79 mmol) were added and the mixture was stirred at RT overnight, TLC (DCM:MeOH=10:1) showed the starting material was consumed. The mixture was washed with brine (15 mL×2), dried over $Na_2SO_4$, filtered and concentrated in vacuo. The residue was purified by chromatography (PE:EA=1:0 to 4:1) to give 67a (150 mg, 23%) as a colorless oil. LC-MS (Agilent): $R_t$ 4.37 min; m/z calculated for $C_{25}H_{30}N_2O_5$ $[M+H]^+$ 439.2, $[M+Na]^+$ 461.2, found $[M+H]^+$ 439.2, $[M+Na]^+$ 461.2.

2. Procedure for the Preparation of 67b

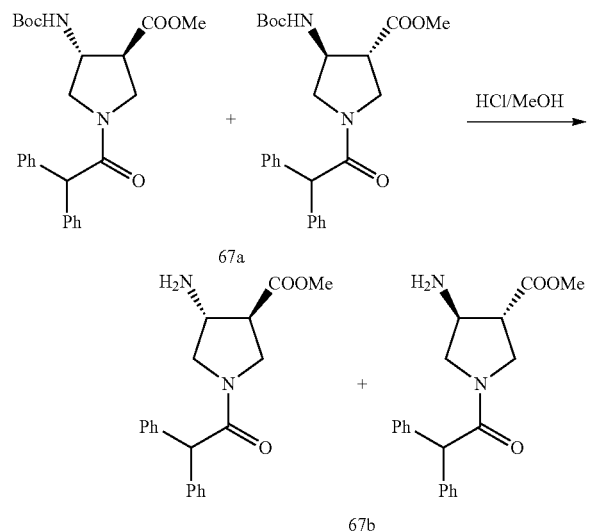

67a (150 mg, 0.34 mmol) was dissolved in a 4 M HCl/MeOH solution (10 mL) and the mixture was stirred at RT overnight, TLC (PE:EA=2:1) showed that the starting material was consumed. The mixture was concentrated in vacuo and the residue was partitioned between DCM (20 mL) and water (15 mL). The aqueous phase was basified to pH 9 with $K_2CO_3$ and the layers were separated. The aqueous layer was further extracted with DCM (10 mL×3) and the combined organic extracts were washed with brine, dried over $Na_2SO_4$, filtered and concentrated in vacuo to give 67b (130 mg, 100%) as a colorless oil which was used directly in the next step. LC-MS (Agilent): $R_t$ 4.13 min; m/z calculated for $C_{20}H_{22}N_2O_3$ $[M+H]^+$ 339.2, found $[M+H]^+$ 339.2.

3. Procedure for the Preparation of 67c

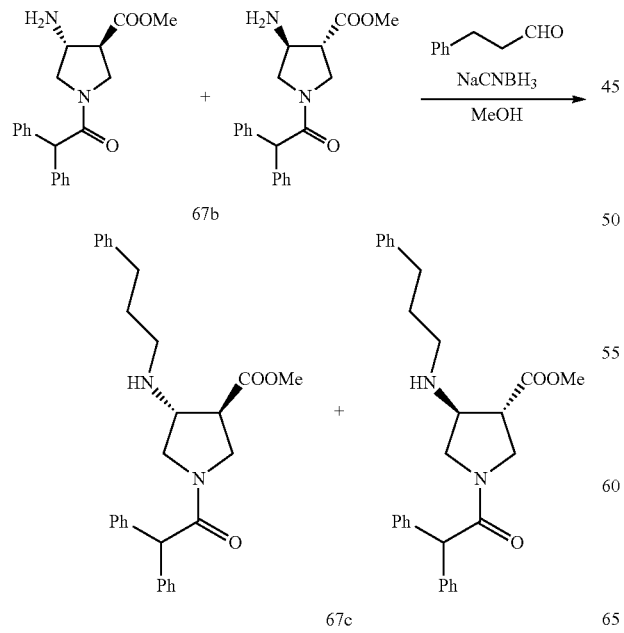

To solution of 67b (130 mg, 0.34 mmol) and 3-phenylpropanal (45 mg, 0.34 mmol) in MeOH (10 mL) was added 1 drop of AcOH and the mixture was stirred at RT for 0.5 h. $NaCNBH_3$ (28 mg, 0.44 mmol) was then added and stirring was continued at RT overnight, TLC (DCM:MeOH=10:1) showed the starting material was consumed. The mixture was concentrated in vacuo and the residue was partitioned between DCM and brine. The organic layer was collected, dried over $Na_2SO_4$, filtered and concentrated in vacuo. The residue was purified by chromatography (PE:EA=1:0 to 2:1) to give 67c (120 mg, 77%) as a colorless oil. LC-MS (Agilent): $R_t$ 3.85 min; m/z calculated for $C_{29}H_{32}N_2O_3$ $[M+H]^+$ 457.2, found $[M+H]^+$ 457.2.

4. Procedure for the Preparation of 67d

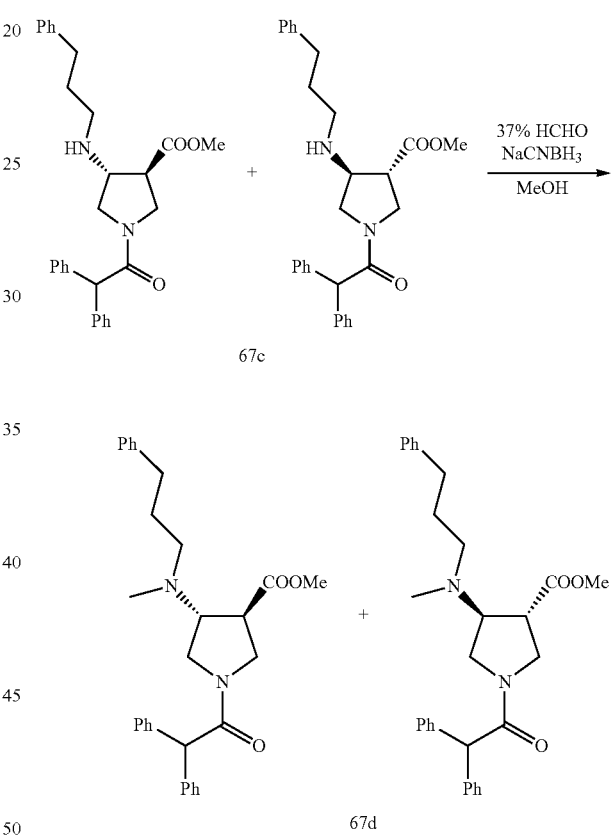

To solution of 67c (120 mg, 0.26 mmol) and 37% aqueous formaldehyde (25 mg, 0.32 mmol) in MeOH (15 mL) at 0° C. was added 2 drops of AcOH and the mixture was stirred at 0° C. for 30 min. $NaCNBH_3$ (20 mg, 0.32 mmol) was added and stirring was continued at RT overnight, TLC (PE:EA=2:1) showed that the starting material was consumed. The mixture was concentrated in vacuo and the residue was partitioned between water (10 mL) and EA (20 mL). The layers were separated and the organic phase was washed with brine (10 mL×2), dried over $Na_2SO_4$, filtered and concentrated in vacuo. The residue was purified by chromatography (PE:EA=5:1 to 3:1) to give 67d (65 mg, 53%) as a colorless oil. LC-MS (Agilent): $R_t$ 3.97 min; m/z calculated for $C_{30}H_{34}N_2O_3$ $[M+H]^+$ 471.3, found $[M+H]^+$ 471.3.

5. Procedure for the Preparation of 67

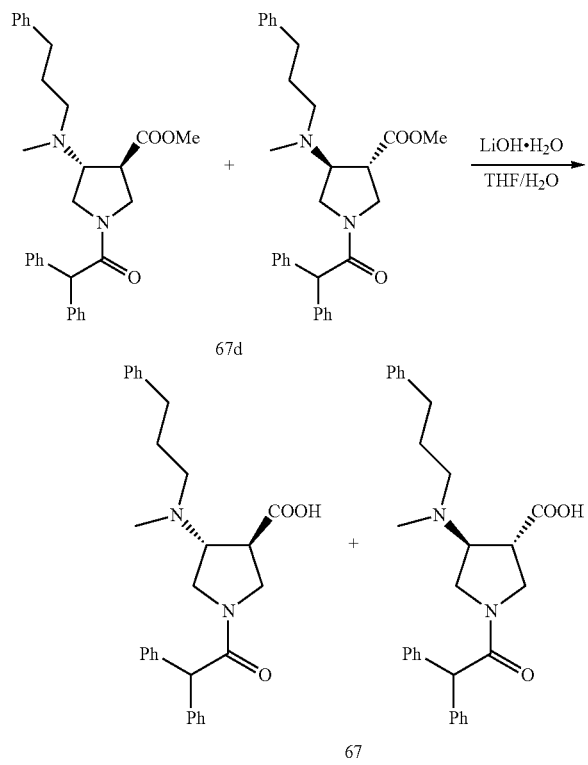

A mixture of 67d (65 mg, 0.14 mmol) and LiOH.H₂O (18 mg, 0.41 mmol) in THF/water (10 mL/2 mL) was stirred at RT overnight, TLC (PE:EA=2:1) showed the starting material was consumed. Most of the THF was removed in vacuo and the residue was dissolved in water H₂O (10 mL), acidified to pH 4~5 with a 3 M aqueous HCl solution and extracted with DCM (10 mL×2). The combined organic extracts were washed with brine (15 mL), dried over Na₂SO₄, filtered and concentrated in vacuo. The residue was purified by preparative HPLC to give 67 (40 mg, 63%) as a white solid. LC-MS (Agilent): R$_t$ 3.78 min; m/z calculated for $C_{28}H_{30}N_2O_3$ [M+H]⁺ 457.3, found [M+H]⁺ 457.3. HPLC (JULY-L) (214 and 254 nm): R$_t$ 8.79 min.

Example 28: Compound 75 (2S,4S)-1-(2,2-diphenylacetyl)-4-(1-oxo-3-phenyl-2,7-diazaspiro[3.5]nonane-7-yl)pyrrolidine-2-carboxylic acid 1. Procedure for the Preparation of 75a

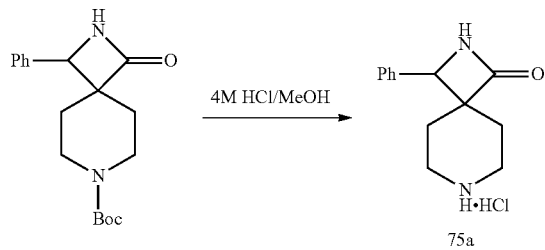

tert-Butyl 1-oxo-3-phenyl-2,7-diazaspiro[3.5]nonane-7-carboxylate (300 mg, 0.94 mmol) was added to a 4 M HCl/MeOH solution (5 mL) at 0° C. and the mixture was stirred at RT for 3 h, after which time a white suspension formed. LCMS analysis showed that the starting material was consumed. EA (3 mL) and diethyl ether (10 mL) were added and the solid material was collected by filtration, washed with diethyl ether (5 mL×2) and dried to give 75a (280 mg, >100%) as a white solid, which was used in the following step without further purification. LC-MS (Agilent): R$_t$ 2.75 min; m/z calculated for $C_{13}H_{16}N_2O$ [M+H]⁺ 217.1, found [M+H]⁺ 217.1.

2. Procedure for the Preparation of 75b

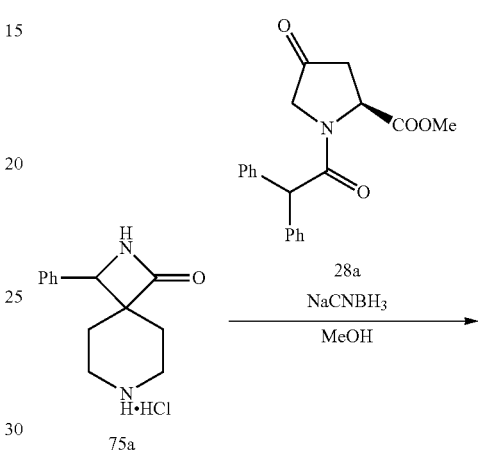

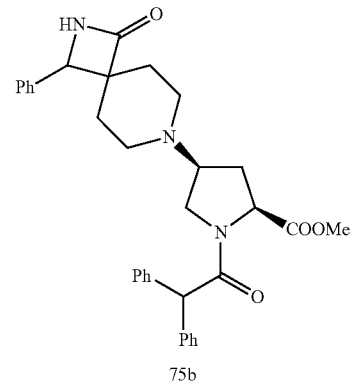

A solution of 28a (100 mg, 0.29 mmol), 75a (75 mg, 0.29 mmol) and Et₃N (33 mg, 0.32 mmol) in MeOH (10 mL) was stirred at RT for 30 min before adding 1 drop of AcOH and NaCNBH₃ (20 mg, 0.32 mmol). The mixture was then allowed to stir at RT overnight, TLC (PE:EA=1:1) showed that the starting material was consumed and 75b was confirmed by LCMS analysis. The reaction was repeated on a larger amount of 75a (200 mg, 0.59 mmol) and the two reaction mixtures were combined and concentrated in vacuo. The residue was dissolved in DCM (30 mL), washed with brine (30 mL) then dried over Na₂SO₄, filtered and concentrated in vacuo. Purification by column chromatography (DCM:MeOH=1:0 to 20:1) gave 75b (60 mg, 12%) as a colorless oil. LC-MS (Agilent): R$_t$ 3.41 min; m/z calculated for $C_{33}H_{35}N_3O_4$ [M+H]⁺ 538.3, [M+Na]⁺ 560.3, found [M+H]⁺ 538.3, [M+Na]⁺ 560.3.

3. Procedure for the Preparation of Compound 75

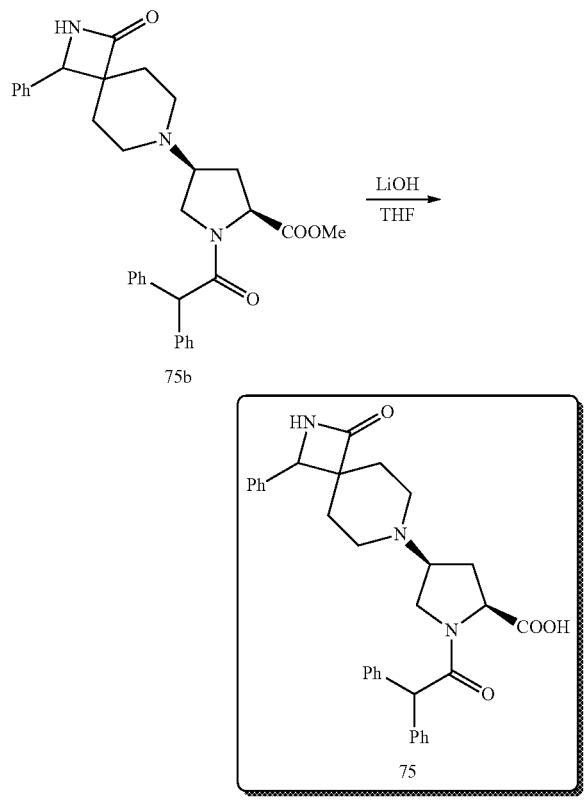

To a mixture of 75b (60 mg, 0.11 mmol) in THF/water (5 mL/1 mL) was added LiOH.H$_2$O (14 mg, 0.33 mmol) and the mixture was stirred at RT overnight, TLC (DCM:MeOH=10:1) showed that the starting material was consumed. Most of THF was removed in vacuo and the residue was dissolved in water (20 mL), acidified to pH 3-4 with a 3 M aqueous HCl solution and extracted with DCM (15 mL×3). The combined organic extracts were washed with brine, dried over Na$_2$SO$_4$, filtered and concentrated in vacuo to give 50 mg of crude product which was suspended in EA (5 mL). The obtained mixture was heated at reflux for 30 min, cooled to RT and the precipitate was collected by filtration then dried to give 75 (25 mg, 43%) as a white solid. LC-MS (Agilent): R$_t$ 3.67 min; m/z calculated for C$_{32}$H$_{33}$N$_3$O$_4$ [M+H]$^+$ 524.3, found [M+H]$^+$ 524.3. HPLC (214 and 254 nm): R$_t$ 8.53 min.

Example 29: Compound 76 (2R,4R)-1-(2,2-diphenylacetyl)-4-(3-phenylpropoxy)-pyrrolidine-2-carboxylic acid

1. Procedure for the Preparation of Compound 76a

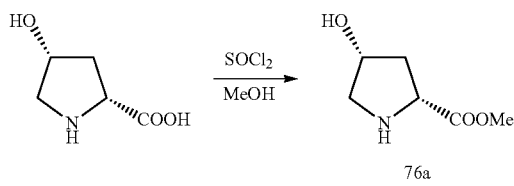 [SMILES: "MeOH" ; O=C(O)[C@H]1C[C@@H](O)CN1 ; "SOCl2" ; COC(=O)[C@H]1C[C@@H](O)CN1]

cis-4-Hydroxy-D-proline was prepared using the procedure described in *Tetrahedron Asymmetry*, 2002, 13, 197. To a solution of cis-4-Hydroxy-D-proline (20 g, 0.15 mol) in MeOH (200 mL) at 0° C. was added SOCl$_2$ (19.9 g, 0.17 mol) dropwise and the mixture was then heated at 70° C. overnight, LCMS analysis showed that the starting material was consumed. The mixture was cooled to RT and concentrated in vacuo to give 76a (22 g, 100%) as brown solid. LC-MS (Agilent): R$_t$ 0.64 min; m/z calculated for C$_6$H$_{11}$NO$_3$ [M+H]$^+$ 146.1, found [M+H]$^+$ 146.1.

2. Procedure for the Preparation of 76b

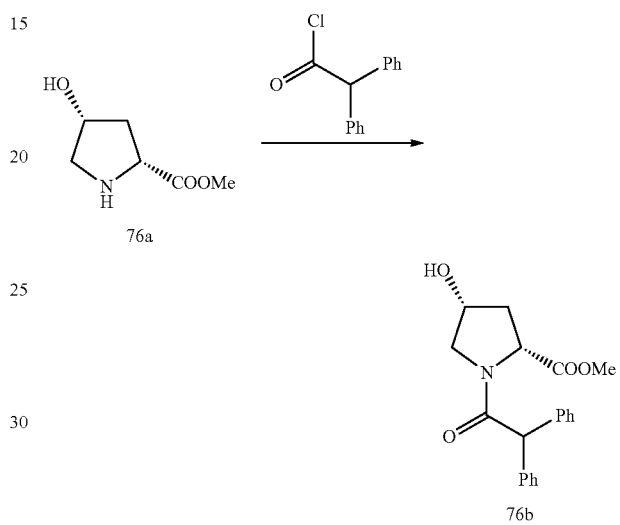

To a solution of diphenylacetic acid (15.9 g, 75.2 mmol) in DCM (150 mL) at 0° C. was added DMF (2 drops) and SOCl$_2$ (11.6 g, 87.7 mmol) and the mixture was heated at reflux for 2 h. The solvent was removed in vacuo and the residue was dissolved in ether (20 mL) and added slowly to a mixture of 76a (15 g, 83 mmol) and K$_2$CO$_3$ (15.6 g, 113 mmol) in water (250 mL) and ether (100 mL) at 0° C. The mixture was stirred at 0° C. for 2 h, TLC (PE:EA=1:1) showed a major new product was formed. The layers were separated and the aqueous layer was extracted with EA (80 mL×2). The combined organic extracts were washed with brine, dried over Na$_2$SO$_4$, filtered and concentrated in vacuo. The residue was purified by column chromatography (PE:EA=10:1 to 3:1) to give 76b (20 g, 80%)' as a yellow solid. LC-MS (Agilent): R$_t$ 3.53 min; m/z calculated for C$_{20}$H$_{21}$NO$_4$ [M+H]$^+$ 340.1 found [M+H]$^+$ 340.1.

3. Procedure for the Preparation of 76c

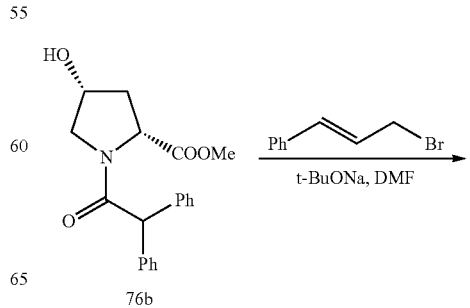

111
-continued

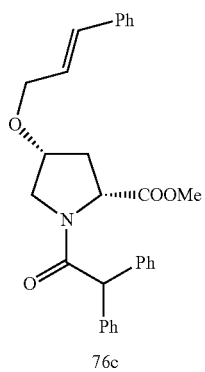

76c

To a stirred solution of 76b (1.0 g, 2.9 mmol) and cinnamyl bromide (0.87 g, 4.4 mmol) in DMF (20 mL) −40° C. was added t-BuONa (0.28 g, 2.9 mmol) in portions and the mixture was stirred at −40° C. for 2 h, TLC (PE:EA=1:1) showed that the starting material was consumed. The mixture was allowed to warm to 0° C., water (100 mL) was added and extracted with EA (30 mL×2). The combined organic extracts were washed with water (20 mL), brine (20 mL×2), dried over $Na_2SO_4$, filtered and concentrated in vacuo. The residue was purified by column chromatography (PE:EA=10:1 to 3:1) to give 76c (0.8 g, 62%) as a white solid. LC-MS (Agilent): $R_t$ 4.03 min; m/z calculated for $C_{29}H_{29}NO_4$ [M+H]$^+$ 456.2, found [M+H]$^+$ 456.1.

4. Procedure for the Preparation of 76d

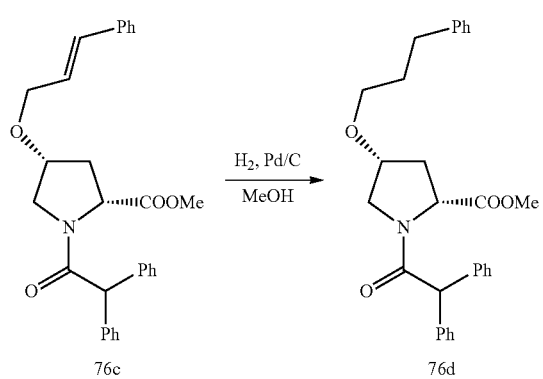 [SMILES: "MeOH" ; COC(=O)[C@H]1C[C@@H](OC/C=C/c2ccccc2)CN1C(=O)C(c1ccccc1)c1ccccc1 ; COC(=O)[C@H]1C[C@@H](OCCCc2ccccc2)CN1C(=O)C(c1ccccc1)c1ccccc1]

To a solution of 76c (400 mg, 0.88 mmol) in MeOH (15 mL) was added 10% Pd/C (40 mg) and the mixture was stirred at RT under a $H_2$ atmosphere (1 atm) overnight, TLC (PE:EA=2:1) showed that the starting material was consumed. The mixture was filtered through Celite and the filtrate was concentrated in vacuo to give 76d (370 mg, 92%) as a colorless oil. LC-MS (Agilent): $R_t$ 4.12 min; m/z calculated for $C_{29}H_{31}NO_4$ [M+H]$^+$ 458.2, found [M+H]$^+$ 458.2.

112

5. Procedure for the Preparation of Compound 76

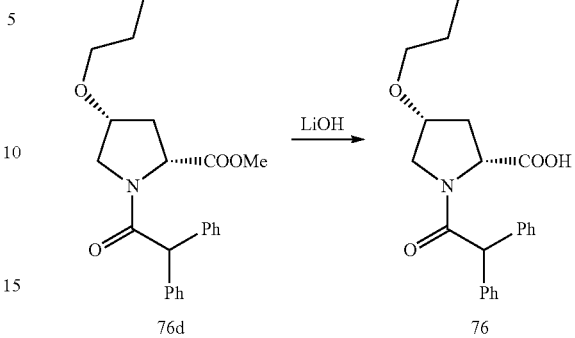

To a stirred solution of 76d (370 mg, 0.8 mmol) in THF/$H_2O$ (10 mL/3 mL) was added LiOH.$H_2O$ (102 mg, 2.4 mmol) and the mixture was heated at 30° C. overnight, TLC (PE:EA=2:1) showed that the starting material was consumed. Most of the THF was removed in vacuo and the residue was dissolved in water (20 mL) and washed with $Et_2O$ (15 mL×2). DCM (15 mL) was added and the aqueous layer was acidified to pH 2-3 with a 3 M aqueous HCl solution. The layers were separated and the aqueous layer was further extracted with DCM (15 mL). The combined organic extracts were washed with brine, dried over $Na_2SO_4$, filtered and concentrated in vacuo to give compound 76 (300 mg, 85%) as a white solid. LC-MS (Agilent): $R_t$ 3.99 min; m/z calculated for $C_{28}H_{29}NO_4$ [M+H]$^+$ 444.2, found [M+H]$^+$ 444.2. HPLC (214 and 254 nm): $R_t$ 9.36 min.

Example 30: Compound 90 (2S,4S)-1-(2,2-diphenylacetyl)-4-(methyl(4-phenylbutyl)-amino)pyrrolidine-2-carboxylic acid 1. Procedure for the Preparation of 90a

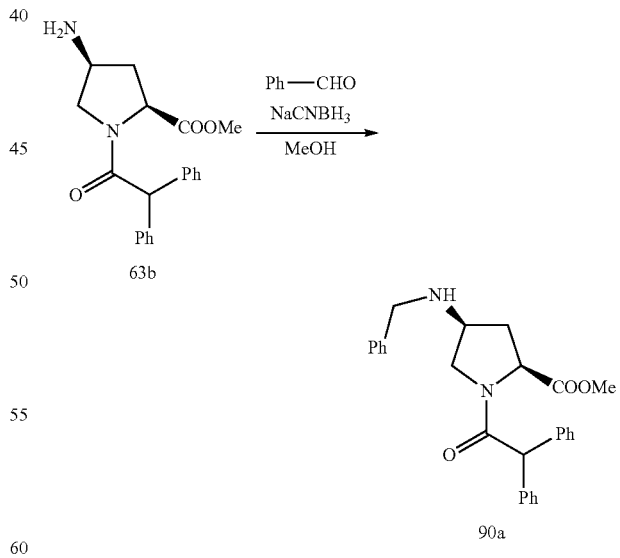

To a stirred solution of 63b (100 mg, 0.29 mmol) and benzaldehyde (25 mg, 0.24 mmol) in MeOH (5 mL) under nitrogen was added 2 drops of AcOH and the mixture was stirred for 1 h then cooled to 0° C. NaCNBH$_3$ (22 mg, 035 mmol) was added and the mixture was allowed to warm slowly to RT and stirred overnight, TLC (DCM:MeOH=10:

1) showed that most of the starting material was consumed. Most of the MeOH was removed in vacuo, water (15 mL) was added and the mixture was extracted with EA (15 mL×2). The combined organic extracts were washed with brine, dried over $Na_2SO_4$ and concentrated in vacuo to give the crude 90a (150 mg) as a yellow oil. The procedure was repeated and the crude batches were combined and purified by column chromatography (PE:EA=10:1 to 1:1) to give 90a (2.0 g, 66%) as a white solid. LC-MS (Agilent): $R_t$ 3.42 min; m/z calculated for $C_{27}H_{28}N_2O_3$ $[M+H]^+$ 429.2, found $[M+H]^+$ 429.2.

2. Procedure for the Preparation of 90b

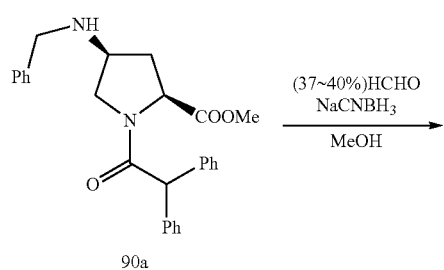

To a stirred solution of 90a (2.00 g, 4.67 mmol) and formaldehyde (37~40% solution in water, 0.56 g, 7.01 mmol) in MeOH (40 mL) under nitrogen was added 3 drops of AcOH and the mixture was stirred for 1 h then cooled to 0° C. $NaCNBH_3$ (0.35 g, 5.60 mmol) was added and the mixture was allowed to warm slowly to RT and stirred overnight, TLC (DCM:MeOH=20:1) showed that most of the starting material was consumed. Most of the MeOH was removed in vacuo, water (20 mL) was added and the mixture was extracted with DCM (30 mL). The organic layer was washed with brine (25 mL), dried over $Na_2SO_4$ and concentrated in vacuo. The residue was purified by chromatography (PE:EA=10:1 to 4:1) to give 90b (1.86 g, 90%) as a white solid. LC-MS (Agilent): $R_t$ 3.50 min; m/z calculated for $C_{28}H_{30}N_2O_3$ $[M+H]^+$ 443.3, found $[M+H]^+$ 443.3.

3. Procedure for the Preparation of 90c

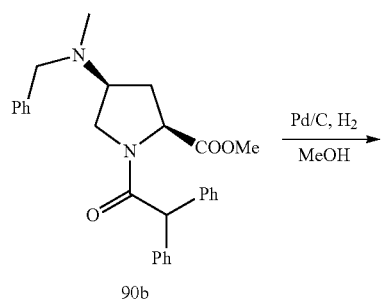

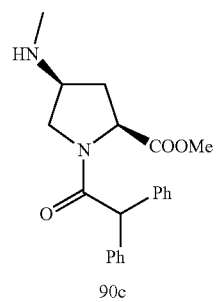

A mixture of 90b (1.86 g, 4.20 mmol) and 10% Pd/C (200 mg) in MeOH (30 mL) was stirred at RT under a $H_2$ atmosphere (1 atm) for 2 days, TLC (DCM:MeOH=10:1) showed that the starting material was consumed. The mixture was filtered and the filtrate was concentrated in vacuo to give 90c (1.40 g, 95%) as colorless oil. LC-MS (Agilent): $R_t$ 3.34 min; m/z calculated for $C_{21}H_{24}N_2O_3$ $[M+H]^+$ 353.2, found $[M+H]^+$ 353.2.

4. Procedure for the Preparation of 90d

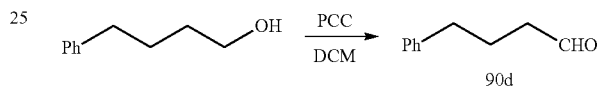

To a solution of 4-phenyl-1-butanol (0.5 g, 3.3 mmol) in DCM (10 mL) was added Celite (0.5 g) followed by PCC (1.8 g, 8.3 mmol) and the mixture was stirred at RT for 3 h, TLC (PE:EA=2:1) showed that the starting material was consumed. The mixture was filtered through a short plug of silica gel using DCM to wash. The filtrate was concentrated in vacuo to give 90d (0.5 g, 100%) as a yellow oil.

5. Procedure for the Preparation of 90e

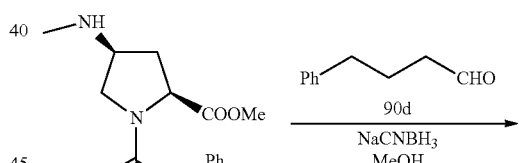

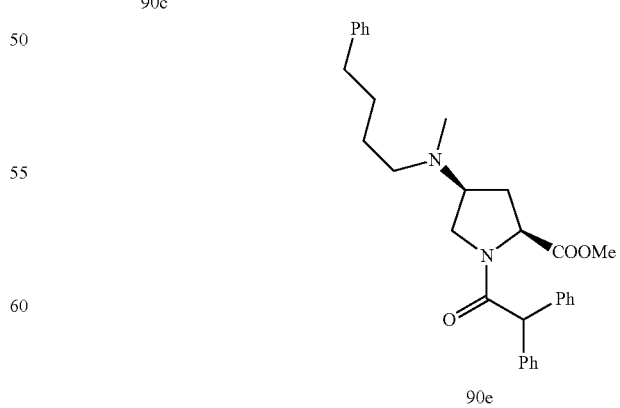

To a stirred solution of 90c (202 mg, 0.57 mmol) and the aldehyde 90d (102 mg, 0.68 mmol) in MeOH (10 mL) at RT was added AcOH (1 drop) and the mixture was stirred for 1 h then cooled to at 0° C. NaCNBH$_3$ (43 mg, 0.68 mmol) was added and the mixture was allowed to warm to RT and stirred overnight, TLC (DCM:MeOH=20:1) showed that the starting material was consumed. The mixture was concentrated in vacuo and the residue was dissolved in water (15 mL) and extracted with DCM. The organic extracts were washed with brine (15 mL×2), dried over Na$_2$SO$_4$, filtered and concentrated in vacuo. Purification by column chromatography (PE:EA=4:1 to 1:1) gave 90e (198 mg, 71%) as thick colorless oil. LC-MS (Agilent): R$_t$ 3.61 min; m/z calculated for C$_{31}$H$_{36}$N$_2$O$_3$ [M+H]$^+$ 485.3, found [M+H]$^+$ 485.3.

6. Procedure for the Preparation of Compound 90

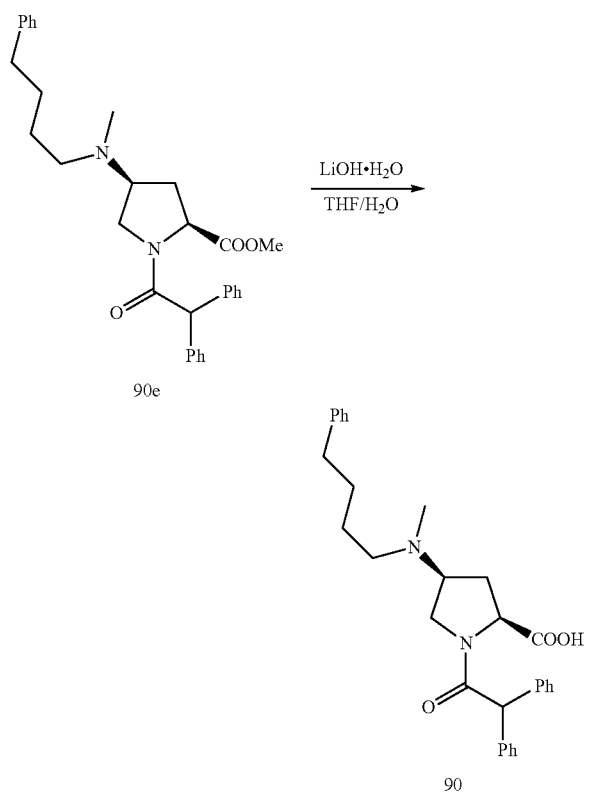

Hydrolysis of 90e (198 mg, 0.41 mmol) was performed as described in Example 27, 5. with 3 equivalents of LiOH.H$_2$O (52 mg, 1.23 mmol) and the mixture was stirred at RT overnight, TLC (DCM:MeOH=20:1). The combined organic extracts were washed with brine (10 mL×2), dried over Na$_2$SO$_4$, filtered and concentrated in vacuo to give 90 (185 mg, 96%) as white solid. LC-MS (Agilent): R$_t$ 3.67 min; m/z calculated for C$_{31}$H$_{36}$N$_2$O$_3$ [M+H]$^+$ 471.3, found [M+H]$^+$ 471.3. HPLC (214 and 254 nm): R$_t$ 8.93 min.

Example 31: Compound 91 (2S,4S)-1-(2,2-diphenylacetyl)-4-((3-(4-fluorophenyl)-propyl)(methyl)amino)pyrrolidine-2-carboxylic acid 1. Procedure for the Preparation of 91a

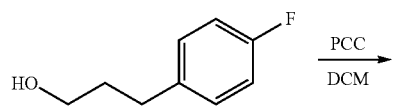

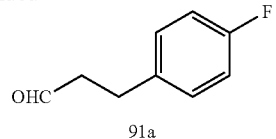

To a solution of the alcohol (1.0 g, 6.5 mmol) in DCM (20 mL) was added Celite (1.5 g) and PCC (3.5 g, 16.2 mmol) and the mixture was stirred at RT for 3 h. TLC (PE:EA=4:1) showed the starting material was consumed. The mixture was charged on to a silica column and flushed with DCM to give 91a (0.8 g, 79%) as a yellow oil, which was used directly in the next step.

2. Procedure for the Preparation of 91b

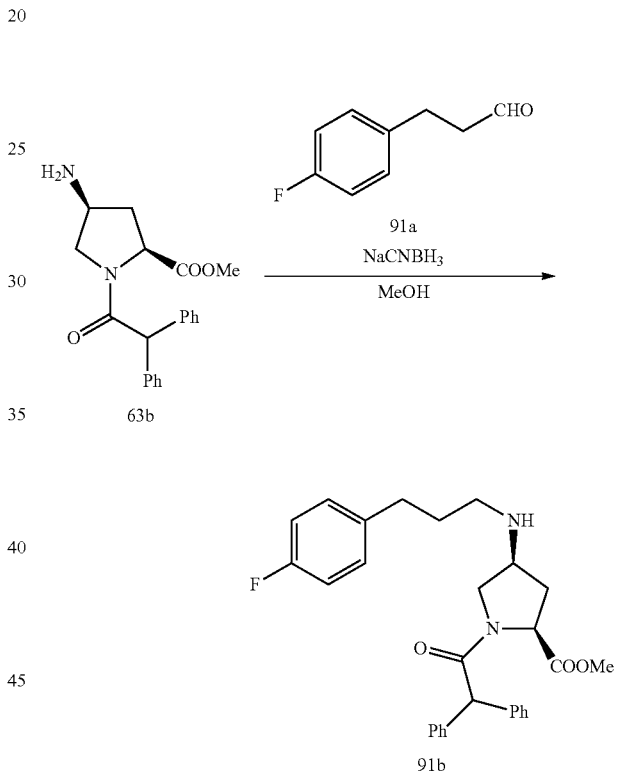

To a solution of 63b (113 mg, 0.33 mmol) and 91a (41 mg 0.27 mmol) in MeOH (10 mL) at 0° C. under a N$_2$ atmosphere was added a drop of AcOH and the mixture was stirred for 30 min. NaCNBH$_3$ (21 mg, 0.33 mmol) was then added and the mixture was allowed to warm slowly to RT and stirred overnight, TLC (DCM:MeOH=10:1) showed most of starting material was consumed. The mixture was concentrated in vacuo to give crude 91b (150 mg) as a yellow oil. The reaction was repeated on a larger batch of 63b (509 mg, 1.5 mmol) and the crude products were combined and purified by column chromatography (DCM:MeOH=50:1 to 20:1) to give 91b (500 mg, 57%) as a white solid. LC-MS (Agilent): R$_t$ 3.37 min; m/z calculated for C$_{29}$H$_{31}$FN$_2$O$_3$ [M+H]$^+$ 475.2, found [M+H]$^+$ 475.3.

3. Procedure for the Preparation of 91c

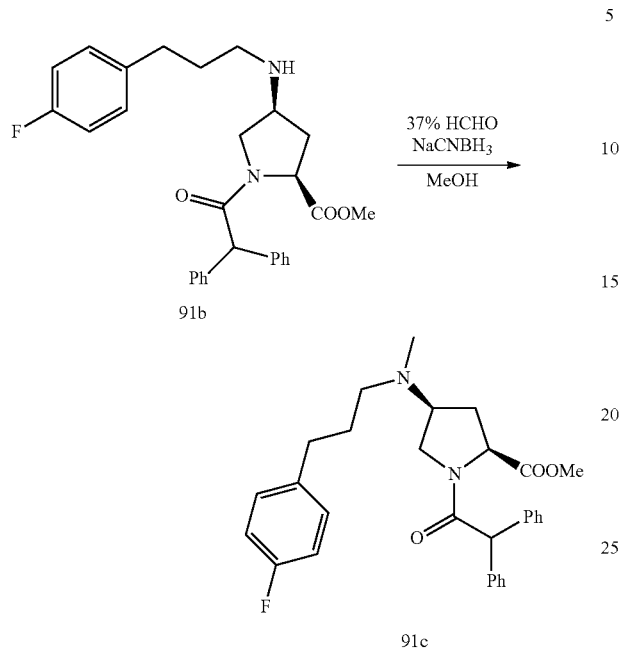

To a solution of 91b (210 mg, 0.44 mmol) and formaldehyde (37% aqueous solution, 72 mg, 0.88 mmol) in MeOH (10 mL) at 0° C. under a $N_2$ atmosphere was added 2 drops of AcOH and the mixture was stirred for 30 min. NaCNBH$_3$ (56 mg, 0.88 mmol) was then added and the mixture was allowed to warm slowly to RT and stirred overnight, TLC (DCM:MeOH=10:1) showed the starting material was consumed. The mixture was concentrated in vacuo and the residue was dissolved in EA (15 mL), washed with water (10 mL), saturated aqueous NaHCO$_3$ solution (15 mL), brine (15 mL) and dried over Na$_2$SO$_4$. The solvent was removed in vacuo and the residue was purified by column chromatography (DCM:MeOH=100:1 to 50:1) to give 91c (170 mg, 79%) as a colorless oil. LC-MS (Agilent): R$_t$ 3.76 min; m/z calculated for $C_{30}H_{33}FN_2O_3$ [M+H]$^+$ 489.3, found [M+H]$^+$ 489.3.

4. Procedure for the Preparation of Compound 91

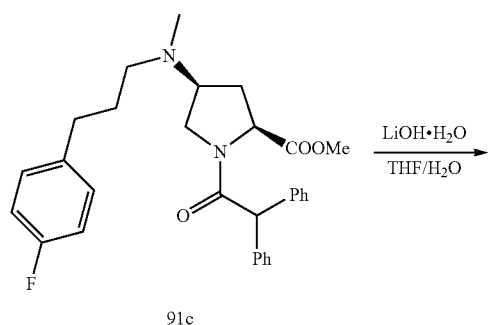

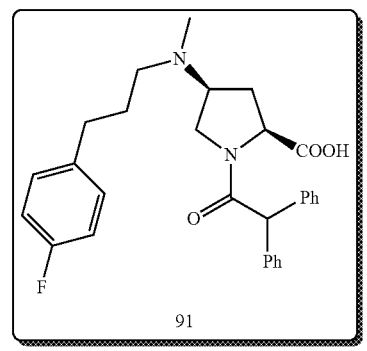

Hydrolysis of 91c (170 mg, 0.35 mmol) was performed using the procedure of Example 9, 3. with about 3 equivalents of LiOH.H$_2$O (44 mg, 1.04 mmol) at RT and the mixture was stirred overnight, TLC (MeOH:DCM=1:10) showed the starting material was consumed. Most of the THF was removed in vacuo and the residue was dissolved in water (15 mL) and washed with Et$_2$O (10 mL×2). The aqueous layer was acidified to pH 2-3 with a 3 M aqueous HCl solution and the resulting precipitate was collected by filtration and dried to give 91 (90 mg, 54%) as a white solid. LC-MS (Agilent): R$_t$ 3.52 min; m/z calculated for $C_{29}H_{31}FN_2O_3$ [M+H]$^+$ 475.2, found [M+H]$^+$ 475.3. HPLC (214 and 254 nm): R$_t$ 8.86 min.

Example 32: Compound 93 (2S,4S)-1-(2,2-diphenylacetyl)-4-(methyl(3-pyridinyl)-propyl)amino)pyrrolidine-2-carboxylic acid

1. Procedure for the Preparation of 93a

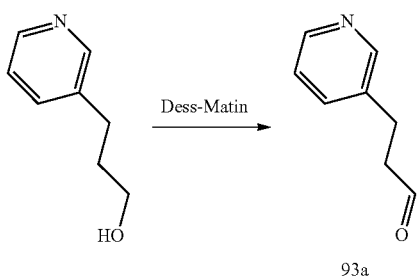 [SMILES: OCCCc1cccnc1 ; O=CCCc1cccnc1]

To a solution of 3-(pyridin-3-yl)propan-1-ol (500 mg, 3.6 mmol) in DCM (10 mL) was added Dess-Martin reagent (1.7 g, 4.0 mmol) and the mixture was stirred at RT overnight, TLC (DCM:MeOH=10:1) showed that the starting material was consumed. Water (20 mL) was added and the solid was removed by filtration. The filtrate layers were separated and the aqueous layer was extracted with DCM (15 mL). The combined organics layers were washed with brine, dried over Na$_2$SO$_4$, filtered and concentrated in vacuo. The residue was purified by chromatography (DCM:MeOH=150:0 to 50:1) to give 93a (200 mg, 40%) as a white solid. LC-MS (Agilent): R$_t$ 0.58 min; m/z calculated for $C_8H_9NO$ [M+H]$^+$ 136.1, found [M+H]$^+$ 136.1.

2. Procedure for the Preparation of 93b.

3. Procedure for the Preparation of Compound 93

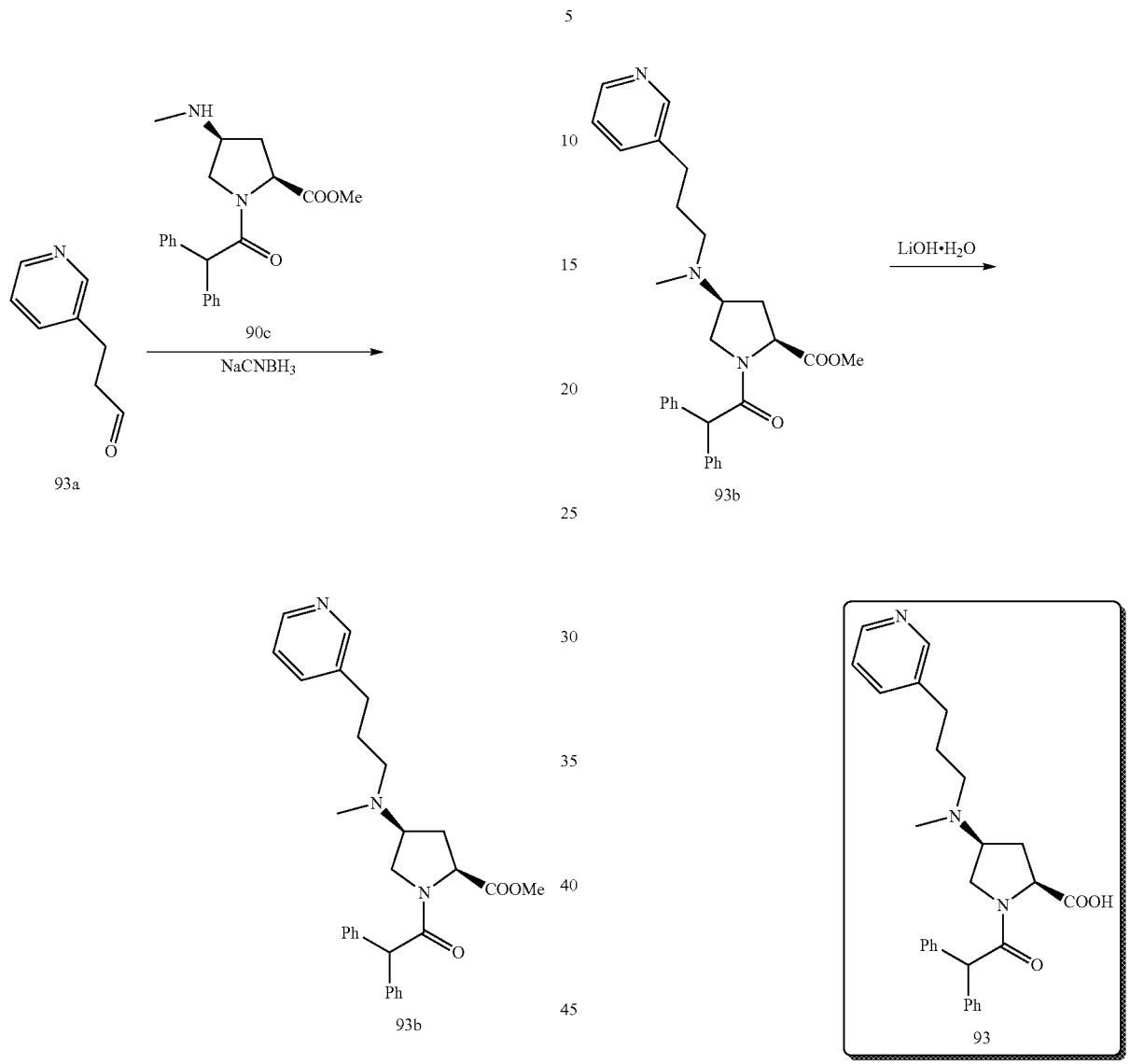

To a solution of 93a (57 mg, 0.42 mmol) and 90c (100 mg, 0.28 mmol) in MeOH (10 mL) was added 2 drops of AcOH and the mixture was stirred at RT for 1 h. NaCNBH$_3$ (27 mg, 0.42 mmol) was added and stirring was continued at RT overnight, TLC (DCM:MeOH=10:1) showed that the starting material was consumed. The mixture was concentrated in vacuo and the residue suspended in water (20 mL) and extracted with EA (15 mL×2). The combined organic extracts were washed with brine, dried over Na$_2$SO$_4$, filtered and concentrated in vacuo. The residue was purified by chromatography (DCM:MeOH=100:1 to 50:1) to give 93b (100 mg, 75%) as a yellow oil. LC-MS (Agilent): R$_t$ 3.52 min; m/z calculated for C$_{29}$H$_{33}$N$_3$O$_3$ [M+H]$^+$ 472.3, found [M+H]$^+$ 472.3.

A mixture of 93b (100 mg, 0.21 mmol) and LiOH.H$_2$O (18 mg, 0.42 mmol) in THF/water (6 mL/2 mL) was stirred at RT overnight, TLC (DCM:MeOH=10:1) showed that the starting material was consumed. Most of the THF was removed in vacuo and the residue was dissolved in water (15 mL) and washed with ether (10 mL). The aqueous layer was acidified to pH 5 with a 3 M aqueous HCl solution and freeze dried to give a white solid, which was suspended in DCM/MeOH and filtered. The filtrate was concentrated in vacuo and the residue was purified by preparative HPLC to give 93 (70 mg, 74%) as a white solid. LC-MS (Agilent): R$_t$ 3.59 min; m/z calculated for C$_{28}$H$_{31}$N$_3$O$_3$ [M+H]$^+$ 458.2, found [M+H]$^+$ 458.2. HPLC (JULY-L) (214 and 254 nm): R$_t$ 8.33 min.

Example 33: Compound 94 (2S,4S)-4-cinnamamido-1-(2,2-diphenylacetyl)-pyrrolidine-2-carboxylic acid 1. Procedure for the Preparation of 94a

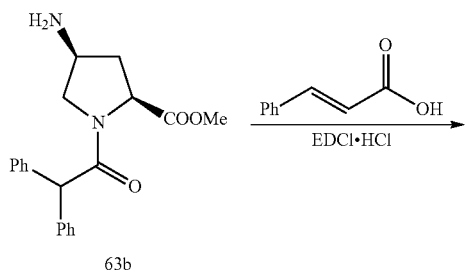

63b

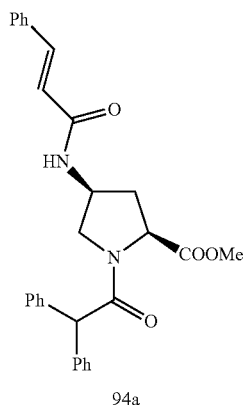

94a

To a solution of 63b (1.05 g, 3.1 mmol) and cinnamic acid (0.46 g, 3.10 mmol) in DCM (40 mL) at RT under nitrogen was added EDCI.HCl (0.65 g, 3.39 mmol) and the mixture was stirred overnight, TLC (DCM:MeOH=10:1) showed the reaction was complete. The mixture was washed with brine (20 mL×2), dried over Na$_2$SO$_4$, filtered and concentrated in vacuo. The residue was purified by column chromatography (PE:EA=1:0 to 1:1) to give 94a (1.28 g, 88%) as a white solid. LC-MS (Agilent): R$_t$ 3.84 min; m/z calculated for C$_{29}$H$_{28}$N$_2$O$_4$ [M+H]$^+$ 469.2, [M+Na]$^+$ 491.2, found [M+H]$^+$ 469.2, [M+Na]$^+$ 491.2.

2. Procedure for the Preparation of Compound 94

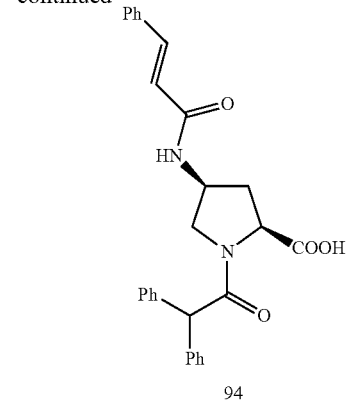

94

To a mixture of 94a (300 mg, 0.64 mmol) in THF/H$_2$O (15 mL/2 mL) was added LiOH.H$_2$O (81 mg, 1.92 mmol) and the mixture was stirred at RT overnight, TLC (DCM:MeOH=10:1) showed the starting material was consumed. Most of the THF was removed in vacuo and the residue was dissolved in water H$_2$O (20 mL), acidified to pH 2-3 with a 3 M aqueous HCl solution and extracted with DCM (25 mL×2). The combined organic extracts were washed with brine (20 mL), dried over Na$_2$SO$_4$, filtered and concentrated in vacuo to give 94 (286 mg, 98%) as a white solid. LC-MS (Agilent): R$_t$ 3.71 min; m/z calculated for C$_{28}$H$_{26}$N$_2$O$_4$ [M+H]$^+$ 455.2, found [M+H]$^+$ 455.2. HPLC (214 and 254 nm): R$_t$ 9.08 min.

Example 34: Compound 95 (2S,4S)-1-(2,2-diphenylacetyl)-4-(N-methylcinnamamido)-pyrrolidine-2-carboxylic acid 1. Procedure for the Preparation of 95a

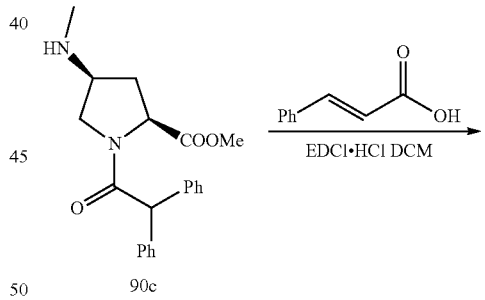

95a

To a stirred solution of 90c (300 mg, 0.85 mmol) and cinnamic acid (126 mg, 0.85 mmol) in DCM (15 mL) at RT under nitrogen was added EDCI.HCl (180 mg, 0.94 mmol)

and the mixture was stirred overnight, TLC (DCM: MeOH=10:1) showed that the starting material was consumed. The mixture was washed with a saturated aqueous NaHCO₃ solution (15 mL×2), a 0.5 M aqueous HCl solution (15 mL×2), brine (15 mL×2), dried over Na₂SO₄ and filtered. The solvent was removed in vacuo and the residue was purified by column chromatography (PE:EA=2:1) to give 95a (300 mg, 73%) as a white solid. LC-MS (Agilent): $R_t$ 3.93 min; m/z calculated for $C_{30}H_{30}N_2O_4$ [M+H]⁺ 483.2, [M+Na]⁺ 505.2, found [M+H]⁺ 483.2, [M+Na]⁺ 505.2.

2. Procedure for the Preparation of 95

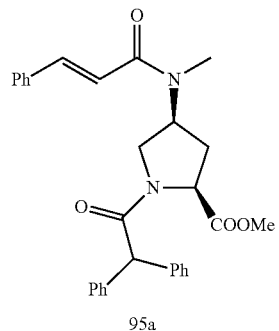

95a

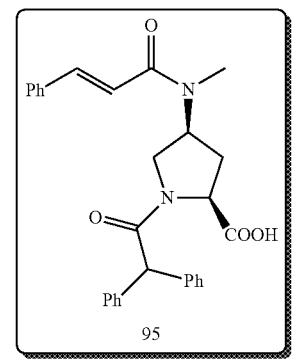

95

To a stirred solution of 95a (300 mg, 0.62 mmol) in THF/water (15 mL/2 mL) was added LiOH.H₂O (78 mg, 1.87 mmol) and the mixture was stirred at RT overnight, TLC (DCM:MeOH=10:1) showed the starting material was consumed. Most of the THF was removed in vacuo and the residue was dissolved in water (20 mL). The solution was acidified to pH-3~4 with a 3 M aqueous HCl solution and extracted with EA (15 mL×2). The combined organic extracts were washed with brine (20 mL), dried over Na₂SO₄, filtered and concentrated in vacuo to give 95 (270 mg, 93%) as a white solid. LC-MS (Agilent): $R_t$ 3.88 min; m/z calculated for $C_{29}H_{28}N_2O_4$ [M+H]⁺ 469.2, [M+Na]⁺ 491.2, found [M+H]⁺ 469.2, [M+Na]⁺ 491.2. HPLC (214 and 254 nm): $R_t$ 9.12 min.

Example 35: Compound 96 (2S,4S)-1-(2,2-diphenylacetyl)-4-(3-phenylpropanamido)-pyrrolidine-2-carboxylic acid

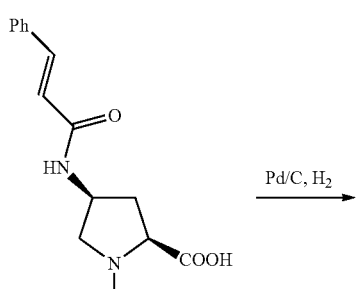

94

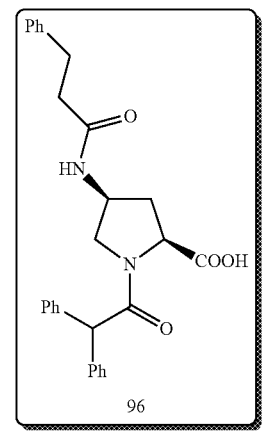

96

To a solution of 94 (170 mg, 0.37 mmol) in EA (30 mL) was added 10% Pd/C (20 mg) and the mixture was stirred at RT under a H₂ atmosphere (1 atm pressure) overnight, TLC (DCM:MeOH=10:1) showed the starting material was consumed. The mixture was filtered and the filtrate was concentrated in vacuo to give 96 (150 mg, 88%) as a white solid. LC-MS (Agilent): $R_t$ 3.80 min; m/z calculated for $C_{28}H_{28}N_2O_4$ [M+H]⁺ 457.2, [M+Na]⁺ 479.2, found [M+H]⁺ 457.2, [M+Na]⁺ 479.2. HPLC (214 and 254 nm): $R_t$ 9.06 min.

Example 36: Compound 97 (2S,4S)-1-(2,2-diphenylacetyl)-4-(N-methyl-3-phenylpropanamido)pyrrolidine-2-carboxylic acid

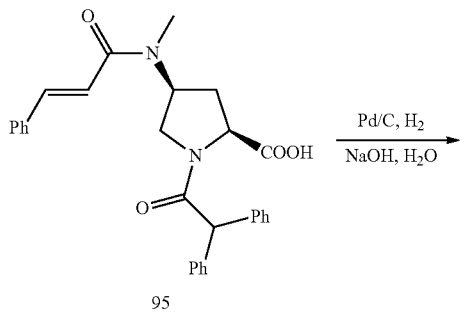

95

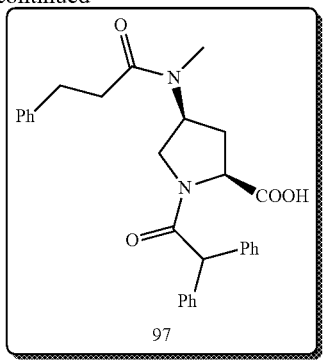

97

To a mixture of 95 (80 mg, 0.17 mmol) and 10% Pd/C (20 mg) in H$_2$O (20 mL) was added NaOH (10 mg, 0.26 mmol) and the mixture was stirred at RT under a H$_2$ atmosphere (1 atm pressure) overnight, LCMS analysis showed the starting material was consumed. The mixture was filtered and the filtrate was acidified to pH=3~4 with a 3 M aqueous HCl solution and extracted with EA (10 mL×3). The combined organic extracts were washed with brine (20 mL×2), dried over Na$_2$SO$_4$ and concentrated in vacuo. The residue was re-crystallized from Et$_2$O to give 97 (15 mg, 19%) as a white solid. LC-MS (Agilent): R$_t$ 3.86 min; m/z calculated for C$_{29}$H$_{30}$N$_2$O$_4$ [M+H]$^+$ 471.2, [M+Na]$^+$ 493.2, found [M+H]$^+$ 471.2, [M+Na]$^+$ 493.2. HPLC (214 and 254 nm): R$_t$ 9.12 min.

Example 37: Compound 98 (2S,4S)-1-(2,2-diphenylacetyl)-4-(N-3-phenylpropyl)-acetamido)pyrrolidine-2-carboxylic acid 1. Procedure for the preparation of 98a

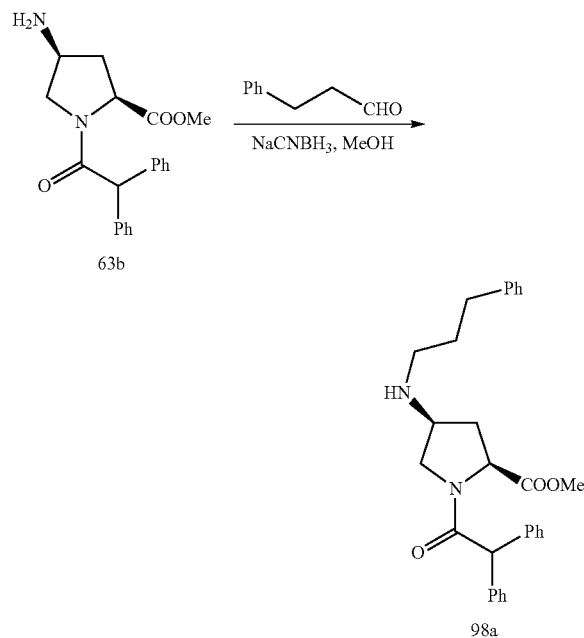

To a solution of 63b (500 mg, 1.5 mmol) and 3-phenylpropanal (161 mg, 1.2 mmol) in MeOH (10 mL) at RT was added AcOH (2 drops) and the mixture was stirred for 1 h. The mixture was cooled to 0° C., NaCNBH$_3$ (113 mg, 1.8 mmol) was added and stirring was continued at RT overnight, TLC (DCM:MeOH=20:1) showed that the starting material was consumed. Most of the MeOH was removed in vacuo and the residue was partitioned between water (20 mL) and EA (15 mL). The layers were separated and the aqueous phase was further extracted with EA (20 mL). The combined organic extracts were washed with brine, dried over Na$_2$SO$_4$, filtered and concentrated in vacuo. The residue was purified by column chromatography (DCM:MeOH=100:1 to 50:1) to give 98a (320 mg, 58%) as a yellow oil. LC-MS (Agilent): R$_t$ 3.46 min; m/z calculated for C$_{29}$H$_{34}$N$_2$O$_3$ [M+H]$^+$ 457.3, found [M+H]$^+$ 457.3.

2. Procedure for the Preparation of 98b

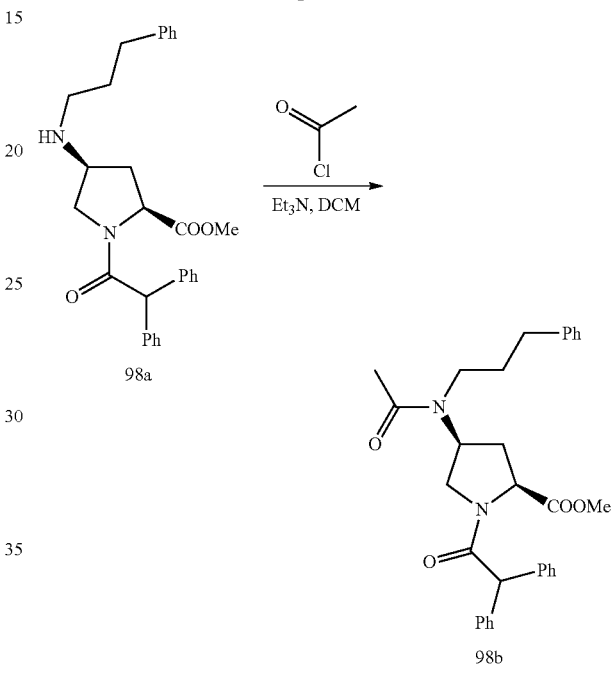

To a solution of 98a (150 mg, 0.33 mmol) in DCM (5 mL) at 0° C. was added Et$_3$N (40 mg, 0.4 mmol) followed by acetyl chloride (28 mg, 0.36 mmol). The mixture was then stirred at RT for 15 min, TLC (DCM:MeOH=20:1) showed that the starting material was consumed. The mixture was washed with brine (10 mL×2) and the organic layer was concentrated in vacuo. Purification by column chromatography (PE:EA=4:1 to 1:1) gave 98b (130 mg, 79%) as a yellow oil. LC-MS (Agilent): R$_t$ 3.89 min; m/z calculated for C$_{31}$H$_{34}$N$_2$O$_4$ [M+Na]$^+$ 521.25, found [M+Na]$^+$ 521.3.

3. Procedure for the Preparation of Compound 98

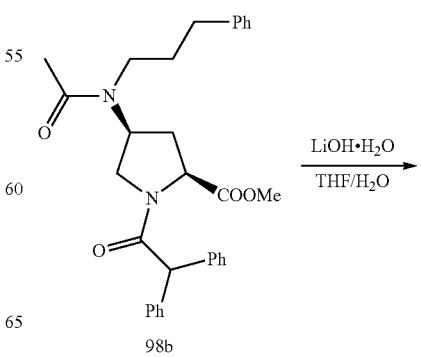

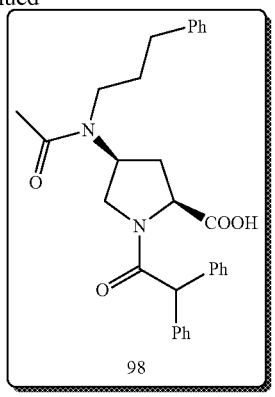

Hydrolysis of 98b (130 mg, 0.26 mmol) was performed as described in Example 5, 3. using 3 equivalents of LiOH.H$_2$O (32 mg, 0.78 mmol) to give 98 (100 mg, 80%) as a light yellow solid. LC-MS (Agilent): R$_t$ 3.85 min; m/z calculated for C$_{30}$H$_{32}$N$_2$O$_4$ [M+H]$^+$ 485.25, found [M+H]$^+$ 485.3. HPLC (214 and 254 nm): R$_t$ 9.19 min.

Example 38: Compound 99 (2S,4S)-1-(2,2-diphenylacetyl)-4-(N-(3-phenylpropyl)-methylsulfonamido)pyrrolidine-2-carboxylic acid 1. Procedure for the Preparation of 99a

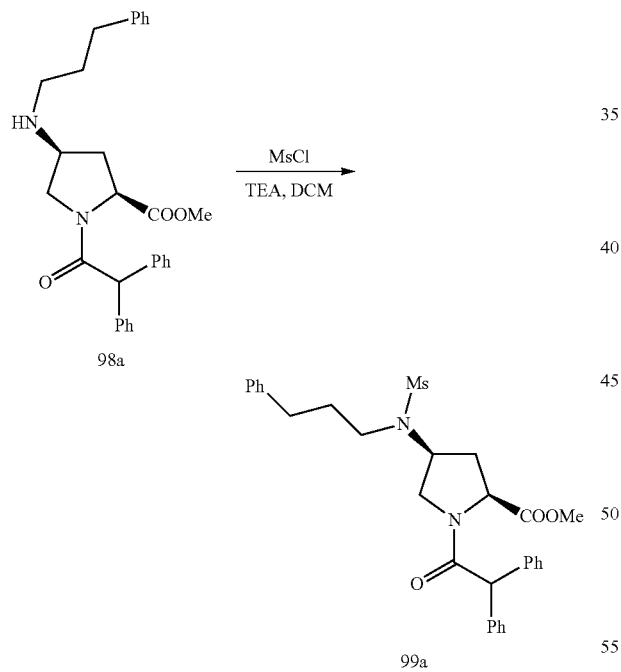

To a cooled mixture of 98a (150 mg, 0.33 mmol) in DCM (5 mL) and TEA (40 mg, 0.4 mmol) at 0° C., was added MSCl (41 mg, 0.36 mmol). The mixture was stirred at RT for 15 min. TLC (DCM:MeOH=20:1) showed that 99a had disappeared, and the mixture was washed with brine. The organic phase was dried over Na$_2$SO$_4$, and evaporated in vacuo. The resulting mixture was purified by silica column (PE:EA=4:1 to 2:1) to give 99a (140 mg, 79%) as white solid. LC-MS (Agilent): R$_t$ 3.86 min; m/z calculated for C$_{30}$H$_{34}$N$_2$O$_5$S [M+H]$^+$ 535.24, found [M+H]$^+$ 535.3.

2. Procedure for the Preparation of Compound 99

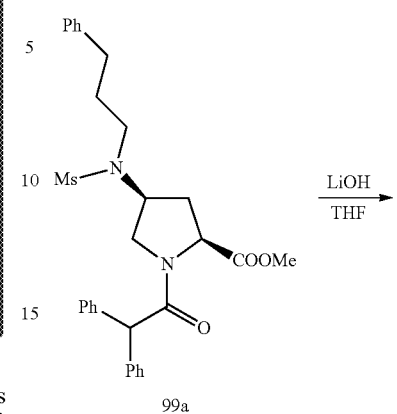

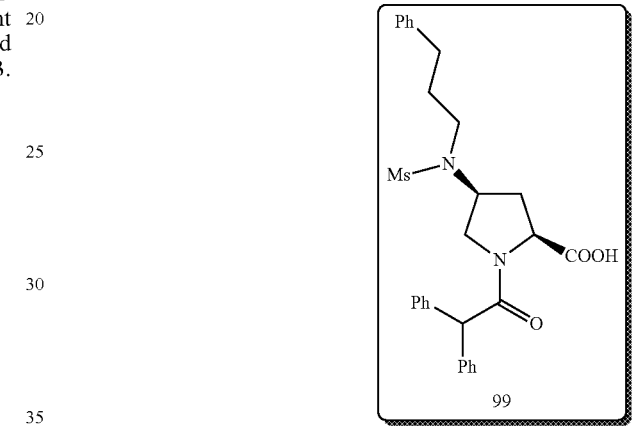

Hydrolysis of 99a (140 mg, 0.26 mmol) was performed as described in Example 25, 3. with about 3 equivalents of LiOH.H$_2$O (33 mg, 0.79 mmol). The precipitate was collected by filter, washed with water (5 mL×2), dried at 50° C. overnight to give 99 (120 mg, 88%) as a white solid. LC-MS (Agilent): R$_t$ 3.87 min; m/z calculated for C$_{29}$H$_{32}$N$_2$O$_5$S [M+H]$^+$ 521.2, [M+Na]$^+$ 543.2, found [M+H]$^+$ 521.3, [M+Na]$^+$ 543.2. HPLC (214 and 254 nm): R$_t$ 9.15 min.

Example 39: Compound 100 (2S,4S)-1-(2,2-diphenylacetyl)-4-(5-phenyl-1H-1,2,3-triazol-1-yl)pyrrolidine-2-carboxylic acid 1. Procedure for the Preparation of 100b

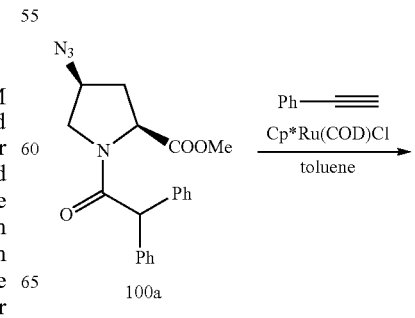

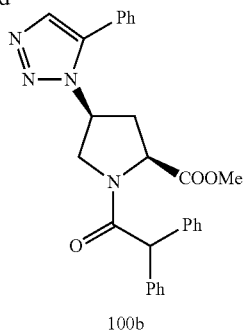

100b

A mixture of 100a (100 mg, 0.27 mmol), phenyl acetylene (42 mg, 0.41 mmol) and Cp*Ru(COD)Cl (10 mg, 0.027 mmol) in toluene (5 mL) was heated at 80° C. under a $N_2$ atmosphere overnight, TLC (PE:EA=1:1) showed that the starting material was consumed. The mixture was cooled to RT, concentrated in vacuo and the residue was purified by column chromatography (PE:EA=1:0 to 1:1) to give 100b (130 mg, 100%) as a white solid. LC-MS (Agilent): $R_t$ 3.80 min; m/z calculated for $C_{28}H_{26}N_4O_3$ [M+H]$^+$ 467.2, [M+Na]$^+$ 489.2, found [M+H]$^+$ 467.2, [M+Na]$^+$ 489.2.

2. Procedure for the Preparation of 100

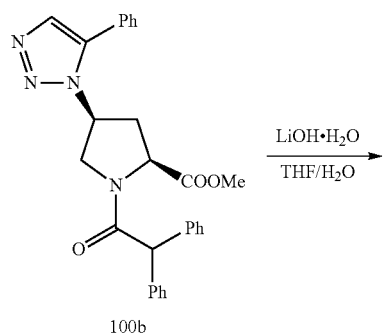

To a mixture 100b (130 mg, 0.28 mmol) in THF/water (10 mL/1.5 mL) was added LiOH·H$_2$O (35 mg, 0.84 mmol) and the mixture was stirred at RT overnight, TLC (DCM:MeOH=10:1) showed that the starting material was consumed. Most of the THF was removed in vacuo and the residue was dissolved in water (15 mL). The aqueous mixture was acidified to pH=5-6 with a 3 M aqueous HCl solution and extracted with DCM (20 mL×2). The combined organic extracts were washed with brine, dried over Na$_2$SO$_4$, filtered and concentrated in vacuo to give 100 (120 mg, 95%) as a white solid. LC-MS (Agilent): $R_t$ 3.87 min; m/z calculated for $C_{27}H_{24}N_4O_3$ [M+H]$^+$ 453.2, [M+Na]$^+$ 475.2, found [M+H]$^+$ 453.2, [M+Na]$^+$ 475.2. HPLC (214 and 254 nm): $R_t$ 8.98 min.

Example 40: Compound 101 (2S,4S)-4-(5-benzyl-1H-1,2,3-triazol-1-yl)-1-(2,2-diphenylacetyl)pyrrolidine-2-carboxylic acid 1. Procedure for the Preparation of 101a

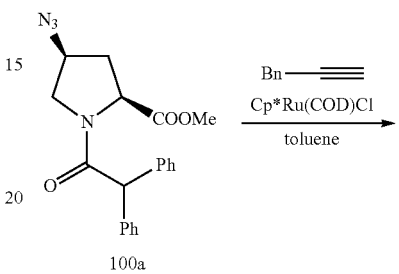

A mixture of 100a (100 mg, 0.27 mmol), 1-(prop-2-ynyl)benzene (48 mg, 0.41 mmo) and Cp*Ru(COD)Cl (10 mg, 0.027 mmol) in toluene (5 mL) was heated at 80° C. under a N$_2$ atmosphere overnight, TLC (PE:EA=1:1) showed that the starting material was consumed. The reaction was cooled to RT and concentrated in vacuo to give 140 mg of crude product. The reaction was repeated and the two batches of crude product were combined and purified by column chromatography (PE:EA=1:0 to 1:1) to give 101a (230 mg, 88%) as a white solid. LC-MS (Agilent): $R_t$ 3.89 min; m/z calculated for $C_{29}H_{28}N_4O_3$ [M+H]$^+$ 481.2, [M+Na]$^+$ 503.2, found [M+H]$^+$ 481.2, [M+Na]$^+$ 503.2.

2. Procedure for the Preparation of 101

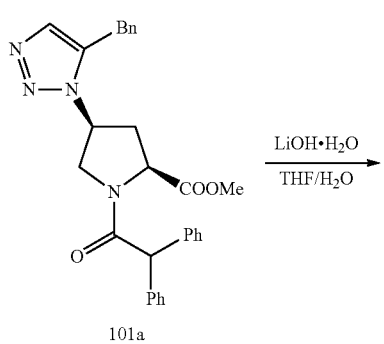

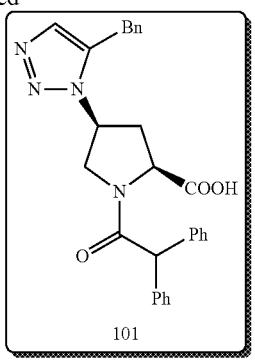

101

Hydrolysis of 101a (230 mg, 0.48 mmol) was performed as described in Example 39, 2. using about 3 equivalents of LiOH.H$_2$O (64 mg, 1.53 mmol) to give 101 (190 mg, 97%) as a white solid. LC-MS (Agilent): R$_t$ 3.82 min; m/z calculated for C$_{28}$H$_{26}$N$_4$O$_3$ [M+H]$^+$ 467.2, [M+Na]$^+$ 489.2, found [M+H]$^+$ 467.2, [M+Na]$^+$ 489.2. HPLC (214 and 254 nm): R$_t$ 9.00 min.

Example 41: Compound 102 (2S,4S)-4-((S)-3-benzyl-5-oxomorpholino)-1-(2,2-diphenylacetyl)pyrrolidine-2-carboxylic acid 1. Procedure for the Preparation of 102a.

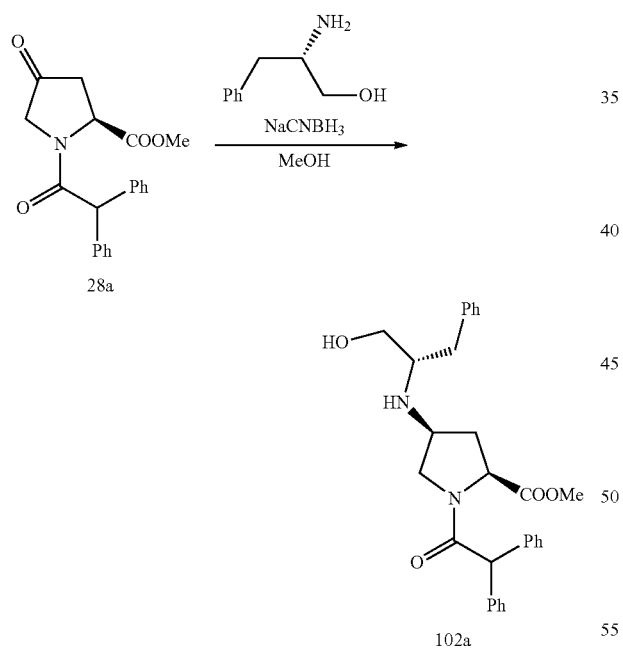

To a solution of 28a (980 mg, 2.90 mmol) and L-phenylglycinol (483 mg, 3.20 mmol) in MeOH (20 mL) at RT under N$_2$ was added AcOH (one drop) and the mixture was stirred for 1 h then cooled to 0° C. NaCNBH$_3$ (219 mg, 3.49 mmol) was added and the mixture was allowed to warm to RT and stirred overnight, TLC (DCM:MeOH=10:1) showed that the starting material was consumed. The mixture was concentrated in vacuo and the residue was dissolved in water (20 mL) and extracted with DCM (25 mL). The organic layer was washed with brine (15 mL×2), dried over Na$_2$SO$_4$, filtered and concentrated in vacuo. The residue was purified by column chromatography (DCM:EA=3:1 to 1:1) to give 102a (395 mg, 29%) as a white solid. LC-MS (Agilent): R$_t$ 3.47 min; m/z calculated for C$_{29}$H$_{32}$N$_2$O$_4$[M+H]$^+$ 473.3, found [M+H]$^+$ 473.3.

2. Procedure for the Preparation of 102b.

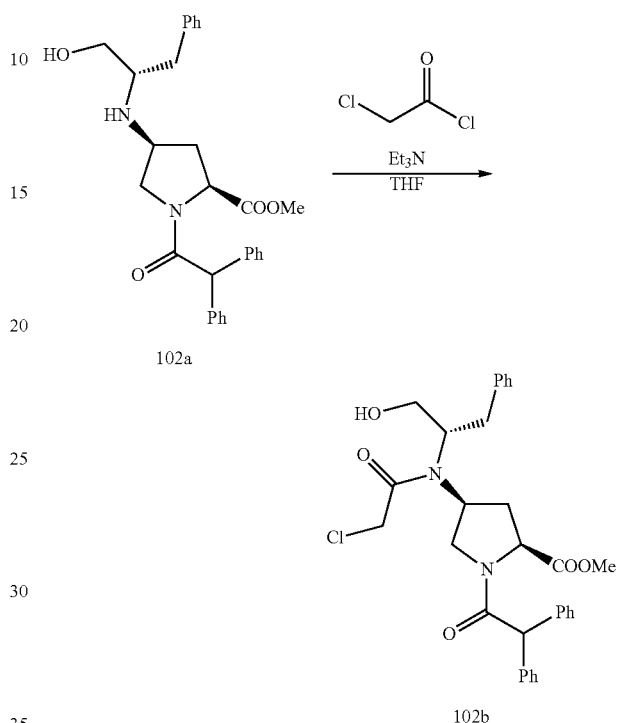

To a stirred solution of 102a (385 mg, 0.83 mmol) and Et$_3$N (101 mg, 1.00 mmol) in THF (15 mL) at 0° C. was added chloroacetyl chloride (95 mg, 0.83 mmol) and the mixture was allowed to warm to RT and stirred overnight, TLC (PE:EA=1:1) showed that the starting material was consumed. Most of the THF was removed in vacuo and the residue was diluted with water (15 mL) and extracted with EA (15 mL×2). The combined organic extracts were washed with brine (20 mL), dried over Na$_2$SO$_4$, filtered and concentrated in vacuo. The residue was purified by column chromatography (PE:EA=10:1 to 3:2) to give 102b (190 mg, 43%) as a white solid. LC-MS (Agilent): R$_t$ 3.83 min; in/z calculated for C$_{31}$H$_{33}$N$_2$O$_5$[M+H]$^+$ 549.2, [M+Na]$^+$ 571.2, found [M+H]$^+$ 549.2, [M+Na]$^+$ 571.2.

3. Procedure for the Preparation of 102c

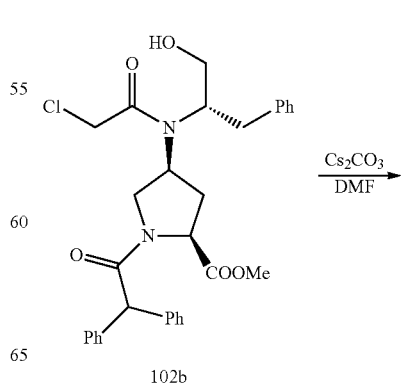

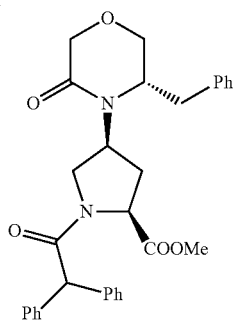

102c

A stirred mixture of 102b (160 mg, 0.30 mmol) and Cs$_2$CO$_3$ (151 mg, 0.46 mmol) in DMF (15 mL) was heated to 90° C. under a N$_2$ atmosphere for 4 h, TLC (PE:EA=1:2) showed that the starting material was consumed. The mixture was cooled to RT, poured into ice-water (100 mL) and extracted with EA (20 mL×2). The combined organic extracts were washed with brine (30 mL), dried over Na$_2$SO$_4$, filtered and concentrated in vacuo to give 102c (100 mg, 67%) as a yellow solid. LC-MS (Agilent): R$_t$ 3.94 min; ink calculated for C$_{31}$H$_{32}$N$_2$O$_5$ [M+H]$^+$ 512.2, [M+Na]$^+$ 535.2, found [M+H]$^+$ 512.2, [M+Na]$^+$ 535.2.

4. Procedure for the Preparation of 102

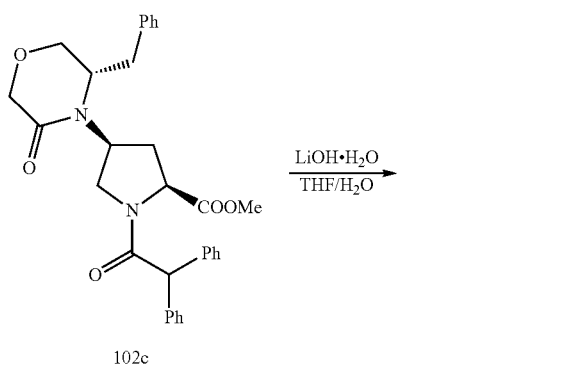

To a solution of 102c (100 mg, 0.20 mmol) in THF/water (10 mL/2 mL) was added LiOH.H$_2$O (25 mg, 0.59 mmol) and the mixture was stirred at RT overnight, TLC (DCM:MeOH=10:1) showed that the starting material was consumed. Most of the THF was removed in vacuo and the residue was dissolved in water (10 mL) and washed with Et$_2$O. The aqueous layer was acidified to pH 4~5 with a 3 M aqueous HCl solution and extracted with DCM (15 mL×2). The combined organic extracts were washed with brine (15 mL×2), dried over Na$_2$SO$_4$, filtered and concentrated in vacuo. The residue was purified by preparative HPLC to give 102 (28 mg, 29%) as white solid. LC-MS (Agilent): R$_t$ 4.03 min; m/z calculated for C$_{29}$H$_{28}$N$_4$O$_3$ [M+H]$^+$ 499.2, found [M+H]$^+$ 499.2. HPLC (214 and 254 nm): R$_t$ 9.14 min.

Example 42: Compound 103 1-((2S,4S)-2-(hydroxymethyl)-4-(3-phenylpropoxy)-pyrrolidine-1-yl)-diphenylethanoate

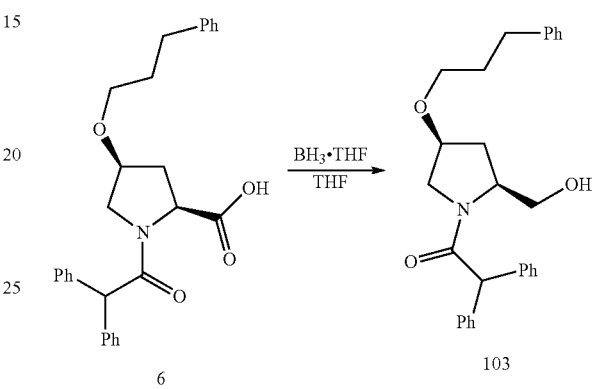

To a solution of Compound 6 (400 mg, 0.9 mmol) in THF (10 mL) at −10° C. under N$_2$ was added BH$_3$.THF (1.0 M solution in THF, 1.0 mL, 1.0 mmol) dropwise and the mixture was stirred at −10° C. for 1 h, TLC (DCM:MeOH=20:1) showed there was no reaction. The reaction mixture was allowed to warm to RT and stirred for 30 min, TLC showed most of the starting material remained. More BH$_3$.THF (1.0 M solution in THF, 0.9 mL, 0.9 mmol) was added and the mixture was stirred at RT overnight, TLC (DCM:MeOH=20:1) showed that most of the starting material was consumed. The mixture was cooled to 0° C., quenched with MeOH, diluted with water (20 mL) and extracted with EA (20 mL×2). The combined organic extracts were washed with a saturated aqueous NaHCO$_3$ solution, a 1 M aqueous HCl solution, brine and dried over Na$_2$SO$_4$, filtered and concentrated in vacuo. The residue was purified by column chromatography (PE:EA=10:1 to 5:1) followed by preparative HPLC to give 103 (30 mg, 7%) as a white solid. LC-MS (Agilent): R$_t$ 4.02 min; m/z calculated for C$_{28}$H$_{31}$NO$_3$ [M+H]$^+$ 430.3, [2M+Na]$^+$ 881.5, found [M+H]$^+$ 430.3, [2M+Na]$^+$ 881.5. HPLC (214 and 254 nm): R$_t$ 9.42 min.

Example 43: Compound 104 (2S,4S)-1-(2,2-diphenylacetyl)-4-(3-(4-fluorophenyl)-propoxy)pyrrolidine-2-carboxylic acid 1. Procedure for the Preparation of 104a

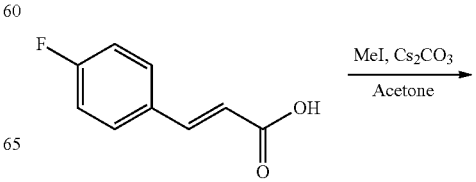

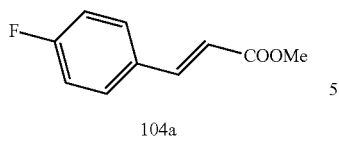

104a

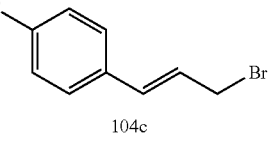

104c

To a solution of 4-fluorocinnamic acid (2.0 g, 12 mmol) in acetone (30 mL) was added $Cs_2CO_3$ (4.7 g, 14.4 mmol) and iodomethane (2.5 g, 18 mmol) and the mixture was stirred at RT for 3 h, TLC (PE:EA=2:1) showed that the starting material was consumed. The mixture was concentrated in vacuo and the residue was partitioned between water (30 mL) and DCM (20 mL). The organic layer was separated, washed with brine, dried over $Na_2SO_4$ and concentrated in vacuo to give 104a (1.9 g, 90%) as a yellow solid. LC-MS. (Agilent): $R_t$ 3.85 min; m/z calculated for $C_{10}H_9FO_2[M+H]^+$ 180.1, found $[M+H]^+$ 180.1.

2. Procedure for the Preparation of 1046

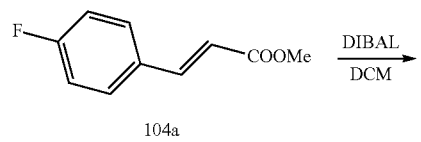

104a

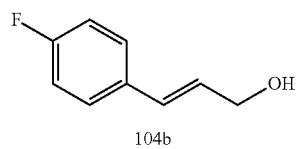

104b

To a solution of 104a (1.9 g, 10.0 mmol) in DCM (20 mL) at −65° C. under $N_2$ was added DIBAL-H (1.2 M solution in toluene, 10.0 mL, 12.0 mmol) dropwise and the mixture was stirred at −65° C. for 1 h, TLC (PE:EA=2:1) showed incomplete reaction. More DIBAL-H (1.2 M solution in toluene, 8.3 mL, 10.0 mmol) was added and stirring was continued for 30 min, TLC (PE:EA=2:1) showed that some starting material remained. More DIBAL-H (1.2 M solution in toluene, 2.5 mL, 3.0 mmol) was added and stirring was continued for 30 min, TLC (PE:EA=2:1) showed that the starting material was consumed. The mixture was allowed to warm to −10° C. and quenched with a 2.5 M aqueous NaOH solution (2.5 eq) then water (50 mL). DCM (30 mL) was added and the resulting precipitate was removed by filtration. The filtrate was collected and the phases were separated. The aqueous layer was extracted with DCM (30 mL) and the combined organic extracts were washed with brine, dried over $Na_2SO_4$, filtered and concentrated in vacuo to give 104b (1.4 g, 93%) as an off-white solid.

3. Procedure for the Preparation of 104c

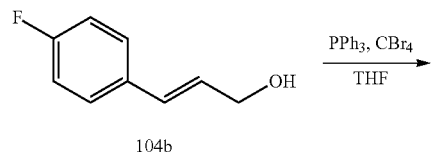

104b

To a stirred suspension of 104b (0.7 g, 4.6 mmol) in THF (10 mL) was added $PPh_3$ (1.4 g, 5.5 mmol) and $CBr_4$ (2.3 g, 6.9 mmol) and the mixture was stirred at RT for 1 h, TLC (PE:EA=10:1) showed that the starting material was consumed. The mixture was concentrated in vacuo and the residue was purified by column chromatography (100% PE) to give 104c (0.9 g, 90%) as a yellow oil.

4. Procedure for the Preparation of 104d

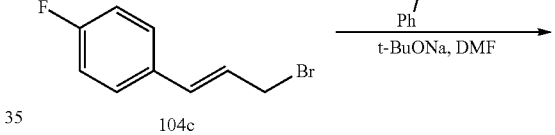

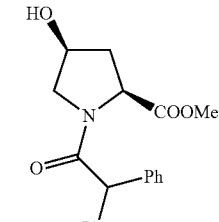

104c

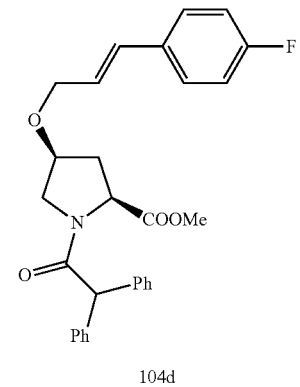

104d

To a stirred solution of 104c (353 mg, 1.6 mmol) and 2e (380 mg, 1.1 mmol) in DMF (10 mL) at −45° C. was added t-BuONa (108 m g, 1.1 mmol) in portions and the mixture was stirred at −40° C. for 1.5 h, TLC (PE:EA=1:1) showed that the starting material was consumed. The reaction was quenched with AcOH and then allowed to warm to −10° C. Water (50 mL) was added and the mixture was extracted with EA (20 mL). The organic layer was washed with brine, dried over $Na_2SO_4$, filtered and concentrated in vacuo. The residue was purified by chromatography (PE:EA=10:1 to 5:1) to give 104d (110 mg, 21%) as a yellow oil. LC-MS (Agilent): $R_t$ 4.05 min; m/z calculated for $C_{13}H_{17}NO_3$ $[M+H]^+$ 474.2, found $[M+H]^+$ 474.2.

5. Procedure for the Preparation of 104e

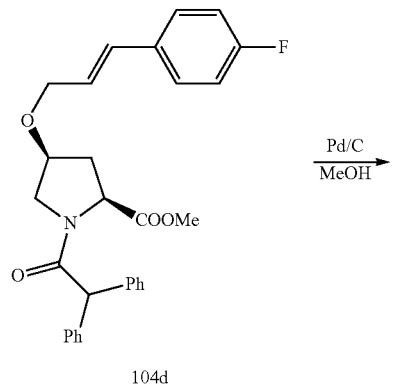

104d

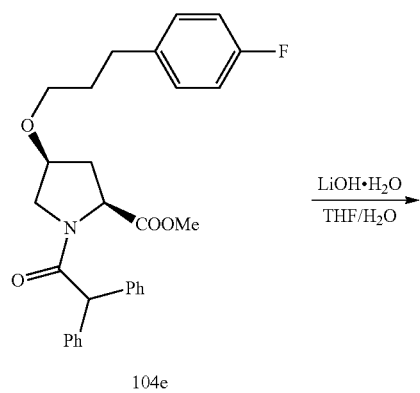

104e

To a stirred solution of 104d (110 mg, 0.23 mmol) in MeOH (10 mL) was added 10% Pd/C (11 mg) and the mixture was stirred at RT under a $H_2$ atmosphere (1 atm) overnight, TLC (PE:EA=2:1) showed that the starting material was consumed. The mixture was filtered and the filtrate was concentrated in vacuo to give 104e (100 mg, 90%) as a colorless oil.

LC-MS (Agilent): $R_t$ 4.08 min; m/z calculated for $C_{29}H_{28}FNO_4$ [M+H]$^+$ 476.2, found [M+H]$^+$ 476.2.

6. Procedure for the Preparation of 104

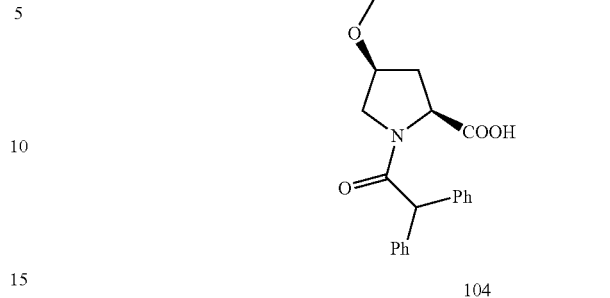

104

To a mixture of 104e (100 mg, 0.2 mmol) in THF/water (8 mL/3 mL) was added LiOH.H$_2$O (26 mg, 0.6 mmol) and the mixture was stirred at RT overnight, TLC (PE:EA=2:1) showed that the starting material was consumed. Most of the THF was removed in vacuo and the residue was dissolved in water (15 mL) and washed with Et$_2$O (15 mL). DCM (15 mL) was added and the aqueous layer was acidified to pH 2-3 with a 1 M aqueous HCl solution. The layers were separated and the aqueous layer was further extracted with DCM (15 mL). The combined organic layers were washed with brine, dried over Na$_2$SO$_4$, filtered and concentrated in vacuo to give 104 (60 mg, 65%) as a white solid. LC-MS (Agilent): $R_t$ 3.96 min; m/z calculated for $C_{28}H_{28}FNO_4$ [M+H]$^+$ 461.2, found [M+H]$^+$ 462.2. HPLC (214 and 254 nm): $R_t$ 9.34 min.

Example 44: Compound 105 (2S,4S)-1-(2,2-diphenylacetyl)-4-((3-(4-methoxy-3-methylphenyl)prop-2-yn-1-yl)(methyl)amino)pyrrolidine-2-carboxylic acid 1. Procedure for the Preparation of 105a

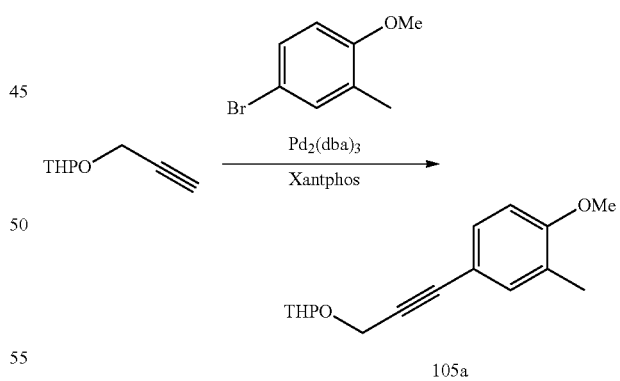

105a

A mixture of 2-(prop-2-ynyloxy)-tetrahydro-2H-pyran (1.4 g, 10.0 mmol), Cs$_2$CO$_3$ (4.8 g, 15.0 mmol), 4-bromo-1-methoxy-2-methylbenzene (2.0 g, 10.0 mmol), Pd$_2$(dba)$_3$ (180 mg, 0.2 mmol) and Xantphos (100 mg, 0.17 mmol) in MeCN (30 mL) was stirred at 80° C. under a N$_2$ atmosphere overnight. TLC (PE:EA=10:1) showed that the starting material was consumed. The mixture was cooled to RT, water (50 mL) was added and extracted with EA (30 mL×2). The combined organic extracts were washed with brine, dried over Na$_2$SO$_4$, filtered and concentrated in vacuo. The residue was purified by column chromatography (PE:EA=1:0 to 50:1) to give 105a (450 mg, 17%) as a yellow oil. LC-MS (Agilent): $R_t$ 4.49 min; m/z calculated for $C_{16}H_{20}O_3$ [M+H]$^+$ 261.1, [M+Na]$^+$ 283.1, found [M+H]$^+$ 261.2, [M+Na]$^+$ 283.1.

2. Procedure for the Preparation of 105b

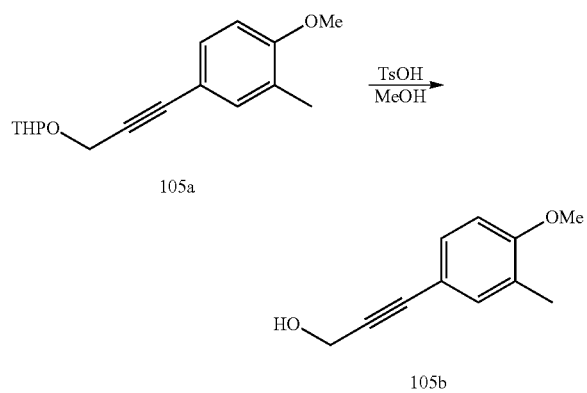

To a stirred solution of 105a (450 mg, 1.7 mmol) in MeOH (10 mL) was added TsOH.H$_2$O (5 mg, 0.03 mmol) and the mixture was stirred at RT overnight, TLC (PE:EA=2:1) showed some of the starting material remained. More TsOH.H$_2$O (5 mg, 0.03 mmol) was added and stirring was continued at RT for 24 h, TLC showed that the starting material was consumed. Most of the MeOH was removed in vacuo and the residue was partitioned between water (30 mL) and EA (20 mL). The layers were separated and the aqueous layer was further extracted EA (20 mL). The combined organic extracts were washed with brine, dried over Na$_2$SO$_4$, filtered and concentrated in vacuo to give 105b (330 mg, >100%) as a yellow oil, which was used directly in the next step. LC-MS (Agilent): $R_t$ 3.56 min; m/z calculated for $C_{11}H_{12}O_{32}$[M+H]$^+$ 177.1, [M+Na]$^+$ 199.1, found [M+H]$^+$ 177.1, [M+Na]$^+$ 199.1.

3. Procedure for the Preparation of 105c

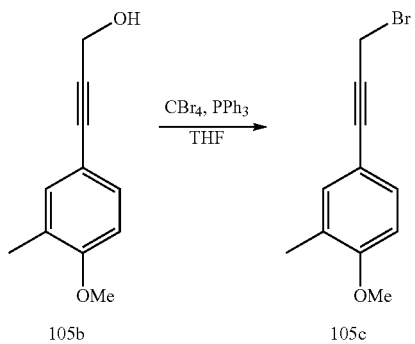

To a stirred suspension of 105b (320 mg, 1.8 mmol) in THF (10 mL) was added PPh$_3$ (518 mg, 1.9 mmol) and CBr$_4$ (782 mg, 2.4 mmol) and the mixture was stirred at RT for 4 h, TLC (PE:EA=4:1) showed that the starting material was consumed. The mixture was concentrated in vacuo and the residue was purified by column chromatography (100% PE) to give 105c (400 mg, 93%) as a yellow oil.

4. Procedure for the Preparation of 105d

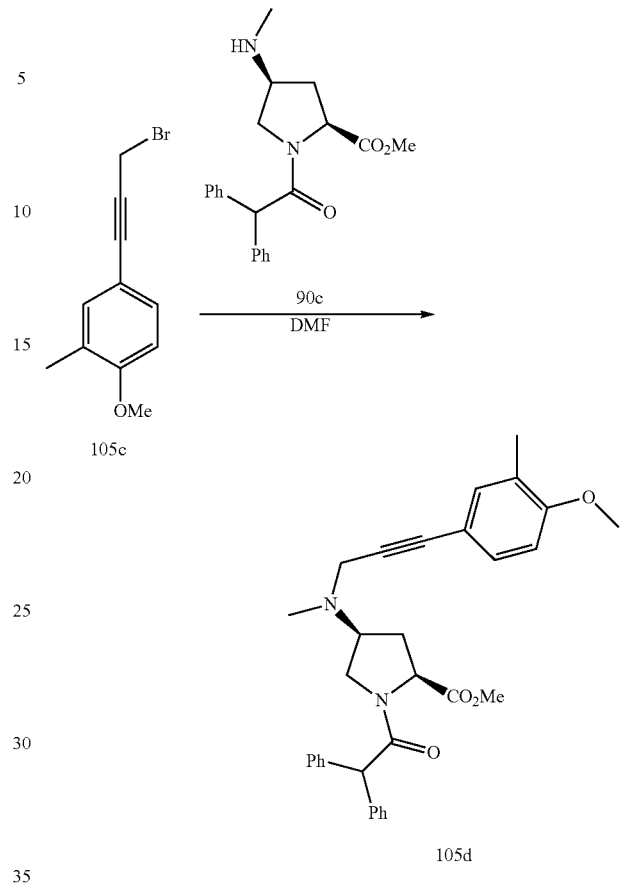

To a solution of 105c (350 mg, 1.0 mmol) and 105c (353 mg, 1.48 mmol) in DMF (10 mL) was added Cs$_2$CO$_3$ (480 mg, 1.48 mmol) and the mixture was heated at 60° C. for 4 h, TLC (DCM:MeOH=20:1) showed that most of 90c was consumed. The mixture was cooled to RT, poured into ice-water (100 mL) and extracted with EA (30 mL×2). The combined organic extracts were washed with brine, dried over Na$_2$SO$_4$, filtered and concentrated in vacuo. The residue was purified by column chromatography (PE:EA=5:1 to 2:1) to give 105d (250 mg, 49%) as a yellow oil. LC-MS (Agilent): $R_t$ 4.07 min; m/z calculated for $C_{32}H_{34}N_2O_4$ [M+H]$^+$ 511.3, found [M+H]$^+$ 511.3.

5. Procedure for the Preparation of 105

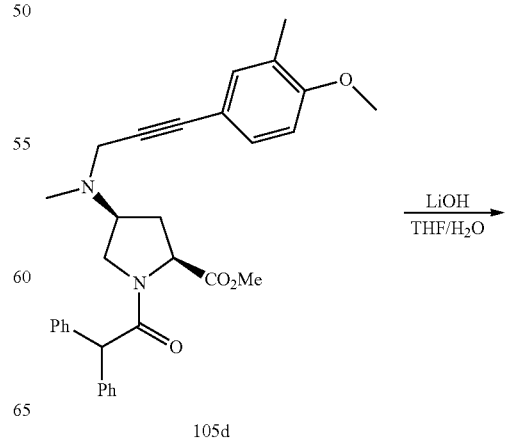

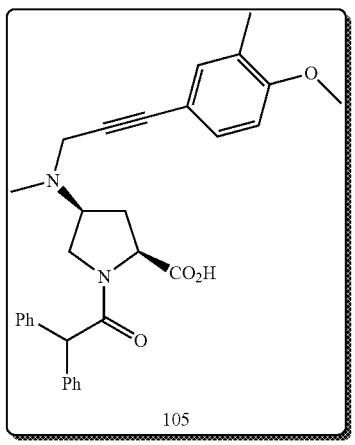

Hydrolysis of 105d (250 mg, 0.49 mmol) was performed as described in Example 9, 3. with 3 equivalents of LiOH.H$_2$O (62 mg, 1.47 mmol). After acidification, the layers were separated and the aqueous layer was further extracted with DCM (20 mL). The combined organic extracts were washed with brine, dried over Na$_2$SO$_4$, filtered and concentrated in vacuo to give 105 (200 mg, 82%) as a yellow solid. LC-MS (Agilent): R$_t$ 3.89 min; m/z calculated for C$_{31}$H$_{32}$N$_2$O$_4$ [M+H]$^+$ 497.2, found [M+H]$^+$ 497.3. HPLC (214 and 254 nm): R$_t$ 9.09 min.

Example 45: Compound 92 (2S,4S)-1-(2,2-diphenylacetyl)-4-((3-(4-methoxy-3-methylphenyl)propyl)(methyl)amino)pyrrolidine-2-carboxylic acid

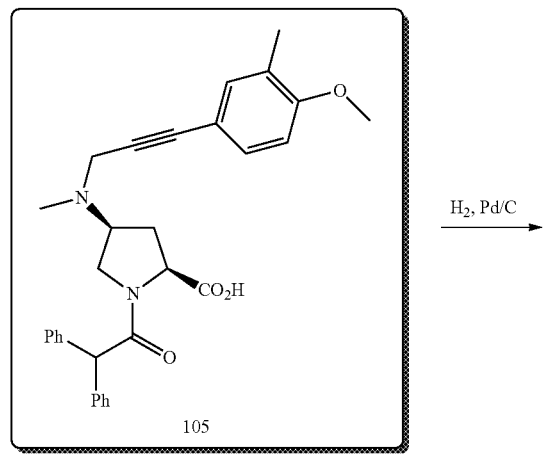

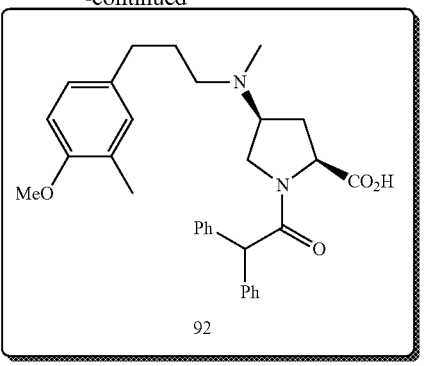

A mixture of Compound 105 (140 mg, 0.28 mmol) and 10% Pd/C (14 mg) in EA (10 mL) was stirred at 30° C. under a H$_2$ atmosphere (1 atm) overnight, LCMS analysis showed that the starting material was consumed. The mixture was filtered through Celite and the filtrate was concentrated in vacuo. The residue was purified by preparative HPLC to give 92 (30 mg, 21%) as a white solid. LC-MS (Agilent): R$_t$ 3.84 min; m/z calculated for C$_{31}$H$_{36}$N$_2$O$_4$ [M+H]$^+$ 501.3, found [M+H]$^+$ 501.3. HPLC (214 and 254 nm): R$_t$ 8.99 min.

Example 46: Compound 106 (2S,4S)-1-(2,2-diphenylacetyl)-4-(4-phenylbutyl)-pyrrolidine-2-carboxylic acid 1. Procedure for the Preparation of 106a

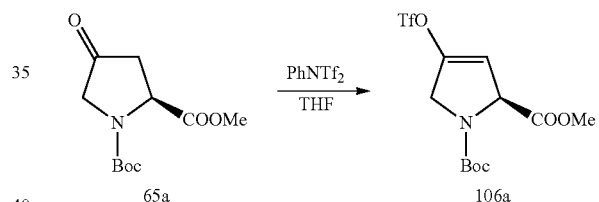

To a solution of 65a (500 mg, 2.05 mmol) in THF (5 mL) at −65° C. was added LiHMDS (1 M solution in THF, 2.26 mL, 2.26 mmol) and the mixture was stirred at −65° C. for 0.5 h. A solution of PhNTf$_2$ (807 mg, 2.26 mmol) in THF (1 mL) was then added slowly and stirring was continued at −65° C. for 3 h before allowing to warm to −30° C. and stirred for a further 2 h. The mixture was then allowed to warm to RT and stirred overnight, TLC (PE:EA=1:1) showed that most of the starting material was consumed. The reaction was quenched with a saturated aqueous NaHCO$_3$ solution and then partitioned between EA and brine. The organic layer was separated, dried over Na$_2$SO$_4$, filtered and concentrated in vacuo. The residue was purified by chromatography (PE:EA=1:0 to 4:1) to give 106a (400 mg, 52%) as a thick colorless oil.

2. Procedure for the Preparation of 106b

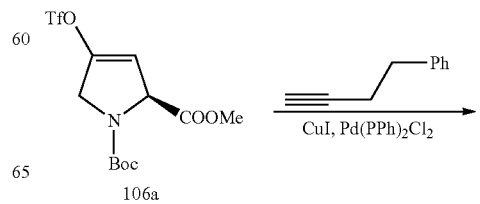

-continued

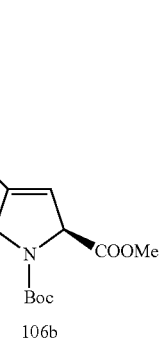

106b

To a solution of 106a (250 mg, 0.66 mmol) in THF (5 mL) at RT under N₂ was added 1-(but-3-ynyl)benzene (104 mg, 0.80 mmol), DIPEA (425 mg, 3.30 mmol), CuI (13 mg, 0.068 mmol) and Pd(PPh)₂Cl₂ (21 mg, 0.033 mmol) and the mixture was stirred at RT for 3 h, TLC (PE:EA=10:1) showed that the starting material was consumed. The mixture was partitioned between brine (20 mL) and EA (20 mL) and the organic layer was separated, dried over Na₂SO₄, filtered and concentrated in vacuo. The residue was purified by chromatography (PE:EA=1:0 to 20:1) to give 106b (120 mg, 51%) as a yellow oil and an impure fraction of 106b (40 mg). LC-MS (Agilent). $R_f$ 4.42 min; m/z calculated for $C_{21}H_{25}NO_4[M+Na]^+$ 378.2, $[M-t-Bu]^+$ 300.1, found $[M+Na]^+$ 378.2, $[M-t-Bu]^+$ 300.1.

3. Procedure for the Preparation of 106c

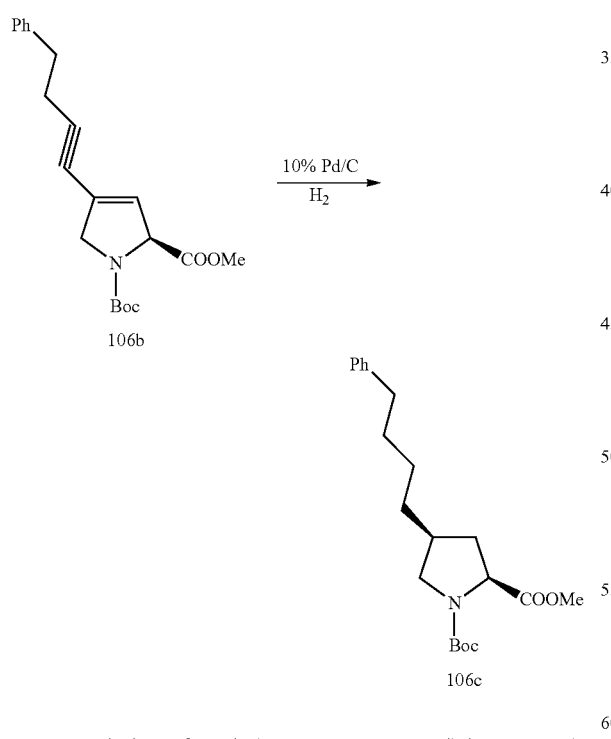

To a solution of 106b (170 mg, 0.48 mmol) in MeOH (5 mL) was added 10% Pd/C (20 mg) and the mixture was stirred under a H₂ atmosphere (1 atm) at RT overnight, TLC (PE:EA=10:1) showed that the starting material was consumed. The mixture was filtered and the filtrate was concentrated in vacuo to give 106c (160 mg, 94%) as colorless oil. LC-MS (Agilent): $R_f$ 4.48 min; m/z calculated for $C_{21}H_{31}NO_4$ $[M+Na]^+$ 384.2, $[M-t-Bu]^+$ 306.2, $[M-boc]^+$ 262.2, found $[M+Na]^+$ 384.2, $[M-t-Bu]^+$ 306.2, $[M-boc]^+$ 262.2.

4. Procedure for the Preparation of 106d

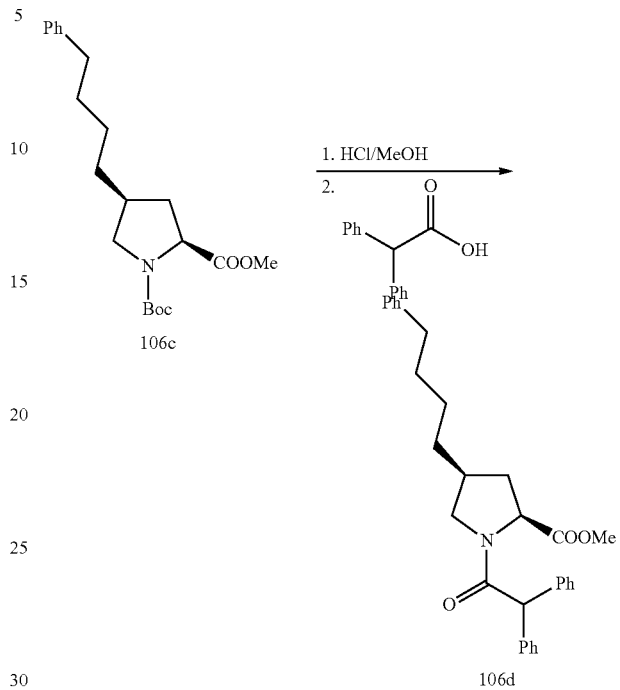

A solution of 106c (160 mg, 0.44 mmol) in a 4 M HCl/MeOH solution (5 mL) was stirred at RT for 3 h, TLC (PE:EA=4:1) showed that the starting material was consumed. The mixture was concentrated in vacuo, the residue was dissolved in water (15 mL), basified to pH 7-8 with K₂CO₃ and extracted with DCM (15 mL×3). The combined organic extracts were washed with brine (15 mL), dried over Na₂SO₄, filtered and concentrated in vacuo to give the product (90 mg) as a yellow oil. NMR analysis revealed the cis/trans ratio to be 6.1:1. To a solution of the deprotected amine (90 mg) in DCM (10 mL) was added diphenyl acetic acid (90 mg, 0.44 mmol) and EDCI.HCl (95 mg, 0.49 mmol) and the mixture was stirred at RT overnight, TLC (DCM:MeOH=10:1) showed that the starting material was consumed. The mixture was washed with brine, dried over Na₂SO₄, filtered and concentrated in vacuo. The residue was purified by chromatography (PE:EA=1:0 to 4:1) to give 106d (120 mg, 59%) as a colorless oil. LC-MS (Agilent): $R_f$ 4.54 min; m/z calculated for $C_{30}H_{33}NO_3[M+H]^+$ 455.2, found $[M+H]^+$ 455.2.

5. Procedure for the Preparation of Compound 106

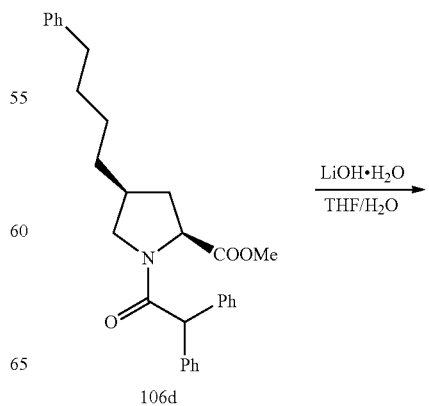

106d

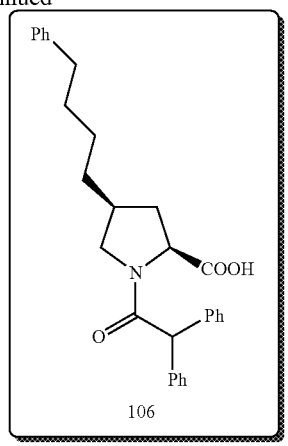

106

Hydrolysis of 106d (120 mg, 0.26 mmol) was performed as described in Example 53, 2. with about 3 equivalents of LiOH.H$_2$O (33 mg, 0.79 mmol). The combined organic extracts were washed with brine (10 mL×2), dried over Na$_2$SO$_4$, filtered and concentrated in vacuo to give 106 (110 mg, 94%) as a colorless gum. LC-MS (Agilent): R$_t$ 4.55 min; m/z calculated for C$_{29}$H$_{31}$NO$_3$ [M+H]$^+$ 442.2, found [M+H]$^+$ 442.2. HPLC (214 and 254 nm): R$_t$ 9.62 min.

Example 47: Compound 139 (S)-1-(2,2-diphenylacetyl)-4-(3-phenylthiophen-2-yl)-2,5-dihydro-1H-pyrrole-2-carboxylic acid 1. Procedure for the Preparation of 139a

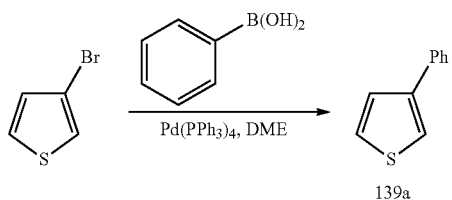

To a solution of 3-bromo thiophene (15.0 g, 92 mmol) and phenyl boronic acid (16.8 g, 138 mmol) in DME (150 mL) was added Pd(PPh$_3$)$_4$, (1.0 g, 0.87 mmol) and the mixture was heated at reflux overnight under a N$_2$ atmosphere, TLC (PE) showed most of the starting material was consumed. The mixture was cooled to RT, washed with brine (100 mL), dried over Na$_2$SO$_4$, filtered and concentrated in vacuo. The residue was purified by column chromatography (PE) to give 139a (4.0 g, 27%) as light yellow solid, which was used directly in the next step.

2. Procedure for the Preparation of 139b

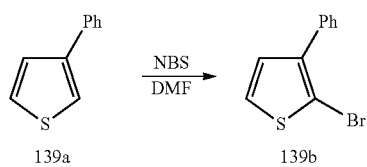

To a stirred solution of 139a (2.0 g, 12.5 mmol) in DMF (40 mL) at 0° C. under N$_2$ was added a solution of NBS (2.43 g, 13.7 mmol) in DMF (20 mL) dropwise and the mixture was stirred at RT overnight, TLC analysis (hexane) showed that the starting material was consumed. The mixture was poured into water (300 mL), extracted with EA (50 mL×2) and the combined organic extracts were washed with water (40 mL), brine, dried over Na$_2$SO$_4$, filtered and concentrated in vacuo to give 139b (3.0 g, 100%) as a yellow oil.

3. Procedure for the Preparation of 139c

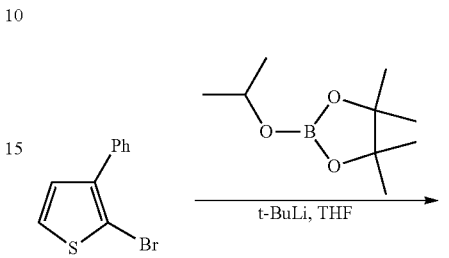

To a stirred solution of 139b (1.0 g, 4.2 mmol) in THF (20 mL) at −70° C., under N$_2$ was added t-BuLi (1.3 M solution in hexane, 3.5 mL, 4.6 mmol) dropwise and the mixture was stirred at −70° C. for 2 h. 2-Isopropoxy-4,4,5,5-tetramethyl-1,3,2-dioxaborolane (950 mg, 5.1 mmol) was added dropwise and stirring was continued at −70° C. for a further 3 h. The mixture was allowed to warm to RT and stirred for a further 1 h, TLC (PE) showed that the starting material was consumed. The mixture was cooled to 0° C., water was added (30 mL) and extracted with EA (20 mL×2). The combined organic extracts were washed with brine, dried over Na$_2$SO$_4$, filtered and concentrated in vacuo. The residue was purified by column chromatography (PE:EA=1:0 to 50:1) to give 139c (700 mg, 58%) as yellow solid. LC-MS (Agilent): R$_t$ 4.64 min; m/z calculated for C$_{16}$H$_{19}$BO$_2$S [M+H]$^+$ 287.1, [M+Na]$^+$ 309.1, found [M+H]$^+$ 287.1, [M+Na]$^+$ 309.1.

4. Procedure for the Preparation of 139d

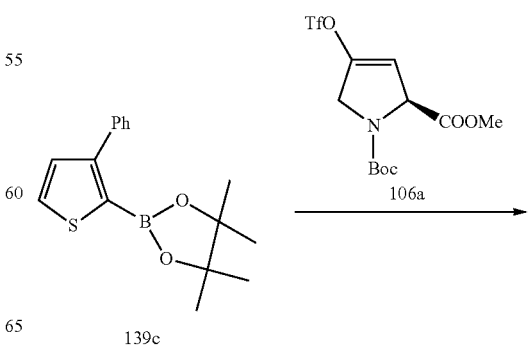

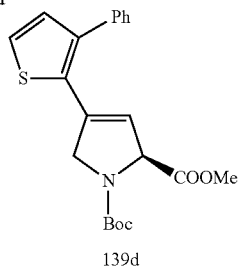

139d

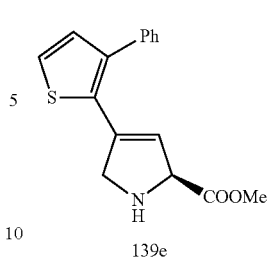

139e

6. Procedure for the Preparation of 139f.

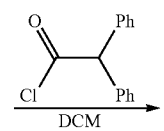

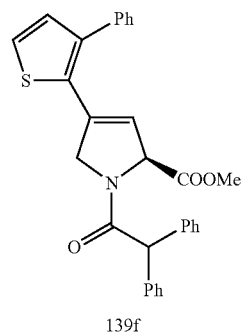

139f

To a mixture of 139c (515 mg, 1.8 mmol) and 106a (675 mg. 1.8 mmol) in toluene (10 mL) was added a 2 M aqueous $Na_2CO_3$ solution (2.7 mL, 5.4 mmol) and $Pd(PPh_3)_4$ (104 mg, 0.09 mmol, 5 mol %) and the mixture was heated at 105° C. overnight under a $N_2$ atmosphere, TLC (PE:EA=10:1) showed that most of the starting materials were consumed. The mixture was cooled to RT, diluted with water (20 mL) and extracted with EA (15 mL×2). The combined organic extracts were washed with brine, concentrated in vacuo and the residue was purified by column chromatography (PE to PE:EA=40:1) to give 139d (600 mg, 86%) as yellow oil. LC-MS (Agilent): $R_t$ 4.60 min; m/z calculated for $C_{21}H_{23}NO_4S$ [M−100]$^+$ 286.1, [M+Na]$^+$ 408.1, [M−56]$^+$ 330.1, found [M−100]$^+$ 286.1, [M+Na]$^+$ 408.1, [M−56]$^+$ 330.1.

5. Procedure for the Preparation of 139e

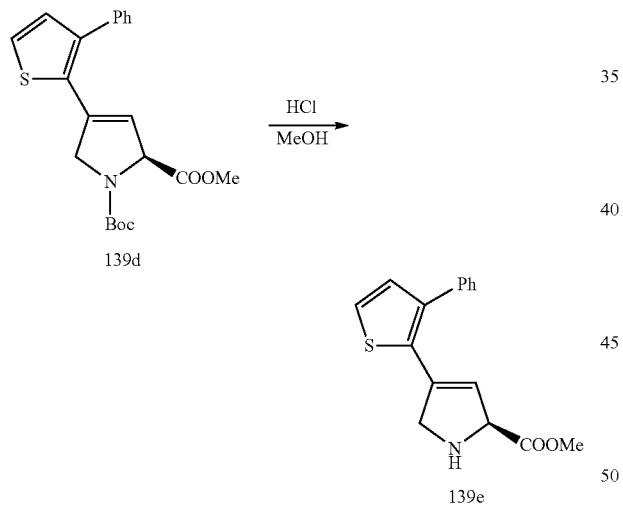

139d (600 mg, 1.56 mmol) was dissolved in a 4 M HCl/MeOH solution (15 mL) and the mixture was stirred at RT overnight, TLC (PE:EA=2:1) showed that the starting material was consumed. Most of the MeOH was removed in vacuo and the residue was diluted with water (20 mL) and washed with $Et_2O$ (15 mL×2). The aqueous layer was basified to pH 8 with a saturated aqueous $Na_2CO_3$ solution and extracted with DCM (15 mL×2). The combined organic extracts were washed with brine, dried over $Na_2SO_4$, filtered and concentrated in vacuo and the residue was purified by column chromatography (PE:EA=15:1 to 5:1) to give 139e (170 mg, 38%) as a yellow oil. LC-MS (Agilent): $R_t$ 3.51 min; m/z calculated for $C_{17}H_{17}NO_2S$ [M+H]$^+$ 286.1, found [M+H]$^+$ 286.1.

To a solution of 139e (160 mg, 0.56 mmol) and $Et_3N$ (85 mg, 0.84 mmol) in DCM (5 mL) at 0° C. was added a solution of diphenylacetyl chloride (155 mg, 0.67 mmol) in DCM (2 mL) and the mixture was stirred at RT for 15 min, TLC (PE:EA=4:1) showed that the starting material was consumed. The mixture was washed with brine, dried over $Na_2SO_4$, filtered and concentrated in vacuo. The residue was purified by column chromatography (PE:EA=15:1 to 8:1) to give 139f (130 mg, 48%) as a yellow solid. LC-MS (Agilent): $R_t$ 4.37 min; m/z calculated for $C_{30}H_{25}NO_3S$ [M+H]$^+$ 480.2, found [M+H]$^+$ 480.2.

7. Procedure for the Preparation of 139

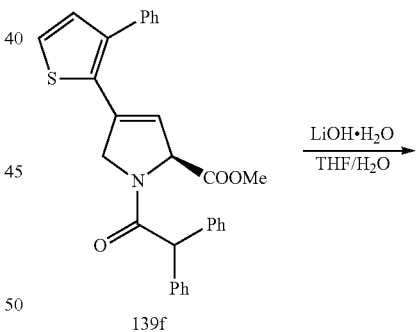

139f

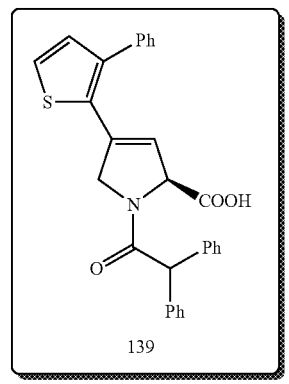

139

To a mixture of 139f (130 mg, 0.27 mmol) in THF/water (6 mL/2 mL) was added LiOH.H$_2$O (23 mg, 0.54 mmol) and the mixture was stirred at RT overnight, TLC (PE:EA=2:1) showed that the starting material was consumed. Most of the THF was removed in vacuo and the residue was partitioned between water (15 mL) and DCM (15 mL) and the aqueous phase was acidified to pH 2-3 with a 1 M aqueous HCl solution. The layers were separated and the aqueous phase was extracted with DCM (15 mL). The combined organic extracts were washed with brine, dried over Na$_2$SO$_4$, filtered and concentrated in vacuo to give 139 (100 mg, 80%) as white solid. LC-MS (Agilent): R$_t$ 4.43 min; m/z calculated for C$_{29}$H$_{23}$NO$_3$S [M+H]$^+$ 466.1 found [M+H]$^+$ 466.1. HPLC (JULY-L) (214 and 254 nm): R$_t$ 9.46 min.

Example 48: Compound 107 (2S,4S)-1-(2,2-diphenylacetyl)-4-(3-phenylthiophen-2-yl)-pyrrolidine-2-carboxylic acid

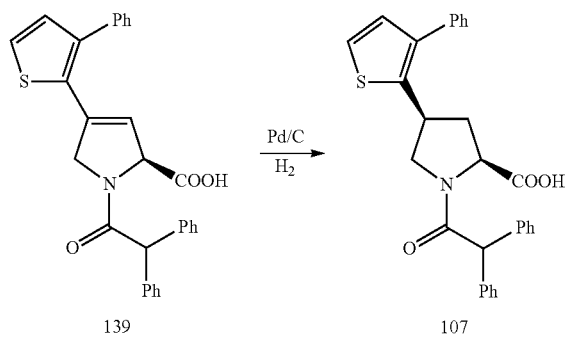 [SMILES: O=C(O)[C@@H]1C=C(c2sccc2-c2ccccc2)CN1C(=O)C(c1ccccc1)c1ccccc1 ; "Pd/C" ; "H2" ; O=C(O)[C@@H]1C[C@H](c2sccc2-c2ccccc2)CN1C(=O)C(c1ccccc1)c1ccccc1]

A mixture of 139 (60 mg, 0.13 mmol) and 10% Pd/C (6 mg) in MeOH (10 mL) was stirred at RT under a H$_2$ atmosphere (1 atm) overnight, TLC (DCM:MeOH=10:1) showed that the starting material was consumed. The mixture was filtered and the filtrate was concentrated in vacuo. The residue was purified by preparative HPLC to give 107 (15 mg, 25%) as white solid. LC-MS (Agilent): R$_t$ 4.51 min; m/z calculated for C$_{29}$H$_{25}$NO$_3$S [M+H]$^+$ 468.1 found [M+H]$^+$ 468.1. HPLC (JULY-L) (214 and 254 nm): R$_t$ 9.44 min.

Example 49: Compound 140 (S)-1-(2,2-diphenylacetyl)-4-(4-phenylbut-1-yn-1-yl)-2,5-dihydro-1H-pyrrole-2-carboxylic acid 1. Procedure for the Preparation of 140a

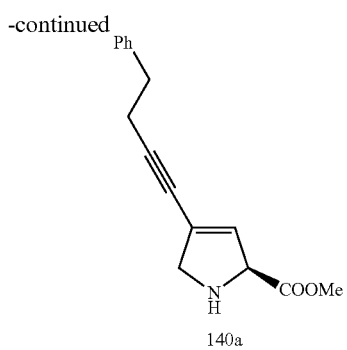

106b (40 mg, 0.089 mmol) was dissolved in a 4 M HCl/MeOH solution (5 mL) at RT and the mixture was stirred for 4 h, TLC (PE:EA=4:1) showed that the starting material was consumed. The mixture was concentrated in vacuo and the residue was dissolved in water (20 mL) and washed with ether (15 mL). DCM (15 mL) was added and the aqueous layer was basified to pH 8 with a saturated aqueous NaHCO$_3$ solution. The layers were separated and the aqueous phase was extracted with DCM (15 mL). The combined organic extracts were washed with brine, dried over Na$_2$SO$_4$, filtered and concentrated in vacuo to give 140a (30 mg, 98%) as a yellow oil. LC-MS (Agilent): R$_t$ 3.55 min; m/z calculated for C$_{16}$H$_{17}$NO$_2$[M+H]$^+$ 256.04, found [M+H]$^+$ 256.1.

2. Procedure for the Preparation of 140b

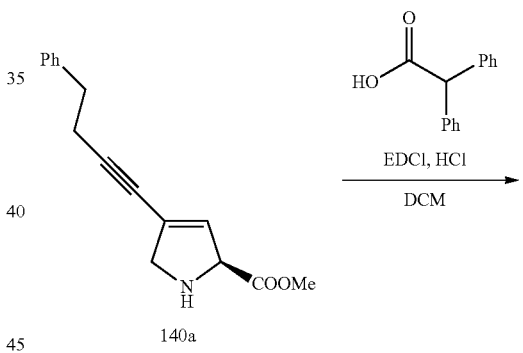

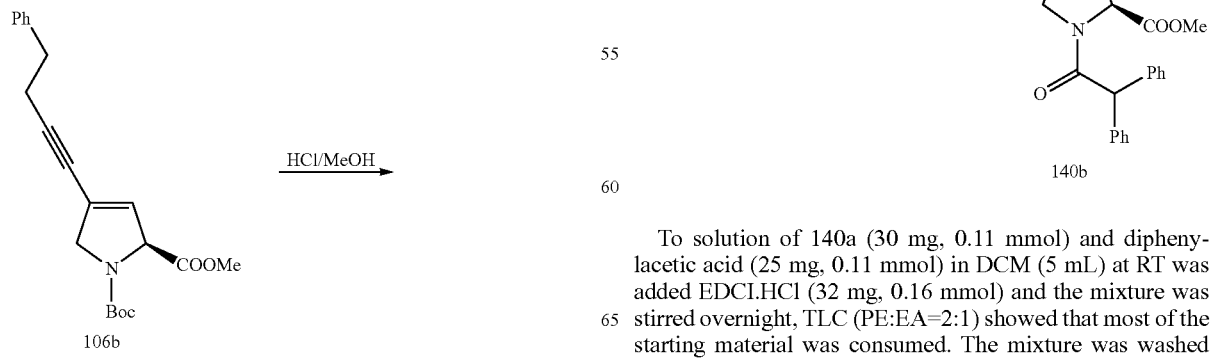

To solution of 140a (30 mg, 0.11 mmol) and diphenylacetic acid (25 mg, 0.11 mmol) in DCM (5 mL) at RT was added EDCI.HCl (32 mg, 0.16 mmol) and the mixture was stirred overnight, TLC (PE:EA=2:1) showed that most of the starting material was consumed. The mixture was washed with brine, dried over Na$_2$SO$_4$, filtered and concentrated in vacuo. The residue was purified by chromatography (PE: EA=1:0 to 4:1) to give 140b (40 mg, 81%) as a yellow solid. LC-MS (Agilent): $R_t$ 4.52 min; m/z calculated for $C_{30}H_{27}NO_3$ [M+H]$^+$ 450.2, found [M+H]$^+$ 450.2.

3. Procedure for the Preparation of 140

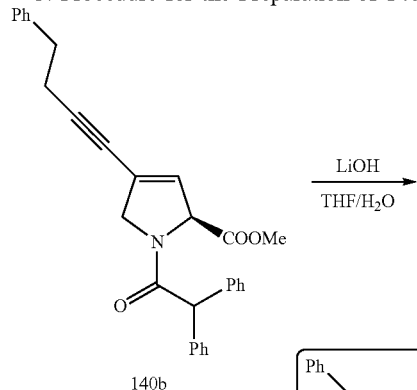

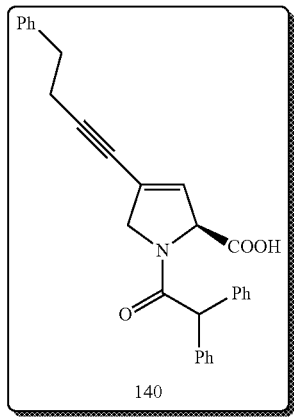

Hydrolysis of 140b (40 mg, 0.089 mmol) was performed as described in Example 9, 3. with about 2 equivalents of LiOH.H$_2$O (7 mg, 0.18 mmol). After acidification, the layers were separated and the aqueous phase was extracted with DCM (10 mL). The combined organic extracts were washed with brine, dried over Na$_2$SO$_4$, filtered and concentrated in vacuo. The residue was purified by preparative HPLC to give 140 (10 mg, 26%) as a white solid. LC-MS (Agilent): $R_t$ 3.95 min; m/z calculated for $C_{29}H_{25}NO_3$ [M+H]$^+$ 436.2, found [M+H]$^+$ 436.2. HPLC (214 and 254 nm): $R_t$ 9.49 min.

Example 50: Compound 112 (2S,4S)—N—(N,N-dimethylsulfamoyl)-1-(2,2-diphenylacetyl)-4-(3-phenylpropoxy)pyrrolidine-2-carboxamide

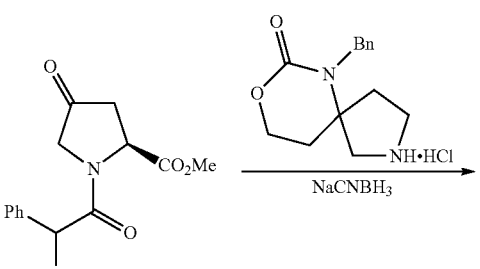

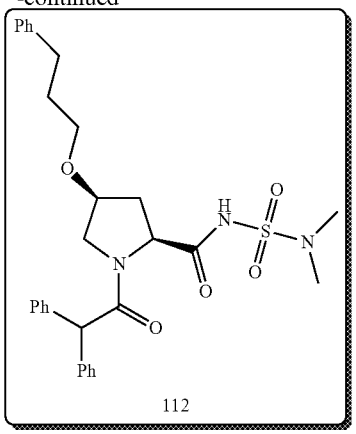

To a solution of Compound 6 (50 mg, 0.11 mmol) and N,N-dimethylsulfamide (15 mg, 0.12 mmol) in DCM (1 mL) was added DCC (27 mg, 0.13 mmol) and the mixture was stirred in a sealed flask at RT overnight, LCMS analysis showed that the starting material was consumed. DCM (5 mL) and PE (3 mL) were added to the mixture and the white solid was removed by filtration. The filtrate was concentrated in vacuo and the residue was purified by preparative HPLC to give 112 (15 mg, 25%) as a white solid. LC-MS (Agilent): $R_t$ 3.25 min; m/z calculated for $C_{30}H_{35}N_3O_5S$ [M+H]$^+$ 550.2, found [M+H]$^+$ 550.3. HPLC (JULY-L) (214 and 254 nm): $R_t$ 9.27 min.

Example 51: Compound 115 (2S,4S)-4-(6-benzyl-7-oxa-2,6-diazaspiro[4,5]decan-2-yl)-1-(2,2-diphenylacetyl)pyrrolidine-2-carboxylic acid 1. Procedure for the Preparation of 115a

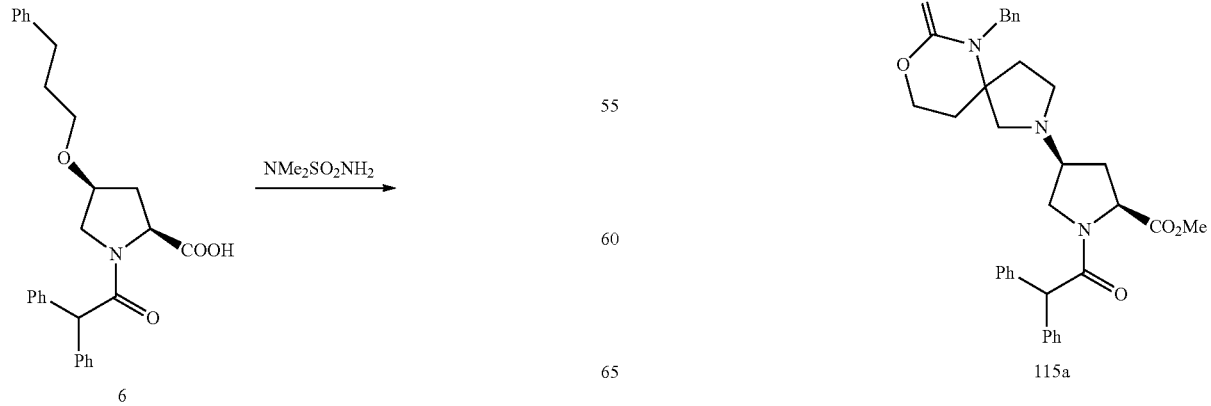

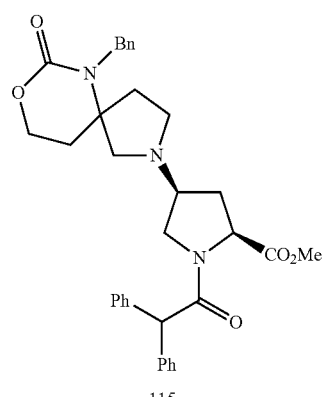

To a solution of 61a (142 mg, 0.42 mmol) and 6-benzyl-8-oxa-2,6-diazaspiro[4.5]decan-7-one hydrochloride (100 mg, 0.42 mmol) in MeOH (10 mL) was added Et₃N (43 mg, 0.42 mmol) followed by 2 drops of AcOH and the mixture was stirred at RT for 1 h. NaCNBH₃ (40 mg, 0.63 mmol) was added and stirring was continued at RT overnight, TLC (DCM:MeOH=10:1) showed that the starting material was consumed. The mixture was concentrated in vacuo and the residue was purified by column chromatography (DCM:MeOH=100:1 to 50:1) to give 115a (100 mg, 42%) as a light yellow solid. LC-MS (Agilent): $R_t$ 3.96 min; m/z calculated for $C_{34}H_{37}N_3O_5$ [M+H]⁺ 568.3, found [M+H]⁺ 568.3.

2. Procedure for the Preparation of 115

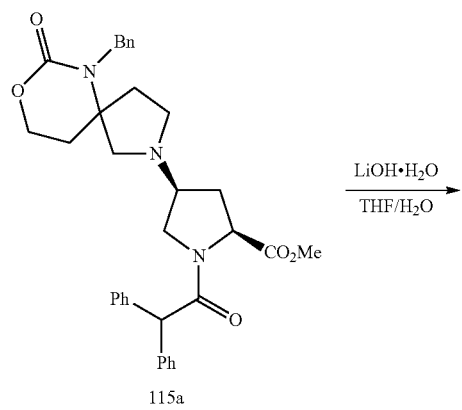

115a

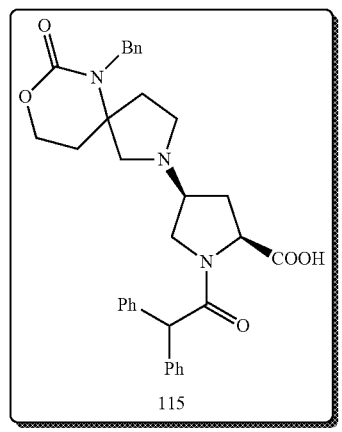

115

Hydrolysis of 115a (20 mg, 0.035 mmol) was performed as described in Example 9, 3. with 2 equivalents of LiOH.H₂O (3 mg, 0.07 mmol). The organic layer was separated, washed with brine, dried over Na₂SO₄, filtered and concentrated in vacuo. The residue was purified by preparative HPLC to give 115 (10 mg, 50%) as a white solid. LC-MS (Agilent): $R_t$ 3.94 min; m/z calculated for $C_{33}H_{35}N_3O_5$ [M+H]⁺ 554.3 found [M+H]⁺ 554.3. HPLC (JULY-L) (214 and 254 nm): $R_t$ 8.77 min.

Example 52: Compound 116 (2S,4S)1-(2,2-diphenylacetyl)-4-(methyl(3-phenylprop-2-yn-1-yl)amino) pyrrolidine-2-carboxylic acid 1. Procedure for the Preparation of 116a

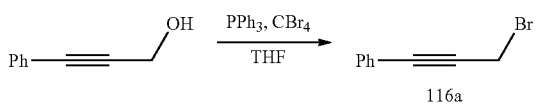

To a solution of 3-phenylprop-2-yn-1-ol (930 mg, 7.04 mmol) and PPh₃ (1.85 g, 7.04 mmol) in THF (20 mL) was added CBr₄ (2.10 g, 6.33 mmol) portion-wise and the mixture was stirred at RT overnight, TLC (100% PE) showed that most of the starting material was consumed. PE (15 mL) was added and the resulting precipitate was removed by filtration. The filtrate was concentrated in vacuo and the residue was purified by chromatography (100% PE) to give 116a (1.10 g, 81%) as a colorless oil.

2. Procedure for the Preparation of 116b

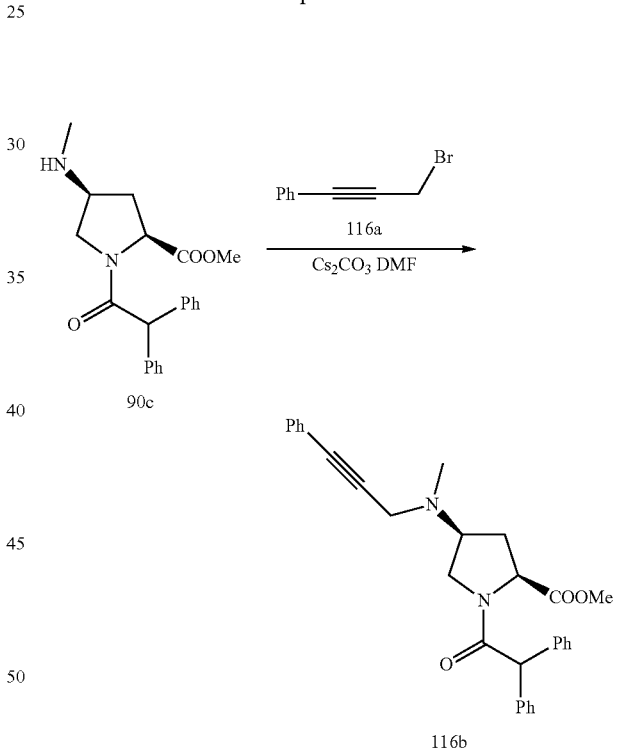

A mixture of 90c (80 mg, 0.23 mmol), 116a (53 mg, 0.27 mmol) and Cs₂CO₃ (89 mg, 0.27 mmol) in DMF (8 mL) was heated at 60° C. overnight, TLC (DCM:MeOH=20:1) showed that most of the starting material was consumed. The mixture was poured into ice-water (40 mL), extracted with EA (20 mL×2) and the combined organic extracts were washed with brine (15 mL), dried over Na₂SO₄, filtered and concentrated in vacuo. The residue was purified by chromatography (PE:EA=1:0 to 2:1) to give 116b (60 mg, 57%) as thick colorless oil. LC-MS (Agilent): $R_t$ 4.24 min; m/z calculated for $C_{30}H_{30}N_2O_3$ [M+H]⁺ 467.2, found [M+H]⁺ 467.2.

3. Procedure for the Preparation of 116

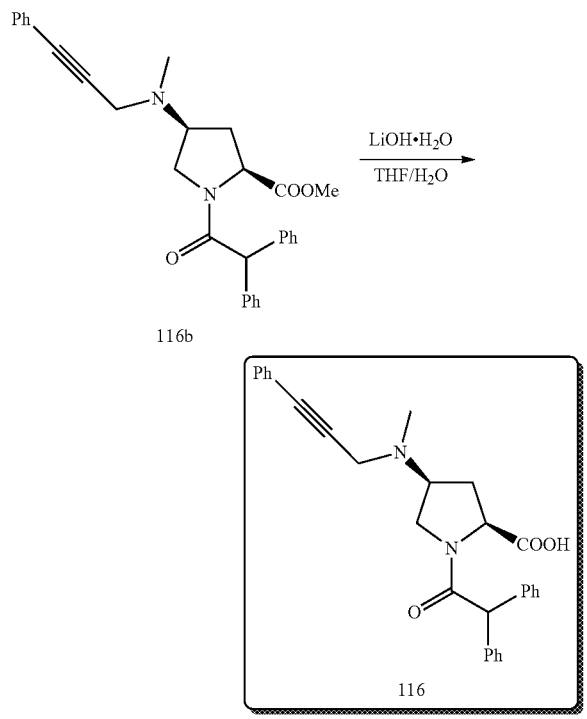

A mixture of 116b (60 mg, 0.13 mmol) and LiOH.H$_2$O (16 mg, 0.39 mmol) in THF/water (8 mL/2 mL) was stirred at RT overnight, TLC (PE:EA=1:1) showed that the starting material was consumed. Most of the THF was removed in vacuo, the residue was dissolved in water (8 mL) and washed with MTBE (6 mL×2). The aqueous layer was then acidified to pH 4~5 with a 4 M aqueous HCl solution. The resulting precipitate was collected by filtration and purified by preparative HPLC to give 116 (32 mg, 55%) as a white solid. LC-MS (Agilent): R$_t$ 3.81 min; m/z calculated for C$_{29}$H$_{28}$N$_2$O$_3$ [M+H]$^+$ 453.2, found [M+H]$^+$ 453.2. HPLC (JULY-L) (214 and 254 nm): R$_t$ 8.91 min.

Example 53: Compound 124 (2S,4S)-1-(2,2-diphenylacetyl)-4-((3-phenylpropyl)thio)-pyrrolidine-2-carboxylic acid 1. Procedure for the Preparation of 124a

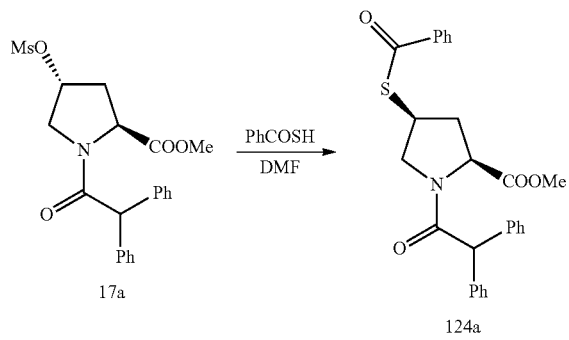

To a solution of PhCOSH (1.42 g, 9.60 mmol) in DMF (70 mL) at 0° C. under N$_2$ was added NaH (0.39 g, 9.60 mmol) slowly and the mixture was stirred at RT for 30 min. 17a (2.00 g, 4.8 mmol) was then added and the mixture was stirred at RT overnight, TLC (PE:EA=1:1) showed that the starting material was consumed. The mixture was poured into water, extracted with EA and the organic extract was washed with a saturated aqueous NaHCO$_3$ solution, brine, dried over Na$_2$SO$_4$, filtered and concentrated in vacuo. The residue was purified by chromatography (PE:EA=1:0 to 5:1) to give 124a (1.61 g, 73%) as a yellow solid. LC-MS (Agilent, P-2): R$_t$ 3.14 min; m/z calculated for C$_{2-4}$H$_{25}$NO$_4$S [M+H]$^+$ 460.1, [M+Na]$^+$ 482.1, found [M+H]$^+$ 460.1, [M+Na]$^+$ 482.1.

2. Procedure for the Preparation of 124b

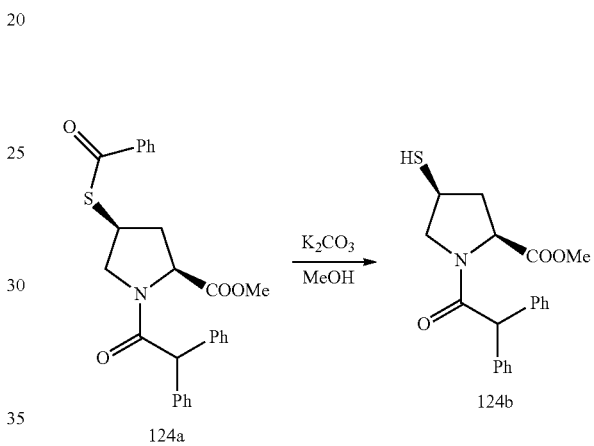

A mixture of 124a (1.61 g, 3.50 mmol) and K$_2$CO$_3$ (968 mg, 7.01 mmol) in MeOH (20 mL) was stirred at RT for 20 min, TLC (PE:EA=2:1) showed that the starting material was consumed. Most of the MeOH was removed in vacuo and the residue was diluted with brine (30 mL) and extracted with EA (30 mL×2). The combined organic extracts were dried over Na$_2$SO$_4$, filtered and concentrated in vacuo to give crude 124b (1.58 g) as thick yellow oil, which was used directly in the next step without purification. LC-MS (Agilent, P-2): R$_t$ 2.93 min; in/z calculated for C$_{20}$H$_{21}$NO$_3$S [M+H]$^+$ 356.1, [M+Na]$^+$ 378.1, found [M+H]$^+$ 356.1, [M+Na]$^+$ 378.1.

3. Procedure for the Preparation of 124c

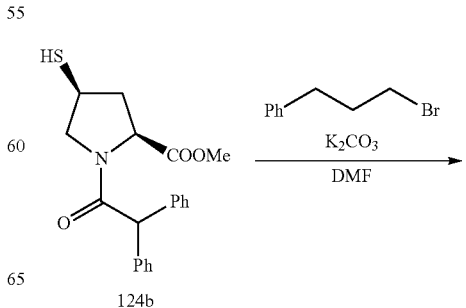

158

Example 54: Compound 125 (2S,4S)-1-(2,2-diphenylacetyl)-4-((3-phenylpropyl)-sulfonyl)pyrrolidine-2-carboxylic acid 1. Procedure for the Preparation of 125a.

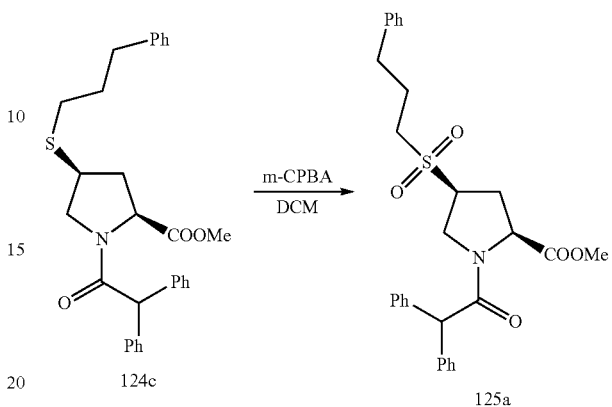

To a solution of 124c (260 mg, 0.55 mmol) in DCM (15 mL) was added 80% m-CPBA (296 mg, 1.37 mmol) and the mixture was stirred at RT overnight, TLC (PE:EA=2:1) showed that the starting material was consumed. The mixture was washed with a saturated aqueous $Na_2CO_3$ solution (15 mL), brine (15 mL×2), dried over $Na_2SO_4$, filtered and concentrated in vacuo. The residue was purified by chromatography (PE:EA=8:1 to 2:1) to give 125a (245 mg, 88%) as a thick colorless oil. LC-MS (Agilent, P-2): $R_t$ 3.03 min; m/z calculated for $C_{29}H_{31}NO_5S$ $[M+H]^+$ 506.2, $[M+Na]^+$ 528.2, found $[M+H]^+$ 506.2, $[M+Na]^+$ 528.2.

2. Procedure for the Preparation of 125

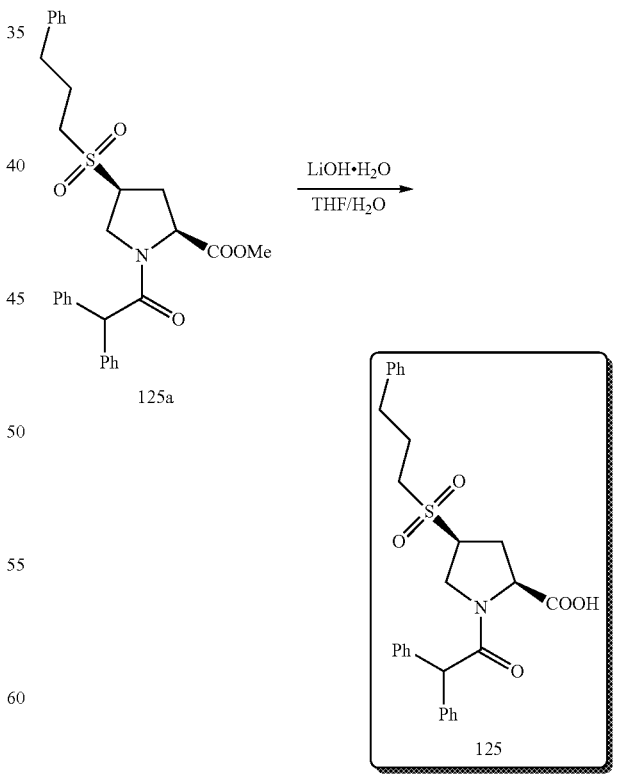

Hydrolysis of 125a (245 mg, 0.48 mmol) was performed as described in Example 53, 2. with about 3 equivalents of $LiOH·H_2O$ (61 mg, 1.45 mmol). The organic extract was

157

-continued

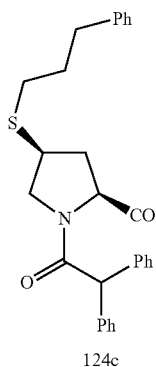

To a stirred mixture of 124b (600 mg, 1.69 mmol) and $K_2CO_3$ (257 mg, 1.86 mmol) in DMF (20 mL) was added 1-bromo-3-phenylpropane (370 mg, 1.86 mmol) and the mixture was heated at 80° C. overnight, TLC (PE:EA=2:1) showed that the starting material was consumed. The mixture was poured into ice-water (100 mL) and EA (40 mL). The organic layer was separated, washed with brine (30 mL×2), dried over $Na_2SO_4$, filtered and concentrated in vacuo. The residue was purified by chromatography (PE:EA=1:0 to 4:1) to give 124c (448 mg, 71%) as a colorless oil. LC-MS (Agilent, P-2): $R_t$ 3.26 min; m/z calculated for $C_{29}H_{31}NO_3S$ $[M+H]^+$ 472.2, $[M+Na]^+$ 496.2, found $[M+H]^+$ 472.2, $[M+Na]^+$ 496.2.

4. Procedure for the Preparation of 124

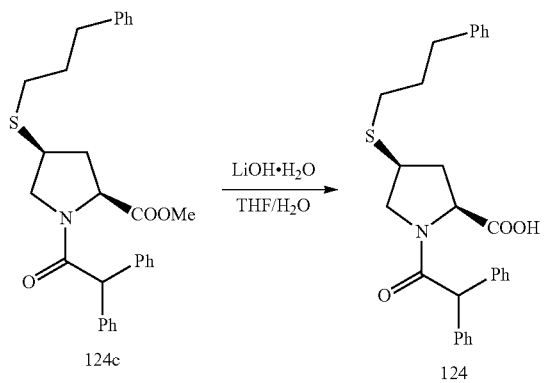 [SMILES: COC(=O)[C@@H]1C[C@H](SCCCc2ccccc2)CN1C(=O)C(c1ccccc1)c1ccccc1 ; "THF/H2O" ; "LiOH·H2O" ; O=C(O)[C@@H]1C[C@H](SCCCc2ccccc2)CN1C(=O)C(c1ccccc1)c1ccccc1]

A mixture of 124c (146 mg, 0.31 mmol) and $LiOH·H_2O$ (39 mg, 0.93 mmol) in THF/water (8 mL/2 mL) was stirred at RT overnight, TLC (PE:EA=2:1) showed that the starting material was consumed. Most of the THF was removed in vacuo, the residue was dissolved in water (10 mL), acidified to pH 4~5 with a 4 M aqueous HCl solution and extracted with DCM (15 mL×2). The combined organic extracts were washed with brine (10 mL×2), dried over $Na_2SO_4$, filtered and concentrated in vacuo. The residue was purified by chromatography (PE:EA=4:0 to 2:1) to give 124 (97 mg, 68%) as a colorless oil. LC-MS (Agilent, P-2): $R_t$ 2.87 min; m/z calculated for $C_{28}H_{29}NO_3S$ $[M+H]^+$ 460.2, $[M+Na]^+$ 482.2, found $[M+H]^+$ 460.2, $[M+Na]^+$ 482.2. HPLC (JULY-L) (214 and 254 nm): $R_t$ 9.41 min.

washed with brine (15 mL×2), dried over $Na_2SO_4$, filtered and concentrated in vacuo to give 125 (215 mg, 90%) as a white solid. LC-MS (Agilent, P-2): $R_t$ 2.73 min; m/z calculated for $C_{28}H_{29}NO_5S$ $[M+H]^+$ 492.2, $[M+Na]^+$ 514.2, found $[M+H]^+$ 492.2, $[M+Na]^+$ 514.2. HPLC (JULY-L) (214 and 254 nm): $R_t$ 8.95 min.

Example 55: Compound 142 (2S,3S)-1-(2,2-diphenylacetyl)-3-(3-phenylpropoxy)-azetidine-2-carboxylic acid and (2R,3R)-1-(2,2-diphenylacetyl)-3-(3-phenylpropoxy)-azetidine-2-carboxylic acid 1. Procedure for the Preparation of 142b

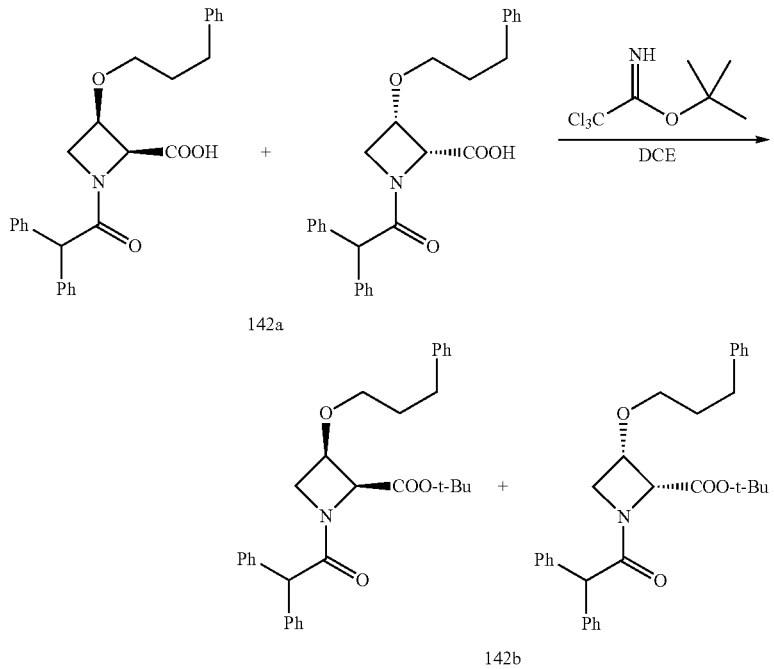

To a mixture of 142a (300 mg, 0.69 mmol) in DCE (10 mL) was added tert-butyl 2,2,2-trichloroacetimidate (168 mg, 0.77 mmol) and the mixture was heated at 60° C. overnight, TLC(DCM:MeOH=10:1) showed that the starting material was consumed. The mixture was washed with brine (10 mL), dried over $Na_2SO_4$, filtered and concentrated in vacuo. The residue was purified by chromatography (PE:EA=1:0 to 4:1) to give 142b (270 mg, 81%) as a white solid. LC-MS (Agilent): $R_t$ 4.81 min; m/z calculated for $C_{31}H_{35}NO_4$ $[M+H]^+$ 486.3, $[M-t-Bu]^+$ 430.2, found $[M+H]^+$ 486.3, $[M-t-Bu]^+$ 430.2.

2. Procedure for the Preparation of 142c

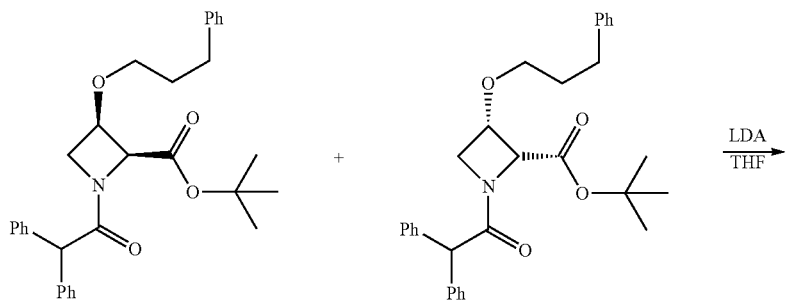

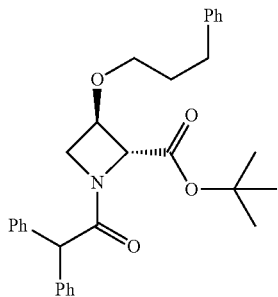 + 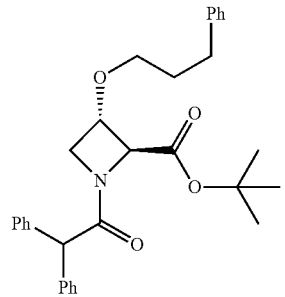

142c

To a stirred solution of 142b (170 mg, 0.35 mmol) in THF (10 mL) at −65° C. under $N_2$ was added LDA (1 M in THF, 0.7 mL, 0.70 mmol) and the mixture was allowed to warm slowly to RT and stirred overnight. The mixture was cooled in an ice-water bath and the reaction was quenched with a saturated aqueous $NH_4Cl$ solution. The mixture was partitioned between EA (20 mL) and brine (30 mL), the organic layer was separated, dried over $Na_2SO_4$, filtered and concentrated in vacuo. The residue was purified by chromatography (PE:EA=1:0 to 10:1) to give the trans-product (70 mg, 41%) as a colorless oil and the cis starting material (50 mg, 29%) as a white solid. LC-MS (Agilent): $R_1$ 4.47 min; m/z calculated for $C_{31}H_{35}NO_4$ $[M+H]^+$ 486.3, $[M-t-Bu]^+$ 430.2, found $[M+H]^+$ 486.3, $[M-t-Bu]^+$ 430.2.

3. Procedure for the Preparation of 142

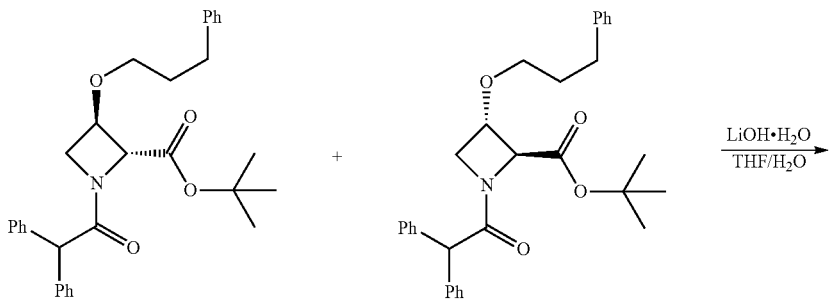

142c

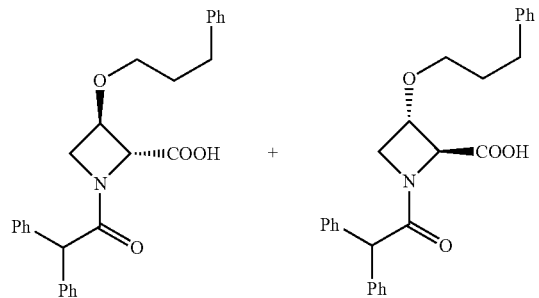

142

To a stirred mixture of 142c (70 mg, 0.14 mmol) in THF/water (3 mL/1 mL) was added LiOH.H$_2$O (18 mg, 0.43 mmol) and the mixture was stirred at RT overnight, TLC (PE:EA=4:1) showed that the starting material was consumed. Most of the THF was removed in vacuo, the residue was dissolved in water (15 mL) and acidified to pH 3-4 with a 3 M aqueous HCl solution. The aqueous mixture was extracted with DCM (15 mL×2) and the combined organic extracts were washed with brine, dried over Na$_2$SO$_4$, filtered and concentrated in vacuo to give 142 (60 mg, 92%) as a white solid. LC-MS (Agilent): R$_t$ 4.36 min; m/z calculated for C$_{27}$H$_{27}$NO$_4$ [M+H]$^+$ 430.2, found [M+H]$^+$ 430.2. HPLC (JULY-L) (214 and 254 nm): R$_t$ 9.33 min.

Example 56: Compound 108 1-((2R,3S)-2-(hydroxymethyl)-3-(3-phenylpropoxy)-azetidin-1-yl)-2,2-diphenylethanone and 14(2S,3R)-2-(hydroxymethyl)-3-(3-phenylpropoxy)-azetidin-1-yl)-2,2-diphenylethanone

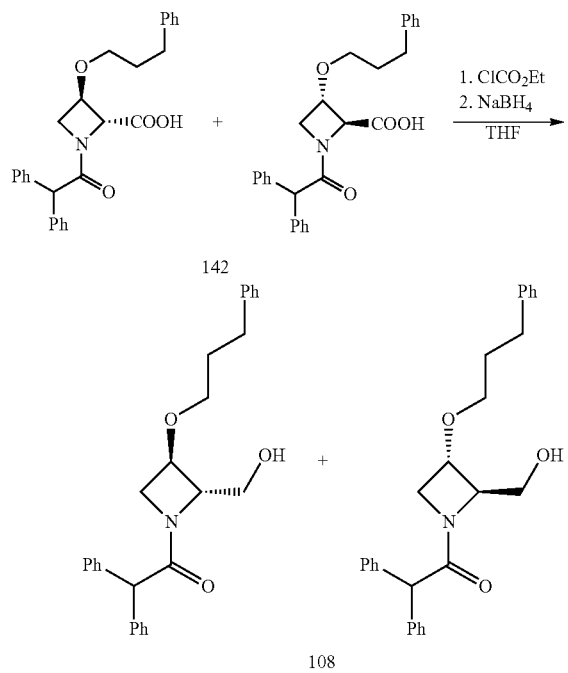

To a solution of 142 (30 mg, 0.07 mmol) in dry THF (10 mL) at 0° C. under N$_2$ was added Et$_3$N (7 mg, 0.07 mmol) followed by ClCO$_2$Et (7.6 mg, 0.07 mmol) and the mixture was stirred at 0° C. for 1 h. NaBH$_4$ (8 mg, 0.21 mmol) was added and stirring was continued at 0° C. for 1 h before allowing to warm slowly to RT and stirred overnight, TLC (PE:EA=2:1) showed that the starting material was consumed. The reaction was quenched with water (30 mL) and the mixture was extracted with EA (15 mL×2). The combined organic extracts were washed with brine, dried over Na$_2$SO$_4$, filtered and concentrated in vacuo. The residue was purified by preparative HPLC to give 108 (15 mg, 51%) as a colorless oil.

LC-MS (Agilent): R$_t$ 4.34 min; m/z calculated for C$_{27}$H$_{29}$NO$_3$ [M+H]$^+$ 416.2, found [M+H]$^+$ 416.2. HPLC (JULY-L) (214 and 254 nm): R$_t$ 9.32 min.

Example 57: Compound 109 (1-((2R,3R)-2-(hydroxymethyl)-3-(3-phenylpropoxy)-azetidin-1-yl)-2,2-diphenylethanone and (1-((2S,3S)-2-(hydroxymethyl)-3-(3-phenylpropoxy)-azetidin-1-yl)-2,2-diphenylethanone 1. Procedure for the Preparation of 109a

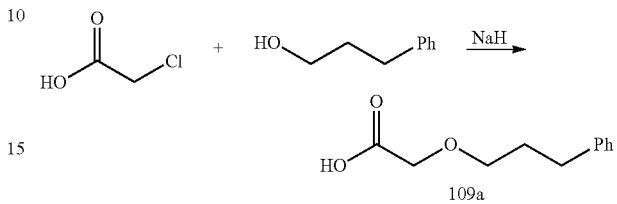

To a solution of 3-phenylpropan-1-ol (54.0 g, 0.40 mol) in DMF (250 mL) at RT was added NaH (60% dispersion in oil, 15.6 g, 0.40 mol) and the mixture was stirred at RT for 1 h, then heated at 61° C. for 1 h. The mixture was cooled to 5° C. and 2-chloroacetic acid (15.0 g, 0.16 mol) was added. The mixture was stirred at RT for 0.5 h, then heated at 60° C. for 3 h, TLC (DCM:MeOH=10:1) showed that a new product was formed. The mixture was allowed to cool to RT, stirred overnight then poured into ice-water (1.5 L) and washed with EA (300 mL×4). The aqueous layer was acidified to pH 5 with a 3 M aqueous HCl solution and extracted with EA (500 mL×2). The combined organic extracts were washed with brine (300 mL×2), dried over Na$_2$SO$_4$, filtered and concentrated in vacuo to give 109a (25 g, 81%) as a pale yellow solid. LC-MS (Agilent): R$_t$ 3.74 min; m/z calculated for C$_{11}$H$_{14}$O$_3$ [M+Na]$^+$ 217.1, found [M+Na]$^+$ 217.1.

2. Procedure for the Preparation of 109b

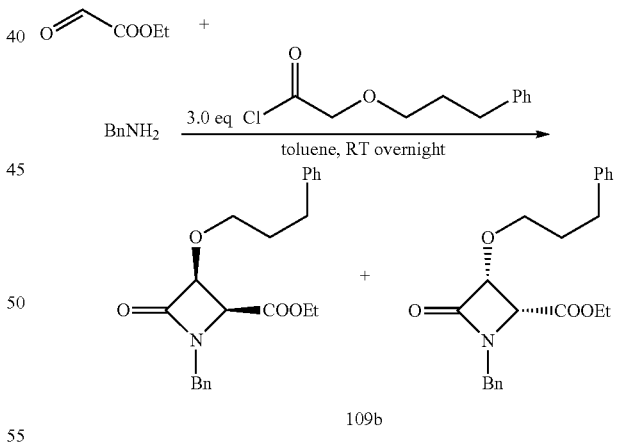

To a solution of 109a (17.1 g, 87.9 mmol) in DCM (150 mL) was added SOCl$_2$ (11.0 g, 92.3 mmol) and the mixture was heated at reflux for 0.5 h, then cooled to RT and concentrated in vacuo to give the acid chloride which was used directly in the next step. To a solution of ethyl glyoxylate (6.00 g, 50% toluene solution, 29.3 mmol) in toluene (60 mL) was added benzyl amine (3.15 g, 29.3 mmol) and the mixture was stirred at RT for 1 h. Triethylamine (10.4 g, 103 mmol) was added and the mixture was cooled in an ice-water bath. A solution of the above-prepared acid chloride in toluene (45 mL) was then added dropwise and the mixture was stirred at RT overnight, TLC (PE:EA=4:1) showed that the product was formed. The mixture was partitioned between EA (60 mL) and brine (100 mL). The organic layer was separated and washed with brine (100 mL), dried over Na$_2$SO$_4$, filtered and concentrated in vacuo. The residue was purified by chromatography (PE:EA=1:0 to 10:1) to give 109b (1.2 g, 11%) as a colorless oil. LC-MS (Agilent): R$_t$ 4.15 min; m/z calculated for C$_{22}$H$_{25}$NO$_4$ [M+H]$^+$ 368.2, [M+Na]$^+$ 390.2, found [M+H]$^+$ 368.2, [M+Na]$^+$ 390.2.

3. Procedure for the Preparation of 109c

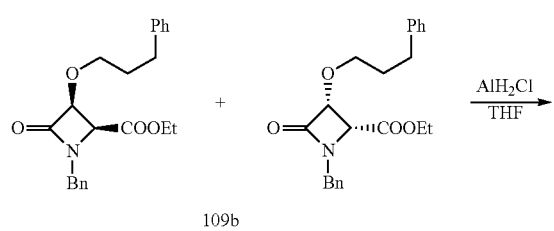

109b

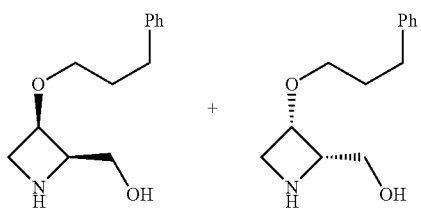

109d

To a mixture of AlCl$_3$ (333 mg, 2.49 mmol) in dry THF (5 mL) at 0° C. under N$_2$ was added LiAlH$_4$ (95 mg, 2.49 mmol) and the mixture was heated at 35° C. for 0.5 h then re-cooled to 0° C. A solution of 109b (200 mg, 0.54 mmol) in THF (2 mL) was then added and the mixture was heated at 35° C. for 3 h, TLC (PE:EA=2:1) showed that the starting material was consumed. The mixture was cooled to 0° C., the reaction was quenched water (1 mL) and then partitioned between EA and brine. The organic layer was separated, dried over Na$_2$SO$_4$, filtered and concentrated in vacuo to give 109c (160 mg, 95%) as a yellow oil. LC-MS (Agilent): R$_t$ 3.37 min; m/z calculated for C$_{20}$H$_{25}$NO$_2$ [M+H]$^+$ 312.2, found [M+H]$^+$ 312.2.

4. Procedure for the Preparation of 109d

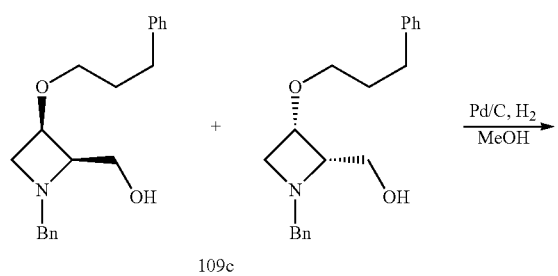

109c

A mixture of 109c (160 mg, 0.51 mmol) and 10% Pd/C (20 mg) in MeOH (5 mL) was stirred at RT under a H$_2$ atmosphere (1 atm) at 35*C overnight, TLC (DCM:MeOH=10:1) showed that the starting material was consumed. The mixture was filtered and the filtrate was concentrated in vacuo to give 109d (100 mg, 87%) as a colorless oil. LC-MS (Agilent): R$_t$ 3.53 min; m/z calculated for C$_{13}$H$_{19}$NO$_2$ [M+H]$^+$ 222.1, found [M+H]$^+$ 222.1.

5. Procedure for the Preparation of 109

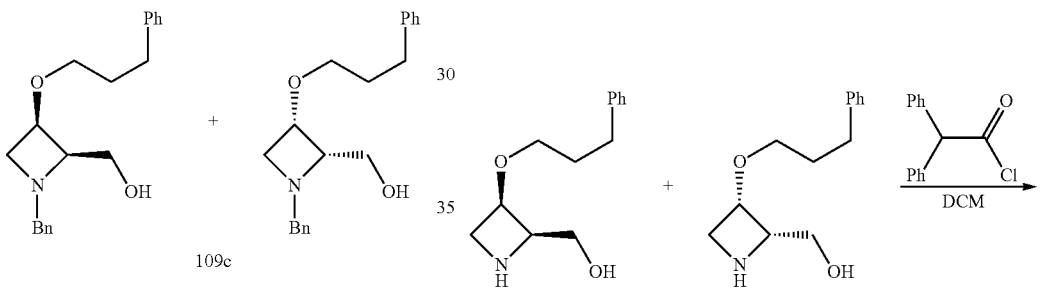

109

To a solution of 109d (100 mg, 0.45 mmol) and Et$_3$N (50 mg, 0.49 mmol) in DCM (10 mL) at 0° C. was added a solution of diphenylacetyl chloride (104 mg, 0.45 mmol) in DCM (1 mL) and the mixture was stirred at 0° C. for 1 h, TLC (DCM:MeOH=10:1) showed that the starting material was consumed. The mixture was washed with brine, dried over Na$_2$SO$_4$, filtered and concentrated in vacuo. The residue was purified by chromatography (PE:EA=1:0 to 4:1) to give 109 (80 mg, 43%) as a colorless oil. LC-MS (Agilent): R$_t$ 3.80 min; in/z calculated for C$_{27}$H$_{29}$NO$_3$ [M+H]$^+$ 416.2, found [M+H]$^+$ 416.2. HPLC (214 and 254 nm): R$_t$ 9.36 min.

Example 58: Compound 143 (2R,3R)-3-(3-phenyl-propoxy)-1-(2,2-diphenylacetyl)-azetidine-2-carboxylic acid and (2S,3S)-3-(3-phenylpropoxy)-1-(2,2-diphenylacetyl)-azetidine-2-carboxylic acid

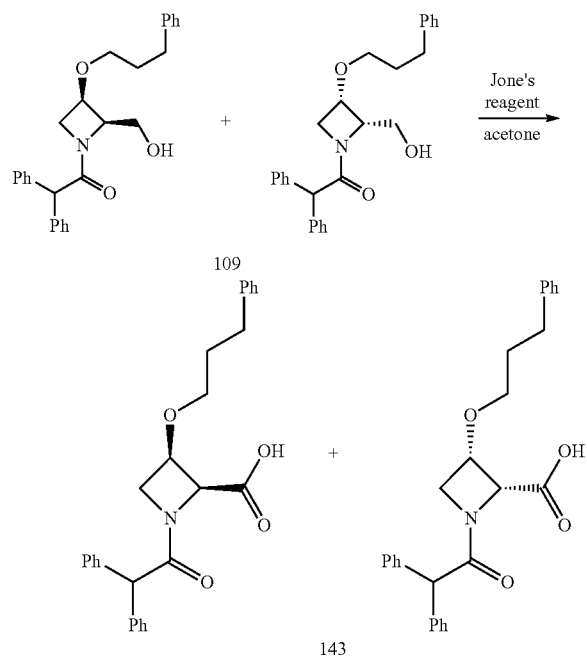

To a stirred solution of 109 (250 mg, 0.60 mmol) in acetone (5 mL) at 0° C. was added Jone's reagent (0.92 mL, 2.40 mmol) and the mixture was stirred at 0° C. for 2 h, TLC (PE:EA=2:1) showed that the starting material was consumed. The reaction was quenched with iso-propanol (1 mL) then diluted with EA (20 mL) and filtered. The filtrate was concentrated in vacuo and the residue was dissolved in EA (20 mL), washed with water (15 mL×2), saturated aqueous EDTA solution (10 mL×2), brine (15 mL×2), then dried over $Na_2SO_4$, filtered and concentrated in vacuo to give crude 143t (240 mg) as a brown oil. A portion (40 mg) of the crude product was purified by preparative TLC (DCM:MeOH=10: 1) to give pure 143 (20 mg) as a white solid. LC-MS (Agilent): $R_t$ 4.27 min; m/z calculated for $C_{27}H_{27}NO_4$ [M+H]$^+$ 430.2, found [M+H]$^+$ 430.2. HPLC (214 and 254 nm): $R_t$ 9.24 min.

Example 59: Compound 54 (2S,4S)-4-((benzyloxymethyl)-1-(2,2-diphenylacetyl)pyrrolidine-2-carboxylic acid 1. Procedure for the Preparation of 54a

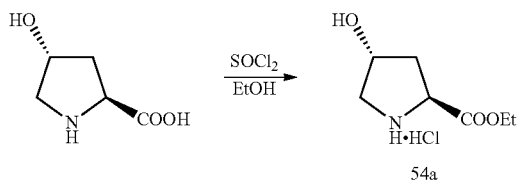

To a stirred solution of trans-4-hydroxy-L-proline (100 g, 0.76 mol) in EtOH (1 L) was added $SOCl_2$ (95.2 g, 0.8 mol) dropwise and the mixture was heated at reflux overnight. The mixture was cooled to RT and concentrated in vacuo to give 54a (140 g, 94%) as a white solid. LC-MS (Agilent): $R_t$ 0.56 min; m/z calculated for $C_{13}H_{17}NO_3$ [m+H]$^+$ 160.1, found [M+H]$^+$ 160.1.

2. Procedure for the Preparation of 54b

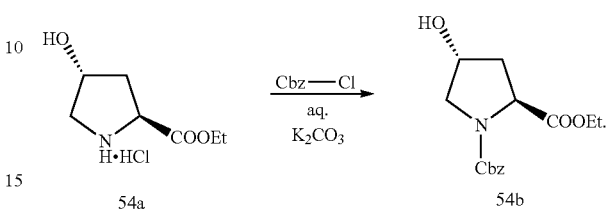

To a stirred mixture 54a (60.0 g, 0.30 mol) in diethyl ether/$H_2O$ (100 mL/600 mL) at 0° C. was added $K_2CO_3$ (104 g, 0.75 mol) and CbzCl (48.0 g, 0.28 mol) dropwise and the mixture was stirred at RT for 2 h, TLC (PE:EA=2:1) showed that a major new product was formed. The layers were separated and the aqueous phase was extracted with EA (100 mL×2) and the combined organic extracts were washed with brine, dried over $Na_2SO_4$, filtered and concentrated in vacuo to give 54b (75.0 g, 83%) as a yellow oil. LC-MS (Agilen, P-2): $R_t$ 2.86 min; m/z calculated for $C_{15}H_{19}NO_5$ [M+H]$^+$ 294.1, [M+Na]$^+$ 316.1 found [M+H]$^+$ 294.1, [M+Na]$^+$ 316.1.

3. Procedure for the Preparation of 54c

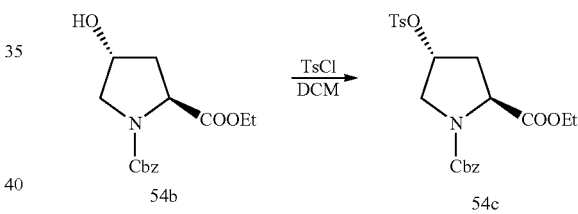

To a stirred solution of 54b (145 g, 0.49 mol) and $Et_3N$ (60.05 g, 0.59 mol) in DCM (1 L) at RT was added TsCl (104 g, 0.54 mol) in portions over 20 min and the mixture was heated at 40° C. overnight, TLC (PE:EA=2:1) showed that the starting material was consumed. The mixture was cooled to RT, washed with water (200 mL×2), brine (200 mL×2), dried over $Na_2SO_4$, filtered and concentrated in vacuo. The residue was purified by chromatography (PE:EA=20:1 to 1:1) to give 54c (128 g, 58%) as a yellow oil. LC-MS (Agilent, P-2): $R_t$ 3.025 min; m/z calculated for $C_{22}H_{25}NO_7S$ [M+H]$^+$ 448.1, [M+Na]$^+$ 470.1, found [M+H]$^+$ 448.2, [M+Na]$^+$ 470.1.

4. Procedure for the Preparation of 54d

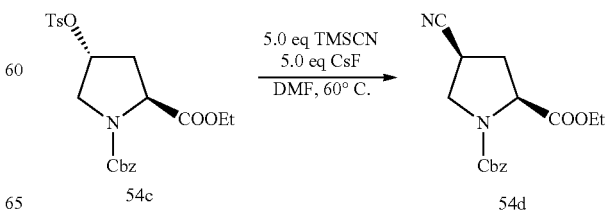

A mixture 54c (34.4 g, 76.8 mmol), CsF (58.4 g, 384 mmol) and TMSCN (38.1 g, 384 mmol) in DMF (300 mL) was heated at 60° C. for 40 h, TLC (PE:EA=2:1) showed about half of the starting material remained. The mixture was cooled to RT and poured into EA/H$_2$O (2 L/800 mL). The organic layer was collected and washed with water (400 mL×2), brine (500 mL×2), dried over Na$_2$SO$_4$, filtered and concentrated in vacuo. The residue was purified by chromatography (PE:EA=10:0 to 1:1) to give 54d (8.00 g, 34%) as a yellow oil and recovered starting material (7.0 g, 20%). LC-MS (Waters): R$_t$ 5.73 min; m/z calculated for C$_{16}$H$_{18}$N$_2$O$_4$ [M+H]$^+$ 303.1, [M+Na]$^+$ 325.1, found [M+H]$^+$ 303.1, [M+Na]$^+$ 325.1.

5. Procedure for the Preparation of 54e

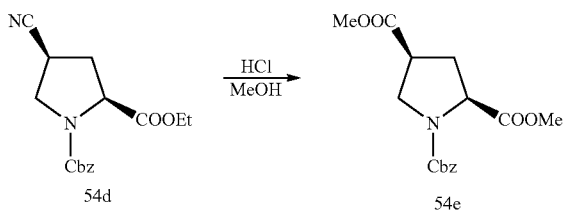 [SMILES: "MeOH" ; CCOC(=O)[C@@H]1C[C@H](C#N)CN1C(=O)OCc1ccccc1 ; Cl ; COC(=O)[C@H]1C[C@@H](C(=O)OC)N(C(=O)OCc2ccccc2)C1]

Acetyl chloride (20.8 g, 0.264 mol) was added to MeOH (40 mL) drop-wise at 0° C. and the mixture was stirred at RT for 1 h. 54d (8.00 g, 26.4 mmol) was then added and stirring was continued at RT for 2 days, TLC (PE:EA=4:1) showed that the starting material was consumed. The reaction was neutralised with solid NaHCO$_3$ until pH 7 and the mixture was filtered. The filtrate was concentrated in vacuo and the residue was partitioned between water (30 mL) and EA (30 mL). The organic layer was collected, washed with brine (30 mL×2), dried over Na$_2$SO$_4$, filtered and concentrated in vacuo. The residue was purified by chromatography (PE:EA=10:1 to 3:1) to give 54e (7.5 g, 88%) as a brown oil. LC-MS (Waters): R$_t$ 5.81 min; m/z calculated for C$_{16}$H$_{19}$NO$_6$ [M+H]$^+$ 322.1, [M+Na]$^+$ 344.1, found [M+H]$^+$ 322.2, [M+Na]$^+$ 344.1.

6. Procedure for the Preparation of 54f

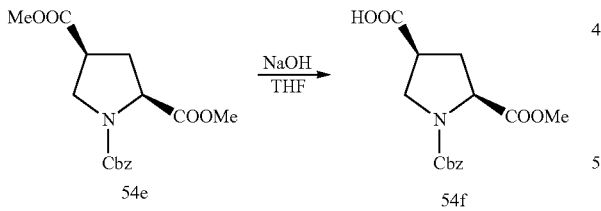

The following procedure was carried out in five parallel reactions using 54e (total of 7.5 g, 23.3 mmol): To a solution of 54e (1.5 g, 4.67 mmol) in THF (10 mL) at 0° C. was added a 1 M aqueous NaOH solution (4.7 mL, 4.7 mmol) and the mixture was stirred at 0° C. for 30 min, then allowed to warm to RT and stirred for a further 1 h, LCMS showed most of the starting material was consumed. The five reaction mixtures were combined and concentrated in vacuo to remove most of the THF and the residue was dissolved in a saturated aqueous NaHCO$_3$ solution and washed with ether. The aqueous layer was acidified to pH 3-4 with a 3 M aqueous HCl solution and extracted with EA. The organic layer was dried over Na$_2$SO$_4$, filtered and concentrated in vacuo to give 54f (6.3 g, 86%) as a yellow oil. LC-MS (Agilent, P-2): R$_t$ 3.71 min; m/z calculated for C$_{15}$H$_{17}$NO$_6$ [M+Na]$^+$ 330.1, found [M+Na]$^+$ 330.1.

7. Procedure for the Preparation of 54 g

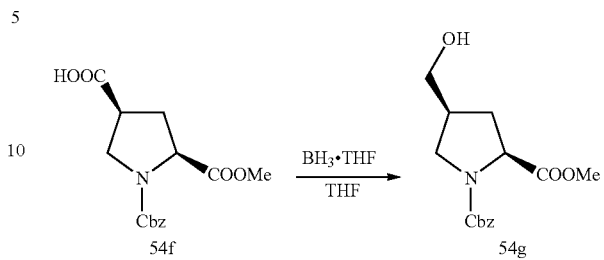

To a stirred solution 54f (3.80 g, 12.4 mmol) in THF (30 mL) at 0° C. under a N$_2$ atmosphere was added BH$_3$.THF (1 M solution in THF, 37 mL, 37 mmol) and the mixture was stirred at 0° C. for 30 min, TLC (DCM:MeOH=10:1) showed that the starting material was consumed. The reaction was quenched with MeOH followed by a 3 M aqueous HCl solution and the mixture was concentrated in vacuo to remove most of THF. The residue was partitioned between EA and brine, the organic layer was separated, dried over Na$_2$SO$_4$, filtered and concentrated in vacuo to give 54 g (3.2 g, 88%) as a colorless oil. LC-MS (Agilent, P-2): R$_t$ 2.82 min; m/z calculated for C$_{15}$H$_{19}$NO$_5$ [M+H]$^+$ 294.1, found [MA-1]$^+$ 294.1.

8. Procedure for the Preparation of 54l,

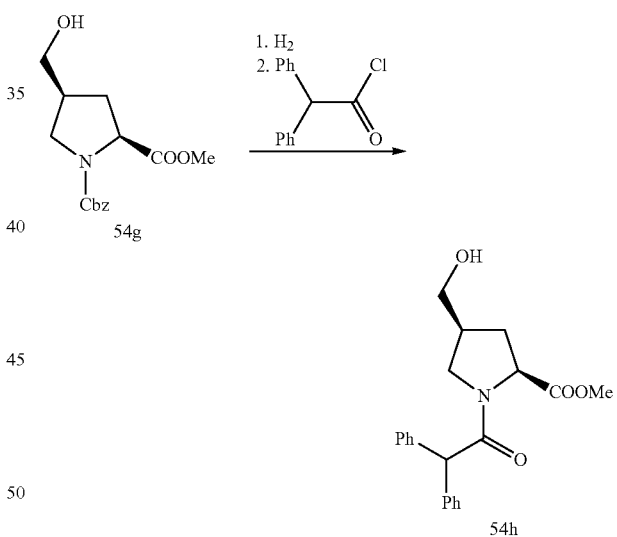

A mixture of 54 g (3.20 g, 11 mmol) and 10% Pd(OH)$_2$/C (300 mg) in MeOH (30 mL) was stirred at RT under a H$_2$ atmosphere (1 atm) overnight, TLC (DCM:MeOH=10:1) showed that the starting material was consumed. The mixture was filtered, the filtrate was concentrated in vacuo and the residue was dissolved in EA/H$_2$O (20 mL/20 mL) then cooled to 0° C. KHCO$_3$ (2.75 g, 2.75 mmol) was added followed by diphenyl acetyl chloride (3.0 g, 13.2 mmol) and the mixture was stirred at 0° C. for 30 min, TLC (DCM:MeOH=10:1) showed that the starting material was consumed. The organic layer was separated, dried over Na$_2$SO$_4$, filtered and concentrated in vacuo. The residue was purified by chromatography (PE:EA=1:0 to 1:1) to give 54 h (2.1 g, 5.5% overall) as a white solid. LC-MS (Agilent, P-2): R$_t$ 2.88 min; m/z calculated for $C_{21}H_{23}NO_4$ [M+H]$^+$ 354.2, [M+Na]$^+$ 376.2, found [M+H]$^+$ 354.1, [M+Na]$^+$ 376.2.

9. Procedure for the Preparation of 54i

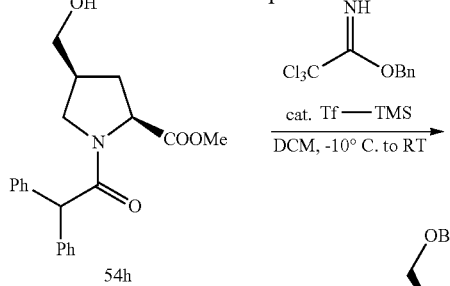

To a solution of 54 h (100 mg, 0.28 mmol) and benzyl trichloroacetimidate (143 mg, 0.56 mmol) in DCM (15 mL) at −10° C. under a N$_2$ atmosphere was added TMS triflate (18 mg, 0.08 mmol) and the mixture was allowed to warm slowly to RT and stirred overnight, TLC (PE:EA=1:1) showed that the starting material was consumed. The mixture was washed with a saturated aqueous NaHCO$_3$ solution, brine, dried over Na$_2$SO$_4$, filtered and concentrated in vacuo. The residue was purified by chromatography (PE:EA=1:0 to 2:1) to give 54i (90 mg, 72%) as a colorless oil. LC-MS (Agilent, P-2): R$_t$ 2.98 min; m/z calculated for $C_{28}H_{29}NO_4$ [M+H]$^+$ 444.2, [M+Na]$^+$ 466.2, found [M+H]$^+$ 444.2, [M+Na]$^+$ 466.2.

10. Procedure for the Preparation of 54

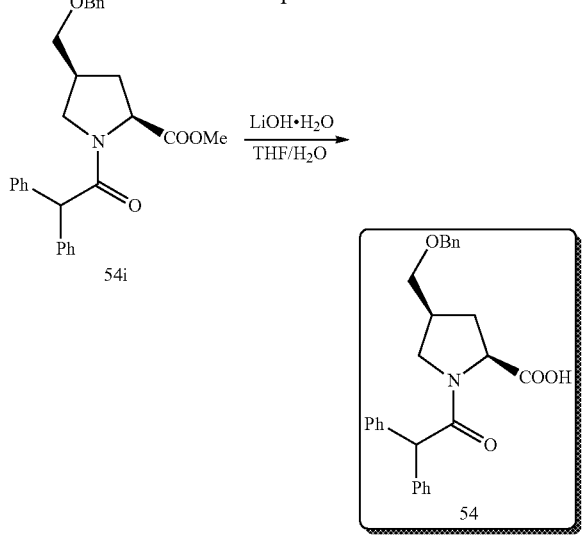

A mixture of 54i (90 mg, 0.20 mmol) and LiOH.H$_2$O (25 mg, 0.60 mmol) in THF/water (3 mL/1 mL) was stirred at RT overnight, TLC (PE:EA=1:1) showed that the starting material was consumed. The mixture was concentrated in vacuo, the residue was dissolved in water (10 mL), acidified to pH 3-4 with a 3 M aqueous HCl solution and extracted with DCM. The organic extracts were washed with brine, dried over Na$_2$SO$_4$, filtered and concentrated in vacuo. The residue was purified by preparative HPLC to give 54 (57 mg, 68%) as a white solid. LC-MS (Agilent, P-2): R$_t$ 3.09 min; m/z calculated for $C_{27}H_{27}NO_4$ [M+H]$^+$ 430.2, found [M+H]$^+$ 430.3. HPLC (JULY-L) (214 and 254 nm): R$_t$ 9.14 min. HPLC (ZSJ-2) (214 and 254 nm): R$_t$ 20.56 min.

Example 60: Compound 56 (2S,4S)-1-(2,2-diphenylacetyl)-4-5-phenyloxazol-2-yl)pyrrolidine-2-carboxylic acid 1. Procedure for the Preparation of 56b

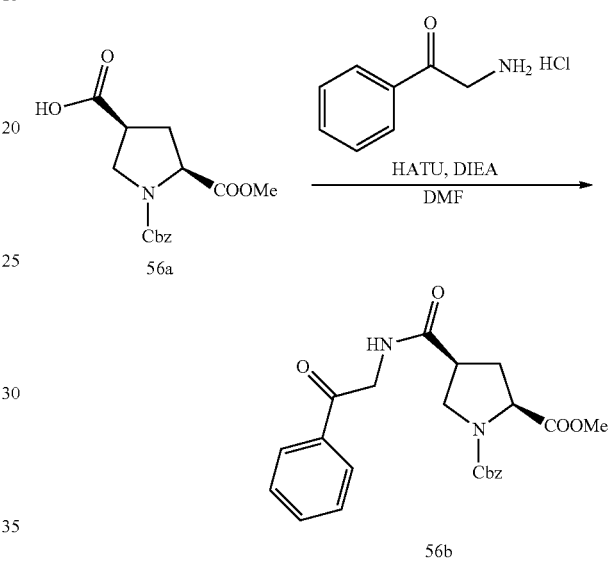

To a stirred solution of 56a (0.5 g, 1.63 mmol) in DMF (20 mL) was added DIPEA (0.63 mL, 4.89 mmol) and HATU (0.74 g, 1.96 mmol) and the mixture was stirred at RT for 30 min. 2-amino-1-phenylethanone hydrochloride (0.36 g, 2.12 mmol) was then added and stirring was continued at RT overnight, TLC (PE:EA=1:1) showed that the starting material was consumed. The mixture was poured into ice-water (40 mL), extracted with EA (40 mL×2) and the combined organic extracts were washed with brine, dried over Na$_2$SO$_4$, filtered and concentrated in vacuo. The residue was purified by chromatography (PE:EA=1:0 to 1:1) to give 56b (260 mg, 37%) as a thick oil. LC-MS (Waters): R$_t$ 5.99 min; ink calculated for $C_{23}H_{24}N_2O_6$ [M+H]$^+$ 425.2, [M+Na]$^+$ 447.2, found [M+H]$^+$ 425.2, [M+Na]$^+$ 447.2.

2. Procedure for the Preparation of 56c

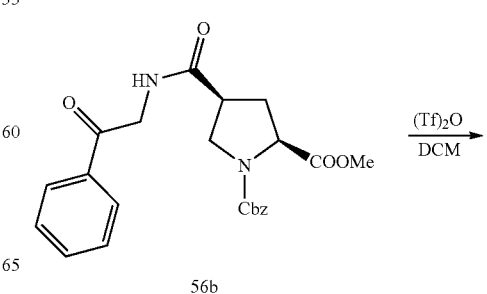

4. Procedure for the Preparation of 56e

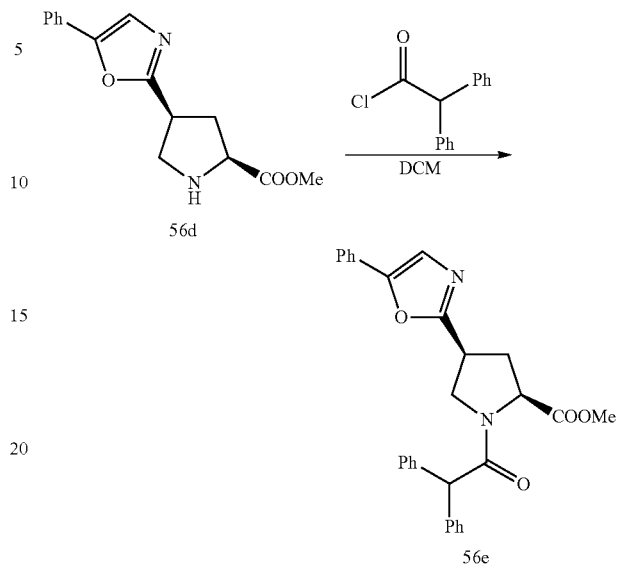

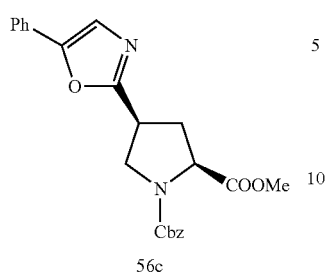

To a solution of 56b (250 mg, 0.59 mmol) in DCM (15 mL) at 0° C. was added pyridine (71 mg, 0.89 mmol) then TFAA (0.2 g, 0.71 mmol) and the mixture was stirred at 0° C. for 15 min then at RT for 3 hours, TLC (PE:EA=2:1) showed that the starting material was consumed. The reaction was quenched with a saturated aqueous $NaHCO_3$ solution, the layers were separated and the aqueous layer was extracted with DCM (30 mL×2). The combined organic extracts were washed with brine, dried over $Na_2SO_4$, filtered and concentrated in vacuo. The residue was purified by chromatography (PE:EA=100:0 to 3:1) to give 56c (100 mg, 41%) as a brown oil. LC-MS (Waters): $R_t$ 6.93 min; m/z calculated for $C_{23}H_{22}N_2O_5$ $[M+H]^+$ 407.2, $[M+Na]^+$ 429.2, found $[M+H]^+$ 407.2, $[M+Na]^+$ 429.2.

3. Procedure for the Preparation of 56d

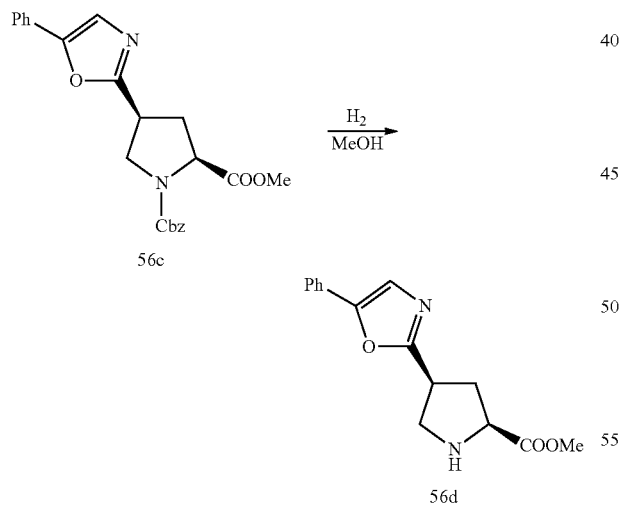

A mixture of 56c (120 mg, 0.3 mmol) and 10% Pd(OH)$_2$/C (20 mg) in methanol (20 mL) was stirred at RT under a $H_2$ atmosphere (1 atm) for 2 h, LC-MS analysis showed that the starting material was consumed. The mixture was filtered and the filtrate was concentrated in vacuo to give 56d (60 mg, 75%) as a white solid. LC-MS (Waters): $R_t$ 4.97 min; m/z calculated for $C_{15}H_{16}N_2O_3[M+H]^+$ 273.1, found $[M+H]^+$ 273.2.

To a solution of 56d (60 mg, 0.22 mmol) in DCM (20 mL) at 0° C. was added DIPEA (85 mg, 0.66 mmol) then 2,2-diphenylacetyl chloride (76 mg, 0.33 mmol) and the mixture was allowed to warm to RT and stirred for 30 min, TLC (PE:EA=2:1) showed that the starting material was consumed. Water was added and the mixture was extracted with DCM (30 mL×2). The combined organic extracts were washed with brine (20 mL×2), dried over $Na_2SO_4$, filtered and concentrated in vacuo. The residue was purified by chromatography (PE:EA=10:1 to 3:1) to give 56e (56 mg, 55%) as a yellow oil. LC-MS (Waters): $R_t$ 7.02 min; m/z calculated for $C_{29}H_{26}N_2O_4[M+H]^+$ 467.2, found $[M+H]^+$ 467.2.

5. Procedure for the Preparation of 56

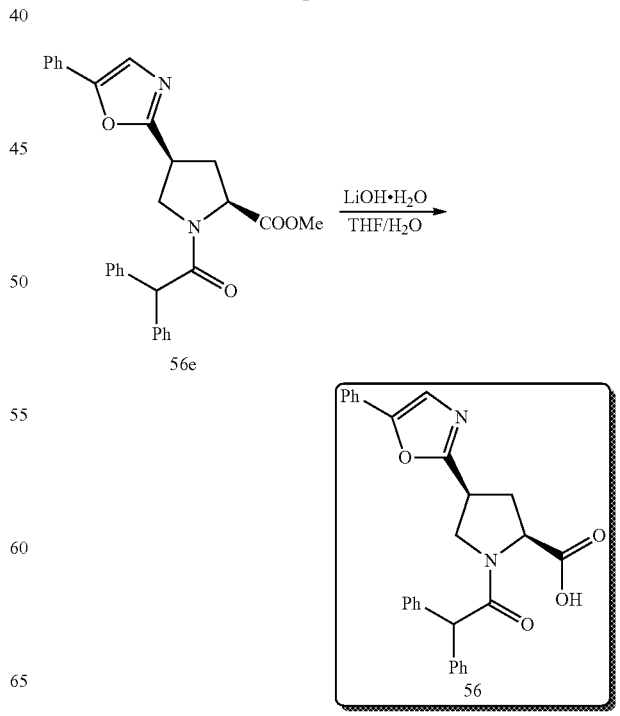

A mixture of 56e (56 mg, 0.12 mmol) and LiOH.H$_2$O (16 mg, 0.38 mmol) in THF/H$_2$O (2.5 mL/0.5 mL) was stirred at RT overnight. The mixture was concentrated in vacuo, the residue was dissolved in water, acidified to pH 4~5 with a 3 M aqueous HCl solution and extracted with DCM (30 mL×3). The combined organic extracts were washed with brine, dried over Na$_2$SO$_4$, filtered and concentrated in vacuo. The residue was purified by preparative HPLC to give 56 (30 mg, 55%) as a white solid. LC-MS (Agilent, P-2): R$_t$ 3.00 min; m/z calculated for C$_{28}$H$_{24}$N$_2$O$_4$ [M+H]$^+$ 453.2, found [M+H]$^+$ 453.2. HPLC (JULY-L) (214 and 254 nm): R$_t$ 9.12 min. HPLC (ZSJ-2) (214 and 254 nm): R$_t$ 20.50 min.

Example 61: Compound 120 (2S,4S)-1-(2,2-diphenylacetyl)-4-((phenethylthio)methyl)pyrrolidine-2-carboxylic acid 1. Procedure for the Preparation of 120b

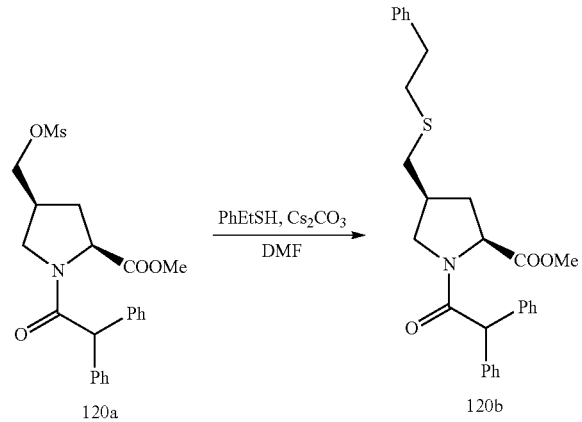

120a

120b

A mixture of 120a (600 mg, 1.39 mmol), 2-phenylethanethiol (385 mg, 2.78 mmol) and Cs$_2$CO$_3$ (906 mg, 2.78 mmol) in DMF (10 mL) was heated at 80° C. overnight, TLC (PE:EA=1:1) showed the starting material was consumed. The mixture was poured into ice-water (50 mL) and extracted with EA (20 mL×2). The combined organic extracts were washed with brine (25 mL×2), dried over Na$_2$SO$_4$, filtered and concentrated in vacuo. The residue was purified by chromatography (PE:EA=10:1 to 3:1) to give 120b (197 mg, 30%) as a colorless oil. LC-MS (Agilent, P-2): R$_t$ 3.30 min; m/z calculated for C$_{29}$H$_{31}$NO$_3$S [M+H]$^+$ 474.2, found [M+H]$^+$ 474.2.

2. Procedure for the Preparation of 120

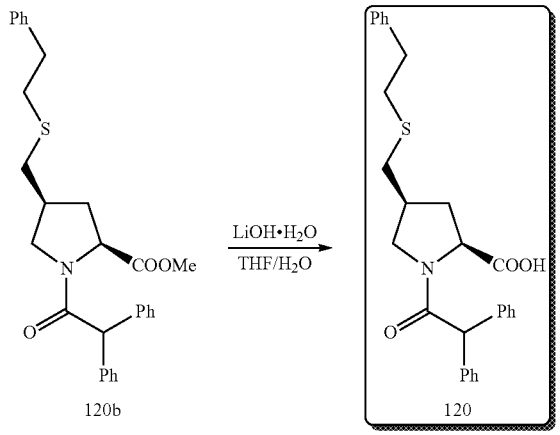

120b

120

Hydrolysis of 120b (70 mg, 0.15 mmol) was performed as described in Example 60, 5. with about 3 equivalents of LiOH.H$_2$O (18 mg, 0.44 mmol) to give 120 (60 mg, 88%) as a white solid. LC-MS (Agilent, P-2): R$_t$ 3.21 min; m/z calculated for C$_{28}$H$_{29}$NO$_3$S [M+H]$^+$ 460.2, found [M+H]$^+$ 460.2. HPLC (JULY-L) (214 and 254 nm): R$_t$ 9.35 min. HPLC (ZSJ-2) (214 and 254 nm): R$_t$ 22.86 min.

Example 62: Compound 58 (2S,S)-1-(2,2-diphenylacetyl)-4-((phenethylsulfonyl)methyl)pyrrolidine-2-carboxylic acid 1. Procedure for the Preparation of 58a

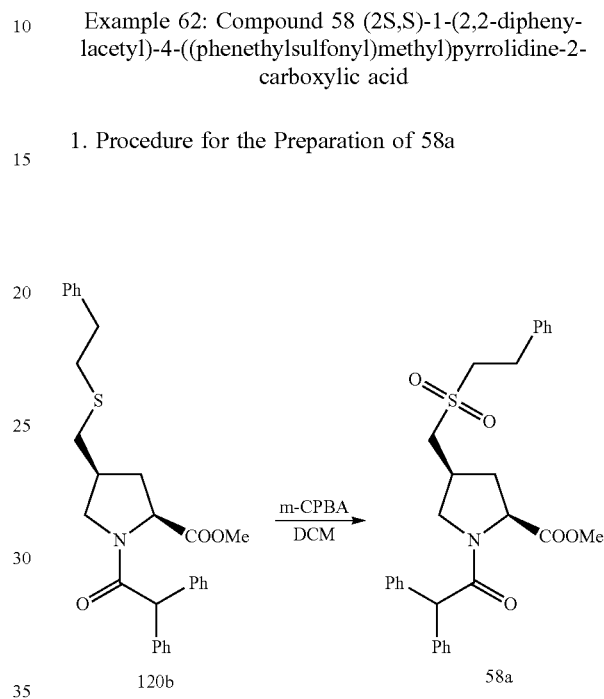

120b

58a

To a solution of 120b (120 mg, 0.25 mmol) in DCM (6 mL) was added 80% m-CPBA (137 mg, 0.63 mmol) and the mixture was stirred at RT overnight, TLC (PE:EA=2:1) showed that the starting material was consumed. The mixture was washed with a saturated aqueous Na$_2$CO$_3$ solution, brine (10 mL), dried over Na$_2$SO$_4$, filtered and concentrated in vacuo. The residue was purified by chromatography (PE:EA=8:1 to 1.5:1) to give 58a (102 mg, 82%) as a white solid. LC-MS (Agilent, P-2): R$_t$ 2.98 min; m/z calculated for C$_{29}$H$_{31}$NO$_5$S [M+H]$^+$ 506.2, [M+Na]$^+$ 528.2, found [M+H]$^+$ 506.2, [M+Na]$^+$ 528.2.

2. Procedure for the Preparation of 58

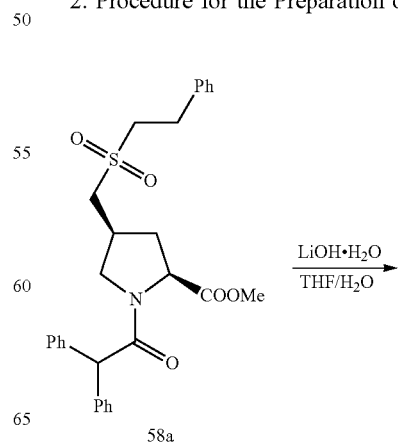

58a

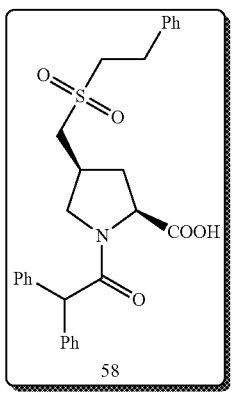

A mixture of 58a (102 mg, 0.20 mmol) and LiOH·H₂O (25 mg, 0.60 mmol) in THF/H₂O (4 mL/1 mL) was stirred at RT overnight, TLC (PE:EA=1:1) showed that the starting material was consumed. The mixture was concentrated in vacuo, the residue was dissolved in water (4 mL), acidified to pH 4~5 with a 3 M aqueous HCl solution and the resulting precipitate was collected by filtration and dried at 60° C. to give 58 (77 mg, 77%) as a white solid. LC-MS (Agilent, P-2): $R_t$ 2.77 min; m/z calculated for $C_{28}H_{29}NO_5S$ [M+H]⁺ 492.2, [M+Na]⁺ 514.2, found [M+H]⁺ 492.2, [M+Na]⁺ 514.2. HPLC (JULY-L) (214 and 254 nm): $R_t$ 8.89 min. HPLC (ZSJ-2) (214 and 254 nm): $R_t$ 18.32 min.

Example 63: Compound 121 (2S,4S)-4-((benzylthio)methyl)-1-(2,2-diphenylacetyl)pyrrolidine-2-carboxylic acid 1. Procedure for the Preparation of 121a

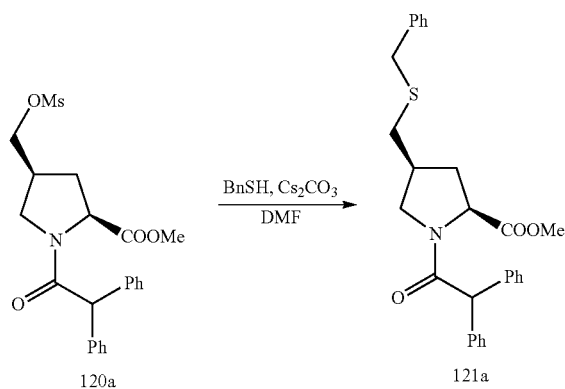

A mixture of 120a (600 mg, 1.39 mmol), BnSH (345 mg, 2.78 mmol) and Cs₂CO₃ (906 mg, 2.78 mmol) in DMF (10 mL) was heated at 80° C. overnight, TLC (PE:EA=1:1) showed that the 120a was consumed. The mixture was poured into ice-water (50 mL) and extracted with EA (20 mL×2). The combined organic extracts were washed with brine (15 mL×2), dried over Na₂SO₄, filtered and concentrated in vacuo. The residue was purified by chromatography (PE:EA=10:1 to 4:1) to give 121a (140 mg, 21%) as colorless oil. LC-MS (Agilent, P-2): $R_t$ 3.10 min; m/z calculated for $C_{28}H_{29}NO_3S$ [M+H]⁺ 460.2, found [M+H]⁺ 460.2.

2. Procedure for the Preparation of 121

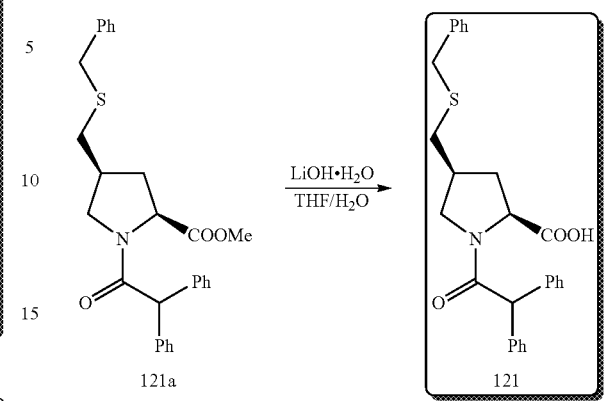

A mixture of 121a (56 mg, 0.12 mmol) and LiOH·H₂O (15 mg, 0.37 mmol) in THF/H₂O (3 mL/1 mL) was stirred at RT overnight, TLC (PE:EA=2:1) showed that the starting material was consumed. The mixture was concentrated in vacuo, the residue was dissolved in water (10 mL), acidified to pH 4~5 with a 3 M aqueous HCl solution and extracted with DCM (10 mL×2). The combined organic extracts were washed with brine (10 mL), dried over Na₂SO₄, filtered and concentrated in vacuo to give 121 (50 mg, 92%) as white solid. LC-MS (Agilent, P-2): $R_t$ 3.16 min; m/z calculated for $C_{27}H_{27}NO_3S$ [M+H]⁺ 446.2, found [M+H]⁺ 446.2. HPLC (JULY-L) (214 and 254 nm): $R_t$ 9.26 min. HPLC (ZSJ-2) (214 and 254 nm): $R_t$ 21.92 min.

Example 64: Compound 122 (2S,4S)-1-(2,2-diphenylacetyl)-4-((phenylthio)methyl)pyrrolidine-2-carboxylic acid 1. Procedure for the Preparation of 120a

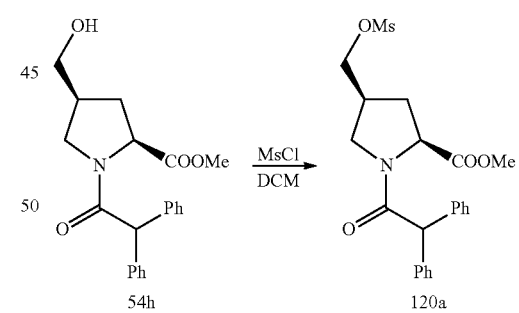

To a solution of 54 h (1.90 g, 5.37 mmol) and Et₃N (0.71 g, 6.98 mmol) in DCM (15 mL) at 0° C. was added MsCl (0.67 g, 5.91 mmol) and the mixture was stirred at 0° C. for 30 min, TLC (PE:EA=1:1) showed that the starting material was consumed. The mixture was washed with brine, dried over Na₂SO₄, filtered and concentrated in vacuo. The residue was purified by chromatography (PE:EA=1:0 to 1:1) to give 120a (2.2 g, 95%) as a white solid. LC-MS (Agilent, P-2): $R_t$ 2.85 min; m/z calculated for $C_{22}H_{26}NO_6S$ [M+H]⁺ 432.2, [M+Na]⁺ 454.1, found [M+H]⁺ 432.2, [M+Na]⁺ 454.1.

2. Procedure for the Preparation of 122a

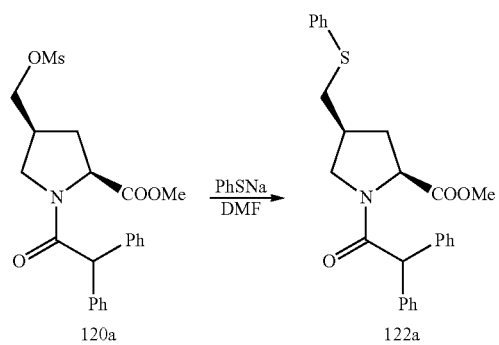

A mixture of 120a (500 mg, 1.39 mmol), and PhSNa (229 mg, 1.74 mmol) in DMF (10 mL) was heated at 80° C. overnight, TLC (PE:EA=2:1) showed that most of the starting material was consumed. The mixture was cooled to RT, poured into ice-water (60 mL) and extracted with EA (20 mL×3). The combined organic extracts were washed with brine, dried over $Na_2SO_4$, filtered and concentrated in vacuo. The residue was purified by chromatography (PE:EA=1:0 to 2:1) to give 122a (150 mg, 29%) as a viscous colorless oil. LC-MS (Agilent, P-2): $R_t$ 3.30 min; m/z calculated for $C_{27}H_{27}NO_3S$ $[M+H]^+$ 446.2, found $[M+H]^+$ 446.2.

3. Procedure for the Preparation of 122

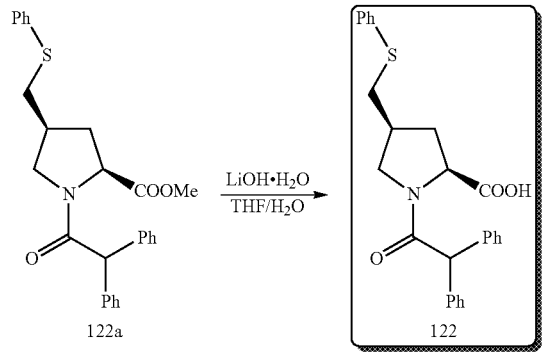

A mixture of 122a (50 mg, 0.11 mmol) and $LiOH \cdot H_2O$ (14 nag, 0.33 mmol) in $THF/H_2O$ (3 mL/1 mL) was stirred at RT overnight, TLC (PE:EA=2:1) showed that the starting material was consumed. The mixture was concentrated in vacuo and the residue was dissolved in water (10 mL), washed with ether then acidified to pH 3~4 with a 3 M aqueous HCl solution and extracted with DCM. The organic extracts were washed with brine, dried over $Na_2SO_4$, filtered and concentrated in vacuo to give 122 (30 mg, 62%) as a white solid. LC-MS (Agilent, P-2): $R_t$ 3.18 min; m/z calculated for $C_{26}H_{25}NO_3S$ $[M+H]^+$ 432.2, $[M+Na]^+$ 454.2, found $[M+H]^+$ 432.2, $[M+Na]^+$ 454.1. HPLC (JULY-L) (214 and 254 nm): $R_t$ 9.24 min. HPLC (ZSJ-2) (214 and 254 nm): $R_t$ 21.70 min.

Example 65: Compound 126 (2S,4S)-1-(2,2-diphenylacetyl)-4-((2-fluorophenoxy)ethyl)(methyl)amino)pyrrolidine-2-carboxylic acid

1. Procedure for the Preparation of 126a

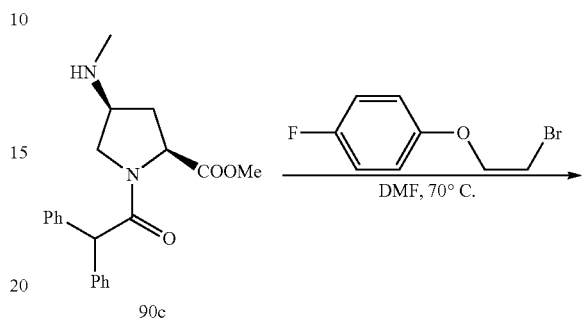

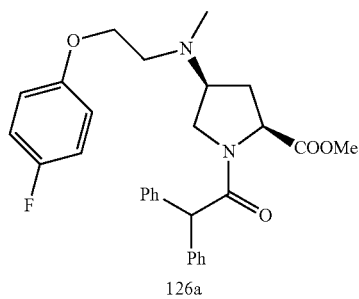

A mixture of 90c (50 mg, 0.14 mmol), $Cs_2CO_3$ (68 mg, 0.21 mmol) and 4-fluorophenylethylbromide (37 mg, 0.17 mmol) in DMF (2 mL) was heated at 70° C. overnight, TLC (DCM:MeOH=20:1) showed that the starting material was consumed. The mixture was cooled to RT, partitioned between EA (30 mL) and $H_2O$ (30 mL) and the organic layer was separated, washed with brine, dried over $Na_2SO_4$, filtered and concentrated in vacuo. The residue was purified by chromatography (PE:EA=10:1 to 1:2) to give 126a (40 mg, 58%) as a yellow oil. LC-MS (Waters): $R_t$ 6.07 min; m/z calculated for $C_{29}H_{31}FN_2O_4$ $[M+H]^+$ 491.1, found $[M+H]^+$ 491.1.

2. Procedure for the Preparation of 126

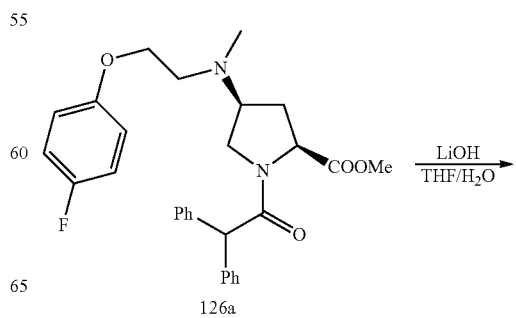

-continued

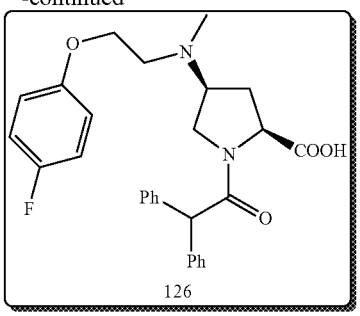

126

A mixture of 126a (127 mg, 0.26 mmol) and LiOH.H₂O (44 mg, 1.04 mmol) in THF/H₂O (3 mL/0.5 mL) was stirred at RT overnight, TLC (DCM:MeOH=20:1) showed that the starting material was consumed. The mixture was concentrated in vacuo, the residue was dissolved in H₂O (3 mL), acidified to pH 5 with a 3 M aqueous HCl solution and extracted with DCM (10 mL×2). The combined organic extracts were dried over Na₂SO₄, filtered and concentrated in vacuo. The residue was purified by preparative HPLC to give 126 (20 mg, 18%) as a white solid. LC-MS (Agilent, P-2): $R_t$ 2.824 min; m/z calculated for $C_{28}H_{29}FN_2O_4$ [M+H]⁺ 477.2, found [M+H]⁺ 477.2. HPLC (ZSJ-2) (214 and 254 nm)): $R_t$ 16.13 min.

Example 66: Compound 133 (2S,4S)-1-(2,2-diphenylacetyl)-4((3-(4-fluorophenyl)propyl)thio)pyrrolidine-2-carboxylic acid 1. Procedure for the Preparation of 133a

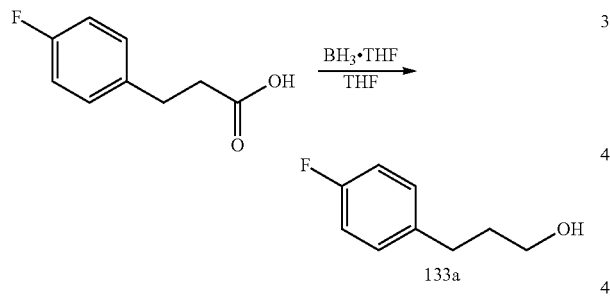

133a

To a solution of 3-(4-fluorophenyl) propanoic acid (6.0 g) in THF (30 mL) at 0° C. under a N₂ atmosphere was added BH₃.THF (1 M in THF, 42.8 mL, 42.8 mmol) dropwise and the mixture was allowed to warm slowly to RT and stirred for 3 h, TLC (PE:EA=2:1) showed that the starting material was consumed. The mixture was re-cooled to 0° C., quenched with MeOH (5 mL) then water (10 mL) and concentrated in vacuo. The residue was diluted with water (20 mL) and extracted with EA. The organic phase was washed with a saturated aqueous NaHCO₃ solution (20 mL) then brine, dried over Na₂SO₄, filtered and concentrated in vacuo to give 133a (5.0 g, 90%) as a colorless oil.

2. Procedure for the Preparation of 133b

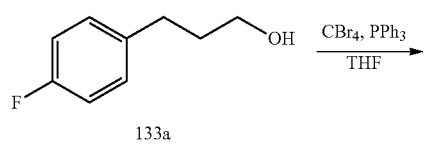

-continued

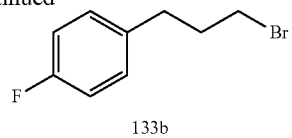

133b

To a solution of 133a (937 mg, 6.08 mmol) and PPh₃ (1.59 g, 6.08 mmol) in THF (20 mL) at 0° C. was added CBr₄ (2.11 g, 6.38 mmol) in portions and the mixture was allowed to warm slowly to RT and stirred for 3 h, TLC (PE:EA=10:1) showed that most of the starting material was consumed. The mixture was filtered the filtrate was concentrated in vacuo. The residue was purified by chromatography (100% PE) to give 133b (724 mg, 54%) as a colorless oil.

3. Procedure for the Preparation of 133c

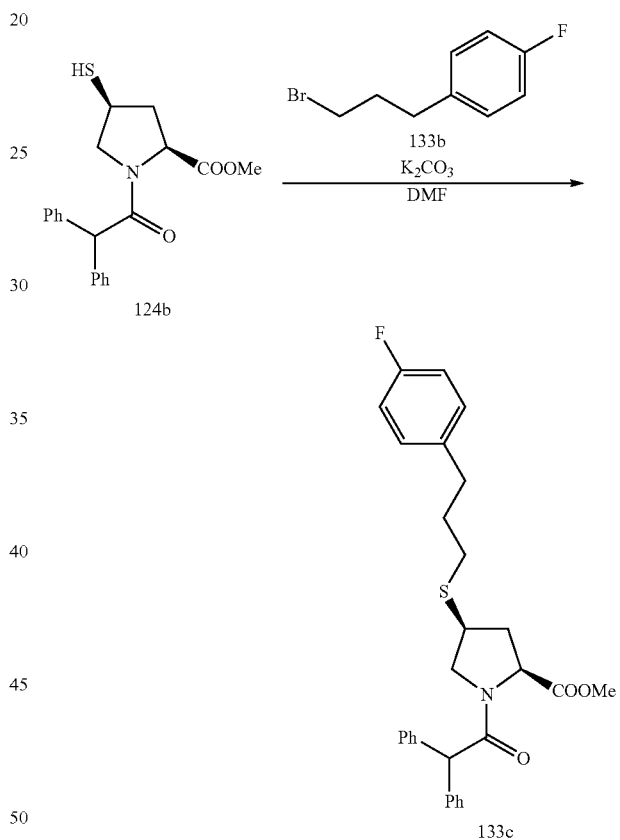

To a solution of 124b (202 mg, 0.57 mmol) in DMF (10 mL) was added K₂CO₃ (87 mg, 0.63 mmol) and 133b (136 mg, 0.63 mmol) and the mixture was heated at 80° C. overnight, TLC (PE:EA=2:1) showed that the starting material was consumed. The mixture was poured into ice-water (30 mL) and extracted with EA (15 mL×2). The combined organic extracts were washed with brine (30 mL), dried over Na₂SO₄, filtered and concentrated in vacuo. The residue was purified by chromatography (PE:EA=8:1 to 5:1) to give 133c (232 mg, 83%) as a colorless oil. LC-MS (Agilent, P-2): $R_t$ 3.26 min; m/z calculated for $C_{29}H_{30}FNO_3S$ [M+H]⁺ 492.2, found [M+H]⁺ 492.2.

4. Procedure for the Preparation of 133

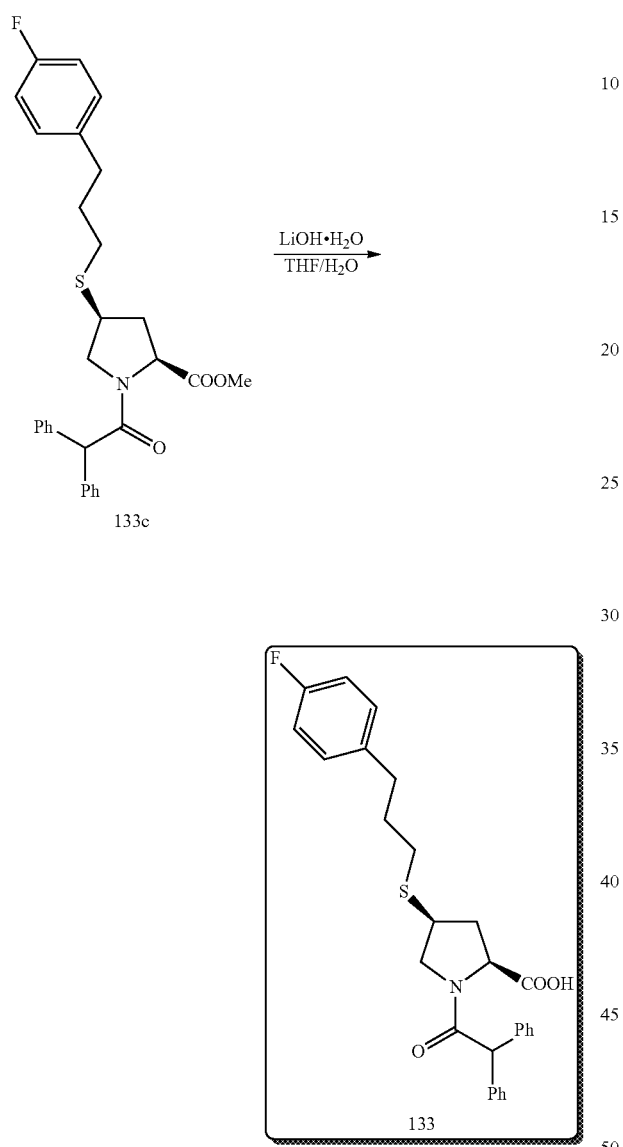

Example 67: Compound 134 (2S,4S)-1-(2,2-diphenylacetyl)-4((3-(4-fluorophenyl)propyl)sulfonyl)pyrrolidine-2-carboxylic acid 1. Procedure for the Preparation of 134a

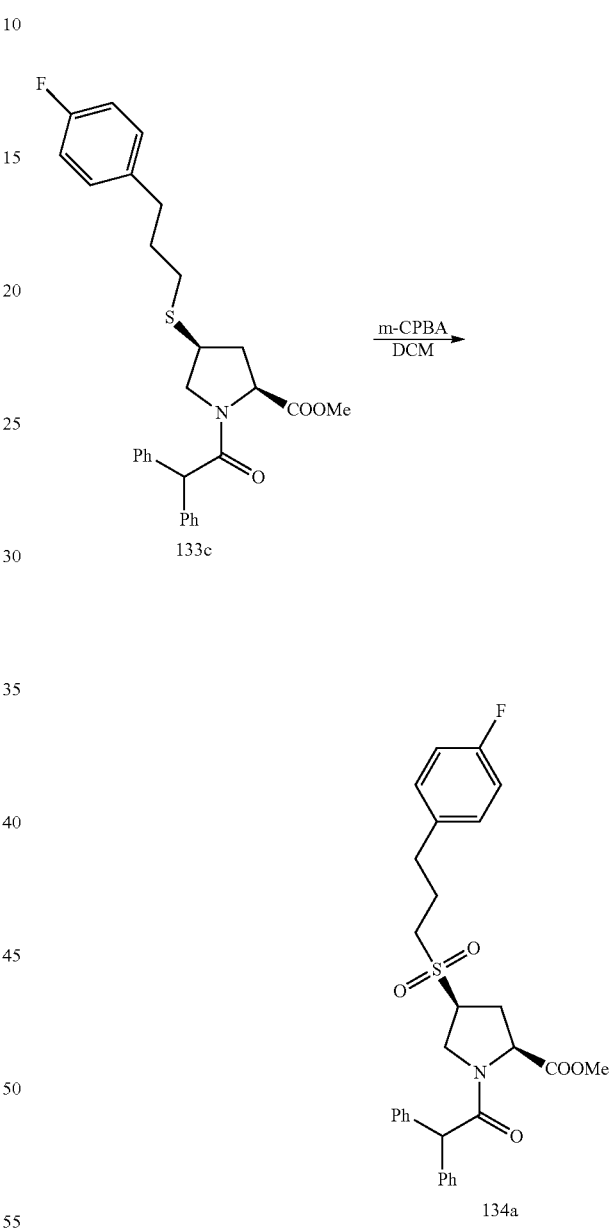

A mixture of 133c (105 mg, 0.21 mmol) and LiOH.H$_2$O (27 mg, 0.63 mmol) in THF/H$_2$O (3 mL/1 mL) was stirred at RT overnight, TLC (PE:EA=1:1) showed that the starting material was consumed. The mixture was concentrated in vacuo, the residue was dissolved in water (10 mL), acidified to pH 4~5 with a 3 M aqueous HCl solution and extracted with DCM. The organic layer was washed with brine, dried over Na$_2$SO$_4$, filtered and concentrated in vacuo to give 133 (100 mg, 98%) as a white solid. LC-MS (Agilent, P-2): R$_t$ 3.29 min; m/z calculated for C$_{28}$H$_{28}$FNO$_3$S [M+H]$^+$ 478.2, found [M+H]$^+$ 478.2. HPLC (JULY-L) (214 and 254 nm): R$_t$ 9.34 min.

To a solution of 133c (105 mg, 0.21 mmol) in DCM (5 mL) was added 80% m-CPBA (115 mg, 0.53 mmol) and the mixture was stirred at RT overnight, TLC (PE:EA=1:1) showed that the starting material was consumed. The reaction was quenched with a saturated aqueous NaHSO$_3$ solution and the mixture was washed with a saturated aqueous Na$_2$CO$_3$ solution (5 mL), then brine (5 mL), dried over Na$_2$SO$_4$, filtered and concentrated in vacuo. The residue was purified by chromatography (PE:EA=8:1 to 2:1) to give 134a (100 mg, 90%) as a colorless oil. LC-MS (Agilent, P-2): $R_t$ 3.04 min; m/z calculated for $C_{29}H_{30}FNO_5S$ [M+H]$^+$ 524.2, [M+Na]$^+$ 546.2, found [M+H]$^+$ 524.2, [M+Na]$^+$ 546.2.

2. Procedure for the Preparation of 134

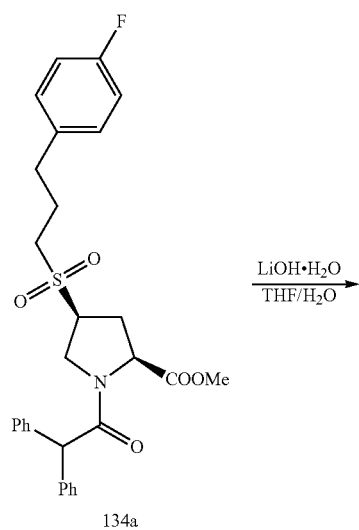

134a

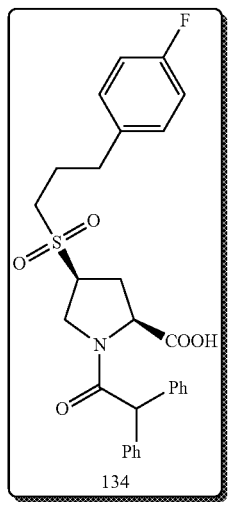

134

A mixture of 134a (100 mg, 0.19 mmol) and LiOH.H$_2$O (24 mg, 0.57 mmol) in THF/H$_2$O (3 mL/1 mL) was stirred at RT overnight, TLC (PE:EA=1:1) showed that the starting material was consumed. The mixture was concentrated in vacuo, the residue was dissolved in water (3 mL), washed with Et$_2$O then acidified to pH 4~5 with a 3 M aqueous HCl solution. The resulting precipitate was collected by filtration and dried at 55° C. to give 134 (60 mg, 61%) as a white solid. LC-MS (Agilent, P-2): $R_t$ 2.94 min; m/z calculated for $C_{28}H_{28}FNO_5S$ [M+H]$^+$ 510.2, [M+Na]$^+$ 532.2, found [M+H]$^+$ 510.2, [M+Na]$^+$ 532.2. HPLC (JULY-L) (214 and 254 nm): $R_t$ 8.91 min.

Example 68: Compound 136 (2S,4S)-1-(2,2-diphenylacetyl)-4-((3-(4-fluorophenyl)propyl)(methyl)amino)pyrrolidine-2-carboxamide

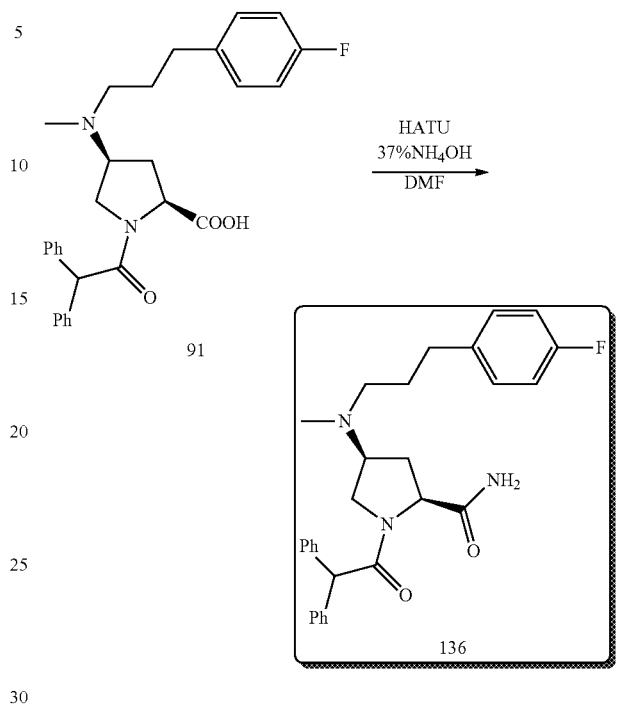

To a solution of 91 (1.2 g, 2.53 mmol) in DMF (20 mL) was added DIPEA (645 mg, 5.03 mmol) and HATU (1.54 g, 4.05 mmol) and the mixture was stirred at RT for 1 h. A 37% aqueous NH$_4$OH solution (1 mL) was then added and stirring was continued at RT overnight, TLC (DCM:MeOH=10:1) showed that the starting material was consumed. Water (30 mL) was added and the mixture was extracted with EA (30 mL×3). The combined organic layers were washed with brine, dried over Na$_2$SO$_4$, filtered and concentrated in vacuo. The residue was purified by column chromatography (DCM:MeOH=1:0 to 20:1) to afford 136 (500 mg, 40%) as a white solid. LC-MS (Agilent, P-2): $R_t$ 2.825 min; m/z calculated for $C_{29}H_{32}FN_3O_2$ [M+H]$^+$ 474.3, found [M+H]$^+$ 474.3. HPLC (JULY-L) (214 and 254 nm): $R_t$ 9.032 min.

Example 69: Compound 137 (2S,4S)-1-(2,2diphenylacetyl)-4-((3-(4-fluorophenyl)propyl)(methyl)amino)pyrrolidine-2-carbonitrile

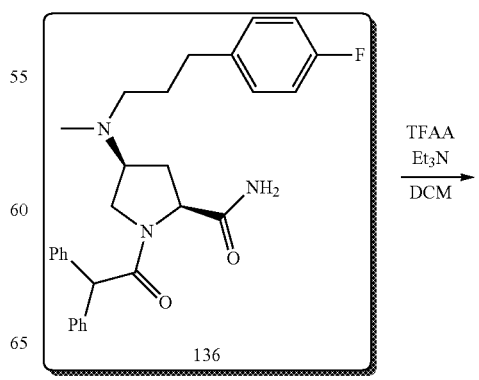

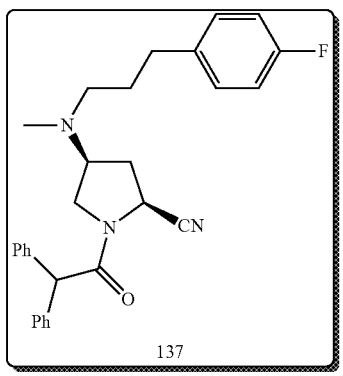

To a solution of 136 (430 mg, 0.91 mmol) in DCM (5 mL) at 0° C. was added TEA (139 mg, 1.37 mmol) and the mixture was stirred at 0° C. for 15 min. TFAA (231 mg, 1.1 mmol) was then added drop-wise at 0° C. and the mixture was stirred at that temperature for 30 min before allowing to warm slowly to RT and stirred overnight, TLC (PE:EA=1:2) showed that the starting material was consumed. The reaction was quenched with a saturated aqueous NaHCO₃ solution, the layers were separated and the aqueous layer was extracted with DCM (15 mL×2). The combined organic layers were washed with brine (15 mL), dried over Na₂SO₄, filtered and concentrated in vacuo. The residue was purified by column chromatography (PE:EA=10:1 to 1:1) to give 137 (320 mg, 77%) as a brown oil. LC-MS (Agilent, P-2): $R_t$ 2.761 min; m/z calculated for $C_{29}H_{30}FN_3O$ [M+H]⁺ 456.2, found [M+H]⁺ 456.2. HPLC (JULY-L) (214 and 254 nm): $R_t$ 8.894 min.

Example 70: Compound 138 1-(2S,4S)-4-((3-(4-fluorophenyl)propyl)(methyl)amino)-2-(1H-tetrazol-5-yl)pyrrolidin-1-yl)-2,2-diphenylethanoate

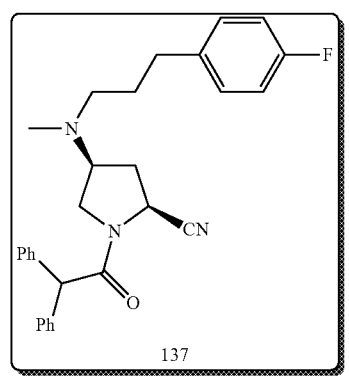

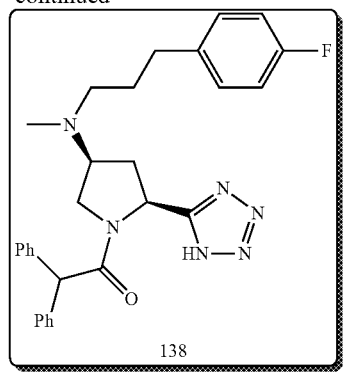

To a solution of 137 (240 mg, 0.53 mmol) in DMF (3 mL) was added NaN₃ (172 mg, 2.64 mmol) and NH₄Cl (192 mg, 3.55 mmol) and the flask was sealed and heated at 100° C. overnight, TLC (DCM:MeOH=50:1) showed that the starting material was consumed. The mixture was partitioned between EA (30 mL) and water (30 mL), the organic layer was collected and washed with brine, dried over Na₂SO₄, filtered and concentrated in vacuo. The residue was purified by chromatography (DCM:MeOH=20:1) to afford 138 (165 mg, 65%) as a white solid. LC-MS (Agilent, P-2): $R_t$ 2.879 min; m/z calculated for $C_{29}H_{31}FN_6O$ [M+H]⁺ 499.3, found [M+H]⁺ 499.3. HPLC (JULY-L) (214 and 254 nm): $R_t$ 8.871 min.

Example 71: Compound 135 (2S,4S)-1-(2,2-diphenylacetyl)-N-(methylsulfonyl)-4-(phenylpropoxy)pyrrolidine-2-carboxamide 1. Procedure for the Preparation of Compound 135b

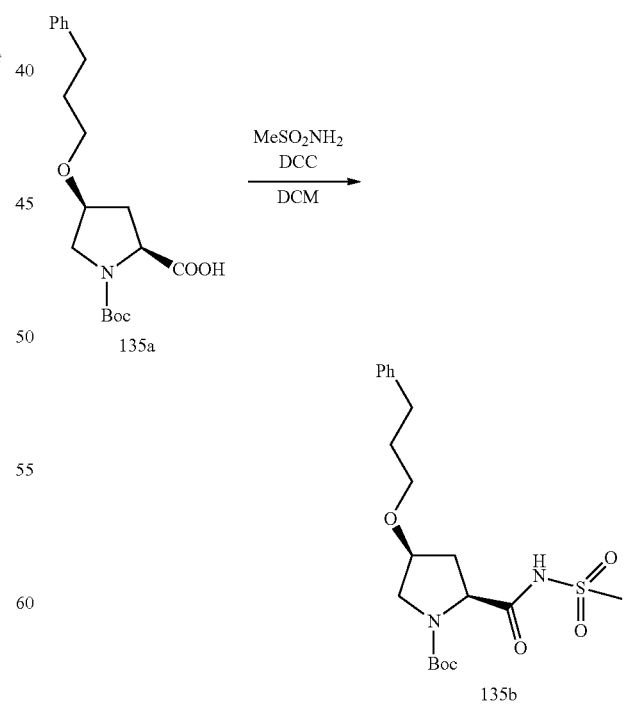

To a stirred solution of 135a (20 mg, 0.057 mmol) in DCM (0.2 mL) was added MeSO₂NH₂ (6 mg, 0.062 mmol), DCC (14 mg, 0.068 mmol) and DMAP (2.0 mg, 0.017 mmol). The flask was sealed and the mixture was stirred at RT for 2 days, LCMS analysis showed that the starting material was consumed. The mixture was concentrated in vacuo to give 135b (50 mg) as a white solid, which was used directly in the next step without purification. LC-MS (Agilent, P-2): $R_t$ 2.78 min; m/z calculated for $C_{20}H_{30}N_2O_6S$ [M+Na]$^+$ 449.2, found [M+Na]$^+$ 449.3.

2. Procedure for the Preparation of 135

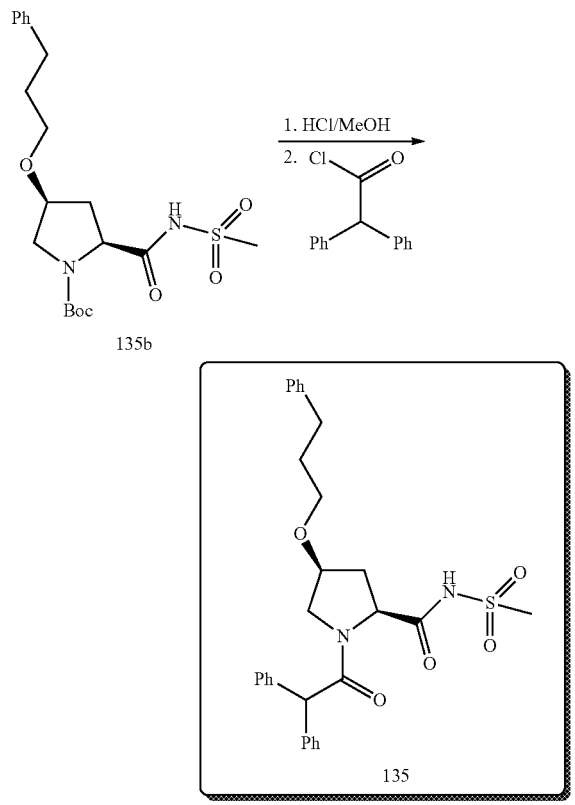

A mixture of 135b (50 mg, assumed 0.057 mmol) and a 4 M HCl/MeOH solution (5 mL) was stirred at RT overnight, LCMS analysis showed that the starting material was consumed. The mixture was concentrated in vacuo, the residue was dissolved in water, basified to pH 8 with $K_2CO_3$ and extracted with DCM. The organic layer was then dried over $Na_2SO_4$ and filtered. To the filtrate was added $Et_3N$ (9 mg, 0.085 mmol) then diphenyl acetyl chloride (16 mg, 0.068 mmol) and the mixture was stirred at RT for 1 h, TLC (DCM:MeOH=10:1) showed a that a major new product formed. The mixture was washed with a 20% aqueous $K_2CO_3$ solution, brine, dried over $Na_2SO_4$, filtered and concentrated in vacuo. The residue was purified by preparative HPLC to give 135 (11 mg, 38% over three steps) as a white solid. LC-MS (Agilent, P-2): $R_t$ 2.68 min; m/z calculated for $C_{29}H_{32}N_2O_5S$ [M+H]$^+$ 521.2, found [M+H]$^+$ 521.2. HPLC (JULY-L) (214 and 254 nm): $R_t$ 9.17 min.

Example 72: Compound 131 (2S,4S)-1-(2,2-diphenylacetyl)-4-(phenethylthio)pyrrolidine-2-carboxylic acid 1. Procedure for the Preparation of 131a

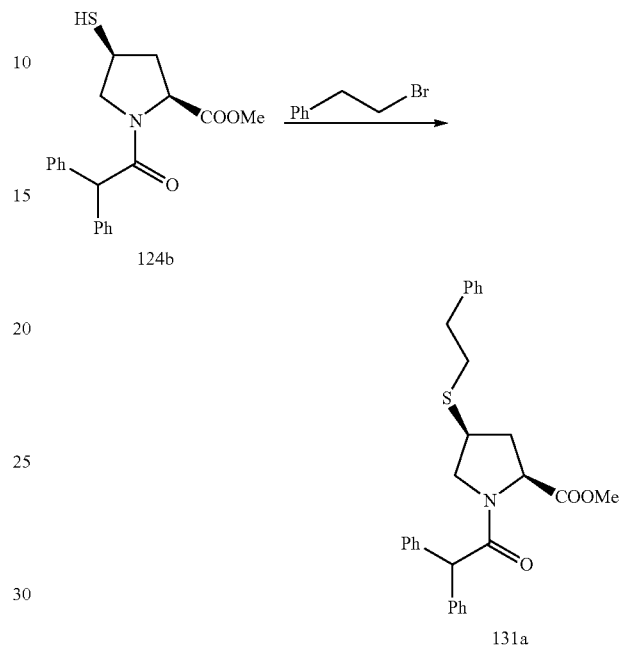

A mixture of 124b (190 mg, 0.53 mmol), 1-(2-bromoethyl)benzene (109 mg, 0.58 mmol) and $K_2CO_3$ (81 mg, 0.58 mmol) in DMF (10 mL) was heated at 80° C. overnight, TLC (PE:EA=2:1) showed that the starting material was consumed. The mixture was cooled to RT, poured into ice-water (60 mL) and extracted with ether (30 mL×2). The combined organic extracts were washed with brine, dried over $Na_2SO_4$, filtered and concentrated in vacuo. The residue was purified by chromatography (PE:EA=1:0 to 4:1) to give 131a (200 mg, 83%) as a colorless oil. LC-MS (Agilent, P-2): $R_t$ 3.15 min; m/z calculated for $C_{28}H_{29}NO_3S$ [M+H]$^+$ 460.2, found [M+H]$^+$ 460.2.

2. Procedure for the Preparation of 131

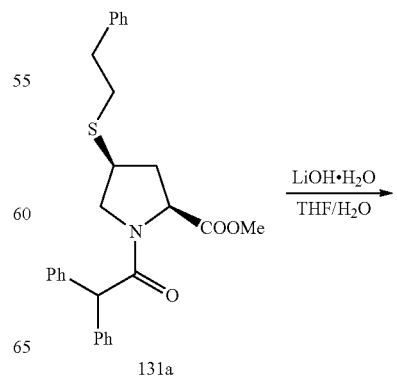

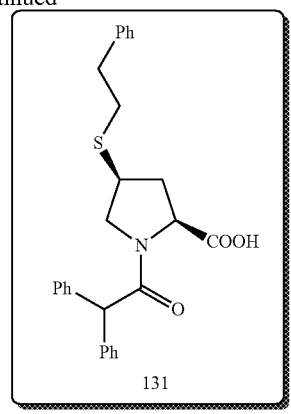

A mixture of 131a (80 mg, 0.17 mmol) and LiOH.H$_2$O (29 mg, 0.69 mmol) in THF/water (3 mL/1 mL) was stirred at RT overnight, TLC (PE:EA=2:1) showed that the starting material was consumed. The mixture was concentrated in vacuo, the residue was dissolved in water (10 mL), acidified to p=3-4 with a 3 M aqueous HCl solution and extracted with DCM (10 mL×2). The combined organic extracts were washed with brine, dried over Na$_2$SO$_4$, filtered and concentrated in vacuo to give 131 (70 mg, 93%) as a white solid. LC-MS (Agilent, P-2): R$_t$ 3.20 min; m/z calculated for C$_{27}$H$_{27}$NO$_3$S [M+H]$^+$ 446.2, found [M+H]$^+$ 446.2. HPLC (JULY-L) (214 and 254 nm): R$_t$ 9.27 min.

Example 73: Compound 132 (2S,4S)-1-(2,2-diphenylacetyl)-4-(phenethylsufonyl)pyrrolidine-2-carboxylic acid 1. Procedure for the Preparation of 132a To a stirred solution of 131a (120 mg, 0.26 mmol) in DCM (10 mL) at 0° C. was added 80% m-CPBA (140 mg, 0.65 mmol) in three portions and the mixture was allowed to warm slowly to RT and stirred overnight, TLC (PE:EA=2:1) showed that the starting material was consumed. The mixture was washed with a saturated aqueous Na$_2$CO$_3$ solution (5 mL×2), brine (5 mL×2) then dried over Na$_2$SO$_4$, filtered and concentrated in vacuo. The residue was purified by chromatography (PE:EA=1:9 to 3:1) to give 132a (110 mg, 86%) as a colorless oil. LC-MS (Agilent, P-2): R$_t$ 3.01 min; m/z calculated for C$_{28}$H$_{29}$NO$_5$S [M+H]$^+$ 492.2, [M+Na]$^+$ 514.2, found [M+H]$^+$ 492.2, [M+Na]$^+$ 514.2.

2. Procedure for the Preparation of 132

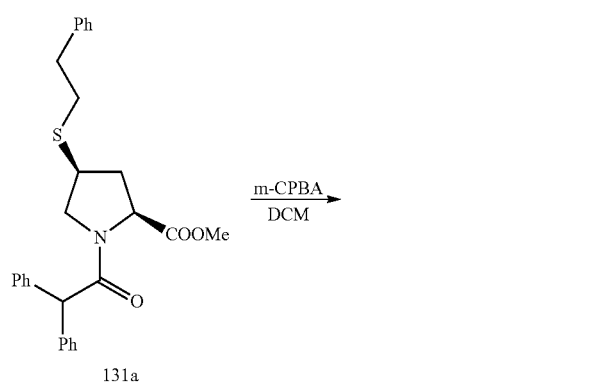

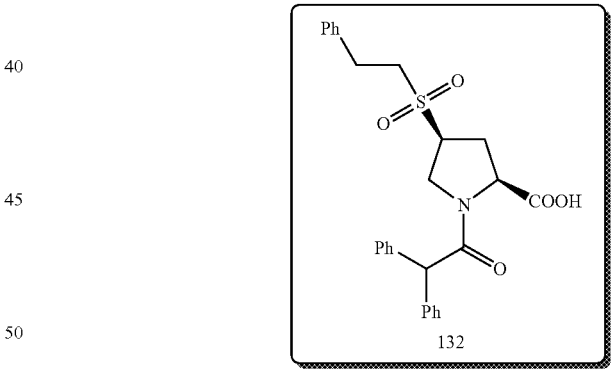

A mixture of 132a (110 mg, 0.22 mmol) and LiOH.H$_2$O (37 mg, 0.88 mmol) in THF/water (3 mL/1 mL) was stirred at RT overnight, TLC (PE:EA=1:1) showed that the starting material was consumed. The mixture was concentrated in vacuo, the residue was dissolved in water (10 mL) and acidified to pH 3-4 with a 3 M aqueous HCl solution. The resulting precipitate was collected by filtration then dried to give 132 (80 mg, 77%) as a white solid. LC-MS (Agilent, P-2): R$_1$ 2.84 min; m/z calculated for C$_{27}$H$_{27}$NO$_5$S [M+H]$^+$ 478.2, found [M+H]$^+$ 478.2. HPLC (JULY-L) (214 and 254 nm): R$_1$ 8.84 min.

Example 74: Compound 118 (2S,4S)-4-((benzylsulfonyl)methyl)-1-(diphenylacetyl)-pyrrolidine-2-carboxylic acid 1. Procedure for the Preparation of 118a

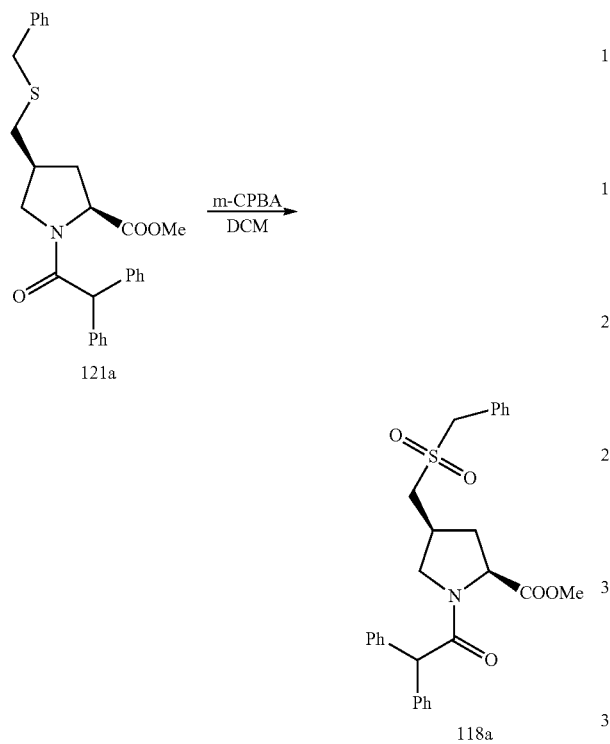

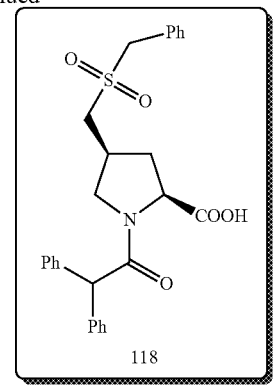

A mixture of 118a (77 mg, 0.16 mmol) and LiOH.H$_2$O (20 mg, 0.47 mmol) in THF/H$_2$O (4 mL/1 mL) was stirred at RT overnight, TLC (PE:EA=1:1) showed that the starting material was consumed. The mixture was concentrated in vacuo, the residue was dissolved in water (5 mL), acidified to pH 4~5 with a 3 M aqueous HCl solution and the resulting precipitate was collected by filtration and dried at 60° C. to give 118 (40 mg, 54%) as a white solid. LC-MS (Agilent, P-2): R$_t$ 2.88 min; m/z calculated for C$_{27}$H$_{27}$NO$_5$S [M+H]$^+$ 478.2, [M+Na]$^+$ 500.2, found [M+H]$^+$ 478.2, [M+Na]$^+$ 500.2. HPLC (JULY-L) (214 and 254 nm): R$_t$ 8.75 min. HPLC (ZSJ-2) (214 and 254 nm): R$_t$ 16.68 min.

Example 75: Compound 119 (2S,4S)-4-((phenylsulfonyl)methyl)-1-(diphenylacetyl)-pyrrolidine-2-carboxylic acid 1. Procedure for the Preparation of 119a

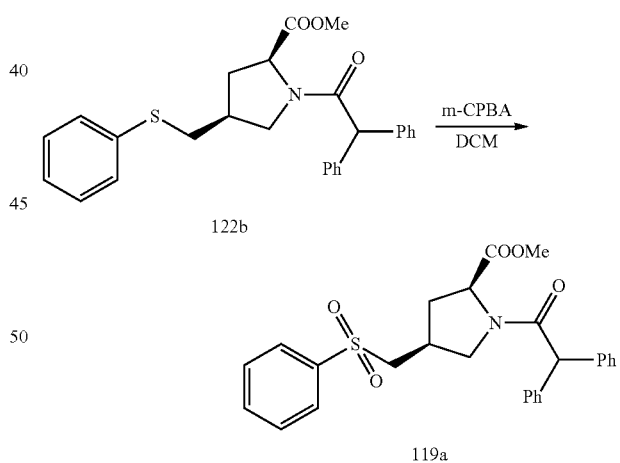

To a solution of 121a (80 mg, 0.17 mmol) in DCM (6 mL) was added 80% m-CPBA (94 mg, 0.43 mmol) and the mixture was stirred at RT overnight, TLC (PE:EA=2:1) showed that the 121a was consumed. The mixture was washed with a saturated aqueous Na$_2$CO$_3$ solution, brine (10 mL), dried over Na$_2$SO$_4$, filtered and concentrated in vacuo. The residue was purified by chromatography (PE:EA=8:1 to 1.5:1) to give 118a (77 mg, 90%) as a white solid. LC-MS (Agilent, P-2): R$_t$ 3.12 min; m/z calculated for C$_{31}$H$_{32}$N$_2$O$_3$ [M+H]$^+$ 492.2, [M+Na]$^+$ 514.2, found [M+H]$^+$ 492.2, [M+Na]$^+$ 514.2.

2. Procedure for the Preparation of 118

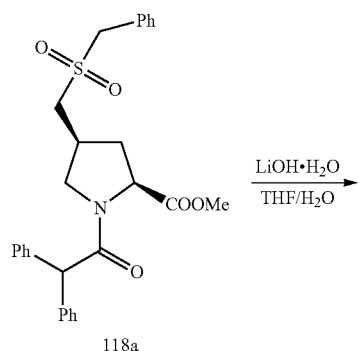

To a solution of 122b (80 mg, 0.18 mmol) in DCM (5 mL) at 0° C. was added 80% m-CPBA (97 mg, 0.45 mmol) and the mixture was allowed to warm slowly to RT and stirred for 3 h, TLC (PE:EA=1:1) showed that the starting material was consumed. A saturated aqueous Na$_2$CO$_3$ solution was added, the layers were separated and the aqueous layer was extracted with DCM (20 mL×3). The combined organic extracts were washed with brine, dried over Na$_2$SO$_4$, filtered and concentrated in vacuo. The residue was purified by chromatography (PE:EA=1:0 to 1:1) to give 119a (55 mg, 64%) as a white solid. LC-MS (Waters): R$_t$ 6.27 min; m/z calculated for $C_{27}H_{27}NO_5S$ [M+H]$^+$ 478.0, [M+Na]$^+$ 500.1 found [M+H]$^+$ 478.0, [M+Na]$^+$ 500.0.

2. Procedure for the Preparation of 119

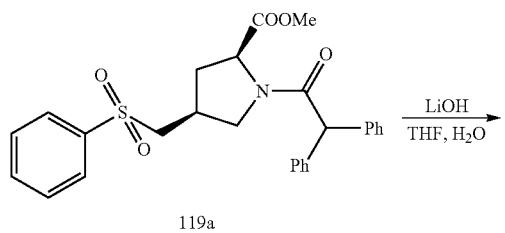

119a

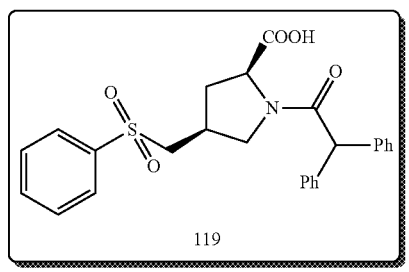

119

A mixture of 119a (55 mg, 0.12 mmol) and LiOH.H$_2$O (15 mg, 0.35 mmol) in THF/H$_2$O (2 mL/0.5 mL) was stirred at RT overnight, TLC (PE:EA=1:1) showed that the starting material was consumed. The mixture was concentrated in vacuo, the residue was dissolved in water, acidified to pH 3~4 with a 3 M aqueous HCl solution and the resulting precipitate was collected by filtration then purified by preparative HPLC to give 119 (30 mg, 50%) as a white solid. LC-MS (Agilent, P-2): R$_t$ 2.917 min; m/z calculated for $C_{26}H_{25}NO_5S$ [M+H]$^+$ 464.2, found [M+H]$^+$ 464.2. HPLC (JULY-L) (214 and 254 nm): R$_t$ 8.73 min. HPLC (ZSJ-2) (214 and 254 nm): R$_t$ 16.36 min.

Example 76: Compound 114 (2S,4S)—N—(N,N-dimethylsulfamoyl)-1-(2,2-diphenylacetyl)-4-((3-(4-fluorophenyl)propyl)(methyl)amino)pyrrolidine-2-carboxylic acid

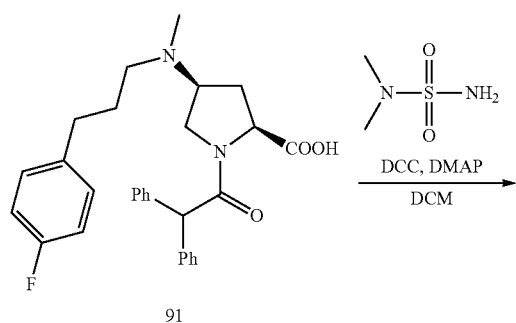

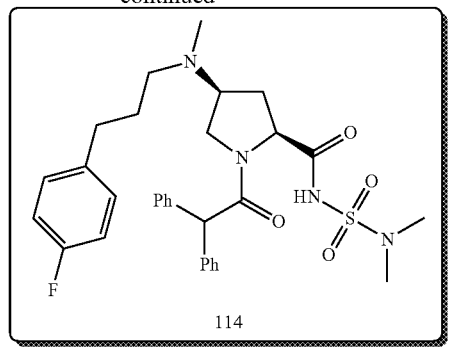

114

To a solution of 91 (100 mg, 0.21 mmol) in DCM (5 mL) was added N,N-dimethylsulfamide (28.8 mg, 0.23 mmol), DMAP (6.3 mg, 0.063 mmol) and DCC (52 mg, 0.25 mmol) and the mixture was stirred at RT for 72 h, TLC (DCM:MeOH=20:1) showed that the starting material was consumed. The mixture was filtered, the filtrate was concentrated in vacuo and the residue was purified by preparative HPLC to give 114 (56 mg, 46%) as a white solid. LC-MS (Agilent, P-2): R$_t$ 2.86 min; m/z calculated for $C_{31}H_{37}FN_4O_4S$ [M+H]$^+$ 581.3, found [M+H]$^+$ 581.3. HPLC (JULY-L) (214 and 254 nm): R$_t$ 8.88 min.

Example 77: Compound 146 (2S,4S)-1-(2,2-diphenylacetyl)-4-methyl(prop-2-yn-1-yl)amino)pyrrolidine-2-carboxylic acid 1. Procedure for the Preparation of 146a

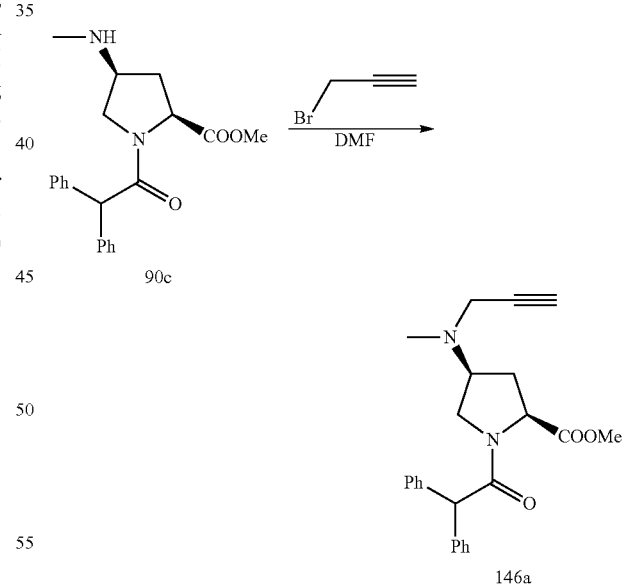

146a

To a solution of 90c (200 mg, 0.57 mmol) in DMF (8 mL) was added Cs$_2$CO$_3$ (222 mg, 0.68 mmol) then 3-bromoprop-1-yne (68 mg, 0.57 mmol). The flask was sealed and the mixture was heated at 40° C. overnight, TLC (PE:EA=1:2) showed that the starting material was consumed. The mixture was poured into ice-water (30 mL) and extracted with EA (15 mL×4). The combined organic extracts were washed with brine, dried over Na$_2$SO$_4$, filtered and concentrated in vacuo. The residue was purified by chromatography (PE:

EA=10:1 to 3:1) to give 146a (61 mg, 27%) as a colorless oil. LC-MS (Agilent, P-2): $R_t$ 2.592 min; m/z calculated for $C_{24}H_{26}N_2O_3$ [M+H]$^+$ 391.2, found [M+H]$^+$ 391.2.

2. Procedure for the Preparation of 146

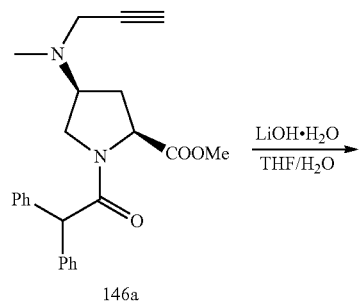

146a

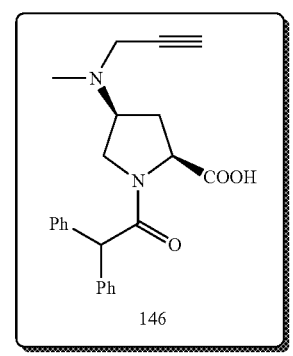

146

A mixture of 146a (61 mg, 0.21 mmol) and LiOH.H$_2$O (20 mg, 0.47 mmol) in THF/H$_2$O (3 mL/1 mL) was stirred at RT overnight, TLC (PE:EA=1:2) showed that the starting material was consumed. The mixture was concentrated in vacuo to remove THF, the residue was dissolved in water (5 mL), acidified to pH 4 with a 4 M aqueous HCl solution and extracted with DCM (5 mL×5). The combined organic extracts were washed with brine, dried over Na$_2$SO$_4$, filtered and concentrated in vacuo to give crude 146 (57 mg) and 27 mg of this crude material was purified by preparative HPLC to give pure 146 (20 mg, 53%) as a viscous colorless oil. LC-MS (Agilent, P-2): $R_t$ 2.51 min; m/z calculated for $C_{23}H_{24}N_2O_3$ [M+H]$^+$ 377.2, found [M+H]$^+$ 377.2. HPLC (JULY-L) (214 and 254 nm): $R_t$ 8.50 min.

Example 78: Compound 147 (2S,4S)-1-(2,2-diphenylacetyl)-4-(methyl(propyl)amino)pyrrolidine-2-carboxylic acid 1. Procedure for the Preparation of 147a

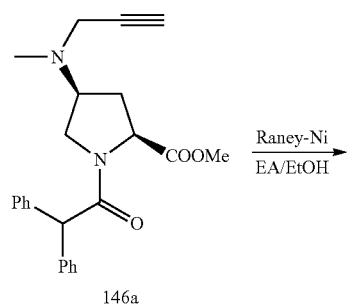

146a

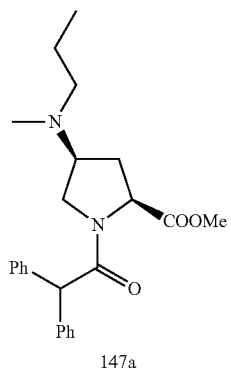

147a

A mixture of 146a (29 mg, 0.074 mmol) and Raney-Ni (50 mg) in EA/EtOH (10 mL/10 mL) was stirred under a H$_2$ atmosphere (1 atm) at 30° C. overnight, LCMS analysis showed that the starting material was consumed. The mixture was filtered and the filtrate was concentrated in vacuo to give 147a (22 mg, 75%) as a colorless oil. LC-MS (Agilent, P-2): $R_t$ 2.75 min; m/z calculated for $C_{24}H_{30}N_2O_3$ [M+H]$^+$ 395.2, found [M+H]$^+$ 395.2.

2. Procedure for the Preparation of 147

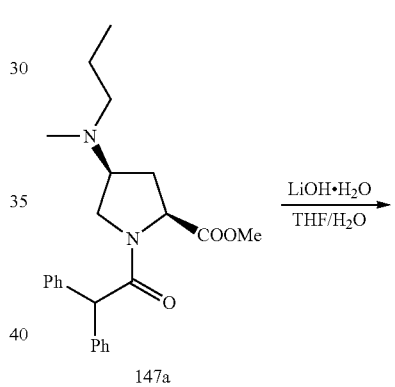

147a

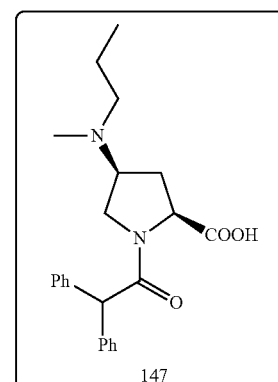

147

A mixture of 147a (22 mg, 0.056 mmol) and LiOH.H$_2$O (7 mg, 0.168 mmol) in THF/H$_2$O (3 mL/1 mL) was stirred at RT for 2 days, LCMS analysis showed that the starting material was consumed. The mixture was concentrated in vacuo to remove the THF, the residue was dissolved in water (5 mL), acidified to pH 4 with a 4 M aqueous HCl solution and concentrated in vacuo. The residue was purified by preparative HPLC to give 147 (7 mg, 33%) as a white solid. LC-MS (Agilent, P-2): $R_t$ 2.47 min; m/z calculated for $C_{23}H_{28}N_2O_3$ [M+H]$^+$ 381.2, found [M+H]$^+$ 381.2. HPLC (JULY-L) (214 and 254 nm): $R_t$ 8.55 min.

Example 79: Compound 148 ((2S,4S)-4-((4,4-dimethylpent-2-yn-1-yl)(methyl)amino)-1-(2,2-diphenylaetyl)pyrrolidine-2-carboxylic acid 1. Procedure for the Preparation of 148a

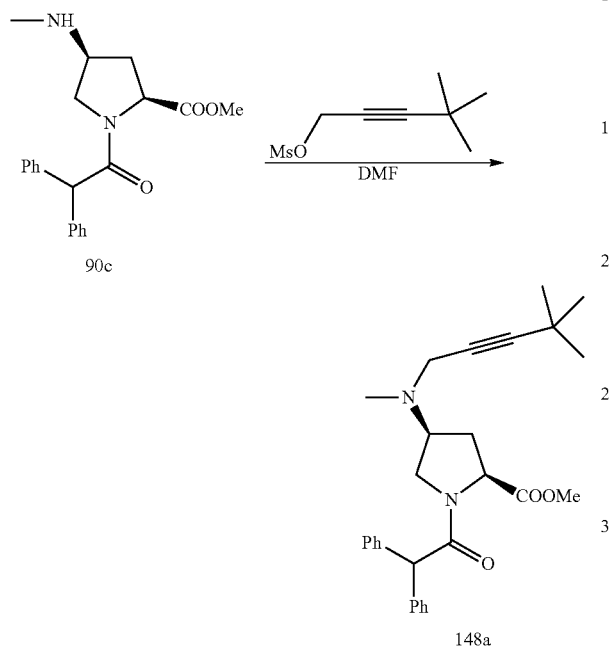

To a solution of 90c (300 mg, 0.85 mmol) in DMF (8 mL) was added $Cs_2CO_3$ (333 mg, 1.02 mmol) then 4,4-dimethylpent-2-ynyl methanesulfonate (194 mg, 1.02 mmol) and the mixture was heated at 40° C. overnight, TLC (PE:EA=1:1) showed that the starting material was consumed. The mixture was poured into ice-water (30 mL) and extracted with EA (15 mL×3). The combined organic extracts were washed with brine (20 mL×2), dried over $Na_2SO_4$, filtered and concentrated in vacuo. The residue was purified by chromatography (PE:EA=10:1 to 4:1) to give 148a (100 mg, 26%) as a colorless oil. LC-MS (Agilent, P-2): $R_t$ 3.60 min; m/z calculated for $C_{28}H_{34}N_2O_3$ [M+H]$^+$ 447.3, found [M+H]$^+$ 447.3.

2. Procedure for the Preparation of 148

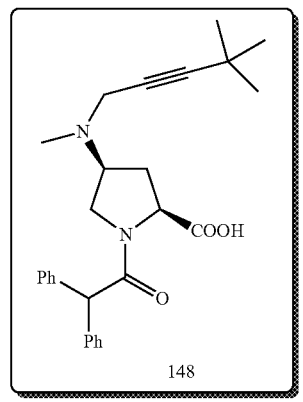

A mixture of 148a (100 mg, 0.22 mmol) and LiOH.H$_2$O (28 mg, 0.67 mmol) in THF/H$_2$O (5 mL/1 mL) was stirred at RT overnight, TLC (PE:EA=1:1) showed that the starting material was consumed. The mixture was concentrated in vacuo to remove THF, the residue was dissolved in water (5 mL), acidified to pH 4 with a 4 M aqueous HCl solution and extracted with DCM (5 mL×4). The combined organic extracts were washed with brine (10 mL×2), dried over $Na_2SO_4$, filtered and concentrated in vacuo to give crude 148 (95 mg) and 35 mg of the crude material was purified by preparative HPLC to give pure 148 (25 mg, 71%) as a white solid. LC-MS (Agilent, P-2): $R_t$ 3.08 min; m/z calculated for $C_{27}H_{32}N_2O_3$ [M+H]$^+$ 433.2, found [M+H]$^+$ 433.2. HPLC (JULY-L) (214 and 254 nm): $R_1$ 9.08 min.

Example 80: Compound 149 ((2S,4S)-4-((4,4-dimethylpentyl)methyl)amino)-1-(2,2-diphenylacetyl)pyrrolidine-2-carboxylic acid

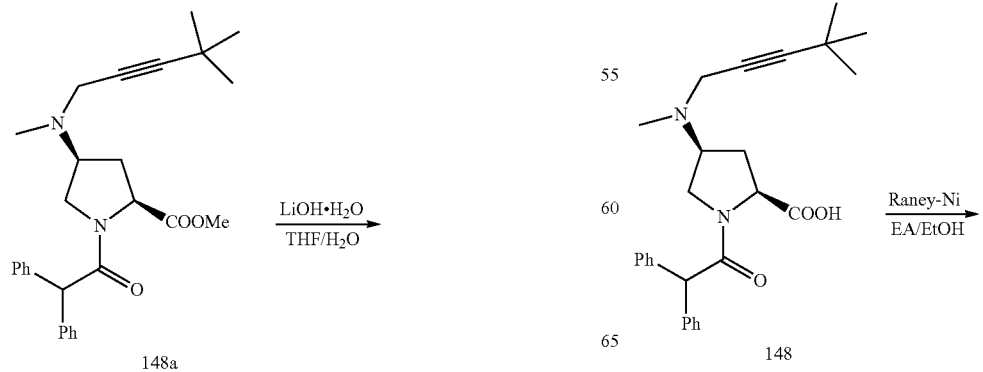

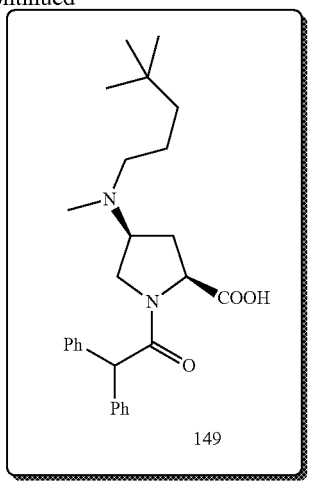

A mixture of 148 (30 mg, 0.069 mmol) and Raney-Ni (50 mg) in EA/EtOH (10 mL/10 mL) was stirred under a $H_2$ atmosphere (1 atm) at 38° C. overnight, LCMS analysis showed that the starting material was consumed. The mixture was filtered and the filtrate was concentrated in vacuo. The residue was purified by preparative HPLC to give 149 (12 mg, 40%) as a white solid. LC-MS (Agilent, P-2): $R_t$ 2.63 min; m/z calculated for $C_{27}H_{36}N_2O_3$ $[M+H]^+$ 4373, found $[M+H]^+$ 437.3. HPLC (JULY-L) (214 and 254 nm): $R_t$ 9.15 min.

Example 81: Compound 16 (2S,4S)-1-(2,2-diphenylacetyl)-4-(((1R,2R)-2-phenylcyclopropyl)methoxy)pyrrolidine-2-carboxylic acid and (2S,4S)-1-(2,2-diphenylacetyl)-4-(((1S,2S)-2-phenylcyclopropyl)methoxy)pyrrolidine-2-carboxylic acid 1. Procedure for the Preparation of 16b

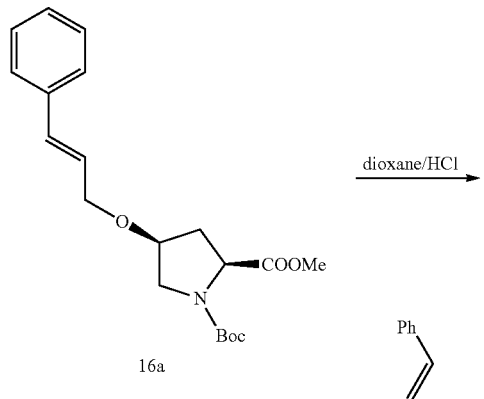

A solution of 16a (12.0 g, 48.8 mmol) in 4 M HCl/diox (60 mL) was stirred at RT overnight, TLC (MeOH:DCM=1:10) showed the starting material was consumed. The mixture was concentrated in vacuo, the residue was dissolved in water (50 mL) and extracted with diethyl ether (100 mL×2). The aqueous layer was basified to pH=9~10 with a saturated aqueous $Na_2CO_3$ solution and extracted with EA (100 mL×2). The combined organic extracts were washed with brine (100 mL×2), dried over $Na_2SO_4$, filtered and concentrated in vacuo to give 16b as a colorless oil (5.0 g, 78%). LC-MS (Agilent): $R_t$ 2.81 min; m/z calculated for $C_{19}H_{15}NO_3$ $[M+H]^+$ 262.1, $[M+Na]^+$ 284.1, found $[M+H]^+$ 262.1, $[M+Na]^+$ 284.1.

2. Procedure for the Preparation of 16c

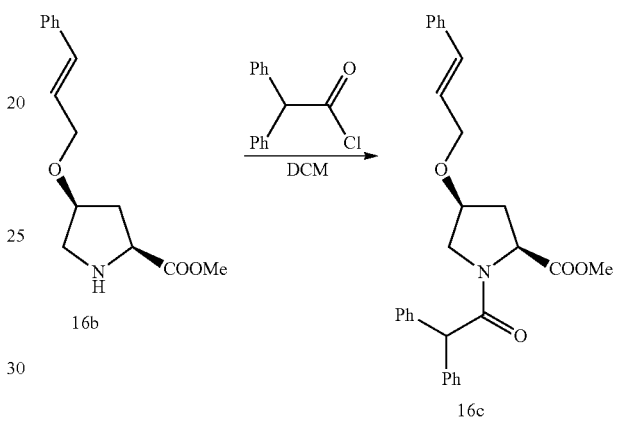

To a solution of 16b (300 mg, 1.15 mmol) and $Et_3N$ (175 mg, 1.72 mmol) in DCM (5 mL) was added diphenylacetyl chloride (318 mg, 1.38 mmol) at 0° C. under $N_2$ and the mixture was stirred at 0° C. for 30 min, TLC (PE:EA=1:1) showed the starting material was consumed. The mixture was washed with brine (3 mL×2), dried over $Na_2SO_4$, filtered and concentrated in vacuo. The residue was purified by chromatography (PE:EA=10:0 to 4:1) to give 16c as a thick oil (300 mg, 57%). LC-MS (Agilent): $R_t$ 3.38 min; m/z calculated for $C_{29}H_{29}NO_4$ $[M+H]^+$ 456.2, $[M+Na]^+$ 478.2, found $[M+H]^+$ 456.2, $[M+Na]^+$ 478.2.

3. Procedure for the Preparation of 16d

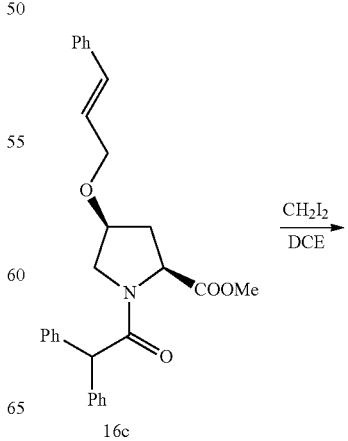

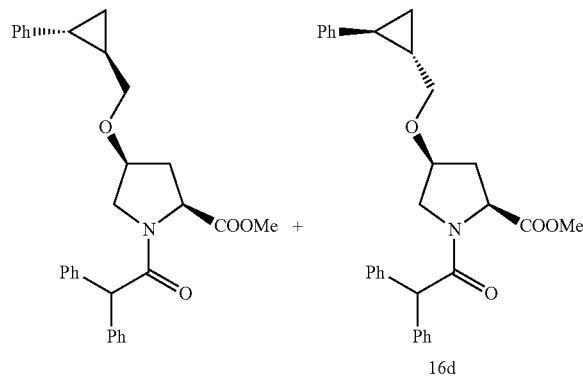

16d

A stirred solution of 16c (150 mg, 0.33 mmol) in dry DCE (5 mL) was cooled to 0° C. under a N₂ atmosphere. A ZnEt₂ solution (1 M in hexane, 0.66 mL, 0.66 mmol) was added followed by CH₂I₂ (354 mg, 1.32 mmol) and the mixture was warmed to RT slowly and stirred overnight. The mixture was re-cooled to 0° C., quenched with a saturated aqueous NH₄Cl solution (10 mL) and extracted with DCM (20 mL). The organic layer was separated, washed with brine, dried over Na₂SO₄ then filtered and concentrated in vacuo. The residue was purified by chromatography (PE:EA=4:1) to give 16d as a thick oil (120 mg, 78%). LC-MS (Agilent): $R_t$ 3.38 min; m/z calculated for $C_{30}H_{31}NO_4$ [M+H]⁺ 470.2, [M+Na]⁺ 492.2, found [M+H]⁺ 470.2, [M+Na]⁺ 492.2.

4. Procedure for the Preparation of 16

16

To a stirred solution of 16d (110 mg, 0.23 mmol) in THF (3 mL) was added a solution of LiOH.H₂O (33 mg, 0.79 mmol) in water (1 mL) and the mixture was stirred at RT overnight, TLC (PE:EtOAc=1:1) showed the starting material was consumed. The mixture was concentrated in vacuo to remove most of the THF and the residue was partitioned between DCM (15 mL) and water (15 mL). The aqueous layer was acidified with a 1 M aqueous HCl solution to pH=3~4, the DCM layer was separated and the aqueous layer was extracted again with DCM (15 mL). The combined organic extracts were washed with brine (30 mL×2), dried over Na₂SO₄, filtered and concentrated in vacuo. The residue was purified by flash chromatography (DCM: MeOH=50:1 to 20:1) to give the product as a white solid (80 mg, 77%). LC-MS (Agilent): $R_t$ 3.39 min; m/z calculated for $C_{29}H_{29}NO_4$ [M+H]⁺ 456.2, [M+Na]⁺ 478.2, found [M+H]⁺ 456.2, [M+Na]⁺ 478.2. HPLC (214 and 254 nm): 13.75 min.

Example 82: Compound 84 (2S,4S)-4-((4aS,7aS)-6-benzoctahydro-1H-pyrrolo[3,4-b]pyridin-1-yl)-1-(2,2-diphenylacetyl)pyrrolidine-2-carboxylic acid 6. Procedure for the Preparation of 84a

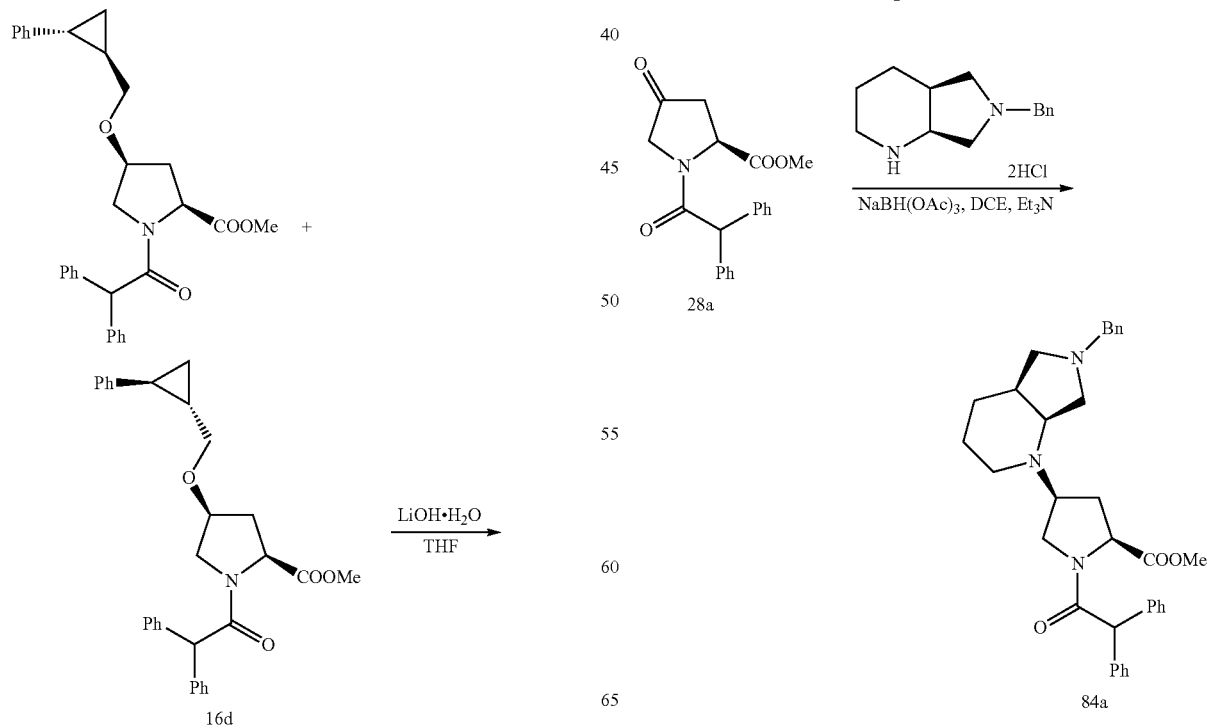

A solution of the amine (257 mg, 0.89 mmol) in DCE (10 mL) was cooled to 0° C. and Et$_3$N (181 mg, 1.78 mmol) was added followed by a solution of 28a (300 mg, 0.89 mmol) in DCE (5 mL). AcOH (0.5 mL) and the mixture was stirred at RT for 30 min. NaBH(OAc)$_3$ (282 mg, 1.34 mmol) was added and stirring was continued at RT overnight, TLC (DCM:MeOH=10:1) showed that some of the 28a remained. NaCNBH$_3$ (1.2 equiv) was added and the mixture was heated at 40° C. overnight, TLC (DCM:MeOH=10:1) showed that most of the ketone was consumed. The mixture was washed twice with brine, dried over Na$_2$SO$_4$, filtered and concentrated in vacuo. The residue was purified by silica column (DCM:MeOH=100:1 to 50:1) to give 84a (90 mg, 18%) as a yellow solid. LC-MS (Agilent): R$_t$ 3.28 min; m/z calculated for C$_{34}$H$_{39}$N$_3$O$_3$ [M+H]$^+$ 538.4, found [M+H]$^+$ 538.4.

7. Procedure for the Preparation of 84

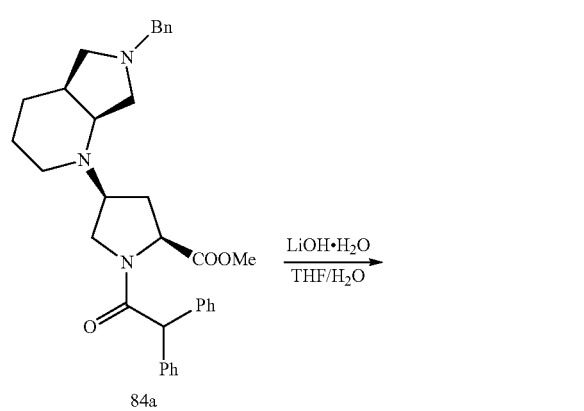

To a mixture of 84a (90 mg, 0.17 mmol) in THF/water (6 mL/2 mL) was added LiOH·H$_2$O (21 mg, 0.51 mmol) and the mixture was stirred at RT overnight, TLC (DCM: MeOH=20:1) showed the starting material was consumed. Most of the THF was removed in vacuo, the residue was dissolved in water (15 mL) and washed with Et$_2$O (10 mL×2). The aqueous layer was then acidified to pH=2-3 with a 1 M aqueous HCl solution and extracted with DCM (10 mL×3). The combined organic extracts were washed with brine, dried over Na$_2$SO$_4$, filtered and concentrated in vacuo and the residue was purified by prep-HPLC to give 84 (25 mg, 28%) as a white solid. LC-MS (Agilent): R$_t$ 3.29 min; m/z calculated for C$_{33}$H$_{37}$N$_3$O$_3$ [M+H]$^+$ 524.28, found [M+H]$^+$ 524.3. HPLC (JULY-L) (214 and 254 nm): R$_t$ 8.67 min.

Example 83: Compound 85 (2S,4S)-4-((4aR,7aR)-6-benzoctahydro-1H-pyrrolo[3,4-b]-pyridin-1-yl)-1-(2,2-diphenylacetyl)pyrrolidine-2-carboxylic acid 2. Procedure for the Preparation of 85a

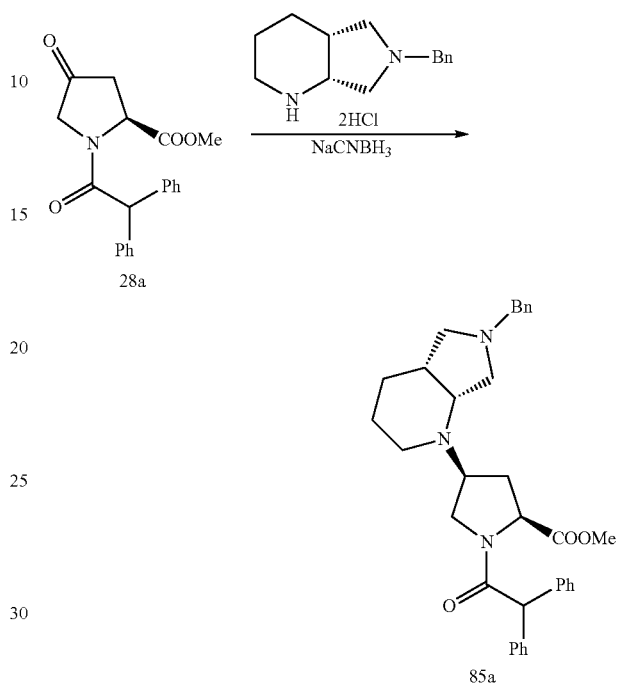

To a solution of 28a (417 mg, 1.24 mmol), amine (300 mg, 1.00 mmol) and Et$_3$N (230 mg, 2.28 mmol) in MeOH (15 mL) was added AcOH (1.0 mL) and the mixture was stirred at RT for 1 h. NaCNBH$_3$ (80 mg, 1.24 mmol) was then added and the mixture was stirred at RT overnight, TLC (DCM:MeOH=10:1) showed that the starting material was consumed. Most of the MeOH was removed in vacuo and the residue was dissolved in water (10 mL) and extracted with DCM (10 mL). The organic layer was washed with brine (10 mL), dried over Na$_2$SO$_4$, filtered and concentrated in vacuo. The residue was purified by silica column (DCM: MeOH=80:1) to give 85a (220 mg, 33%) as a white solid. LC-MS (Agilent): R$_t$ 3.30 min; m/z calculated for C$_{34}$H$_{39}$N$_3$O$_3$ [M+H]$^+$ 538.3, found [M+H]$^+$ 538.3.

3. Procedure for the Preparation of 85

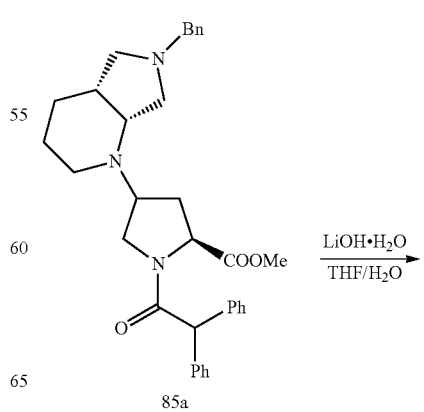

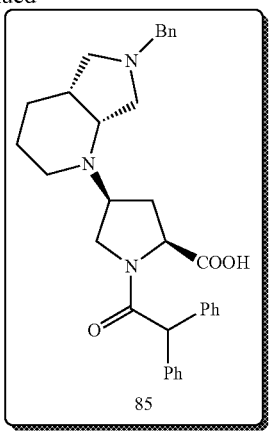

85

To a mixture of 85a (220 mg, 0.41 mmol) in THF/water (10 mL/1.5 mL) was added LiOH.H$_2$O (52 mg, 1.23 mmol) and the mixture was stirred at RT overnight, TLC (DCM:MeOH=10:1) showed that the starting material was consumed. Most of the THF was removed in vacuo and the residue was dissolved in water (15 mL) and acidified to pH=3~4 with a 3 M aqueous HCl solution. The resulting precipitate was collected by filtration then purified by prep-HPLC to give 85 (66 mg, 30%) as a white solid. LC-MS (Agilent): R$_t$ 3.28 min; m/z calculated for C$_{33}$H$_{37}$N$_3$O$_3$ [M+H]$^+$ 524.3, found [M+H]$^+$ 524.3. HPLC (JULY-L) (214 and 254 nm): R$_t$ 8.75 min.

Example 84: Compound 86 (3S,3'S,5'S)-1-(2,2-diphenylacetyl)-3-(phenyl-[1,3'-bipyrrolidine]-5'-carboxylic acid 1. Procedure for the Preparation of 86a

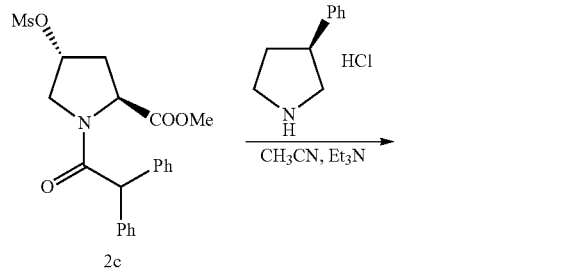

2c

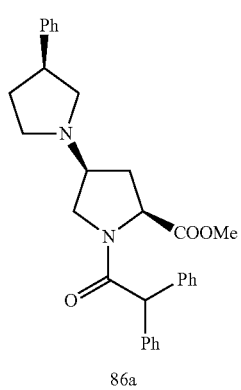

86a

To a stirred mixture of (S)-3-phenyl-pyrolidine.hydrochloride (528 mg, 2.8 mmol) in CH$_3$CN (10 mL) was added Et$_3$N (285 mg, 2.8 mmol) followed by 2c (600 mg, 1.4 mmol) and the mixture was heated at 110° C. in a sealed tube overnight. The solvent was removed in vacuo and the residue was partitioned between water (20 mL) and EA (15 mL). The aqueous layer was separated and further extracted with EA (15 mL). The combined organic extracts were washed with brine, dried over Na$_2$SO$_4$, filtered and concentrated in vacuo. The residue was purified by silica column (DCM:MeOH=100:1 to 50:1) to give 86a (230 mg, 35%) as a yellow solid. LC-MS (Agilent): R$_t$ 3.27 min; m/z calculated for C$_{30}$H$_{32}$N$_2$O$_3$ [M+H]$^+$ 469.24, found [M+H]$^+$ 469.3.

2. Procedure for the Preparation of 86

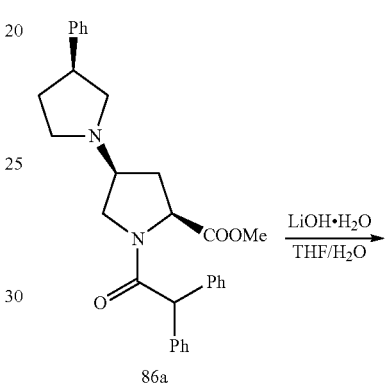

86a

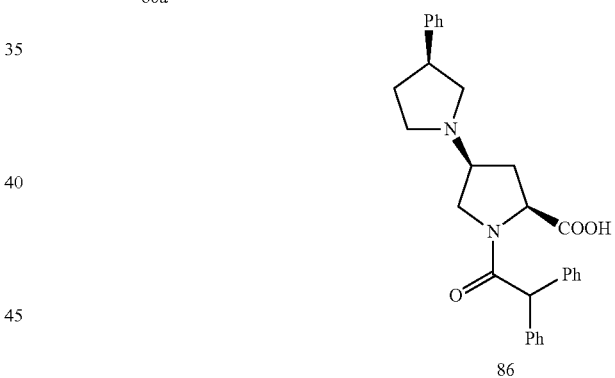

86

To a mixture of 86a (220 mg, 0.47 mmol) in THF/water (8 mL/3 mL) was added LiOH.H$_2$O (59 mg, 1.41 mmol) and the mixture was stirred at RT overnight, TLC (DCM:MeOH=20:1) showed the starting material was consumed. Most of the THF was removed in vacuo and the residue was dissolved in water (20 mL) and washed with Et$_2$O (15 mL×2). The aqueous layer was then acidified to pH=2-3 with a 1 M aqueous HCl solution and extracted with DCM (15 mL×2). The combined organic extracts were washed with brine, dried over Na$_2$SO$_4$, filtered and concentrated in vacuo. The residue was purified by prep-HPLC to give 86 (50 mg, 23%) as a white solid. LC-MS (Agilent): R$_t$ 3.53 min; m/z calculated for C$_{29}$H$_{30}$N$_2$O$_3$ [M+H]$^+$ 455.24, found [M+H]$^+$ 455.3. HPLC (JULY-L) (214 and 254 nm): R$_t$ 8.80 min.

Example 85: Compound 87 (3R,3'S,5'S)-1-(2,2-diphenylacetyl)-3-(phenyl-[1,3'-bipyrrolidine]-5'-carboxylic acid 1. Procedure for the Preparation of 87a

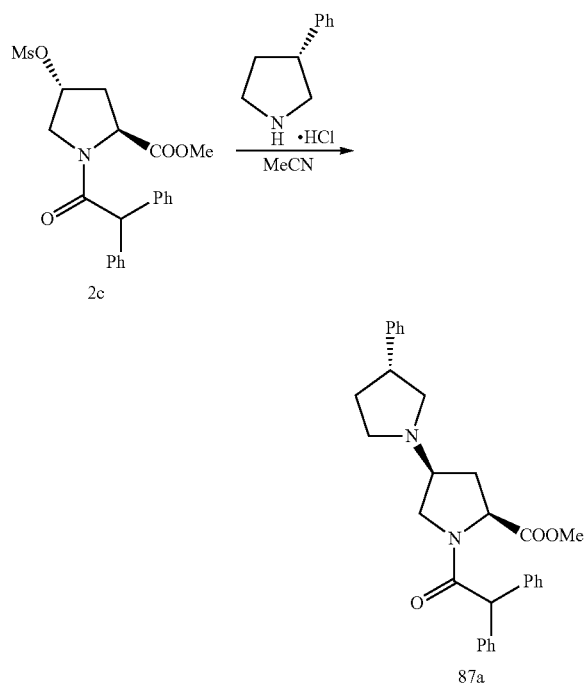

2c

A mixture of 2c (500 mg, 1.19 mmol), (R)-3-phenylpyrrolidine hydrochloride (660 mg 3.59 mmol) and Et₃N (363 mg, 3.59 mmol) in CH₃CN (10 mL) was heated at 110° C. in a sealed tube overnight, TLC (DCM:MeOH=10:1) showed most of the starting material was consumed. The mixture was cooled to RT, concentrated in vacuo and the residue was purified by chromatography (DCM:MeOH=1:0 to 50:1) to give 87a (200 mg, 35%) as a white solid. LC-MS (Agilent): $R_t$ 3.35 min; m/z calculated for $C_{30}H_{32}N_2O_3$ [M+H]⁺ 469.2, found [M+H]⁺ 469.3.

2. Procedure for the Preparation of 87

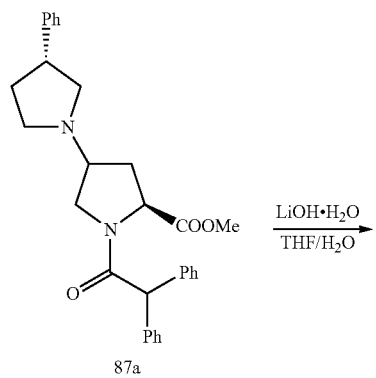

87a

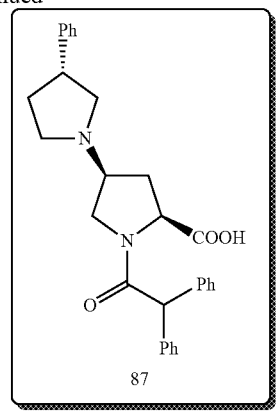

87

To a mixture of 87a (200 mg, 0.43 mmol) in THF/water (5 mL/1 mL) was added LiOH.H₂O (54 mg, 1.28 mmol) and the mixture was stirred at RT overnight, TLC (DCM:MeOH=10:1) showed the starting material was consumed. Most of the THF was removed in vacuo and the residue was dissolved in water (15 mL) and washed with ether (15 mL×2). The aqueous layer was then cooled in an ice water bath and acidified to pH=3'4 with a 1 M aqueous HCl solution. The resulting precipitate was collected by filtration, washed with water (5 mL×3) and dried at 45° C. overnight to give 87 (70 mg, 36%) as a white solid. LC-MS (Agilent): $R_t$ 3.48 min; m/z calculated for $C_{29}H_{30}N_2O_3$ [M+H]⁺ 455.2, found [M+H]⁺ 455.3. HPLC (JULY-L) (214 and 254 nm): $R_t$ 8.77 min.

Biological Example 1: AT₂ Receptor Binding

Media and Solutions
1. Trypsin-EDTA (for preparation of 100 mL)
   Trypsin 0.25 g
   2% EDTA 2 mL
   PBS 98 mL
   Dissolve trypsin in 2% EDTA and PBS completely; sterilize the solution by passing through a 0.20 μM membrane filter; store at 4° C.
2. DMEM medium (for preparation of 1 L)
   The powder was dissolved into 950 mL of distilled water with gentle stirring until the solution becomes clear.
   Add. NaHCO₃ 1.176 g for DMEM medium.
   Adjust pH of medium to 0.2-0.3 below final working pH using 1 M NaOH or 1 M
   HCl. Add slowly with stirring.
   Dilute to 1 liter with ddH₂O.
   Sterilize the medium immediately by filtration.
   Store at 4° C.
3. TE buffer
   20 mM Tris-HCl, pH 7.4,
   5 mM EDTA
4. Binding Assay Buffer
   50 mM Hepes, pH 7.4
   5 mM MgCl₂
   1 mM CaCl₂
   0.2% BSA
5. Wash Buffer
   50 mM Hepes, pH 7.4

Procedures for HEK293/AT$_2$ Receptor Transient Cell Transfection

Cells were plated into 150 mm dish at 50% density for transient transfection. Cells were ready for transfection after overnight incubation (the confluence reaches around 80%).

75 µL Lipofectamine™2000 diluted in 6.25 mL OptiMEM I Reduced Serum Medium, was mixed gently, and incubated at room temperature for 5 minutes. 50 µg expression plasmid DNA diluted in 6.25 mL OptiMEM I Reduced Serum Medium without serum was mixed gently.

After the 5 minute incubation, the diluted DNA was combined with the diluted Lipofectamine™2000 (total volume is 12.5 mL). The mixture was mixed gently and incubated for 30 minutes at room temperature to allow the DNA-Lipofectamine™2000 complexes to form.

The 12.5 mL DNA-Lipofectamine™ 2000 complexes were added into the 150 mm dish and mixed gently by rocking the dish back and forth.

The cells were incubated at 37° C. with 5% CO$_2$ for 48 hours.

Cells were collected and stored frozen at −80° C.

Procedures for HEK293/AT$_2$ Receptor Cell Membrane Preparation

Frozen HEK293/AT$_2$ receptor (transient transfected) cells were homogenized in ice cold TE buffer for 10 s.

The homogenate was centrifuged at 25,000 g for 30 minutes.

The pellet was resuspended in ice cold tissue buffer.

Protein concentrations were determined using Bradford assay method with BSA as standard.

The membrane protein was frozen under −80° C.

Compound Preparation

Solutions of all compounds were prepared by microplate liquid handling equipment such as Janus or Precision 2000. Compounds, dissolved in DMSO were stored in a Freezer. Compounds were prepared from 30 mM in 100% DMSO.

Step 1: Dose Plate Preparation (96 Well Plate)

Add the 3 µL [30 mM] compound stock to column 1 on the plate.

Add 15 pt of 100% DMSO to column 1.

Add 10.81 µL of 100% DMSO to column 2-12.

Transfer 5 µL from column 1 into column 2 (half log dilution).

Transfer 5 µL from column 2 into column 3 (half log dilution).

Transfer 5 µL from column 3 into column 4 (half log dilution).

Transfer 5 µL from column 4 into column 5 (half log dilution).

Transfer 5 µL from column 5 into column 6 (half log dilution).

Transfer 5 µL from column 6 into column 7 (half log dilution).

Transfer 5 µL from column 7 into column 8 (half log dilution).

Transfer 5 µL from column 8 into column 9 (half log dilution).

Transfer 5 µL from column 9 into column 10 (half log dilution)

Transfer 5 µL from column 10 into column 11 (half log dilution)

Transfer 5 µL from column 11 into column 12 (half log dilution).

All the compounds were diluted using Precision 2000 microplate liquid handling equipment. The top concentration of compound was 5 mM with 100% DMSO.

Step 2: Working Plate Preparation (96 Well Plate)

Compounds were diluted 50-fold with buffer.

49 µL buffer was added to the well of 96 well plate.

1 µL compound solution from dose plate was transferred to the corresponding well of working plate.

The top concentration of compound was 100 µM with 2% DMSO.

Step 3: Assay Plate Preparation (96 Well Plate)

15 µL of compound solution was transferred from each well of working plate to the well of assay plate by Janus. Each compound was assayed in duplicate in each plate and there were 4 compounds per plate.

Procedures for AT$_2$ Receptor Binding Assay

120 µL membrane (5 mg protein/well) was incubated with 15 µL of [$^{125}$I]-CGP42112A and 15 µL of compound at RT for 1.5 hrs.

The binding reaction was stopped by rapid filtration through Unifilter GF/C plates (presoaked in 0.3% (v:v) BSA).

Plate was washed three times with ice cold wash buffer.

The filtration plates were dried at 37° C. overnight.

50 µL of scintillation cocktail was added to each well.

Radioactivity was determined using MicroBetaTriluxmicroplate scintillation counter.

Data Analysis

Data was analyzed through 4 parameter logic using Prism 5.0 software.

The results are shown in the following Table:

| Compound | IC$_{50}$ (nM) |
|---|---|
| 2 | 113.9 |
| 3 | 192.9 |
| 5 | 89.96 |
| 6 | 181.3 |
| 9 | 98.62 |
| 15 | 54.47 |
| 16 | 6654 |
| 17 | 3974 |
| 21 | 62.14 |
| 22 | 384.1 |
| 23 | 290.3 |
| 28 | 86.86 |
| 35 | 539.9 |
| 36 | 1664 |
| 46 | 2257 |
| 48 | 89.43 |
| 49 | 58.81 |
| 50 | 67.27 |
| 51 | 50.33 |
| 53 | 43.88 |
| 54 | 154.8 |
| 55 | 386.4 |
| 56 | 315.5 |
| 58 | 3050 |
| 61-A | 83.34 |
| 61-B | 107.0 |
| 62 | 540.2 |
| 63 | 482.9 |
| 64 | 3358 |
| 65 | 1605 |
| 67 | 3665 |
| 70-B | 1340 |
| 70-A | 49.08 |
| 75 | 3829 |
| 76 | 3604 |
| 84 | 75.75 |
| 85 | 102.6 |
| 86 | 817.4 |
| 87 | 43.6 |

-continued

| Compound | IC$_{50}$ (nM) |
|---|---|
| 90 | 64.23 |
| 91 | 12.01 |
| 92 | 133.8 |
| 93 | 125.6 |
| 8 | 512.1 |
| 96 | 2248 |
| 97 | 457.5 |
| 98 | 240.5 |
| 99 | 535.5 |
| 100 | 18 |
| 101 | 400.5 |
| 102 | 498.6 |
| 104 | 1316 |
| 105 | 2489 |
| 106 | 426.2 |
| 107 | 461 |
| 108 | 2054 |
| 109 | 650.4 |
| 112 | 255.1 |
| 114 | 17.05 |
| 52 | 63.23 |
| 115 | 321.3 |
| 116 | 649.6 |
| 118 | 313.7 |
| 119 | 2647 |
| 120 | 1199 |
| 121 | 57.67 |
| 122 | 142.6 |
| 124 | 363.4 |
| 125 | 1244 |
| 126 | 20.48 |
| 131 | 652.1 |
| 133 | 1738 |
| 134 | 954.5 |
| 135 | 240.2 |
| 136 | 89.03 |
| 137 | 173.4 |
| 138 | 3.519 |
| 139 | 2533 |
| 140 | 673.7 |
| 142 | 992.9 |
| 143 | 372.3 |

Biological Example 2: AT$_1$ Receptor Binding

The same media, solutions, cell procedures and compound preparation was used as for Biological Example 1 but using HEK293/AT$_1$ Receptor Transient Cells. The binding assay was then performed as follows:

- 120 µL membrane (5 mg protein/well) was incubated with 15 µL of [$^{125}$I]-Sar1-Ile8-Angiotensin II and 15 µL of compound at RT for 1.5 hrs.
- The binding reaction was stopped by rapid filtration through Unifilter GF/C plates (presoaked in 0.3% (v:v) BSA).
- Plate was washed three times with ice cold wash buffer.
- The filtration plates were dried at 37° C. overnight.
- 50 µL of scintillation cocktail was added to each well.
- Radioactivity was determined using MicroBetaTriluxmicroplate scintillation counter.

The IC$_{50}$ binding results for a known selective AT$_2$ receptor antagonist PD-126,055, known selective AT$_1$ receptor antagonist, Losartin, angiotensin II and compound 21 are shown in the following Table.

| Compound | IC$_{50}$ (nM) | Ki (nM) |
|---|---|---|
| PD-126,055 | — | — |
| Compound 21 | — | — |
| Losartin | 11.01 | 5.505 |
| Angiotensin II | 1.797 | 0.8985 |

—: No significant inhibition of binding of the radiolabelled ligand even at top concentration tested (10 µM). Compounds 6, 112, 136 and 138 were also analysed in a similar assay and showed no AT$_1$ receptor binding at 10 µM.

Biological Example 3: AT$_2$ Receptor Neurite Outgrowth Assay

The general methodology of Wallinder (2008) and references cited therein was used to assess the effect of the compounds of the present invention on neurite outgrowth. The assay was adapted for high content screening.

Figure 2:
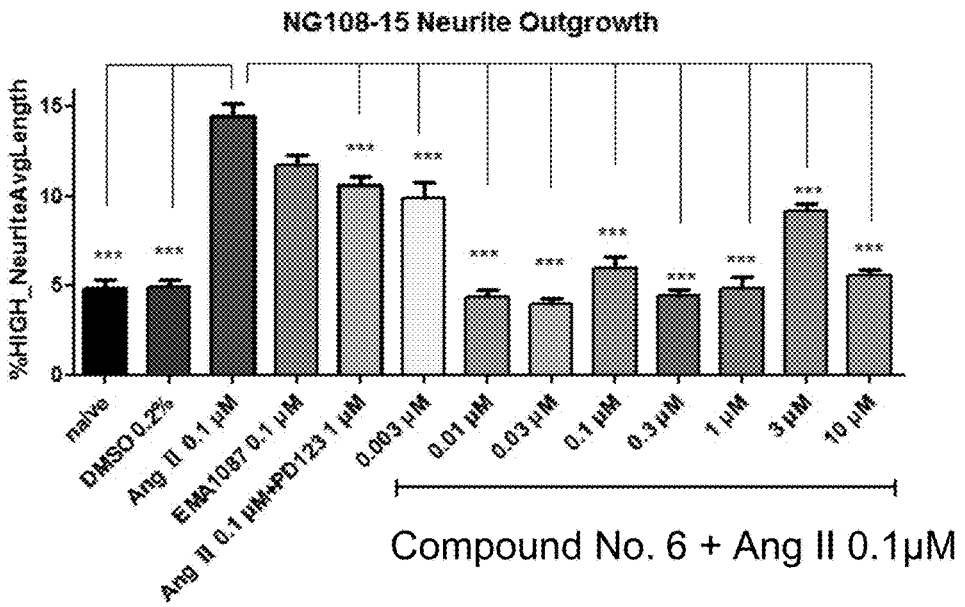
FIG. 2 is a graphical representation of the inhibition of neurite outgrowth in the presence of angiotensin II 0.1 μM and compound 6 at 0.003 μM, 0.01 μM, 0.03 μM, 0.1 μM, 0.3 μM, 1 μM, 3 μM and 10 μM.
Figure 3:
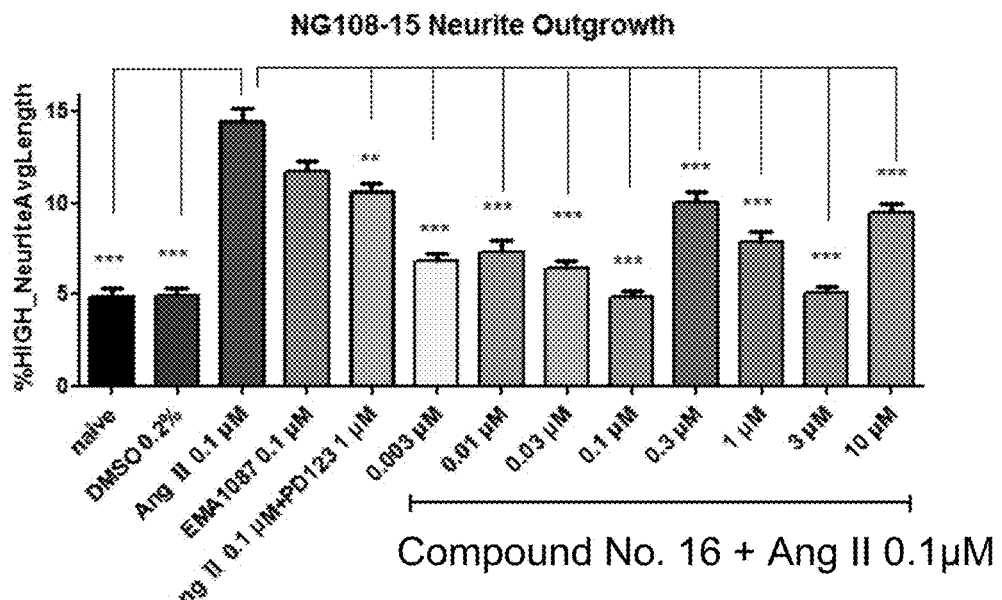
FIG. 3 is a graphical representation of the inhibition of neurite outgrowth in the presence of angiotensin II 0.1 μM and compound 16 at 0.003 μM, 0.01 μM, 0.03 μM, 0.1 μM, 0.3 μM, 1 μM, 3 μM and 10 μM.
Figure 4:
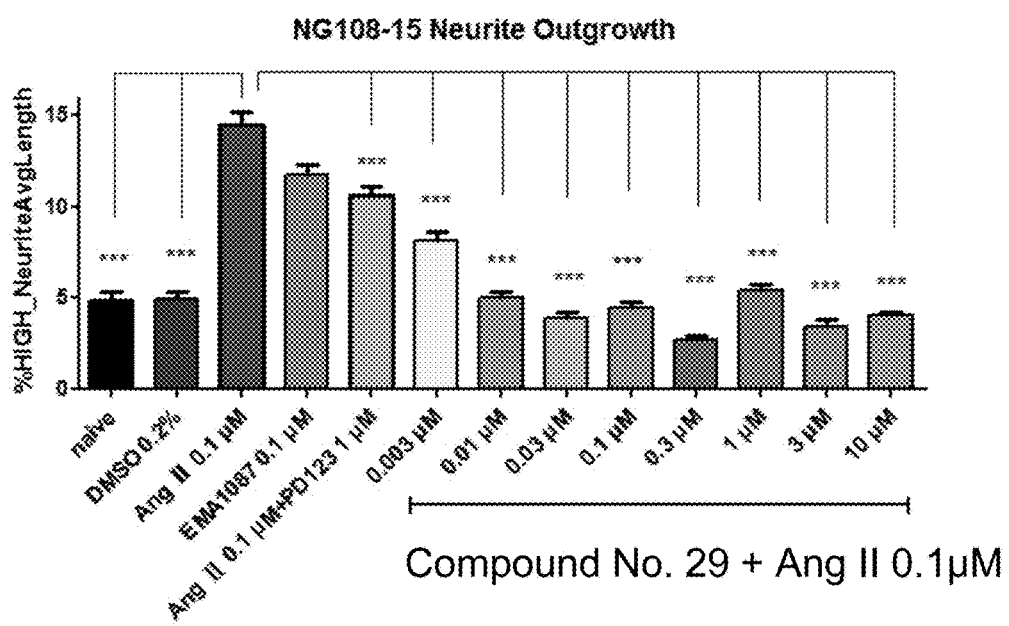
FIG. 4 is a graphical representation of the inhibition of neurite outgrowth in the presence of angiotensin II 0.1 μM and compound 29 at 0.003 μM, 0.01 μM, 0.03 μM, 0.1 μM, 0.3 μM, 1 μM, 3 μM and 10 μM.
Figure 5:
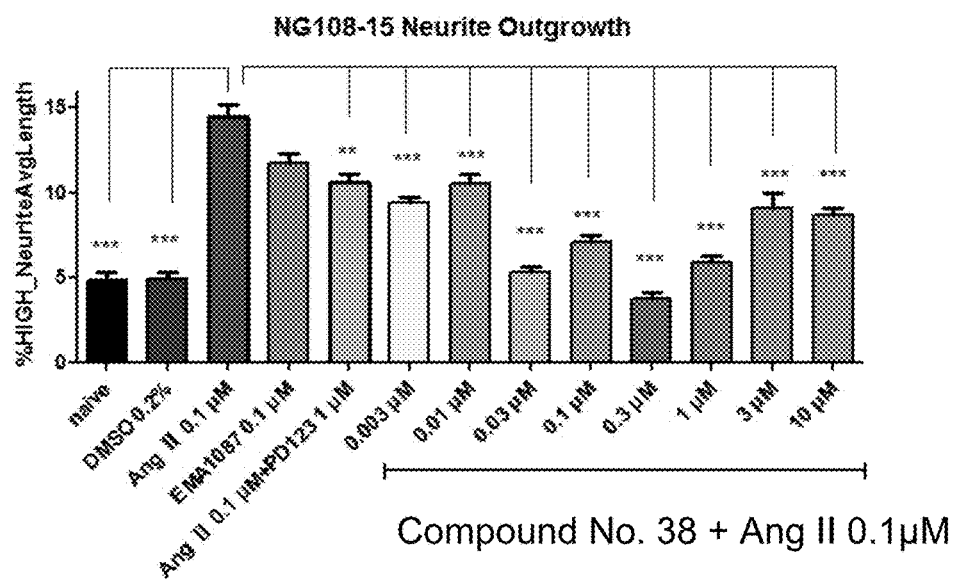
FIG. 5 is a graphical representation of the inhibition of neurite outgrowth in the presence of angiotensin II 0.1 μM and compound 38 at 0.003 μM, 0.01 μM, 0.03 μM, 0.1 μM, 0.3 μM, 1 μM, 3 μM and 10 μM.

The compounds screened against NG108-15 neurite cells were the known AT$_2$ selective antagonist PD-126,055, compound 6, compound 15, compound 21 and compound 28. The controls used were naïve cells, DMSO 0.2% treated cells, cells treated with Angiotensin II (Ang II) 0.1 µM, EMA1087 0.1 µM and Ang II 0.1 µM+PD-123,319 (PD-123) 1 µM. EMA1087 is a known AT$_2$ receptor agonist described as "compound 21" in Wan et al. 2004. PD-123,319 is a known, commercially available AT$_2$ receptor antagonist. The results were analyzed by immunofluorescence quantitative analysis. Neurite outgrowth was quantified with neurite average length using Cellomics software. Results are expressed as the mean±SEM, each conducted in triplicate. Statistical significance, compared with Ang II control: *p<0.05, p<0.01, and *p<0.001. NS: no significant difference. ND: not determined. FIGS. 1 to 5 show neurite outgrowth was inhibited by the AT$_2$ receptor antagonists, PD-126,055 and compounds 6, 15, 21 and 28.

REFERENCES

Chakrabarty et al., 2008, Estrogen elicits dorsal root ganglion axon sprouting via a rennin-angiotensin system. *Endocrinology*, 149(7):3452-3460.

Clere et al., 2010, Deficiency or blockade of angiotensin II type 2 receptor delays tumorigenesis by inhibiting malignant cell proliferation and angiogenesis. *Int. J. Cancer*, 127: 2279-2291.

Izu et al., 2009, Angiotensin II Type 2 receptor blockade increases bone mass. *J. Biol. Chem.*, 284(8):4857-4864.

Steckelings et al., 2005, The AT$_2$ receptor A matter of love and hate. *Peptides*, 26:1401-1409.

Wallinder et al., 2008, Selective angiotensin II AT$_2$ receptor agonists: Benzamide structure-activity relationships. *Bioorganic & Medicinal Chemistry*, 16:6841-6849.

Wan et al., 2004, Design, Synthesis and biological evaluation of the first selective nonpeptide AT$_2$ receptor agonist. *J. Med. Chem.*, 47:5995-6008.

Wexler et al., 1996, Nonpeptide angiotensin II receptor antagonists: The next generation in antihypertensive therapy. *J. Med. Chem.*, 39(3):325-656.

What is claimed is:
1. A compound of formula (I):

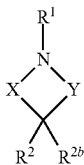

wherein:
X is absent and Y is —CHR³CHR⁴CH₂—, —CH₂CHR³CHR⁴, —CH₂CH₂CHR³—, —CR³=CHCH₂—, —CH=CHR³CH₂— or —CH₂CH=CR³—; or
X is —CHR⁵ and Y is —CHR³CHR⁴—, —CHR³CR⁴=, —CH₂CHR³—, —CR³=CH— or —CH=CR³—, wherein when Y is —CHR³CR⁴=, R²ᵇ is absent, or
X is —CH₂CHR⁵— or C(=O)CHR⁵— and Y is —CHR³—;
R¹ is —C(=O)CH(aryl)(aryl), —C(=O)CH(aryl)(cycloalkyl), —C(=O)CH(cycloalkyl)(cycloalkyl), —C(=O)N(aryl)(aryl), —C(=O)N(aryl)(cycloalkyl) or —C(=O)N(cycloalkyl)(cycloalkyl);
R² is —C₁₋₄alkylenearyl, —OC₁₋₃alkylenearyl, —OC₂₋₃alkenylenearyl, —OC₂₋₃alkynylenearyl, —OC₁₋₃alkylenecycloalkylaryl, -OarylOaryl, —SC₁₋₃alkylenearyl, —SO₂C₁₋₃alkylenearyl, —NHC₁₋₈alkyl, —NHC₁₋₃alkylenearyl, —NHC₁₋₃alkyleneheteroaryl, —NHC₂₋₃alkynylenearyl, —N(CH₃)C₁₋₈alkyl, —N(CH₃)C₁₋₃alkylenearyl, —N(CH₃)C₁₋₃alkyleneheteroaryl, —N(CH₃)C₂₋₃alkynylenearyl, —CH₂OC₁₋₃alkylenearyl, —N(CH₃)C₁₋₃alkylenecycloalkyl or —NHC₁₋₃alkylenecycloalkyl;
R²ᵇ is hydrogen;
R³ is CO₂H, —CH₂CO₂H, —C(=O)C(=O)OH, —C(=O)NHSO₂C₁₋₆alkyl, —C(=O)NHSO₂phenyl, —C(=O)NHSO₂CF₃, —SO₃H or —PO₃H₂;
R⁴ is hydrogen or R³ and R⁴ together form a group:

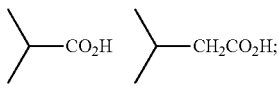

R⁵ is hydrogen;
and
wherein each cycloalkyl, cycloalkenyl, aryl, heterocyclyl and heteroaryl may be optionally substituted with one or more optional substituents selected from the group consisting of C₁₋₆alkyl, C₂₋₆alkenyl, C₃₋₆cycloalkyl, oxo(=O), —OH, —SH, C₁₋₆alkylO—, C₂₋₆alkenylO—, C₃₋₆cycloalkylO—, C₁₋₆alkylS—, C₂₋₆alkenylS—,
C₃₋₆cycloalkylS—, —CO₂H, —CO₂C₁₋₆alkyl, —NH₂, —NH(C₁₋₆alkyl), —N(C₁₋₆alkyl)₂, —NH(phenyl), —N(phenyl)₂, —CN, —NO₂, -halogen, —CF₃, —OCF₃, —SCF₃, —CHF₂, —OCHF₂, —SCHF₂, -phenyl, -heterocyclyl, -heteroaryl, -Oheteroaryl, -Oheterocyclyl, -Ophenyl, —C(O)phenyl, —C(O)C₁₋₆ alkyl;
wherein heterocyclyl is selected from the group consisting of azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl;
or a pharmaceutically acceptable salt thereof.

2. A compound according to claim 1, or a pharmaceutically acceptable salt thereof, wherein X is absent and Y is —CHR³CHR⁴CH₂—, —CH₂CHR³CHR⁴— or —CH₂CH₂CHR³— or X is —CHR⁵— and Y is —CHR³CHR⁴—, —CH₂CHR³—, —CR³=CH— or —CH=CR³— or X is —CH₂CHR⁵— and Y is —CHR₃—.

3. A compound according to claim 1, or a pharmaceutically acceptable salt thereof, wherein R¹ is —C(=O)CH(phenyl)(phenyl), —C(=O)CH(phenyl)(cyclohexyl), —C(=O)CH(cyclohexyl)(cyclohexyl), —C(=O)N(phenyl)(phenyl), —C(=O)N(phenyl)(cyclohexyl) or —C(=O)N(cyclohexyl)(cyclohexyl) wherein each phenyl or cyclohexyl is optionally substituted with one or more substituents selected from —C₁₋₃ alkyl, —OC₁₋₃ alkyl and halo.

4. A compound according to claim 1, or a pharmaceutically acceptable salt thereof, wherein R³ is —CO₂H.

5. A compound according to claim 1, or a pharmaceutically acceptable salt thereof, wherein R⁴ is H.

6. A pharmaceutical composition comprising a compound of formula (I) according to claim 1, or a pharmaceutically acceptable salt thereof, and a pharmaceutically acceptable carrier.

7. A method of treating neuropathic pain or inflammatory pain in a subject comprising administering a compound of formula (I) according to claim 1 or a pharmaceutically acceptable salt thereof.

8. A method of treating a condition characterized by neuronal hypersensitivity, impaired nerve conduction velocity, a cell proliferative disorder, or a disorder associated with an imbalance between bone resorption and bone formation in a subject comprising administering a compound of formula (I) according to claim 1 or a pharmaceutically acceptable salt thereof.

9. A method of producing analgesia in a subject comprising administering a compound of formula (I) according to claim 1 or a pharmaceutically acceptable salt thereof.

10. A compound according to claim 1 selected from group consisting of:
(2S,4S)-4-(benzyloxy)-1-(2,2-diphenylacetyl)pyrrolidine-2-carboxylic acid,
(2S,4R)-4-(benzyloxy)-1-(2,2-diphenylacetyl)pyrrolidine-2-carboxylic acid,
(2S,4S)-4-cinnamyloxy-1-(2,2-diphenylacetyl)pyrrolidine-2-carboxylic acid,

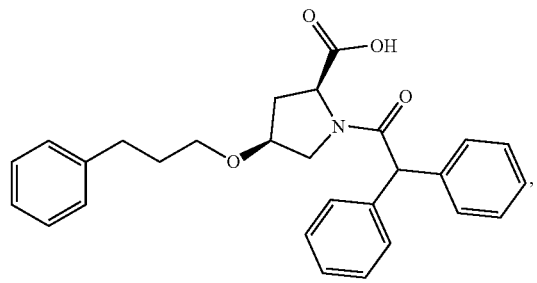 [SMILES: O=C(O)[C@@H]1C[C@H](OCCCc2ccccc2)CN1C(=O)C(c1ccccc1)c1ccccc1]

(2S,4R)-4-(cinnamyloxy)-1-(2,2-diphenylacetyl)pyrrolidine-2-carboxylic acid,
(2S,4R)-1-(2,2-diphenylacetyl)-4-(3-phenylpropoxy)pyrrolidine-2-carboxylic acid,
(2S,4S)-1-(2,2-diphenylacetyl)-4-(((1R,2S)-2-phenylcyclopropyl)methoxy)pyrrolidine-2-carboxylic acid,
(2S,4S)-1-(2,2-diphenylacetyl)-4-(((1 S,2R)-2-phenylcyclopropyl)methoxy)pyrrolidine-2-carboxylic acid,
(2S,4S)-1-(2,2-diphenylacetyl)-4-(methyl(3-phenylpropyl)amino)pyrrolidine-2-carboxylic acid,

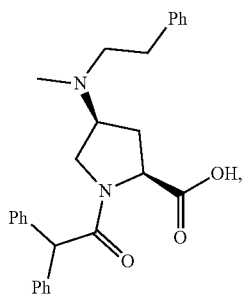 [SMILES: CN(CCc1ccccc1)[C@H]1C[C@@H](C(=O)O)N(C(=O)C(c2ccccc2)c2ccccc2)C1]

(2S,4S)-1-(2,2-diphenylacetyl)-4-(2-phenoxyphenoxy)-pyrrolidine-2-carboxylic acid,
(2S,4S)-1-(2,2-diphenylacetyl)-4-((3-phenylprop-2-yn-1-yl)-oxy)pyrrolidine-2-carboxylic acid,
(2S,4S)-1-(2,2-diphenylacetyl)-4-(phenethylamino)-pyrrolidine-2-carboxylic acid,
(2S,4S)-1-(2-cyclohexyl-2-phenylacetyl)-4-(methyl(3-phenylpropyl)amino)pyrrolidine-2-carboxylic acid,
(2S,4S)-1-(2,2-diphenylacetyl)-4-(methyl((2-phenylcyclopropyl)methyl)amino)pyrrolidine-2-carboxylic acid,

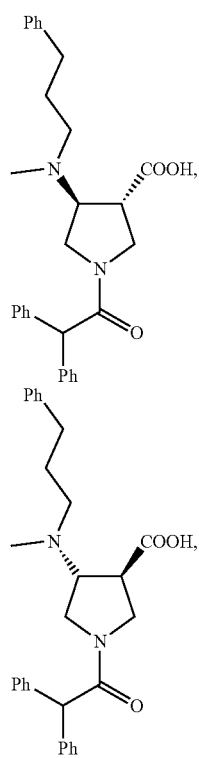

(2R,4R)-1-(2,2-diphenylacetyl)-4-(3-phenylpropoxy)-pyrrolidine-2-carboxylic acid,
(2S,4S)-1-(2,2-diphenylacetyl)-4-((3-(4-fluorophenyl)propyl)(methyl)amino)pyrrolidine-2-carboxylic acid,

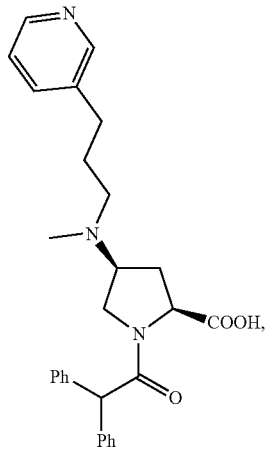 [SMILES: CN(CCCc1cccnc1)[C@H]1C[C@@H](C(=O)O)N(C(=O)C(c2ccccc2)c2ccccc2)C1]

(2S,4S)-1-(2,2-diphenylacetyl)-4-(3-(4-fluorophenyl)propoxy)pyrrolidine-2-carboxylic acid,
(2S,4S)-1-(2,2-diphenylacetyl)-4-((3-(4-methoxy-3-methylphenyl)prop-2-yn-1-yl)(methyl)amino)pyrrolidine-2-carboxylic acid,
(2S,4S)-1-(2,2-diphenylacetyl)-4-((3-(4-methoxy-3-methylphenyl)propyl) (methyl)amino)pyrrolidine-2-carboxylic acid,
(2S,4S)-1-(2,2-diphenylacetyl)-4-(4-phenylbutyl)-pyrrolidine-2-carboxylic acid,

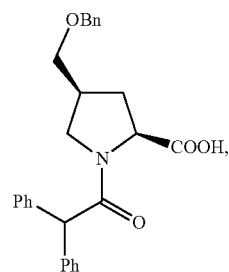 [SMILES: O=C(O)[C@@H]1C[C@H](COCc2ccccc2)CN1C(=O)C(c1ccccc1)c1ccccc1]

(2S,4S)-1-(2,2-diphenylacetyl)-4((3-(4-fluorophenyl)propyl)thio)pyrrolidine-2-carboxylic acid,
(2S,4S)-1-(2,2-diphenylacetyl)-4((3-(4-fluorophenyl)propyl)sulfonyl)pyrrolidine-2-carboxylic acid,
(2S,4S)-1-(2,2-diphenylacetyl)-N-(methylsulfonyl)-4-(phenylpropoxy)pyrrolidine-2-carboxamide,
(2S,4S)-1-(2,2-diphenylacetyl)-4-(phenethylthio)pyrrolidine-2-carboxylic acid,
(2S,4S)-1-(2,2-diphenylacetyl)-4-(((1R,2R)-2-phenylcyclopropyl)methoxy)pyrrolidine-2-carboxylic acid, and
(2S,4S)-1-(2,2-diphenylacetyl)-4-(((1S,2S)-2-phenylcyclopropyl)methoxy)pyrrolidine-2-carboxylic acid,
or a pharmaceutically acceptable salt thereof.

11. A pharmaceutical composition comprising a compound of formula (I) according to claim 10, or a pharmaceutically acceptable salt thereof, and a pharmaceutically acceptable carrier.

12. A method of treating neuropathic pain or inflammatory pain in a subject comprising administering a compound of formula (I) according to claim 10 or a pharmaceutically acceptable salt thereof.

13. A method of treating a condition characterized by neuronal hypersensitivity, impaired nerve conduction velocity, a cell proliferative disorder, or a disorder associated with an imbalance between bone resorption and bone formation in a subject comprising administering a compound of formula (I) according to claim 10 or a pharmaceutically acceptable salt thereof.

14. A method of producing analgesia in a subject comprising administering a compound of formula (I) according to claim 10 or a pharmaceutically acceptable salt thereof.

15. A compound of formula (I):

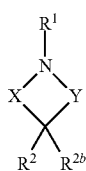

wherein:

X is absent and Y is —CHR$^3$CH$_2$—, —CH$_2$CHR$^3$; or X is —CHR$^5$— and Y is —CHR$^3$—;

R$^1$ is —C(=O)CH(aryl)(aryl), —C(=O)CH(aryl)(cycloalkyl), —C(=O)CH(cycloalkyl)(cycloalkyl), —C(=O)N(aryl)(aryl), —C(=O)N(aryl)(cycloalkyl) or —C(=O)N(cycloalkyl)(cycloalkyl);

R$^2$ is heterocyclyl, heteroaryl, —C$_{1-4}$alkylenearyl, —OC$_{1-3}$alkylenearyl, —OC$_{2-3}$alkenylenearyl, —OC$_{2-3}$ alkynylenearyl, —OC$_{1-3}$alkylenecycloalkylaryl, -OarylOaryl, SC$_{1-3}$alkylenearyl, —SO$_2$C$_{1-3}$alkylenearyl, —NHC$_{1-5}$alkyl, NHC$_{1-3}$alkylenearyl, —NHC$_{1-3}$alkyleneheteroaryl, —NHC$_{2-3}$alkynylenearyl, —N(CH$_3$)C$_{1-8}$alkyl, —N(CH$_3$)C$_{1-3}$alkylenearyl, —N(CH$_3$)C$_{1-3}$ alkyleneheteroaryl, —N(CH$_3$)C$_{2-3}$alkynylenearyl, —CH$_2$OC$_{1-3}$alkylenearyl, —N(CH$_3$)C$_{1-3}$alkylenecycloalkyl or —NHC$_{1-3}$alkylenecycloalkyl;

R$^{2b}$ is hydrogen;

R$^3$ is CO$_2$H, —CH$_2$CO$_2$H, —C(=O)C(=O)OH, —C(=O)NHSO$_2$C$_{1-6}$alkyl, —C(=O)NHSO$_2$phenyl, —C(=O)NHSO$_2$CF$_3$, —SO$_3$H or —PO$_3$H$_2$;

R$^5$ is hydrogen; and wherein each cycloalkyl, cycloalkenyl, aryl, heterocyclyl and heteroaryl may be optionally substituted with one or more optional substituents selected from the group consisting of C$_{1-6}$alkyl, C$_{2-6}$alkenyl, C$_{3-6}$cycloalkyl, oxo(=O), —OH, —SH, C$_{1-6}$alkylO—, C$_{2-6}$alkenylO—, C$_{3-6}$cycloalkylO—, C$_{1-6}$alkylS—, C$_{2-6}$alkenylS—, C$_{3-6}$cycloalkylS—, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$, -phenyl, -heterocyclyl, -heteroaryl, -Oheteroaryl, -Oheterocyclyl, -Ophenyl, —C(O)phenyl, —C(O)C$_{1-6}$alkyl;

wherein heterocyclyl is selected from the group consisting of azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl;

or a pharmaceutically acceptable salt thereof.

16. A compound according to claim 15, or a pharmaceutically acceptable salt thereof, wherein R$^1$ is —C(=O)CH(phenyl)(phenyl), —C(=O)CH(phenyl)(cyclohexyl), —C(=O)CH(cyclohexyl)(cyclohexyl), —C(=O)N(phenyl)(phenyl), —C(=O)N(phenyl)(cyclohexyl) or —C(=O)N(cyclohexyl)(cyclohexyl) wherein each phenyl or cyclohexyl is optionally substituted with one or more substituents selected from —C$_{1-3}$alkyl, —OC$_{1-3}$alkyl and halo.

17. A compound according to claim 15, or a pharmaceutically acceptable salt thereof, wherein R$^3$ is —CO$_2$H.

18. A pharmaceutical composition comprising a compound of formula (I) according to claim 15, or a pharmaceutically acceptable salt thereof, and a pharmaceutically acceptable carrier.

19. A method of treating or preventing neuropathic pain or inflammatory pain in a subject comprising administering a compound of formula (I) according to claim 15 or a pharmaceutically acceptable salt thereof.

20. A method of treating a condition characterized by neuronal hypersensitivity, impaired nerve conduction velocity, a cell proliferative disorder, or a disorder associated with an imbalance between bone resorption and bone formation in a subject comprising administering a compound of formula (I) according to claim 15 or a pharmaceutically acceptable salt thereof.

21. A method of producing analgesia in a subject comprising administering a compound of formula (I) according to claim 15 or a pharmaceutically acceptable salt thereof.

22. A compound according to claim 15 selected from the group consisting of:

(2S,3S)-1-(2,2-diphenylacetyl)-3-(3-phenylpropoxy)-azetidine-2-carboxylic acid, (2R,3R)-1-(2,2-diphenylacetyl)-3-(3-phenylpropoxy)-azetidine-2-carboxylic acid, (2R,3R)-3-(3-phenylpropoxy)-1-(2,2-diphenylacetyl)-azetidine-2-carboxylic acid, and (2S,3S)-3-(3-phenylpropoxy)-1-(2,2-diphenylacetyl)-azetidine-2-carboxylic acid, or a pharmaceutically acceptable salt thereof.

23. A pharmaceutical composition comprising a compound of formula (I) according to claim 22, or a pharmaceutically acceptable salt thereof, and a pharmaceutically acceptable carrier.

24. A method of treating neuropathic pain or inflammatory pain in a subject comprising administering a compound of formula (I) according to claim 22 or a pharmaceutically acceptable salt thereof.

25. A method of treating a condition characterized by neuronal hypersensitivity, impaired nerve conduction velocity, a cell proliferative disorder, or a disorder associated with an imbalance between bone resorption and bone formation in a subject comprising administering a compound of formula (I) according to claim 22 or a pharmaceutically acceptable salt thereof.

26. A method of producing analgesia in a subject comprising administering a compound of formula (I) according to claim 22 or a pharmaceutically acceptable salt thereof.

* * * * *